US008637511B2

(12) United States Patent  
Binch et al.

(10) Patent No.: US 8,637,511 B2
(45) Date of Patent: Jan. 28, 2014

(54) AMINOPYRIMIDINES USEFUL AS KINASE INHIBITORS

(75) Inventors: Hayley Binch, Encinitas, CA (US); Michael Mortimore, Burford (GB); Chris Davis, Salisbury (GB); Dean Boyall, Faringdon (GB); Simon Everitt, Beaconsfields (GB); Daniel Robinson, Abingdon (GB); Sham Ramaya, Burghfield Common (GB); Damien Fraysse, Abingdon (GB); John Studley, Witney (GB); Andrew Miller, Upton (GB); Michael O'Donnell, Abingdon (GB); Alistair Rutherford, Abingdon (GB); Joanne Pinder, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 18 days.

(21) Appl. No.: 12/796,297

(22) Filed: Jun. 8, 2010

(65) Prior Publication Data

US 2010/0310675 A1 Dec. 9, 2010

Related U.S. Application Data

(62) Division of application No. 11/592,114, filed on Nov. 3, 2006, now Pat. No. 7,767,672.

(60) Provisional application No. 60/732,951, filed on Nov. 3, 2005, provisional application No. 60/733,557, filed on Nov. 4, 2005.

(51) Int. Cl.
| A61K 31/506 | (2006.01) |
| A61K 31/5355 | (2006.01) |
| A61P 29/00 | (2006.01) |
| A61P 19/08 | (2006.01) |
| A61P 3/00 | (2006.01) |
| A61P 25/28 | (2006.01) |
| A61P 35/00 | (2006.01) |
| A61P 9/00 | (2006.01) |
| A61P 37/08 | (2006.01) |

(52) U.S. Cl.
USPC ...................................... 514/235.8; 514/274

(58) Field of Classification Search
USPC ......... 514/230.8, 234.5, 274, 272, 235.8, 269
See application file for complete search history.

(56) References Cited

U.S. PATENT DOCUMENTS

| 3,133,081 A | 5/1964 | Lafferty et al. |
| 3,755,322 A | 8/1973 | Winter et al. |
| 3,935,183 A | 1/1976 | Baron et al. |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,569,499 B2 | 5/2003 | Grammatica et al. |
| 6,579,983 B1 | 6/2003 | Batchelor et al. |
| 6,589,958 B1 | 7/2003 | Frietze |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,641,579 B1 | 11/2003 | Bernardi et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,716,851 B2 | 4/2004 | Cai et al. |
| 6,727,251 B2 | 4/2004 | Bebbington et al. |
| 6,743,791 B2 | 6/2004 | Cao et al. |

(Continued)

FOREIGN PATENT DOCUMENTS

| DE | 2458965 | 6/1976 |
| EP | 0019811 | 12/1980 |

(Continued)

OTHER PUBLICATIONS

Demidov, et al., The Plant Cell, vol. 17, 836-848, Mar. 2005.*
Carmena, et al., Current Opinion in Cell Biology 2009, 21:796-805.*
Bain, et al., Biochem. J. (2007) 408, 297-315.*
D'Alise, et al., Mol. Cancer Ther., 2008;7:1140-1149.*
Andrews, et al., Current Opinion in Cell Biology 2003, 15:672-683.*
Gadea, et al., Molec. Biol. of the Cell, vol. 16, 1305-1318, Mar. 2005.*
Jambhekar, S.S., "Biopharmaceutical Properties of Drug Substances" in Principles of Medicinal Chemistry, 4th ed., 12-24, (1995).

(Continued)

Primary Examiner — James O Wilson
Assistant Examiner — Cecilia M Jaisle
(74) Attorney, Agent, or Firm — Rory C. Stewart

(57) ABSTRACT

The present invention relates to compounds useful as inhibitors of protein kinases. The invention also provides pharmaceutically acceptable compositions comprising those compounds and methods of using the compounds and compositions in the treatment of various disease, conditions, and disorders. The invention also provides processes for preparing compounds of the invention.

2 Claims, No Drawings

(56) References Cited

U.S. PATENT DOCUMENTS

| | | |
|---|---|---|
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,919,338 B2 | 7/2005 | Mortlock et al. |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 7,345,054 B2 | 3/2008 | Hale et al. |
| 7,361,665 B2 | 4/2008 | Ledeboer et al. |
| 7,390,815 B2 | 6/2008 | Davies et al. |
| 7,427,681 B2 | 9/2008 | Bebbington et al. |
| 7,473,691 B2 | 1/2009 | Davies et al. |
| 7,491,730 B2 | 2/2009 | Forster et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,579,349 B2 | 8/2009 | Nowak et al. |
| 7,625,913 B2 | 12/2009 | Bebbington et al. |
| 7,691,853 B2 | 4/2010 | Bebbington et al. |
| 7,737,151 B2 | 6/2010 | Mortimore et al. |
| 7,767,672 B2 | 8/2010 | Binch et al. |
| 7,820,685 B2 | 10/2010 | Binch et al. |
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0026664 A1 | 2/2003 | Mongrain |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington et al. |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0049032 A1 | 3/2004 | Charrier et al. |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0167141 A1 | 8/2004 | Bebbihngdon et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0049246 A1 | 3/2005 | Bemis et al. |
| 2005/0228005 A1 | 10/2005 | Moon et al. |
| 2005/0234059 A1 | 10/2005 | Hale et al. |
| 2006/0270660 A1 | 11/2006 | Charrier et al. |
| 2007/0179125 A1 | 8/2007 | Fraysse et al. |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0261722 A1* | 10/2010 | Guillemont et al. ....... 514/235.8 |
| 2010/0267628 A1 | 10/2010 | O'Harte et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0137037 A1 | 6/2011 | Durrant et al. |
| 2011/0269732 A1 | 11/2011 | Golec et al. |

FOREIGN PATENT DOCUMENTS

| | | |
|---|---|---|
| EP | 136976 | 4/1985 |
| EP | 0302312 | 2/1989 |
| GB | 2052487 | 1/1981 |
| JP | 10-130150 | 5/1998 |
| JP | 2000-026421 | 1/2000 |
| JP | 06-65237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0039101 | 6/2000 |
| WO | 0038675 | 7/2000 |
| WO | 0042029 | 7/2000 |
| WO | 0059509 | 10/2000 |
| WO | 0078757 | 12/2000 |
| WO | 0112621 | 2/2001 |
| WO | 0139777 | 6/2001 |
| WO | 0140215 | 6/2001 |
| WO | 0144242 | 6/2001 |
| WO | 0147879 | 7/2001 |
| WO | 0147897 | 7/2001 |
| WO | 0160816 | 8/2001 |
| WO | 0164655 | 9/2001 |
| WO | 0179198 | 10/2001 |
| WO | 0174768 | 11/2001 |
| WO | 0125220 | 12/2001 |
| WO | 0208244 | 1/2002 |
| WO | 0218346 | 3/2002 |
| WO | 0222601 | 3/2002 |

(56) References Cited

FOREIGN PATENT DOCUMENTS

| WO | 0222602 | 3/2002 |
|---|---|---|
| WO | 0222603 | 3/2002 |
| WO | 0224667 | 3/2002 |
| WO | 0247690 | 6/2002 |
| WO | 0250065 | 6/2002 |
| WO | 0250066 | 6/2002 |
| WO | 02057259 | 7/2002 |
| WO | 02059111 | 8/2002 |
| WO | 02059112 | 8/2002 |
| WO | 02062789 | 8/2002 |
| WO | 02066461 | 8/2002 |
| WO | 02068415 | 9/2002 |
| WO | 0279197 | 10/2002 |
| WO | 03026664 | 4/2003 |
| WO | 03077921 | 9/2003 |
| WO | 03078426 | 9/2003 |
| WO | 03078427 | 9/2003 |
| WO | 04000833 | 12/2003 |
| WO | 2004013140 | 2/2004 |
| WO | 2004037814 | 5/2004 |
| WO | 2007023382 | 1/2007 |
| WO | 2007041358 | 4/2007 |
| WO | 2007/056221 | 5/2007 |
| WO | 2007056163 A | 5/2007 |
| WO | 2007056164 A1 | 5/2007 |
| WO | 2007059299 | 5/2007 |
| WO | 2008057940 | 5/2008 |
| WO | WO2008077086 | 6/2008 |

OTHER PUBLICATIONS

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).

Medwid, J.B. et al., "Preparation of Triazolo[1,5-c]pyrimidines as Potential Antiasthma Agents," J. Med. Chem. 33, 1230-1241 (1990).

Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

Cohen, P., "Dissection of the Protein Phosphorylation Cascades Involved in Insulin and Growth Factor Action", Biochem. Soc. Trans., 21, 555-567 (1993).

Haq, S. et al., "Glycogen Synthase Kinase-3β Is a Negative Regulator of Cardiomyocyte Hypertrophy", J. Cell Biol., 151(1), 117-129 (2000).

Fischer, P.M. et al., "Inhibitors of Cyclin-Dependent Kinases as Anti-Cancer Therapeutics", Current Med. Chem., 7, 1213-1245 (2000).

Mani, S. et al., "Cyclin-dependent kinase: novel anticancer agents", Exp. Opin. Invest. Drugs., 8, 1849-1870 (2000).

Fry, D.W. et al., "Inhibitors of cyclin-dependent kinases as therapeutic agents for the treatment of cancer", Current Opin. Oncol. Endoc. & Metab. Investig., 2-40-59 (2000).

Bokemeyer, D. et al., "Multiple intracellular MAP kinase signaling cascades", Kidney Int., 49, 1187-1198 (1996).

Anderson, N.G. et al., "Multiple intracellular MAP kinase signaling cascades", Nature, 343, 651-653 (1990).

Crews, C.M. et al., "The Primary Structure of MEK, a Protein Kinase That Phosphorylates the ERK Gene Product", Science, 258, 478-480 (1992).

Bjorbaek, C. et al, "Divergent Functional Roles for p90rsk Kinase Domains", J. Biol. Chem., 270(32), 18848-18552 (1995).

Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).

Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).

Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).

Moodie, S.A. et al., "Complexes of Ras-GTP with Raf-1 and Mitogen-Activated Protein Kinase Kinase", Science, 260 (5114), 1658-1661 (1993).

Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).

Sivaraman, V.S., et al., "Hyperexpression of Mitogen-activated Protein Kinase in Human Breast Cancer", J. Clin. Invest., 99(7), 1478-1483 (1997).

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).

Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).

Kazuhiko, N. et al., "Akt/Protein Kinase B Prevents Injury-Induced Motoneuron Death and Accelerates Axonal Regeneration", J. of Neuroscience, 20(8), 2875-2986 (2000).

Molina, T.J. et al., "Profound block in thymocyte development in mice lacking p56lck", Nature, 357, 161-164 (1992).

Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).

IUPAC Compendium of Chemical Terminology on a definition of "aliphatic compounds" found from http://www.chemsoc.org/chembytes/goldbook/index.htm (last visited on Nov. 18, 2007).

Caravajal et al., Aurora Kinases: New Targets for Cancer Therapy, Clin Cancer Res 2006:12(23), pp. 6869-6875, Dec. 1, 2006.

Johnson et al., Relationships between drug activity in NCI preclinical in vitro and in vivo models and early clinical trials, British Journal of Cancer (2001) 64(1 0): 1424-1431.

Gura, Systems for identifying New Drugs Are Often Faulty, Cancer Models, Science, vol. 278, No. 5340, pp. 1041-1042, Nov. 1997.

The International Search Report received in the corresponding PCT Application No. PCT/US 06/43096, 2006.

Alonso, M. et al., "GSK-3 Inhibitors: Discoveries and Developments", Current Medicinal Chemistry, 11, 755-763 (2004).

Anonymous, "Vertex Inhbitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-I-(2-cyanophenyl) triazenes into 3-Arylqu i nazol i n-4(3H) -ones with Formamide" J. Chem. Soc. Perkin Trans. I, 3765-2766 (1984).

Bischoff, J.R., et al., "A homologue of Drosophila aurora kinase is oncogenic and amplified in human colorectal cancers", The EMBO Journal, 17(11): 3052-3065 (1998).

Bischoff, J.R., et al., "The Aurora/Ipl1p kinase family: regulators of chromosome segregation and cytokinesis", Cell Biology, 9, 454-459 (1999).

Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).

Wolff, M.E., "Burger's Medicinal Chemistry and Drug Discovery," 5th ed., vol. 1: Principles and Practice, 975-977 (1995).

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).

Harrington, E.A. et al., "VX-680, a potent and selective small-molecule inhibitor of the Aurora kinases, suppresses tumor growth in vivo," Nat. Med., 10(3): 262-267 (2004).

Heutink, P., "Untangling tau-related dementia", Hum. Mol. Genet., 9(6): 979-986 (2000).

Nigg, E.A., "Mitotic Kinases as Regulators of Cell Division and its Checkpoints," Nat. Rev. Mol. Cell Biol., 2: 21-32 (2001).

(56) References Cited

OTHER PUBLICATIONS

Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).
Nakajima, Y. et al., "Pyrazoles agricultural and horticultural bactericides," CAPLUS listing Accession No. 1994:292136, JP 06065237 (1994).
Kelarev, V.I. et al., "Synthesis of amino derivatives of 1,3,5-triazine containing 1,3-4-thiadiazole fragments," Databaseca "Online!" Chemical Abstract Service, Columbus, OH, US; Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim, L. et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).
Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997).
Ali, N.M. et al., "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
Rueeger, H et al., "Design, synthesis and SAR of a series of 2-substituted 4-amino-quinazoline neuropeptide Y Y5 receptor antagonists", Bioorg. Med. Chem. Lett, 10(11), 1175-1180 (2000).
Glossary of Class Names of Organic Compounds and Reactive Intermediates Based on Structure found from http://www.chem.qmul.ac.uk/iupac/class/index.html (last visited on Nov. 18, 2007).
Nomenclature found from http://www.cem.msu.edu/~reusch/VirtualText/nomen1.htm (last visited on Nov. 18, 2007).
Coghlan, M.P. et al., "Selective small molecule inhibitors of glycogen synthase kinase-3 modulate glycogen metabolism and gene transcription", Chemistry & Biology, 7, 793-83 (2000).
Klein, P.S. et al., "A molecular mechanism for the effect of lithium on development", PNAS, 93: 8455-8459 (1996).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Massillon, D. et al., "Identification of the glycogenic compound 5-iodotubercidin as a general protein kinase inhibitor", Biochem J., 299: 123-128 (1994).
Fox T. et al., "A single amino acid substitution makes ERK2 susceptible to pyridinyl imidazole inhibitors of p38 MAP kinase", Protein Sci., 7: 2249-2255 (1998).
Takayanagi, H. et al., "Suppression of arthritic bone destruction by adenovirus-mediated csk gene transfer to synoviocytes and osteoclasts", J. Clin. Invest., 104, 137-146 (1999).
Boschelli et al., "Small molecule inhibitors of Src family kinases", Drugs of the Future, 25(7): 717-736 (2000).
Talamonti, M.S. et al., "Increase in activity and level of pp60c-src in progressive stages of human colorectal cancer", J Clin Invest., 91(1): 53-60 (1993).
Lutz, M.L. et al., "Overexpression and Activation of the Tyrosine Kinase Src in Human Pancreatic Carcimona", Biochem. Biophys. Res. 243, 503-508 (1998).
Rosen, N. et al., "Analysis of pp60c-src Protein Kinase Activity in Human Tumor Cell Lines and Tissues", J.Biol. Chem., 261, 13754-13759 (1986).
Bolen, J.B. et al., "Activation of pp60c-src protein kinase activity in human colon carcinoma", PNAS, 84, 2251-2255 (1987).
Masaki, T. et al., "pp60c-src Activation in Hepatocellular Carcinoma of Humans and LEC Rats", Hapatology, 27, 1257 (1998).
Biscardi, J.S. et al., "c-Src, Receptor Tyrosine Kinases, and Human Cancer", Adv. Cancer Res., 76, 61 (1999).
Lynch, S.A. et al., "Increased Expression of the src Proto-Oncogene in Hairy Cell Leukemia and a Subgroup of B-Cell Lymphomas", Leukemia, 7(9), 1416-1422 (1993).
Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).
Staley, C.A. et al., "Decreased Tumorigenicity of a Human Colon Adenocarcinoma Cell Line by an Antisense Expression Vector Specific for c-Src", Cell Growth Diff., 8, 269-274 (1997).
Singhal, N. et al., "Synthesis and Antimalarial Activity of Some New Quinazoline Derivatives", Indian Chem. Soc., 61, 690-693 (1984).
Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).
Namikowa et al., "Akt/Protein Kinase B Prevents Injury-Induced Motoneuron Death and Accelerates Axonal Regeneration", The Journal of Neuroscience, Apr. 15, 2000, 20(8):2875-2886.
Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).
Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).
Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).
Charpiot, B. et al., "Quinazolines: Combined type 3 and 4 phosphodiesterase inhibitors", Bioorg. Med. Chem. Lett., 8 (20), 2891-2896 (1998).
Shikhaliev, K.S. et al., "Heterocyclization of quinazol-2-ylguanidines. 1. Reaction with amino acids", Chem. Heterocycl. Compd., 35 (7), 818-820 (1999).
Singh, S.P. et al., "Synthesis & Mass Spectra of Some Substituted 2-(2'-Benzazolylamino)pyrimidines", Indian J. Chem. Sect. B, 22(1); 37-42 (1983).
Ti, J. et al., "Anticandidal activity of pyrimidine-peptide conjugates", J. Med. Chem., 23(8), 913-918 (1980).
Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).
Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).
Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett, 7, 4, 421-424 (1997).

(56) References Cited

OTHER PUBLICATIONS

Agarwal, N. et al., "Suitably functionalised pyrimidines as potential antimycotic agents", Bioorg. Med. Chem. Lett., 10, 8, 703-706 (2000).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Noell, C.W. et al., "Potential Purine Antagonists. XX. The Preparation and Reactions of Some Methylthiopurines", J. Am. Chem. Soc., 81(22), 5997-6007 (1959).

Lubbers, T. et al., "Design, synthesis, and structure—activity relationship studies of ATP analogues as DNA gyrase inhibitors", Bioorg. Med. Chem. Lett., 10, 8, 821-826 (2000).

D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f)quinozalines and their oxides", Indian J. Chem. Sect. B, 34, 9, 778-790 (1995).

Curd, F.H.S. et al, "Synthetic antimalarials. Part XVII. Some aminoalkylaminoquinoline derivatives", J. Chem. Soc., 899-909 (1947).

Haworth, R.D. et al., "Synthetic antimalarials. Part XXVII. Some derivatives of phthalazine, quinoxaline, and isoquinoline", J. Chem. Soc., 777-782 (1948).

Nair, M.D., et al., "3-Chloroisocarbostyril & Its Chlorination Products", Indian J. Chem., 467-470 (1967).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Gnecco, D. et al., "An Improved Preparation of 1-Methyl-4-Cyano-4-phenylpiperidine", Org. Prep. Proced. Int., 18 (4), 478-480 (1996).

Fedorynski, M. et al., "Synthesis of 1-Arycyclopropanecarbonitriles under Phase-transfer Catalytic Conditions", Org. Prep. Proced. Int., 27(3), 355-359 (1995).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Prasad, G. et al., "18-Crown-6 as a catalyst in the dialkylation of o-nitrophenacyl derivatives", J. Org. Chem., 25, 7188-7190 (1991).

Moss, R.A. et al., "Conversion of 'Obstinate' Nitriles to Amidines by Garigipati's Reaction", Tetrahedron Lett., 36(48), 8761-8764 (1995).

Garigipati, R.S., "An efficient conversion of nitriles to amidines", Tetrahedron Lett., 31(14), 1969-1972 (1990).

Warner, S.L. et al, "Targeting Aurora-2 Kinase in Cancer," Mol. Cancer Thera., 2, 589-585, 2003.

Wagman, A.S. et all, "Discovery and Development of GSK3 Inhibitors for the Treatment of Type 2 Diabetes," Current Pharmaceutical Design, 10, 1105-1137 (2004).

Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).

Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).

Soriano, P. et al., "Targeted Disruption of the C-SIC Pmto-Oncogene Leads to Osteopetrosis in Mice," Cell, 64: 693-702, (1991).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).

Casanova, B. et al., "Revisión crítica de la patogenia actual de la esclerosis múltiple y futuras direcciones posibles," Rev. Neurol., 28 (9): 909-915 (1999).

Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).

Simone, J.V., "Oncology: Introduction" in Cecil Textbook in Medicine, 20th ed., vol. 1, 1004-1010 (1996).

Coleman, R.A., "The Biological Evaluation of New Compounds" in Medicinal Chemistry: Principles and Practice, King, Frank D. ed, Royal Society of Chemistry, 53-66 (1994).

The Condensed Chemical Dictionary, Sixth Edition by Arthur and Elizabeth Rose, 38 (1961).

Damasio, A.R., "Alzheimer's Disease and Related Dementia," in Cecil Textbook of Medicine, 20th ed., 2: 1992-1996 (1996).

Rogers, E. et al., "The aurora kinase AIR-2 functions in the release of chromosome cohesion in Caenorhabditis elegans meiosis," J. Cell Biol., 157(2): 219-229 (2002).

Fisher A., "Therapeutic Strategies in Alzheimer's Disease: M1 Muscarinic Agonists," Jpn. J. Pharmacol., 84(2):101-12 (2000).

Frame, M.C., "Src in cancer: deregulation and consequences for cell behaviour," Biochimica et Biophysica Acta, 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Ganellin, C.R., "Past Approaches to Discovering New Drugs as Medicines" in Medicinal Chemistry, Principles and Practices. King, Frank D. ed, Royal Society of Chemistry, 189-205 (1994).

Hamdane, M. et al., "A Therapeutic Target in Alzheimer Neurodegeneration," J. Mol. Neurosci., 19(3): 275-87 (2002).

Hardt, S.E. et al., "Glycogen Synthase Kinase-3β—A Novel Regulator of Cardiac Hypertrophy and Development," Circulation Research, 90: 1055-1063 (2002).

Parnell, E.W., "2-Cyano-4-nitrophenylhydrazine and 3-Amino-5-nitroindazole", J. Chem. Soc., 2363-2365 (1959).

Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).

Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Okafor, C.O., "Studies in the Heterocyclic Series. X. 1,3,9-Triazaphenothiazine Ring System, a New Phenothiazine Ring," J. Org. Chem., 40(19): 2753-2755 (1975).

* cited by examiner

AMINOPYRIMIDINES USEFUL AS KINASE INHIBITORS

CROSS REFERENCE TO RELATED APPLICATIONS

This application is a divisional of U.S. Ser. No. 11/592,114 filed Nov. 3, 2006, which claims benefit, under 35 U.S.C. §119, to U.S. Provisional Application Nos. 60/732,951, filed Nov. 3, 2005, and 60/733,557, filed Nov. 4, 2005. The entire teachings of these applications are incorporated herein by reference.

TECHNICAL FIELD OF THE INVENTION

The present invention relates to compounds useful as inhibitors of kinases. The invention also relates to pharmaceutically acceptable compositions comprising the compounds of the invention, methods of using the compounds and compositions in the treatment of various disorders, and processes for preparing the compounds.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families.

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function.

These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

The Aurora proteins are a family of three related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative antibodies or neutralizing antibodies disrupts progression through mitosis with accumulation of cells with 4N DNA, and in some cases this is followed by endoreduplication and cell death.

Protein kinases are attractive and proven targets for new therapeutic agents to treat a range of human diseases, with examples of kinase inhibitors including Gleevec® and Tarceva®. The Aurora kinases are especially attractive targets due to their association with numerous human cancers and the roles they play in the proliferation of these cancer cells. Therefore, there is a need for compounds that inhibit protein kinases.

SUMMARY OF THE INVENTION

This invention provides compounds and pharmaceutically acceptable compositions thereof that are useful as inhibitors of protein kinases. These compounds are represented by formula I:

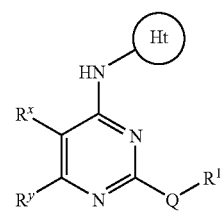

or a pharmaceutically acceptable salt thereof, wherein $R^1$, $R^X$, $R^Y$, Q, and Ht are as defined herein.

These compounds and pharmaceutically acceptable compositions thereof are useful for inhibiting kinases in vitro, in vivo, and ex vivo. Such uses include treating or preventing a variety of diseases, disorders or conditions, including, but not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Other uses include the study of kinases in biological and pathological phenomena; the study of intracellular signal transduction pathways mediated by such kinases; and the comparative evaluation of new kinase inhibitors.

DETAILED DESCRIPTION OF THE INVENTION

The present invention provides a compound of formula I:

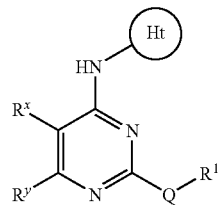

or a pharmaceutically acceptable salt thereof, wherein:

Ht is thiazole or pyrazole, wherein each Ht is optionally and independently substituted with $R^2$ and $R^{2'}$;

Q is —O—, —NR'—, —S—, or —C(R')$_2$—;

$R^X$ is $T^1$-$R^3$ or L-Z—$R^3$;

$R^Y$ is $T^2$-$R^{10}$ or L-Z—$R^{10}$;

$R^1$ is $T^3$-(Ring D);

Ring D is a 5-7 membered monocyclic ring or 8-10 membered bicyclic ring selected from an aryl or heteroaryl ring, said heteroaryl ring having 1-4 ring heteroatoms selected from nitrogen, oxygen or sulfur, wherein each substitutable ring carbon of Ring D is independently substituted by oxo, $T^4$-$R^5$, or V—Z—$R^5$, and each substitutable ring nitrogen of Ring D is independently substituted by —$R^4$;

each T, $T^1$, $T^2$, $T^3$, and $T^4$ is independently a $C_{1-4}$ alkylidene chain or is absent;

Z is a $C_{1-4}$ alkylidene chain or is absent;

L is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^8$)CON(R$^8$)—;

$R^2$ and $R^{2'}$ are independently —R, -T-W—$R^6$, or $R^8$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

each $R^3$ and $R^5$ is independently —R, -halo, —OR, —C(=O)R, —CO$_2$R, —COCOR, COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$ (C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is hydrogen, a $C_{1-6}$ aliphatic group, a $C_{6-10}$ aryl ring, a heteroaryl ring having 5-10 ring atoms, or a heterocyclyl ring having 4-10 ring atoms, the heteroaryl or heterocyclyl ring having 1-4 ring heteroatoms selected from nitrogen, oxygen, or sulfur, the aliphatic group and each R ring being optionally substituted by $R^9$;

each $R^4$ is —$R^7$, —COR', —CO$_2$ (optionally substituted $C_{1-6}$ aliphatic), —CON(R$^7$)$_2$, or —SO$_2$R$^7$;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)$_2$OC(O)—, —C(R$^6$)$_2$OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each $R^6$ is independently hydrogen or an optionally substituted $C_{1-6}$ aliphatic group, or two $R^6$ groups on the same nitrogen atom are taken together with the nitrogen atom to form an optionally substituted 4-6 membered heterocyclyl or heteroaryl ring; and each $R^7$ is independently hydrogen or an optionally substituted $C_{1-6}$ aliphatic group, or two $R^7$ on the same nitrogen are taken together with the nitrogen to form an optionally substituted 5-8 membered heterocyclyl or heteroaryl ring;

each $R^8$ is halogen, —CN, or —NO$_2$;

each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N(R')$_2$, —OC(=O)R', —N(R')COR', —N(R')CO$_2$(C$_{1-6}$ aliphatic), —N(R')N(R')$_2$, —C=NN(R')$_2$, —C=N—OR', —N(R')CON(R')$_2$, —N(R')SO$_2$N(R')$_2$, —N(R')SO$_2$R', or —OC(=O)N(R')$_2$;

each $R^{10}$ is a 4-membered heterocyclic ring containing 1-2 heteroatoms selected from O, NR$^{11}$, and S; each $R^{10}$ is optionally substituted with 0-3 occurrences of J;

each J is independently -halo, —OR, oxo, $C_{1-6}$ aliphatic, —C(=O)R, —CO$_2$R, —COCOR, COCH$_2$COR, —NO$_2$, —CN, —S(O)R, —S(O)$_2$R, —SR, —N(R$^4$)$_2$, —CON(R$^7$)$_2$, —SO$_2$N(R$^7$)2, —OC(=O)R, —N(R$^7$)COR, —N(R$^7$)CO$_2$ (C$_{1-6}$ aliphatic), —N(R$^4$)N(R$^4$)$_2$, =NN(R$^4$)$_2$, =N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$; or 2 J groups, on the same atom or on different atoms, together with the atom(s) to which they are bound, form a 3-8 membered saturated, partially saturated, or unsaturated ring having 0-2 heteroatoms selected from O, N, or S;

each $R^{11}$ is —$R^7$, —COR$^7$, —CO$_2$ (optionally substituted $C_{1-6}$ aliphatic), —CON(R$^7$)$_2$, or —SO$_2$R$^7$;

each R' is independently hydrogen or a $C_{1-6}$ aliphatic group optionally substituted with 0-4 occurrences of NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic; or, two R', together with the atom(s) to which they are attached, form an optionally substituted 3-6 membered carbocyclyl or heterocyclyl.

In some embodiments, the present invention provides a compound of formula I:

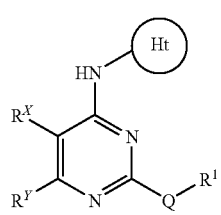

or a pharmaceutically acceptable salt thereof, wherein:

Ht is thiazole or pyrazole, wherein each ring is optionally and independently substituted with $R^2$ and $R^{2'}$;

Q is —O—, —NR'—, —S—, or —C(R')$_2$—;

$R^X$ is H, $C_{1-6}$aliphatic, $NO_2$, CN, halo, $NH_2$, $N(C_{1-4}$aliphatic), $N(C_{1-4}$aliphatic)$_2$, $O(C_{1-4}$aliphatic), OH, or —N(C=O)($C_{1-4}$aliphatic); wherein said aliphatic is optionally substituted with 1-3 fluoro;

$R^Y$ is $T^2$-$R^{10}$ or L-Z—$R^{10}$;

$R^1$ is $T^3$-(Ring D);

Ring D is a 5-7 membered monocyclic aryl or heteroaryl ring, wherein said heteroaryl has 1-4 ring heteroatoms selected from O, N, or S; Ring D can optionally be fused with Ring D';

Ring D' is a 5-8 aromatic, partially saturated, or fully unsaturated ring containing 0-4 ring heteroatoms selected from nitrogen, oxygen or sulfur;

each substitutable ring carbon of Ring D and Ring D' is independently substituted by oxo, $T^4$-$R^5$, or V—Z—$R^5$;

each substitutable ring nitrogen of Ring D and Ring D' is independently substituted by —$R^4$;

each T, $T^3$, and $T^4$ is independently a $C_{1-4}$ alkylidene chain or is absent;

Z is a $C_{1-4}$ alkylidene chain or is absent;

L is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

$T^2$ is independently absent or a $C_{1-10}$ alkylidene chain wherein up to six C units of the alkylidene chain are optionally replaced by —O—, —C(=O)—, —S(O)—, —S(O)$_2$—, —S—, or —N(R$^4$)—; $T^2$ is optionally substituted with 0-6 $J^T$ groups;

$R^2$ and $R^{2'}$ are independently —R, -T-W—$R^6$, or $R^8$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^5$ is —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$(C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is hydrogen, a $C_{1-10}$ aliphatic group, a $C_{6-10}$ aryl ring, a heteroaryl ring having 5-10 ring atoms, or a heterocyclyl ring having 4-10 ring atoms, the heteroaryl or heterocyclyl ring having 1-4 ring heteroatoms selected from nitrogen, oxygen, or sulfur, the aliphatic group and each R being optionally substituted by 0-6 $R^9$;

each $R^4$ is —$R^7$, —COR', —CO$_2$ (optionally substituted $C_{1-6}$ aliphatic), —CON(R$^7$)$_2$, or —SO$_2$R$^7$;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —O(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)$_2$CO(O)—, —C(R$^6$)$_2$OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each $R^6$ is independently hydrogen or $C_{1-6}$ aliphatic optionally substituted with 0-3 $J^6$; or two $R^6$ groups on the same nitrogen atom are taken together with the nitrogen atom to form a 4-8 membered heterocyclyl or heteroaryl ring; wherein said heterocyclyl or heteroaryl ring is optionally substituted with 0-4 $J^6$;

each $R^7$ is independently hydrogen; $C_{1-6}$ aliphatic; a 5-membered heteroaryl containing 0-4 heteroatoms selected from O, N, or S; or phenyl; each $R^7$ is optionally substituted with 0-3 $J^7$; or two $R^7$ on the same nitrogen are taken together with the nitrogen to form an optionally substituted 4-8 membered heterocyclyl or heteroaryl ring; wherein said heterocyclyl or heteroaryl ring is optionally substituted with 0-4 $J^7$;

each $R^8$ is halogen, —CN, or —NO$_2$;

each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N(R')$_2$, —OC(=O)R', —N(R')COR', —N(R')CO$_2$(C$_{1-6}$ aliphatic), —N(R')N(R')$_2$, —N(R')CON(R')$_2$, —N(R')SO$_2$N(R')$_2$, —N(R')SO$_2$R', —OC(=O)N(R')$_2$, =NN(R')$_2$, =N—OR', =NR', or =O;

each $R^{10}$ is a 4-membered heterocyclic ring containing 1 heteroatom selected from O, NR$^{11}$, and S; each R$^{11}$ is optionally substituted with 0-6 occurrences of J;

each J and $J^T$ is independently R, -halo, —OR, —C(=O)R, —CO$_2$R, —COCOR, COCH$_2$COR, —NO$_2$, —CN, —S(O)R, —S(O)$_2$R, —SR, —N(R$^4$)$_2$, —CON(R$^7$)$_2$, —SO$_2$N(R$^7$)2, —OC(=O)R, —N(R$^7$)COR, —N(R$^7$)CO$_2$ (C$_{1-6}$ aliphatic), —N(R$^4$)N(R$^4$)$_2$, =NN(R$^4$)$_2$, =N—OR, =NR', =O, —N(R$^7$)CON(R$^7$)$_2$, —N(R$^7$)SO$_2$N(R$^7$)$_2$, —N(R$^4$)SO$_2$R, —OC(=O)N(R$^7$)$_2$, or —OP(=O)(OR")$_2$; or each $J^6$ and $J^7$ is independently NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic;

2 J or $J^T$ groups, on the same atom or on different atoms, together with the atom(s) to which each set of J or $J^T$ atoms are bound, form a 3-8 membered saturated, partially saturated, or unsaturated ring having 0-2 heteroatoms selected from O, N, or S; wherein 1-4 hydrogen atoms on the ring formed by the 2 J or $J^T$ groups is optionally replaced with halo, C$_{1-3}$alkyl, or —O(C$_{1-3}$alkyl); wherein said C$_{1-3}$alkyl is optionally substituted with 1-3 fluorine; or two hydrogen atoms on the same atom in the ring formed by the 2 J or $J^T$ groups are optionally replaced with oxo;

each $R^{11}$ is —$R^7$, —$COR^7$, —$CO_2$ (optionally substituted $C_{1-6}$ aliphatic), —$CON(R^7)_2$, or —$SO_2R^7$;

each R' is independently hydrogen or a $C_{1-6}$ aliphatic group optionally substituted with 0-4 occurrences of $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), $CONH_2$, $CONH(C_{1-4}$aliphatic), $CON(C_{1-4}$aliphatic$)_2$, $O(haloC_{1-4}$ aliphatic), or halo$C_{1-4}$aliphatic; or, two R', together with the atom(s) to which they are attached, form =O, an optionally substituted 3-6 membered carbocyclyl, or heterocyclyl;

each R" is independently H or $C_{1-2}$alkyl.

In some embodiments, Ht is

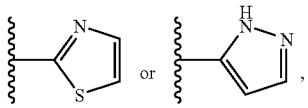 [SMILES: *c1nccs1 ; *c1ccn[nH]1]

wherein each ring is optionally and independently substituted with $R^2$ and $R^{2'}$.

In some embodiments, Q is a heteroatom selected from —O—, —NR'— or —S—. In some embodiments, Q is —NR'— or —S—. In some embodiments, Q is —NR'— or —O—. In some embodiments, Q is —S—. In other embodiments is —O—. In yet other embodiments, Q is —NR'—.

In some embodiments, $R^1$ is $T^3$-(Ring D);

In some embodiments, Ring D is an optionally substituted 5-7 membered aryl or heteroaryl. In other embodiments, Ring D is an optionally substituted 8-10 membered aryl or heteroaryl. In some embodiments, Ring D is an optionally substituted 5-10 membered aryl ring. In other embodiments, Ring D is an optionally substituted 5-10 membered heteroaryl ring. In some embodiments, Ring D is a 5-6 membered monocyclic aryl or heteroaryl ring. In some embodiments, Ring D' is fused with ring D.

In some embodiments, Ring D is phenyl. In some embodiments, Ring D' is phenyl or imidazole. In some embodiments, the bicyclic ring formed by the fusion of Ring D' and Ring D (Ring D-D') is naphthyl, benzimidazole, quinoline, or isoquinoline. In other embodiments, Ring D-D' is benzimidazole, isoquinoline, quinoline, or isoindolinone.

As would be understood by a skilled practitioner, when two rings are fused, the two rings share two adjacent atoms and also the bond or bonds between the adjacent atoms. For example, phenyl fused with pyrimidine could form quinazoline.

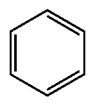

fused with

could form

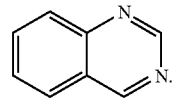

Phenyl fused with pyrrolidine could form indoline.

fused with

could form

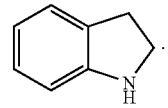

The fused ring can be rotated in any chemically stable orientation. For example, a phenyl fused with an imidazole could form one of three possible compounds:

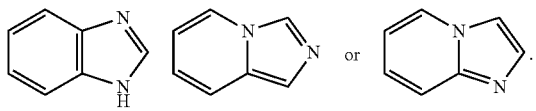

In some embodiments, Ring D is mono-substituted in the 4-position with $T^4$-$R^5$ or V—Z—$R^5$. In some embodiments, Ring D is optionally substituted in the 4-position with V—Z—$R^5$.

In some embodiments, V is —$N(R^6)CO$—, —$C(O)N(R^6)$—, —O—, —$N(R^6)$—, or —$N(R^6)SO_2$—. In other embodiments, V is —$N(R^6)CO$— or —$C(O)N(R^6)$—.

In some embodiments, $T^3$ is absent.

In other embodiments, $T^3$ is a $C_{1-4}$ alkylidene chain.

In other embodiments, $T^2$ is a $C_{1-10}$ alkylidene chain wherein up to six C units of the alkylidene chain are optionally replaced by —O—, —C(=O)—, —S(O)—, —S(O)$_2$—, —S—, or —N($R^4$)—.

In some embodiments, Z is a $C_{1-4}$ alkylidene chain. In other embodiments, Z is absent.

In certain embodiments, the substituents in $R^6$ and $R^7$ are independently selected from $R^9$.

In another embodiment, the optionally substituted aliphatic group of $R^6$ is a $C_{1-4}$ aliphatic group.

In another embodiment, $R^2$ is H or $C_{1-6}$ aliphatic (which is unsubstituted in certain embodiments).

In another embodiment, $R^2$ is H or $C_{1-3}$ aliphatic (which is unsubstituted in certain embodiments).

In another embodiment, $R^{2'}$ is H or $C_{1-3}$ aliphatic (which is unsubstituted in certain embodiments).

In some embodiments, $R^2$ is $C_{1-6}$ aliphatic and $R^{2'}$ is H.

In one embodiment, $R^X$ is —R, halogen, —NO$_2$, —CN, —CO$_2$R, —OR, or —SR.

In another embodiment, $R^X$ is H, halogen, —NO$_2$, or —CN.

In another embodiment, $R^X$ is H or F. In some embodiments, $R^X$ is H.

In one embodiment, $R^Y$ is $T^2$-$R^{10}$. In some embodiments, $T^2$ is absent. In other embodiments, $R^{10}$ is an optionally substituted 4-membered heterocyclic ring containing 1 heteroatom. In some embodiments, $R^{10}$ is an optionally substituted azetidine. In some embodiments, $R^{10}$ is represented by formula i:

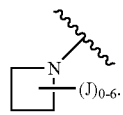

i

In another embodiment, $R^Y$ is L-Z—$R^{10}$. In some embodiments, L is —O—, —N(R$^6$)—, or —S—. In some embodiments, Z is a $C_{1-4}$ alkylidene chain. In other embodiments, Z is absent. In some embodiments, $R^Y$ is represented by formula ii-a:

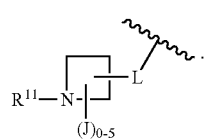

ii-a

In other embodiments, $R^Y$ is represented by formula ii-b:

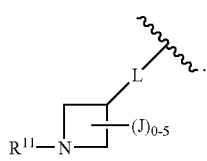

ii-b

In some embodiments, $R^{11}$ is H. In other embodiments, $R^{11}$ is an optionally substituted $C_{1-6}$ aliphatic group. In yet other embodiments, $R^{11}$ is —COR', —CO$_2$ (optionally substituted $C_{1-6}$ aliphatic), —CON(R$^7$)$_2$, or —SO$_2$R$^7$.

In one embodiment, a compound of this invention is represented by formula Ia:

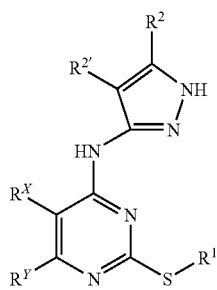

Ia wherein the variables are as defined herein.

In one embodiment, a compound of this invention is represented by formula Ib:

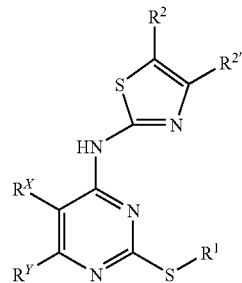

Ib wherein the variables are as defined herein.

In one embodiment of formula Ib, $R^{2'}$ is hydrogen.

In one embodiment, a compound of this invention is represented by formula II-a:

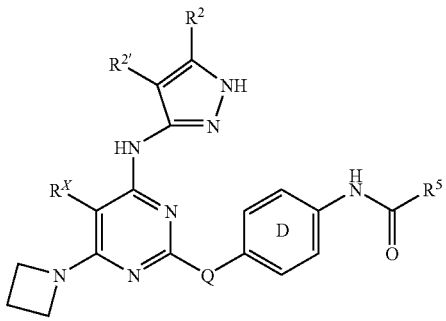

II-a wherein $R^2$, $R^{2'}$, $R^X$, and Q, are as defined herein;

Ring D is a 6-membered aryl or heteroaryl; and $R^5$ is a $C_{6-10}$ aryl optionally substituted with $R^9$.

In some embodiments, Ring D is phenyl.

In other embodiments, $R^5$ is phenyl optionally substituted with $R^9$. In some embodiments, said phenyl is substituted in the ortho position with $R^9$. In some embodiments, $R^9$ is halogen, CF$_3$, $C_{1-3}$alkyl, —S—(C$_{1-3}$alkyl), or OCF$_3$.

In another embodiment, a compound of this invention is represented by formula II-b:

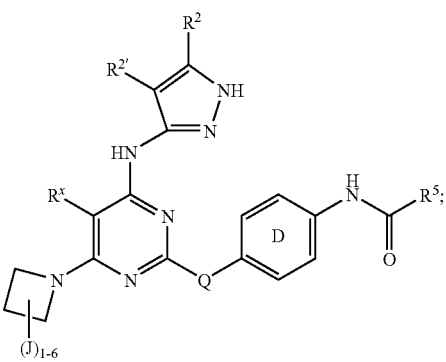

II-b wherein $R^2$, $R^{2'}$, $R^X$, Q, and J are as defined herein;

Ring D is phenyl or a 6-membered heteroaryl containing 1-2 heteroatoms selected from O, N, or S; and $R^5$ is a $C_{6-10}$ aryl optionally substituted with $R^9$.

In some embodiments, Ring D is phenyl.

In other embodiments, $R^5$ is phenyl optionally substituted with $R^9$. In some embodiments, said phenyl is substituted in the ortho position with $R^9$. In some embodiments, $R^9$ is halogen, $CF_3$, —S—($C_{1-3}$alkyl), or $OCF_3$. In other embodiments, J is $C_{1-4}$alkyl, $C_{3-6}$alkyl O($C_{1-34}$alkyl), OH, CN, or F. In yet other embodiments, J is $CH_3$, $OCH_3$, $O(CH_2CH_3)$, $OCH(CH_3)_2$, $OC(CH_3)_3$, OH, CN, or F.

In yet another embodiment, a compound of this invention is represented by formula II-c:

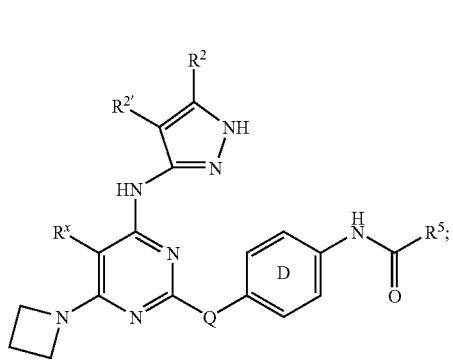

II-c wherein
$R^2$, $R^{2'}$, $R^X$, and Q, are as defined herein;
Ring D is phenyl or a 6-membered heteroaryl containing 1-2 heteroatoms selected from O, N, or S; and
$R^5$ is a $C_{1-6}$ alkyl optionally substituted with $R^9$.

In some embodiments, $R^5$ is optionally substituted with 1-6 halogen groups. In some embodiments, 1-3 halogen groups. In some embodiments, said halogen is fluoro.

In another embodiment, a compound of this invention is represented by formula II-d:

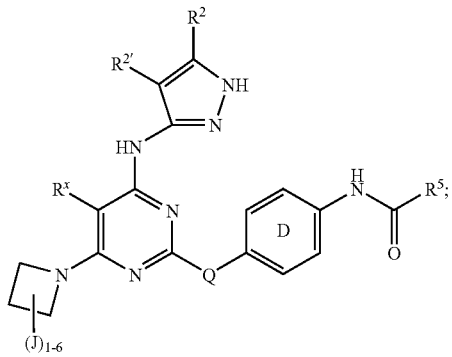

II-d wherein
$R^2$, $R^{2'}$, $R^X$, Q, and J are as defined herein;
Ring D is phenyl or a 6-membered heteroaryl containing 1-2 heteroatoms selected from O, N, or S; and
$R^5$ is $C_{1-6}$alkyl or $C_{3-6}$cycloaliphatic, wherein said $C_{1-6}$alkyl or $C_{3-6}$cycloaliphatic is optionally substituted with 0-6 $R^9$.
In some embodiments, Ring D is phenyl.

In some embodiments, $R^5$ is substituted with 1-6 $R^9$. In some embodiments, $R^9$ is halogen. In other embodiments, $R^9$ is $CF_3$. In some embodiments, $R^5$ is substituted with a $CF_3$ group.

In some embodiments, the azetidine of formula II-d is substituted with 1-2 J groups wherein J is selected from $C_{1-6}$ aliphatic, $C_{3-6}$cycloaliphatic, halogen, OH, OR, $NH_2$, $NH(C_{1-6})$, $N(C_{1-6})_2$, CN, or a 4-7 membered heterocyclyl containing 1-2 heteroatoms selected from O, N, and S.

In some embodiments, said heterocyclyl group is a 3-6 membered heterocyclyl containing 1-2 heteroatoms selected from O, N, or S. In some embodiments, said heterocyclyl is azetidine, morpholine, piperidine, piperazine, or pyrrolidine.

In some embodiments, the azetidine of formula II-d is mono-substituted with a 4-7 membered heterocyclyl containing 1-2 heteroatoms selected from O, N, and S.

In other embodiments, the azetidine of formula II-d is substituted with 2 J groups. In some embodiments, J is selected from $C_{1-6}$ aliphatic, $C_{3-6}$cycloaliphatic, or halogen. In some embodiments, J is $C_3$cycloaliphatic.

In other embodiments, the azetidine of formula II-d is substituted with two J groups: a 4-7 membered heterocyclyl containing 1-2 heteroatoms selected from O, N, and S; and a $C_{1-3}$ alkyl group. In some embodiments, said $C_{1-3}$ alkyl group is methyl.

In some embodiments, the 4-7 membered heterocyclyl is attached to the azetidine via a nitrogen atom. In some embodiments, the 4-7 membered heterocyclyl is attached at the 3-position of the azetidine. In some embodiments, said heterocyclyl is azetidine, morpholine, piperidine, piperazine, or pyrrolidine.

In some embodiments, the halogen of J is fluoro.

In another embodiment, a compound of this invention is represented by formula II-e:

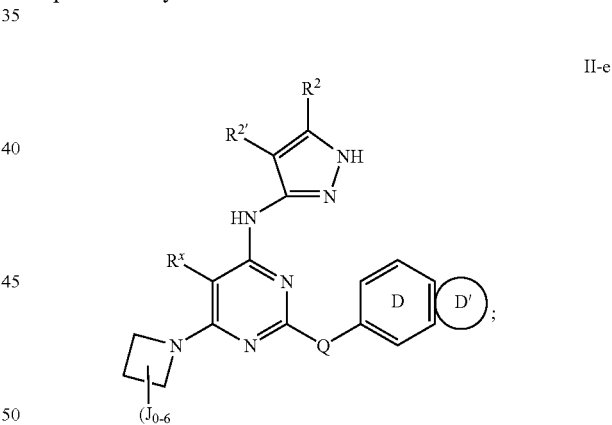

II-e wherein
$R^2$, $R^{2'}$, $R^X$, Q, J, and Ring D' are as defined herein;
Ring D is phenyl or a 6-membered heteroaryl containing 1-2 heteroatoms selected from O, N, or S; and
$R^5$ is $C_{1-6}$ aliphatic, $C_{3-6}$cycloaliphatic, or halogen, wherein said $C_{1-6}$ aliphatic or $C_{3-6}$cycloaliphatic is optionally substituted with $R^9$. In some embodiments, $R^9$ is halogen. In other embodiments, Ring D' is phenyl, a 5-6 membered heteroaryl, or a 5-6 membered heterocyclyl; wherein said heteroaryl or heterocyclyl contains 1-2 heteroatoms selected from O, N, or S. In yet other embodiments, the azetidine of formula II-e is substituted with 1-2 J groups wherein J is selected from $C_{1-6}$ aliphatic, $C_{3-6}$cycloaliphatic, halogen, OH, OR, $NH_2$, NH(C$_{1-6}$), N(C$_{1-6}$)$_2$, CN, or a 4-7 membered heterocyclyl containing 1-2 heteroatoms selected from O, N, and S. In some embodiments, D-D' is benzimidazole, isoquinoline, quinoline, or isoindolinone.

In yet another embodiment, a compound of this invention is represented by formula II-f:

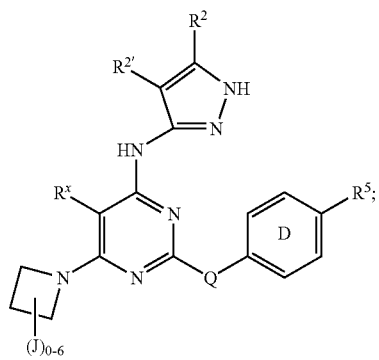

II-f wherein

R$^2$, R$^{2'}$, R$^x$, Q, J, and Ring D are as defined herein;

Ring D is phenyl or a 6-membered heteroaryl containing 1-2 heteroatoms selected from O, N, or S; and R$^5$ is a C$_{6-10}$ aryl ring, a heteroaryl ring having 5-10 ring atoms, or a heterocyclyl ring having 4-10 ring atoms, the heteroaryl or heterocyclyl ring having 1-4 ring heteroatoms selected from nitrogen, oxygen, or sulfur.

In one embodiment, a compound of this invention is represented by formula II-g:

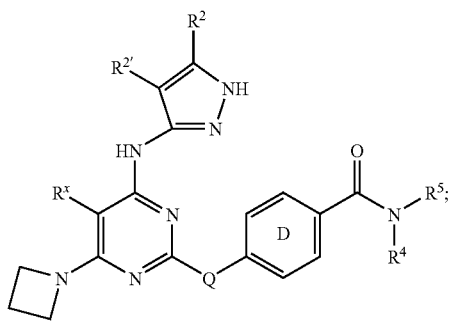

II-g wherein

R$^2$, R$^{2'}$, R$^x$, J, R$^4$, and Ring D are as defined herein;

Ring D is phenyl or a 6-membered heteroaryl containing 1-2 heteroatoms selected from O, N, or S; and R$^5$ is C$_{1-6}$ alkyl optionally substituted with R$^9$.

In some embodiments, Q is O, —NR'—, or S.

In some embodiments, Q is O or S; in some embodiments, Q is S.

In another embodiment, a compound of this invention is represented by formula II-h:

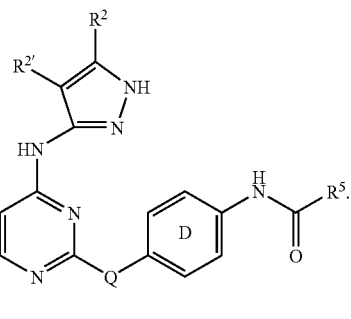

II-h

In some embodiments, the variables are as depicted in the compounds of Table 1 or Table 2.

In one embodiment, this invention includes a compound selected from Table 1 (or a pharmaceutically acceptable salt thereof):

TABLE 1

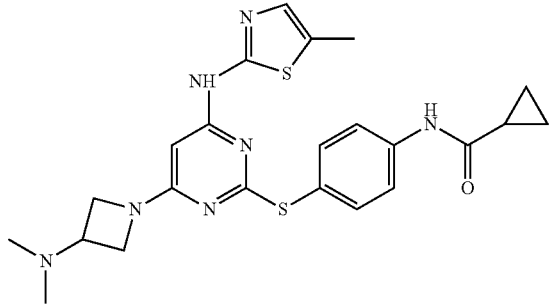

I-1

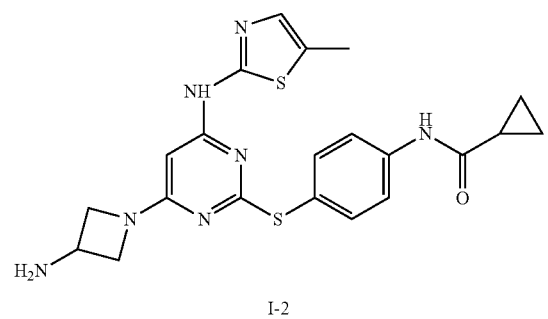

I-2

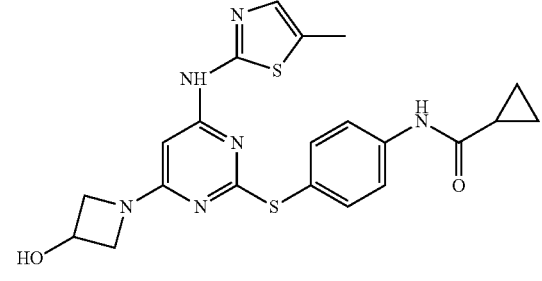

I-3

TABLE 1-continued
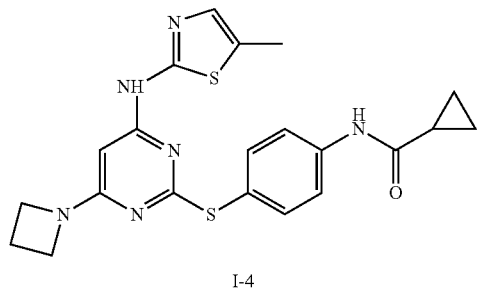
I-4
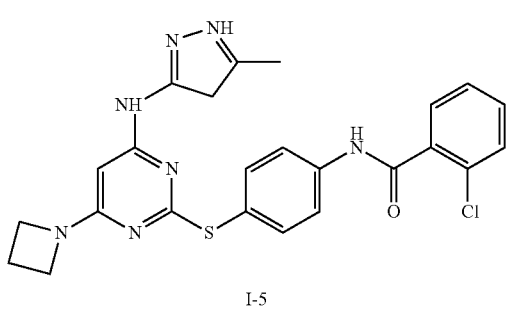
I-5
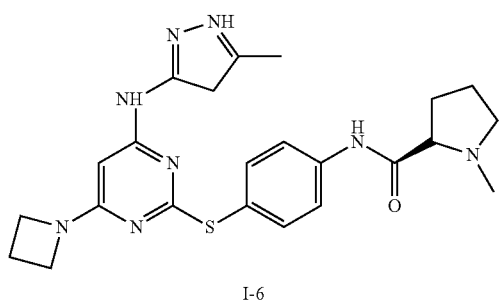
I-6
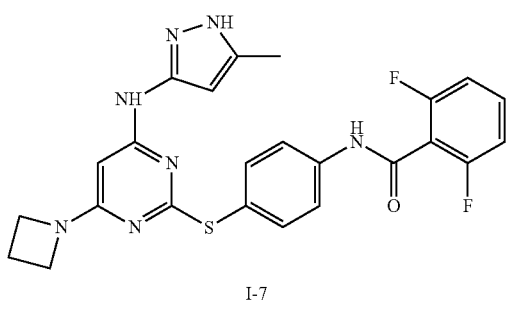
I-7
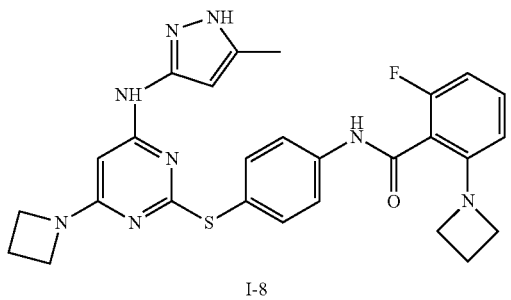
I-8
TABLE 1-continued
I-9
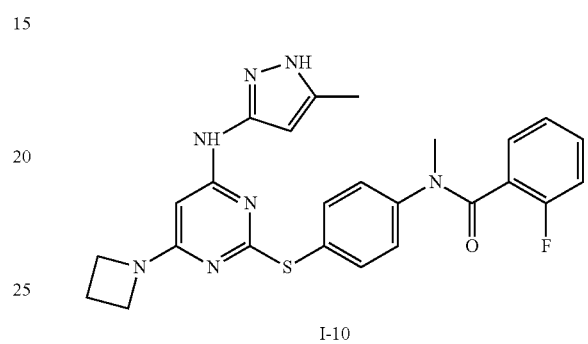
I-10
I-11
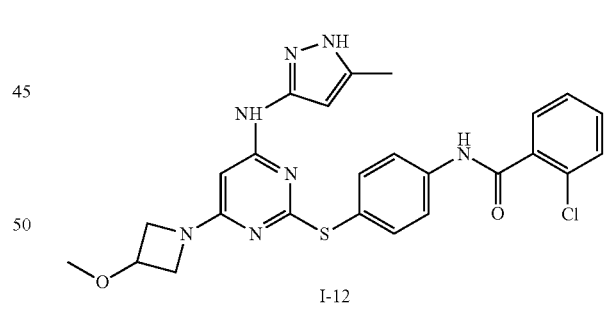
I-12
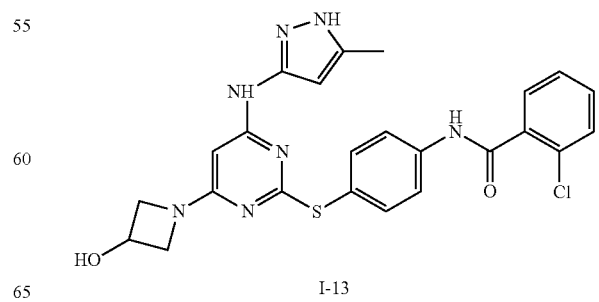
I-13

TABLE 1-continued
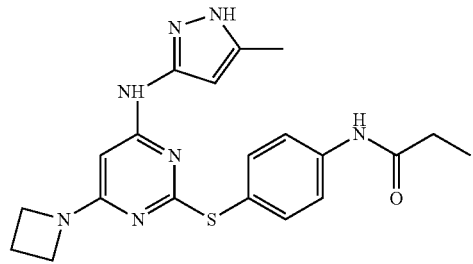
I-14
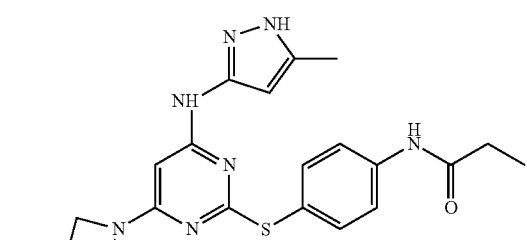
I-15
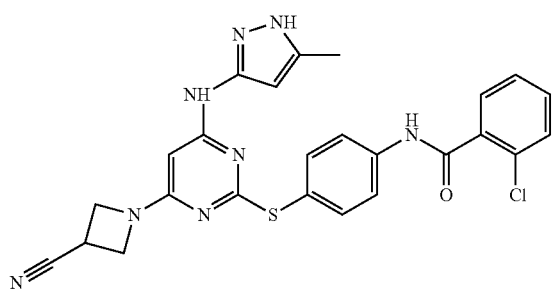
I-16
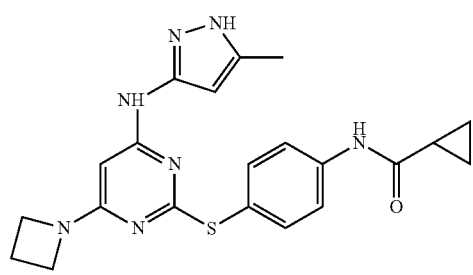
I-17
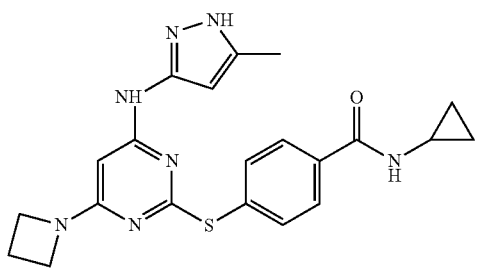
I-18
TABLE 1-continued
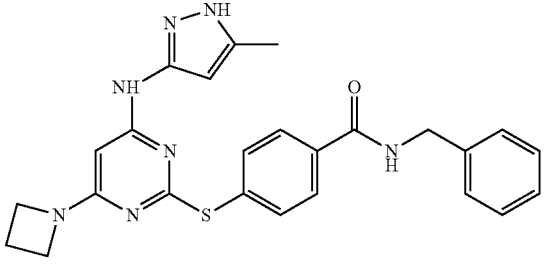
I-19
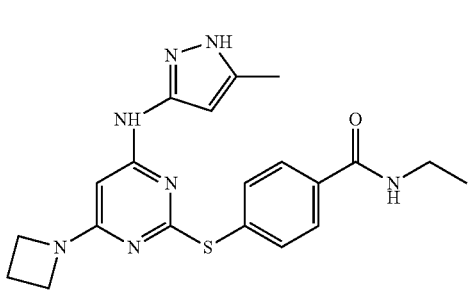
I-20
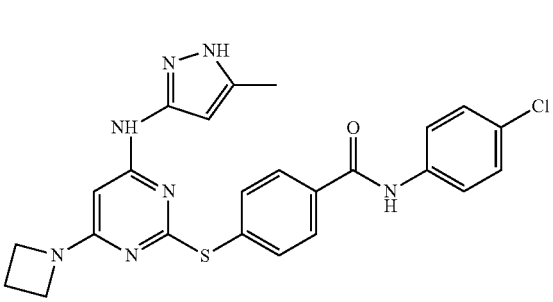
I-21
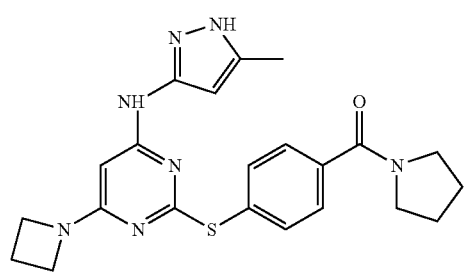
I-22
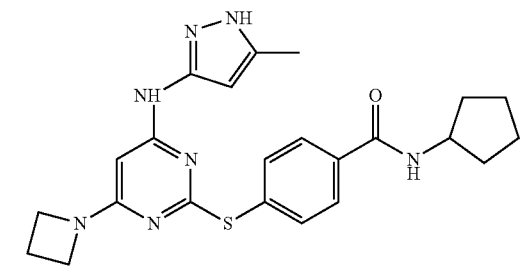
I-23

TABLE 1-continued
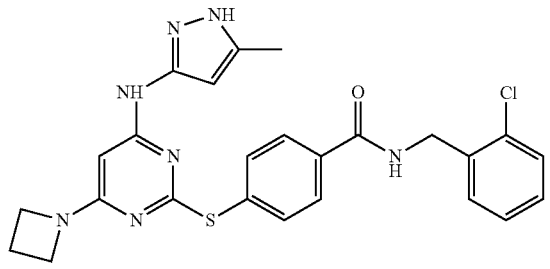
I-24
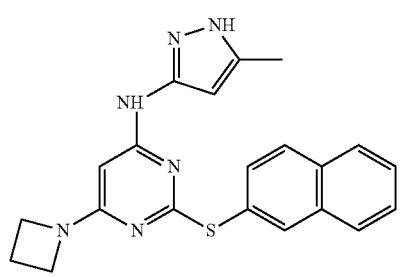
I-25
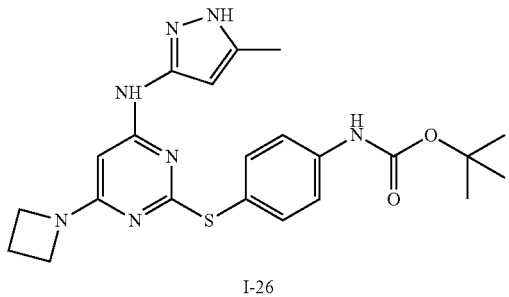
I-26
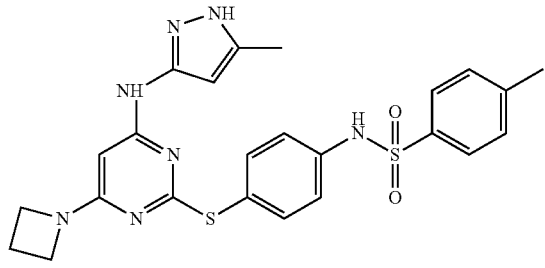
I-27
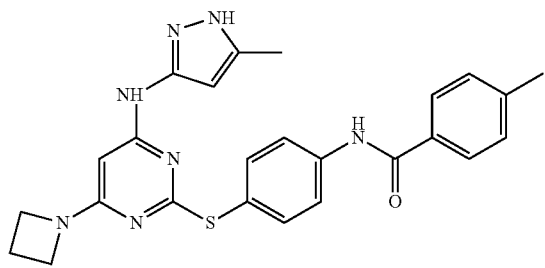
I-28
TABLE 1-continued
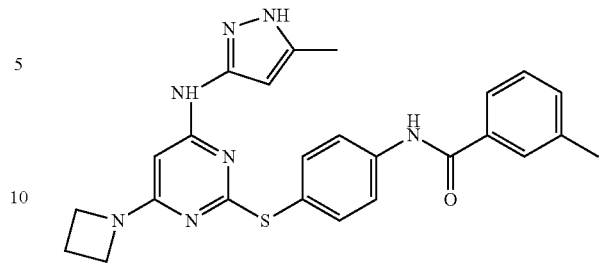
I-29
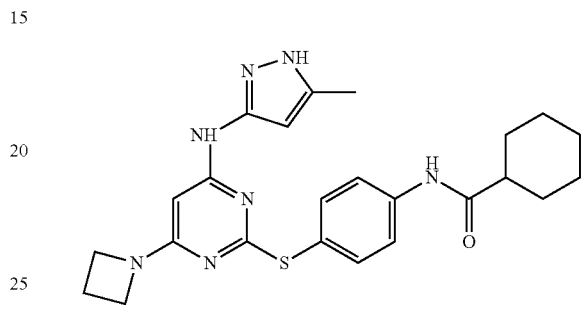
I-30
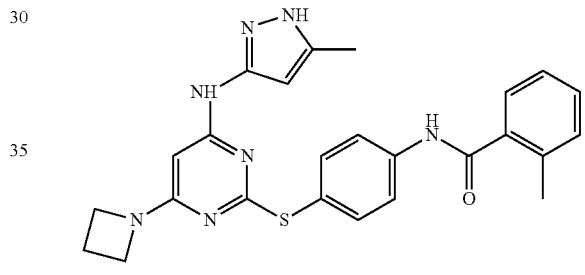
I-31
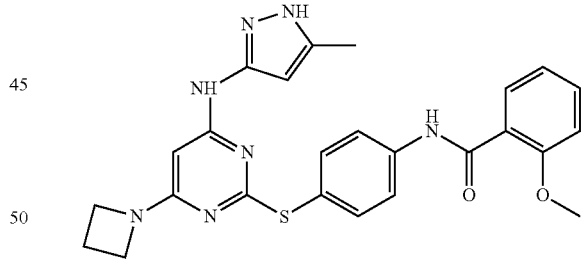
I-32
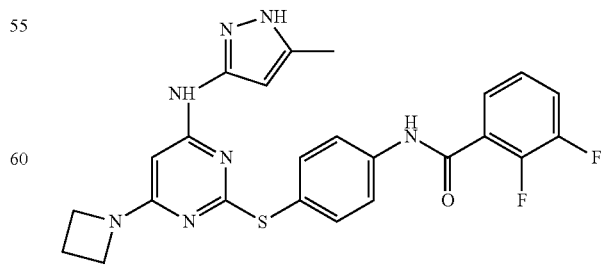
I-33

TABLE 1-continued
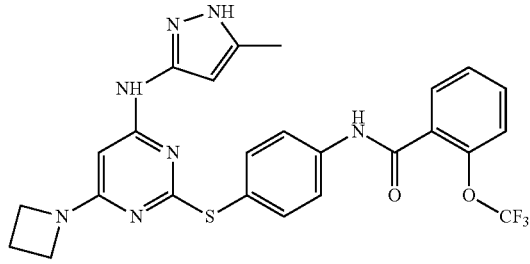
I-34
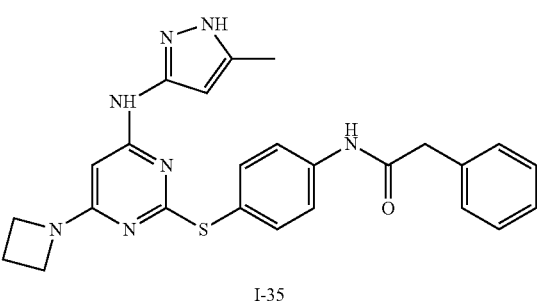
I-35
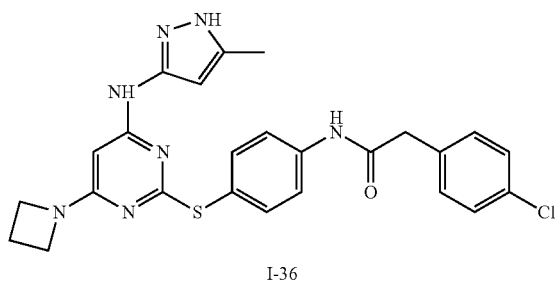
I-36
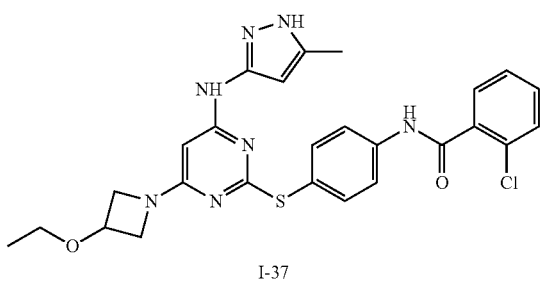
I-37
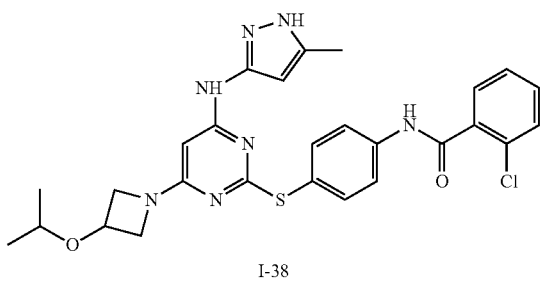
I-38
TABLE 1-continued
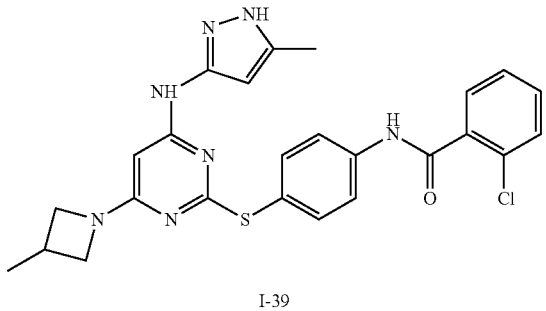
I-39
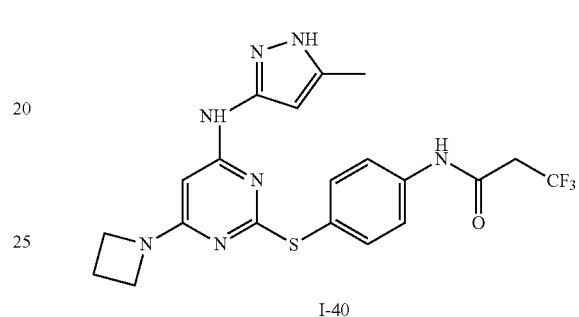
I-40
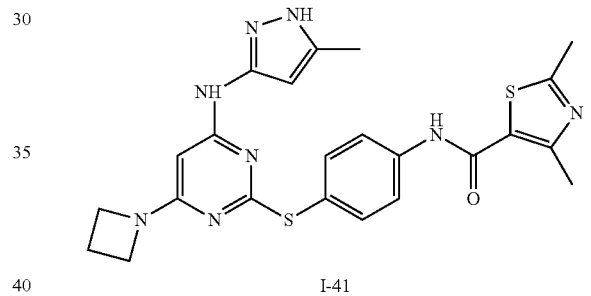
I-41
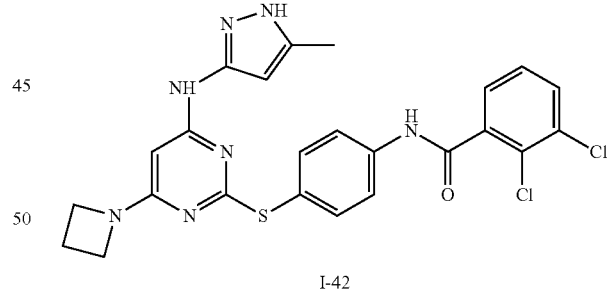
I-42
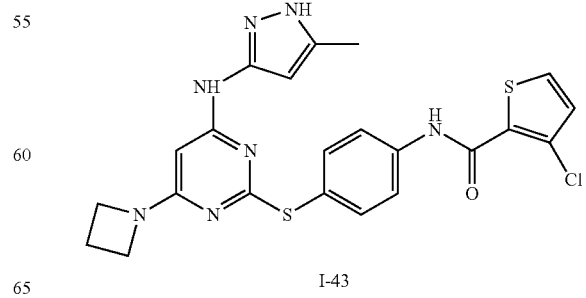
I-43

TABLE 1-continued
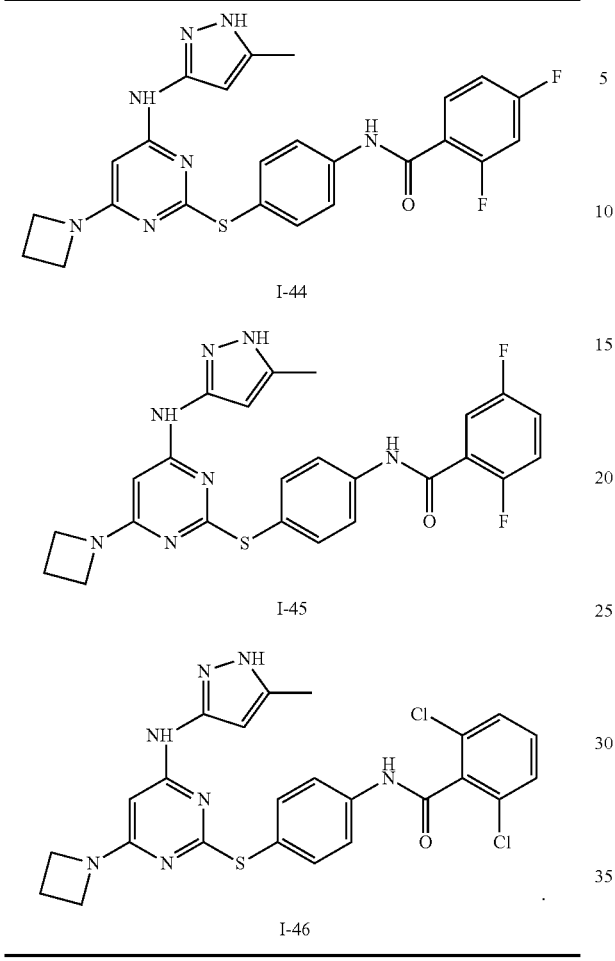
In another embodiment, this invention includes a compound selected from Table 2 (or a pharmaceutically acceptable salt thereof):
TABLE 2
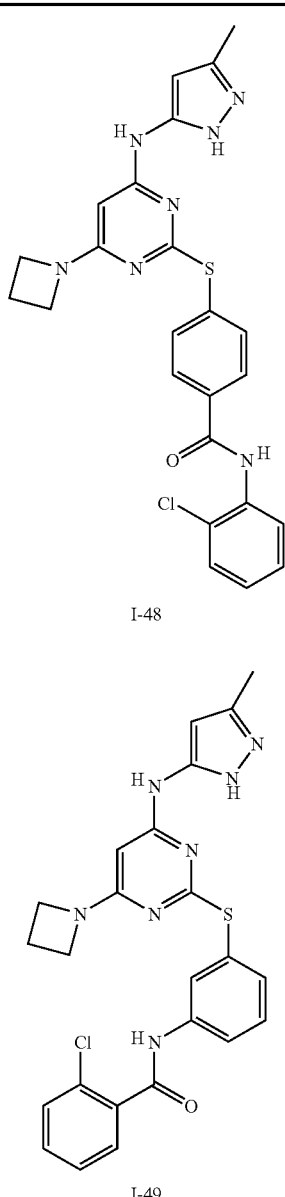
TABLE 2-continued
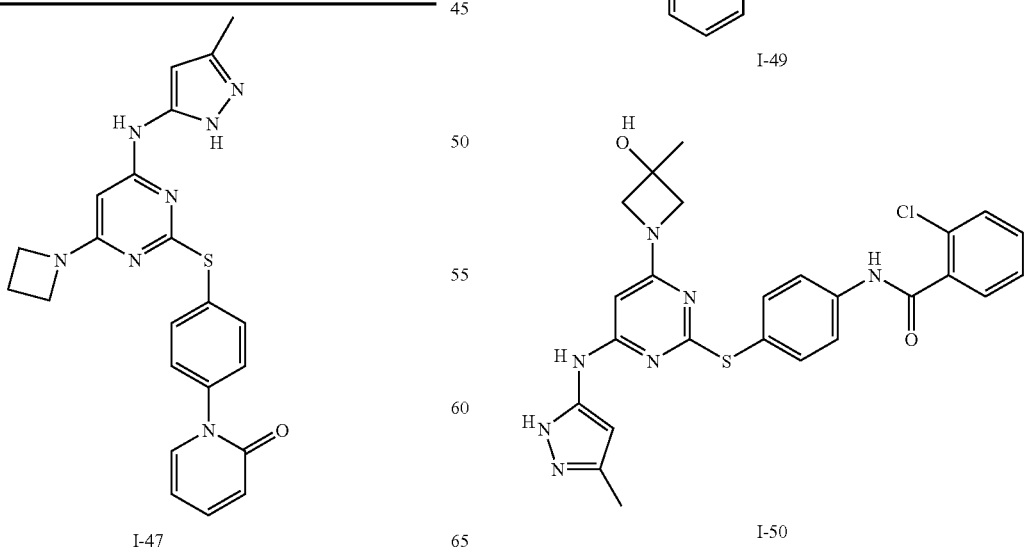

TABLE 2-continued
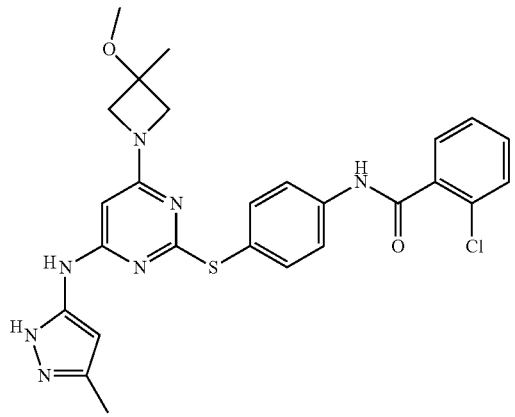
I-51
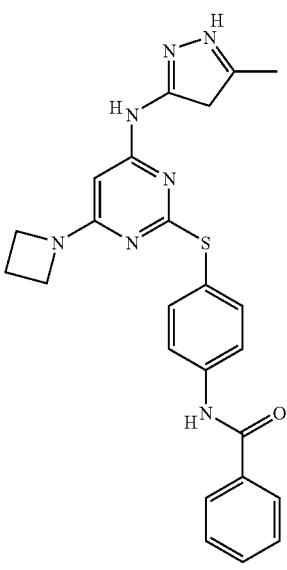
I-52
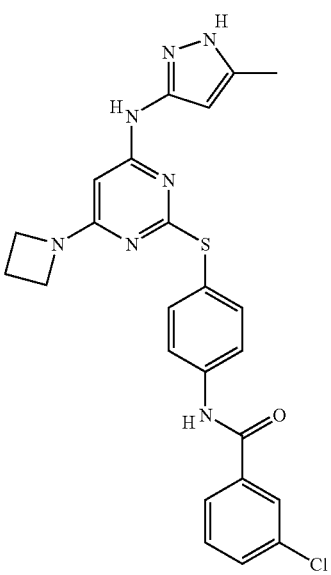
I-53
TABLE 2-continued
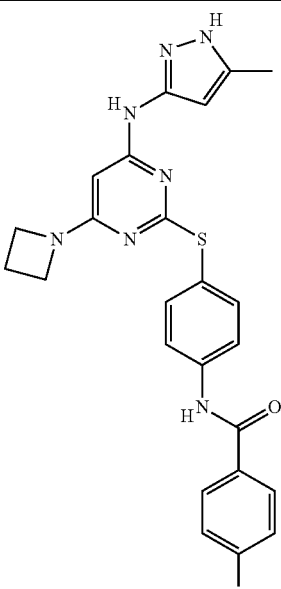
I-54
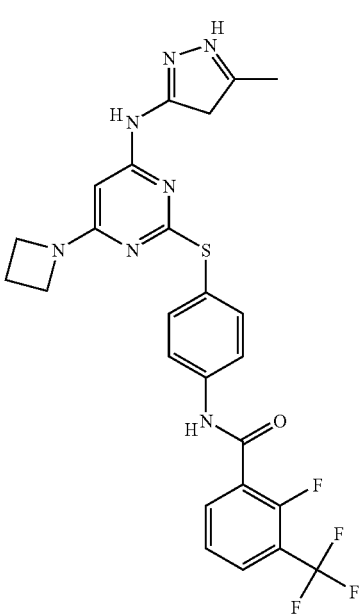
I-55

TABLE 2-continued
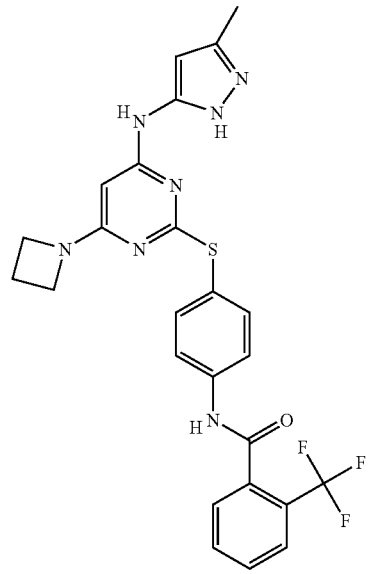
I-56
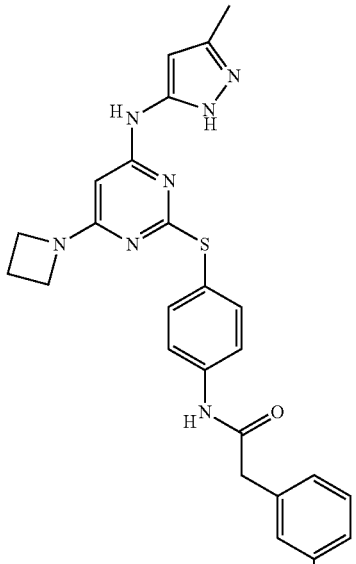
I-58
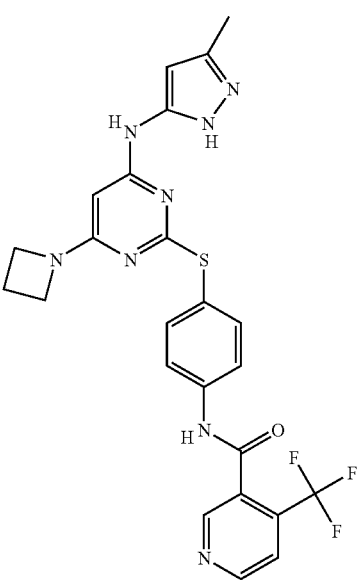
I-59
I-57

TABLE 2-continued
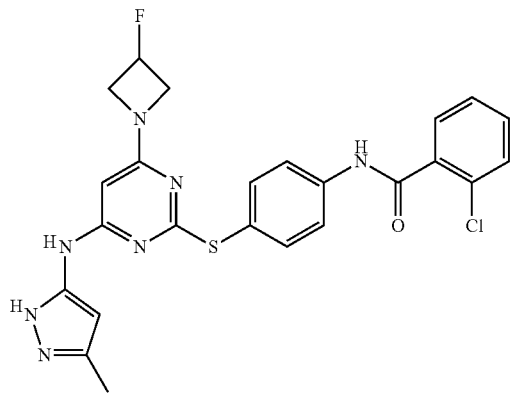
I-60
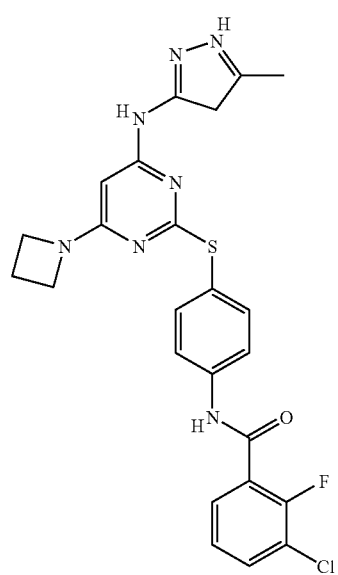
I-61
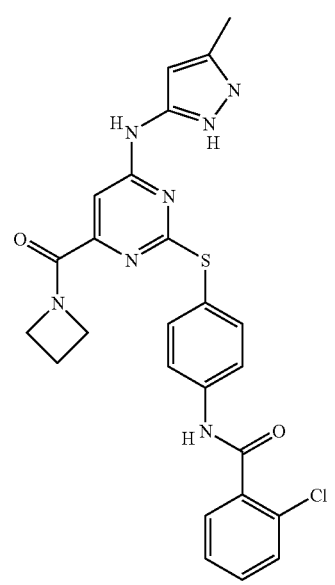
I-62
TABLE 2-continued
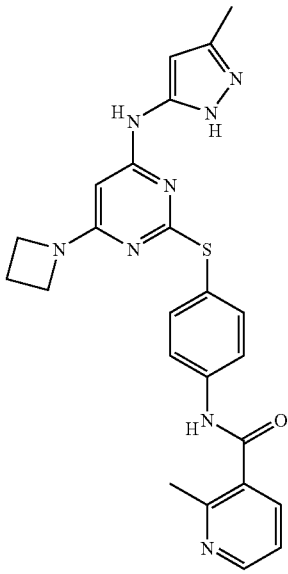
I-63
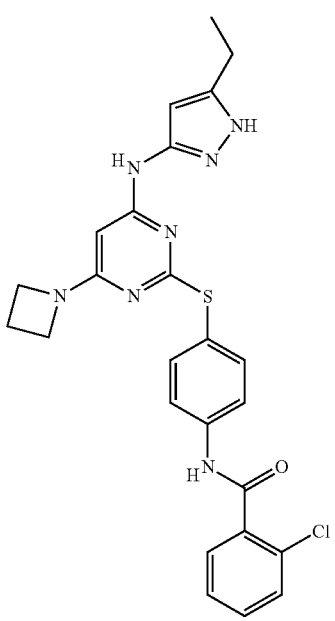
I-64

TABLE 2-continued
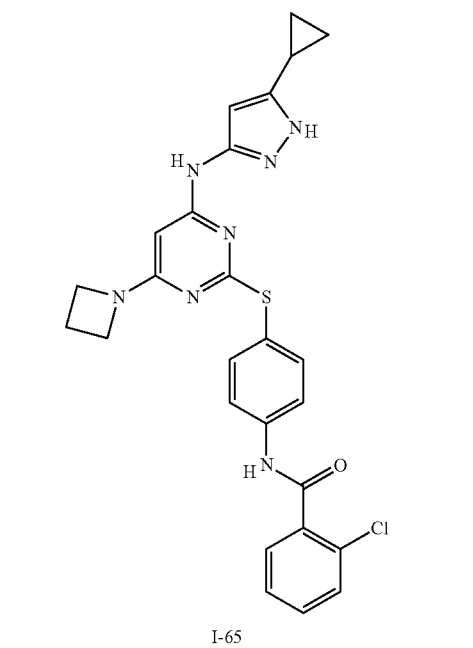
I-65
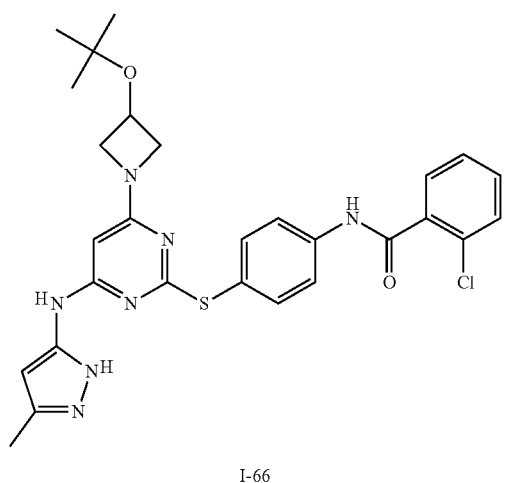
I-66
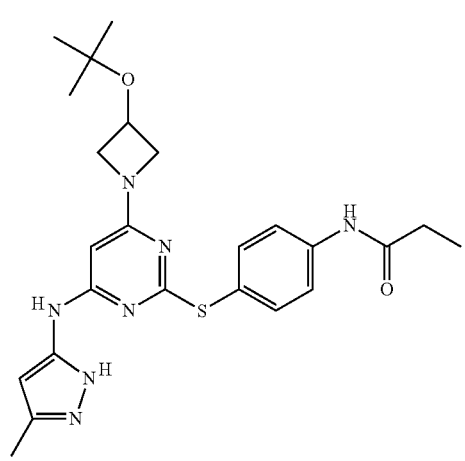
I-67
TABLE 2-continued
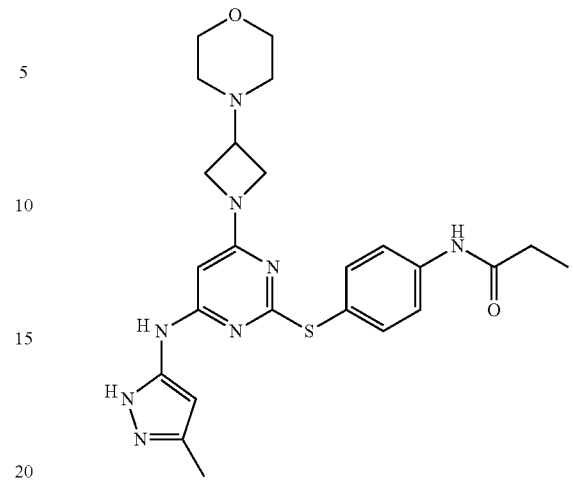
I-68
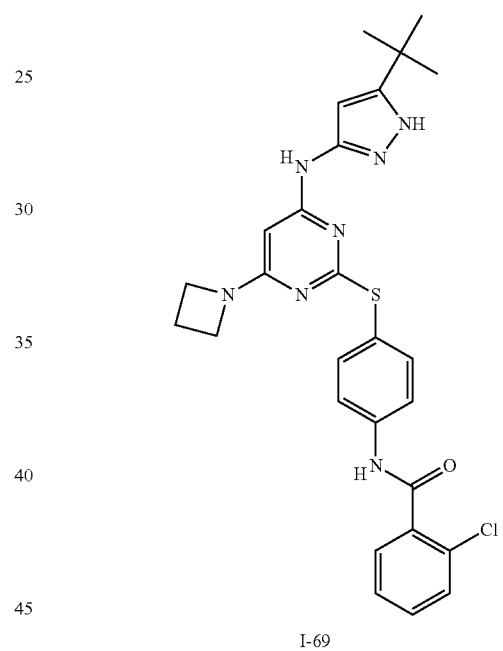
I-69
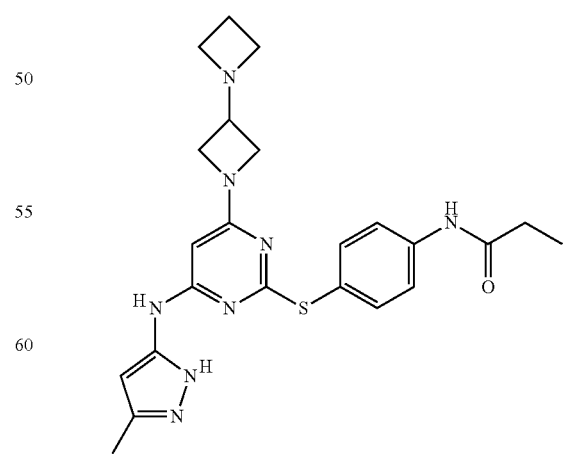
I-70

TABLE 2-continued
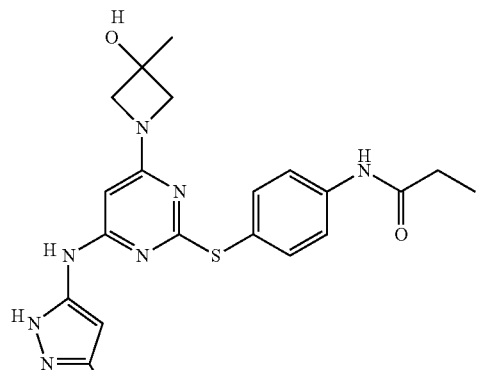
I-71
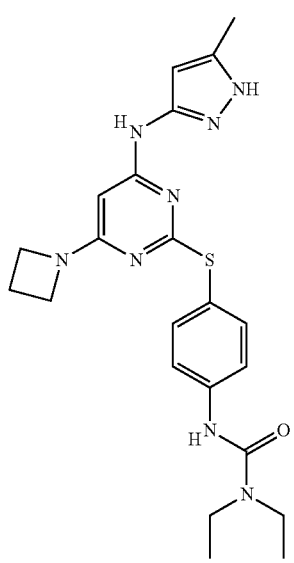
I-72
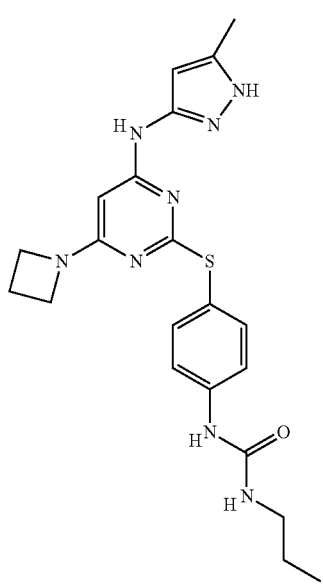
I-73
TABLE 2-continued
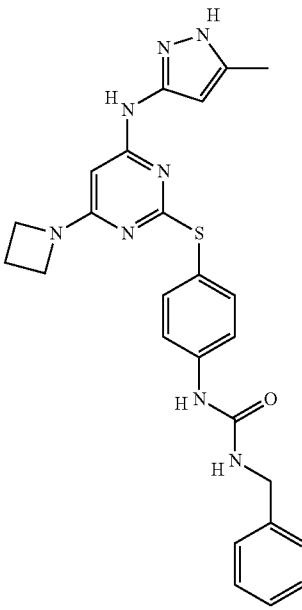
I-74
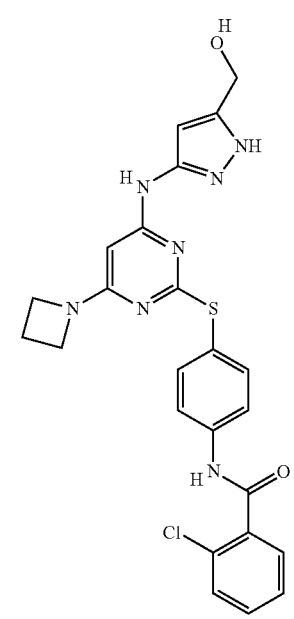
I-75

TABLE 2-continued
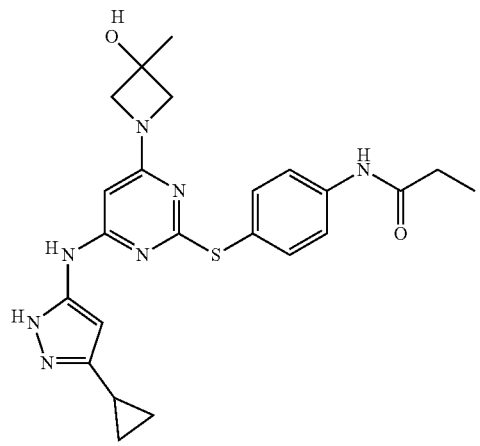
I-76
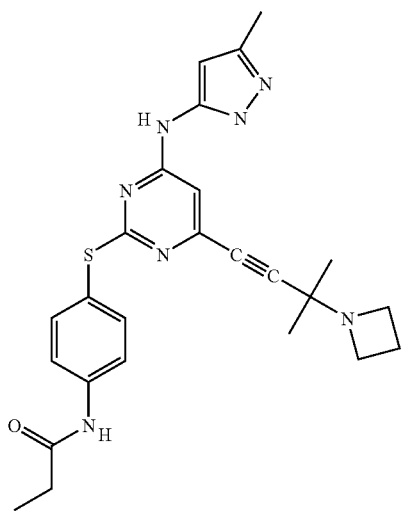
I-77
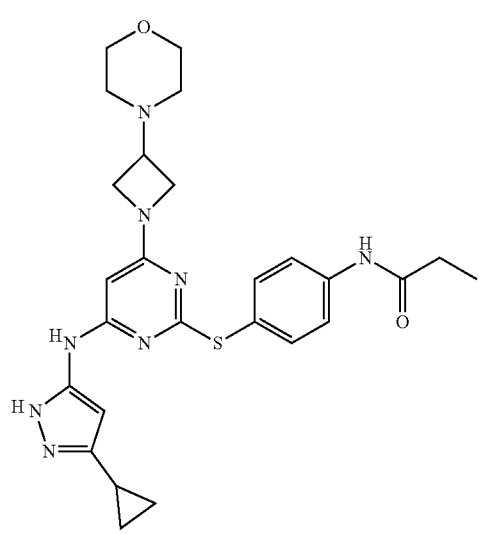
I-78
TABLE 2-continued
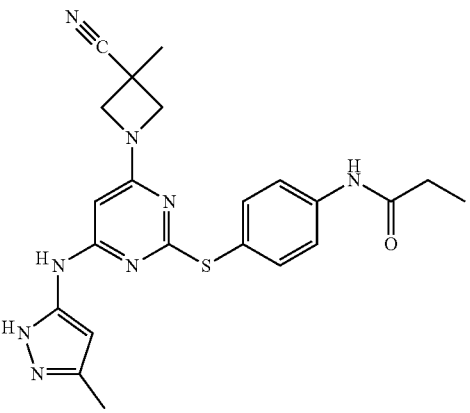
I-79
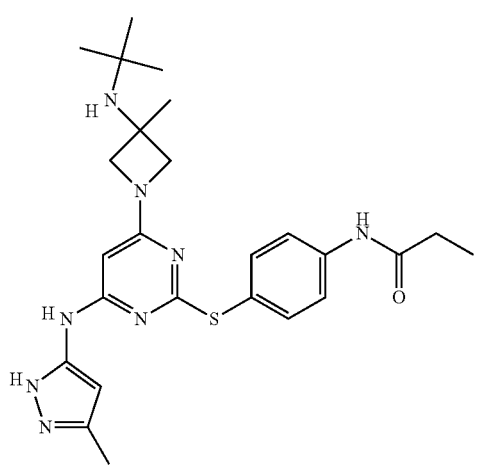
I-80
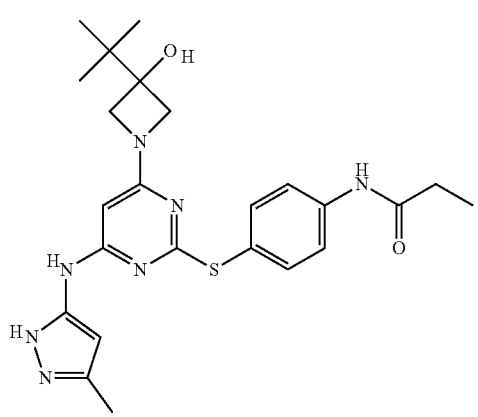
I-81

TABLE 2-continued
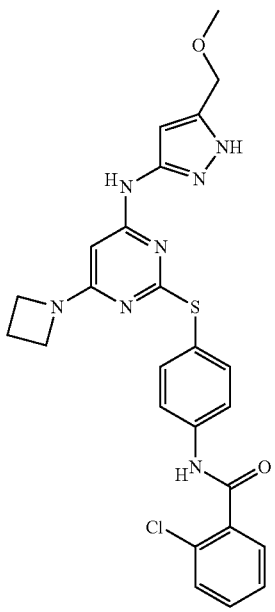
I-82
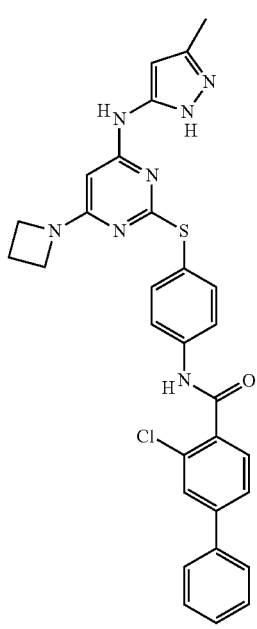
I-83
TABLE 2-continued
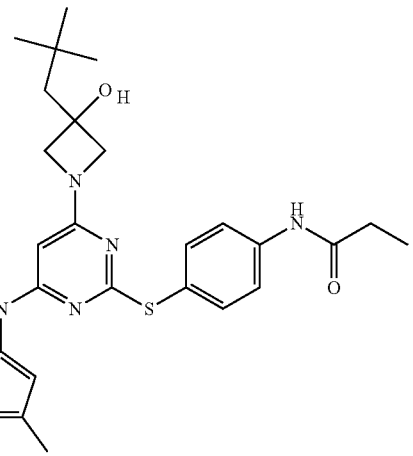
I-84
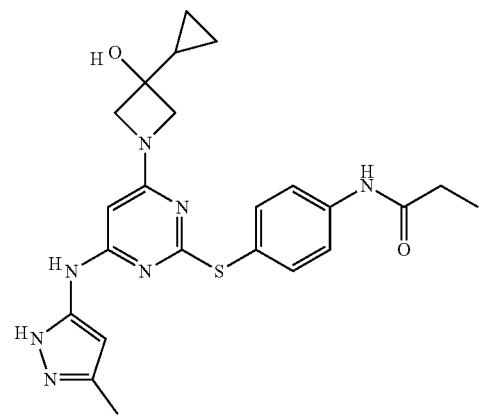
I-85
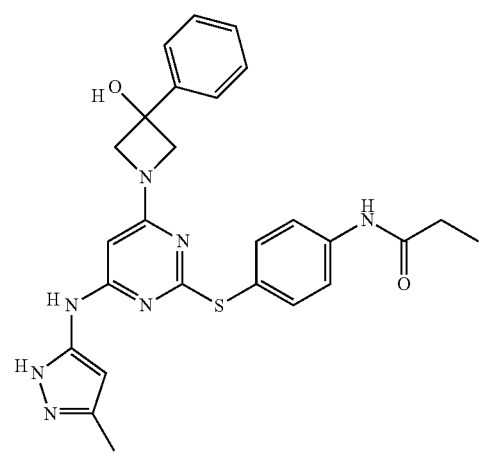
I-86

TABLE 2-continued
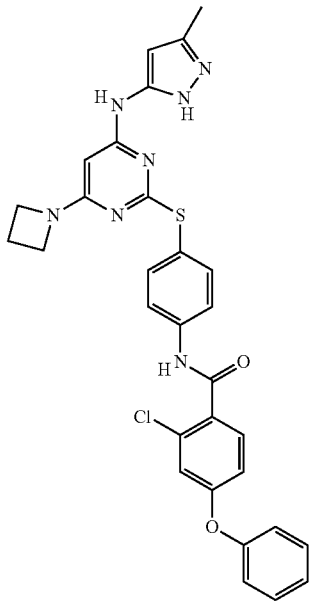
I-87
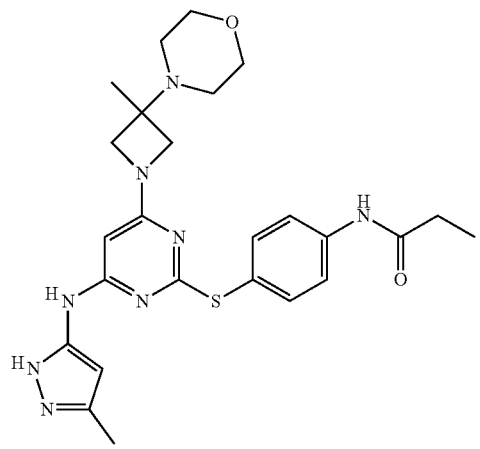
I-88
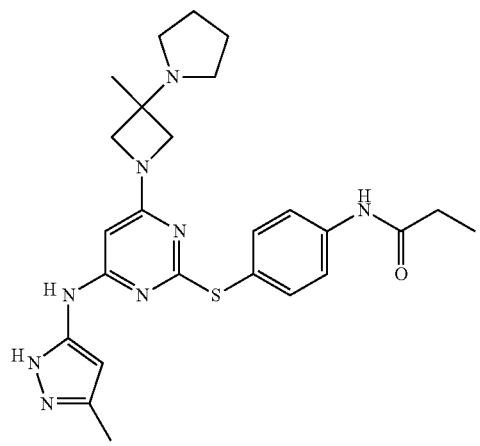
I-89
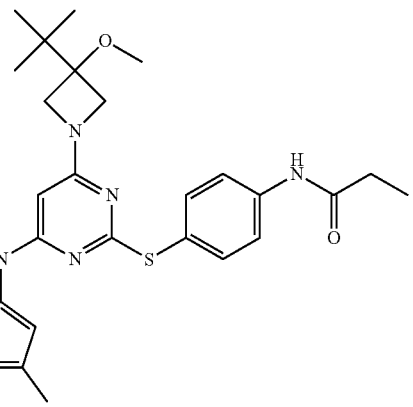
I-90
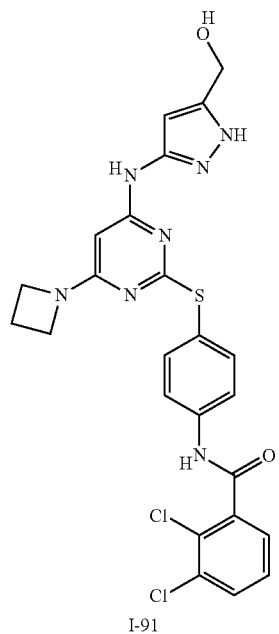
I-91
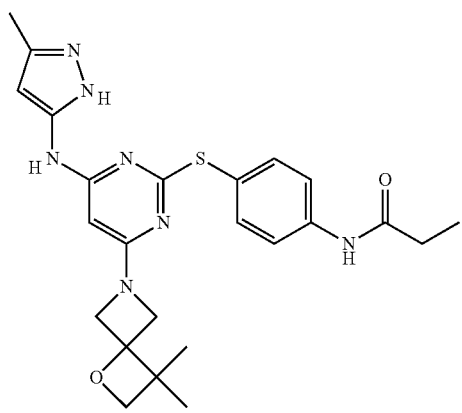
I-92

TABLE 2-continued
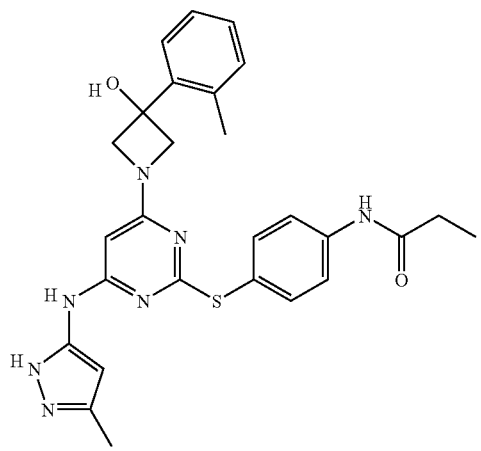
I-93
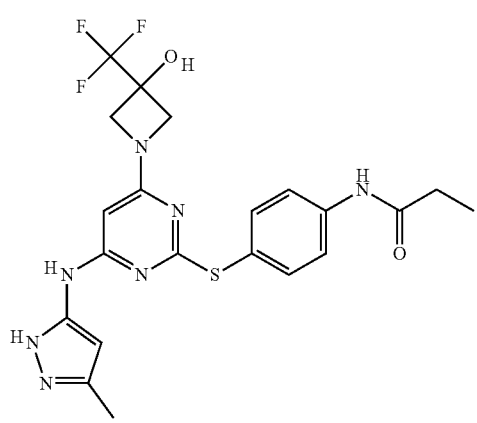
I-94
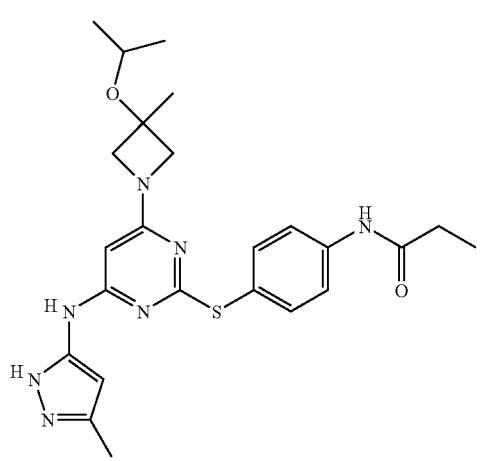
I-95
TABLE 2-continued
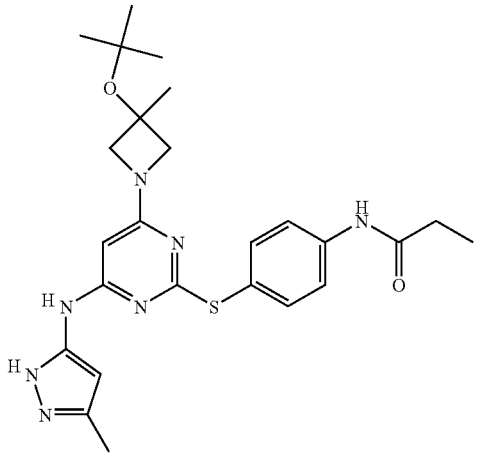
I-96
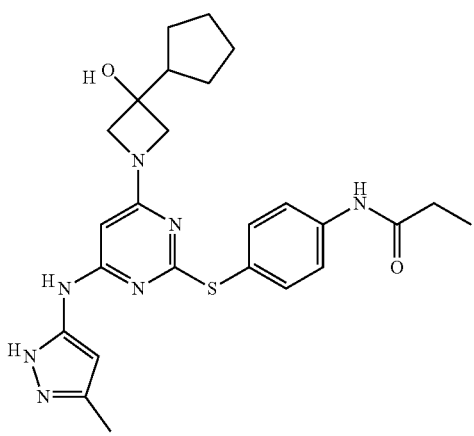
I-97
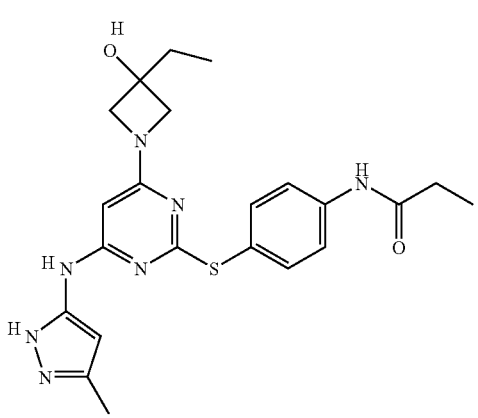
I-98

TABLE 2-continued
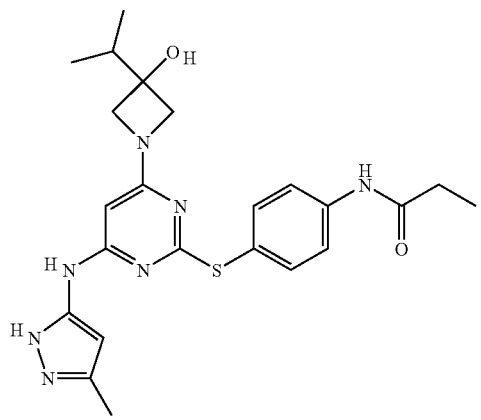
I-99
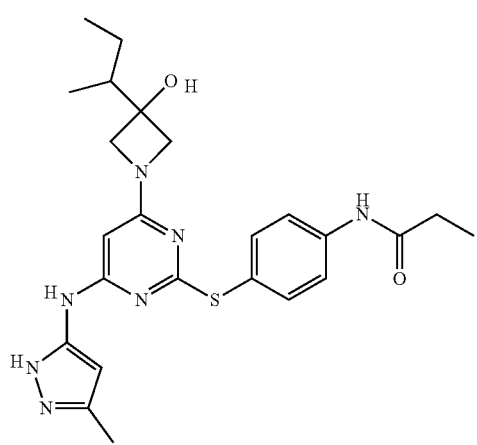
I-100
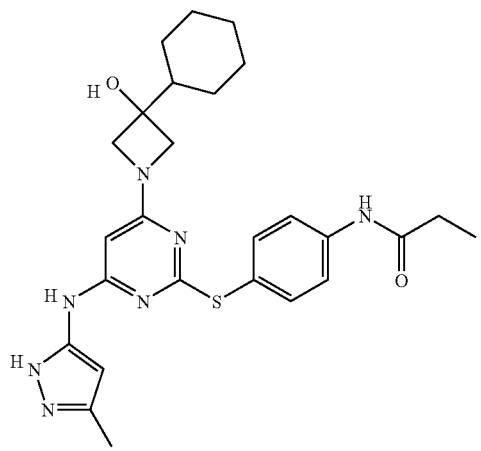
I-101
TABLE 2-continued
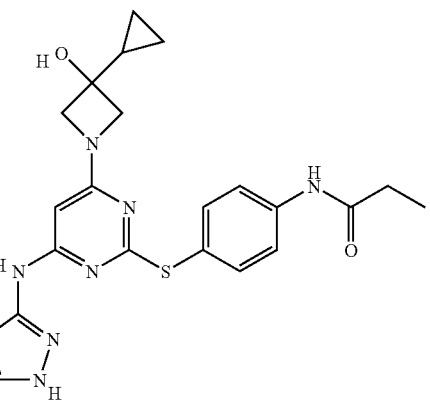
I-102
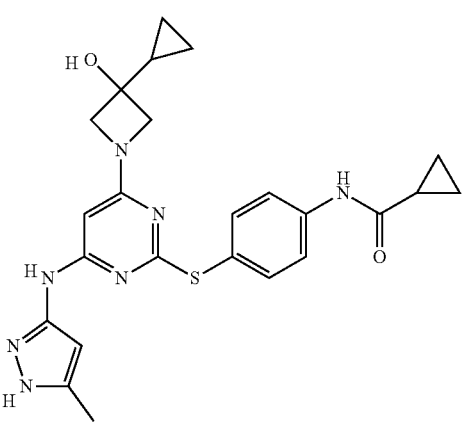
I-103
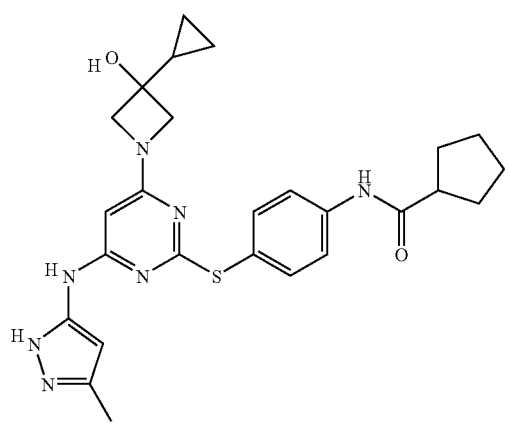
I-104

TABLE 2-continued
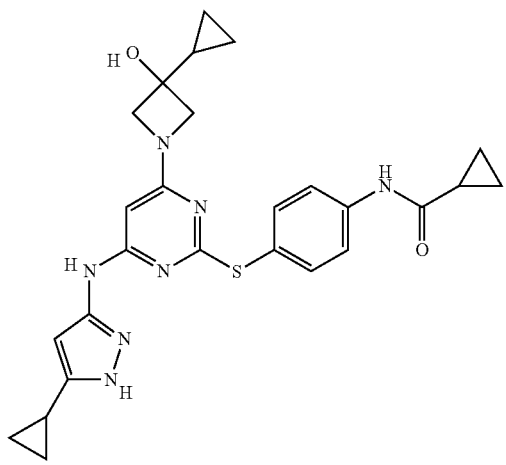
I-105
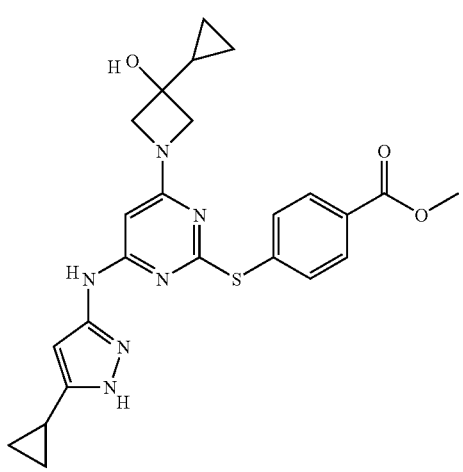
I-106
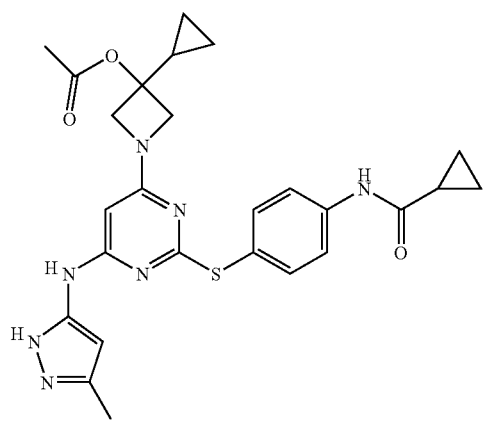
I-107
TABLE 2-continued
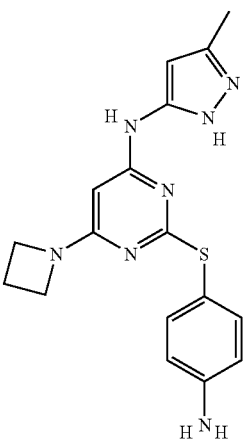
I-108
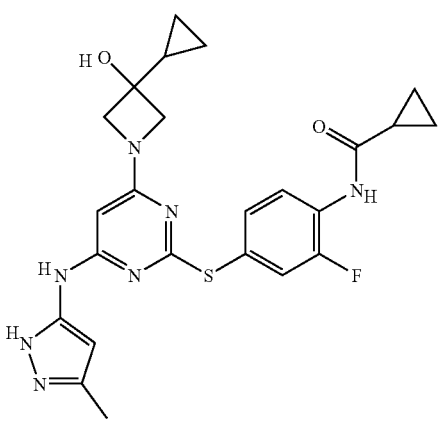
I-109
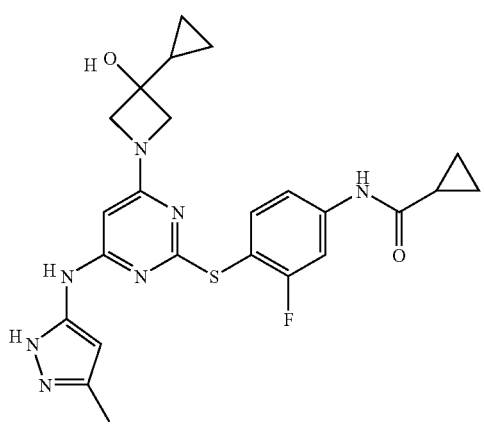
I-110

TABLE 2-continued
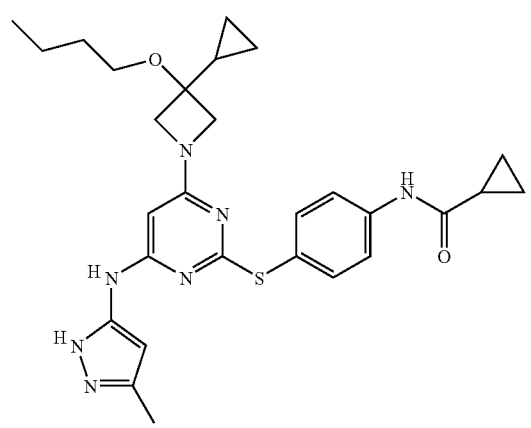
I-111
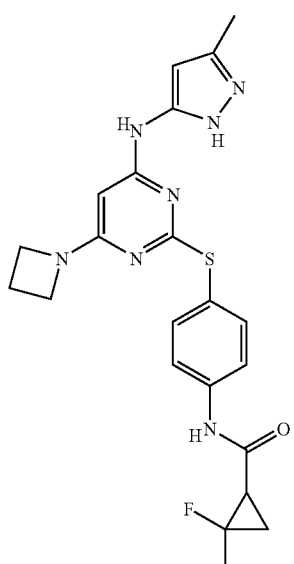
I-112
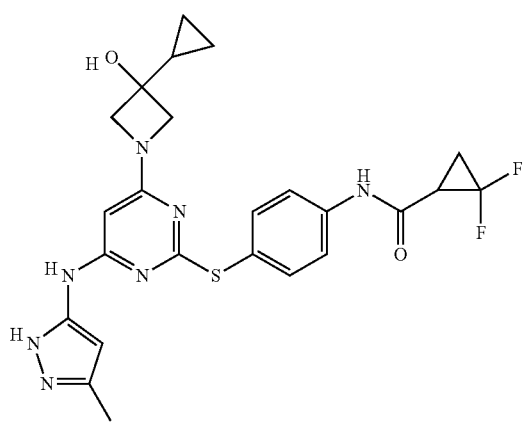
I-113
TABLE 2-continued
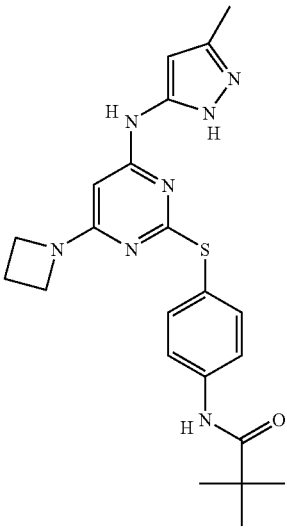
I-114
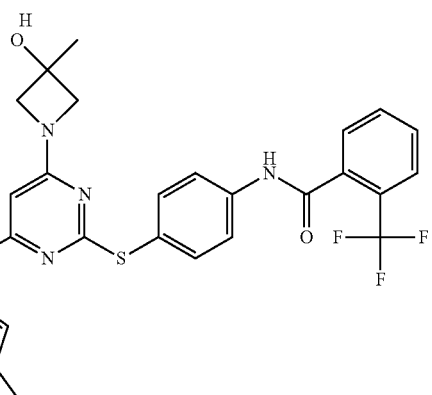
I-115
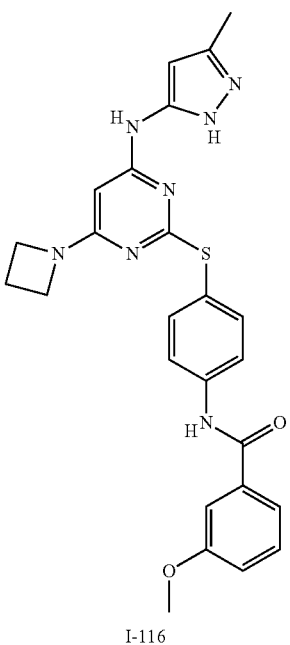
I-116

TABLE 2-continued
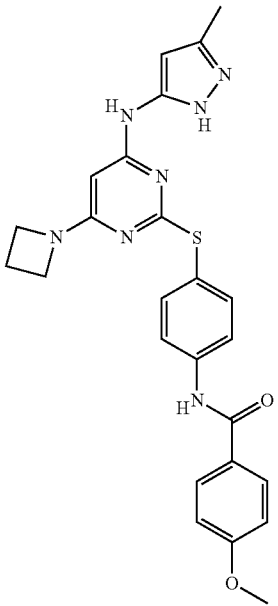
I-117
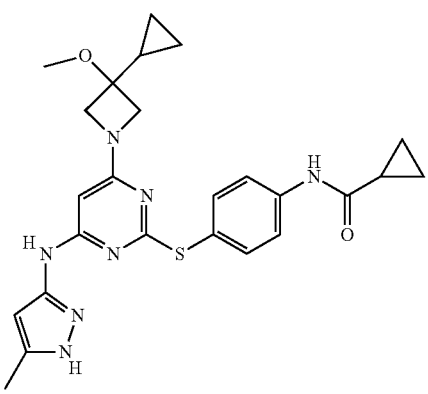
I-118
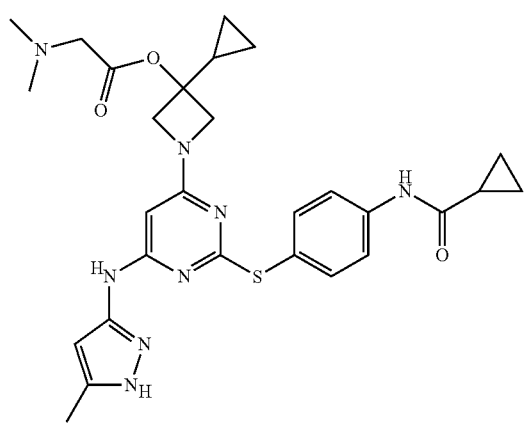
I-119
TABLE 2-continued
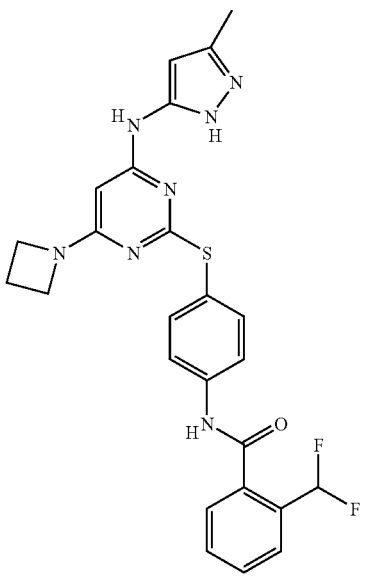
I-120
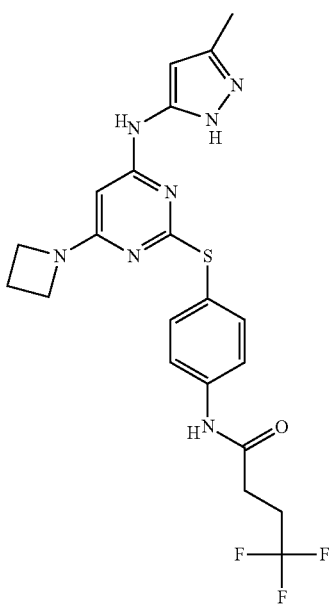
I-121

TABLE 2-continued
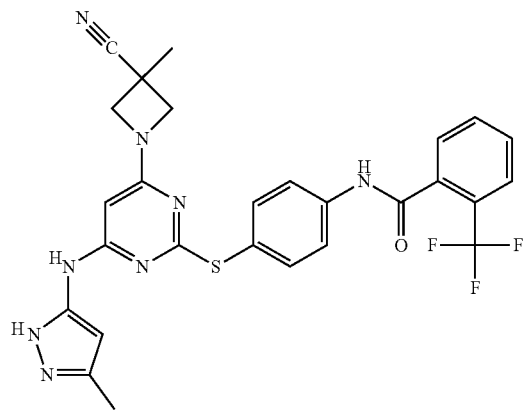
I-122
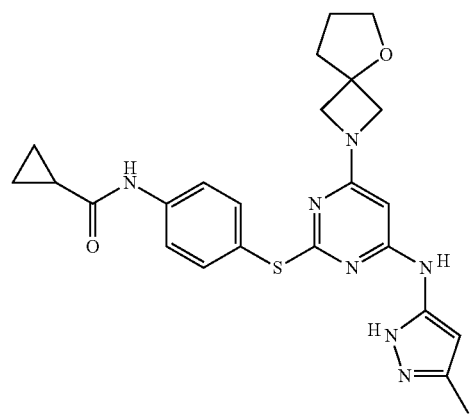
I-123
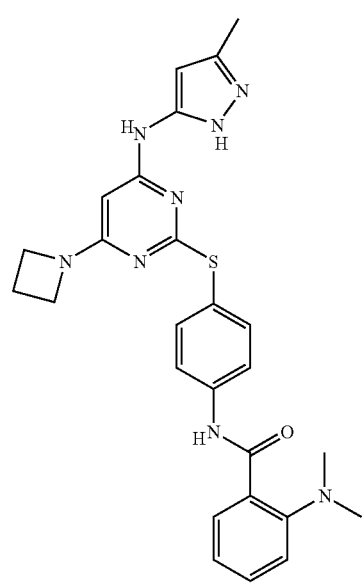
I-124
TABLE 2-continued
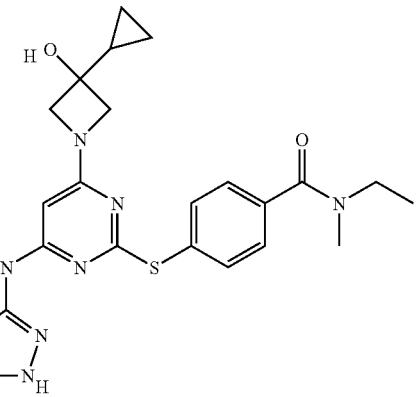
I-125
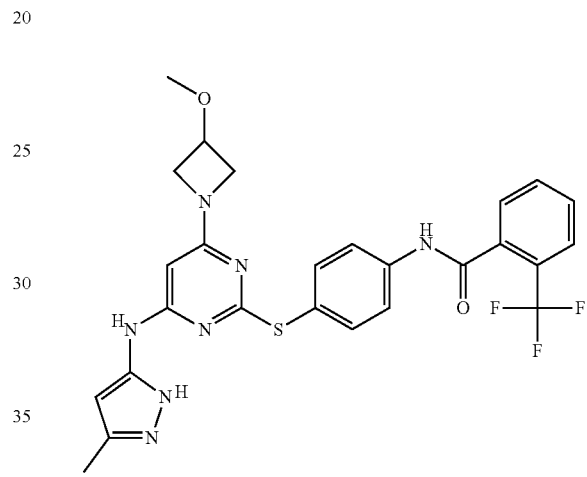
I-126
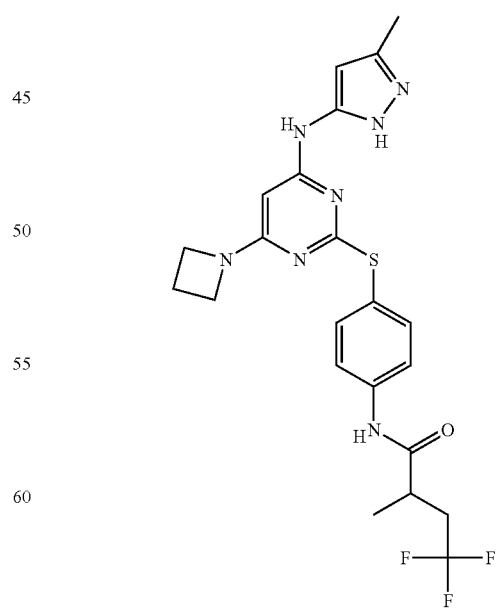
I-127

TABLE 2-continued
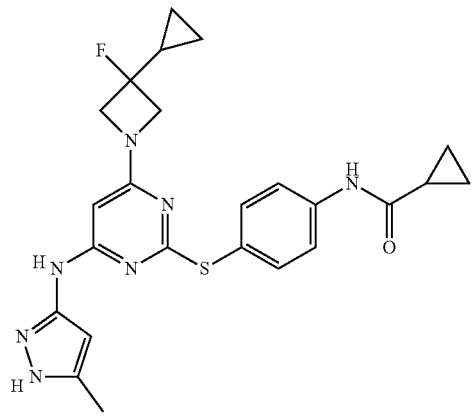
I-128
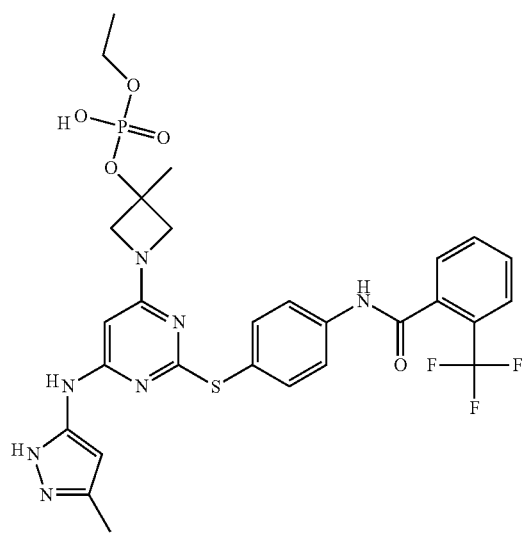
I-129
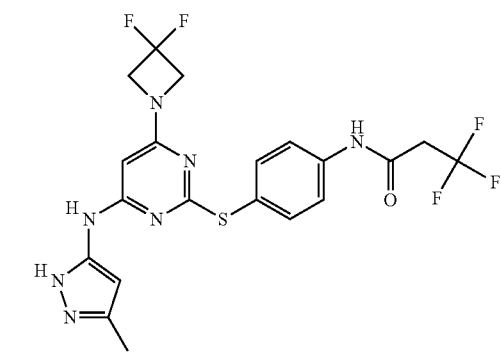
I-130
TABLE 2-continued
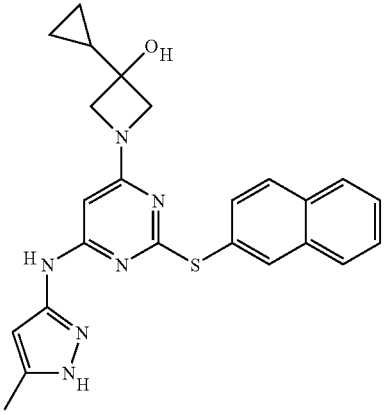
I-131
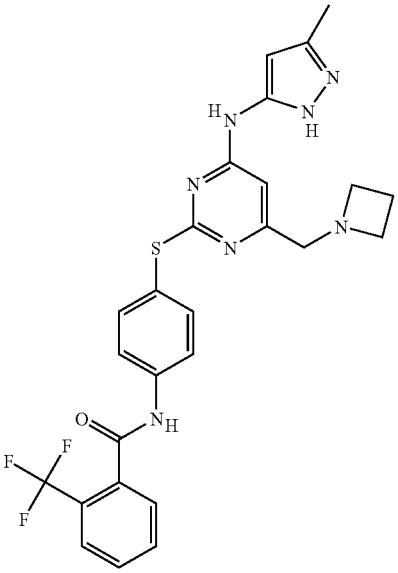
I-132
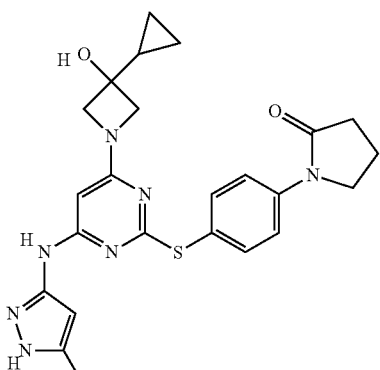
I-133

TABLE 2-continued
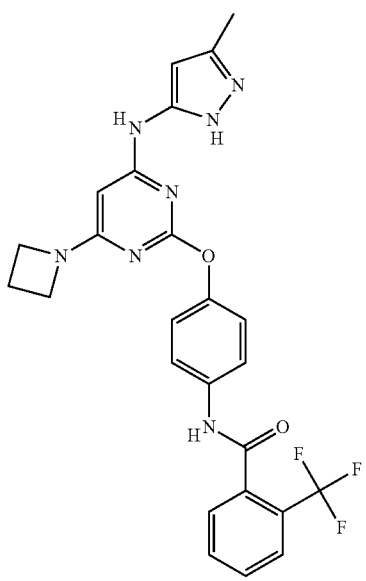
I-134
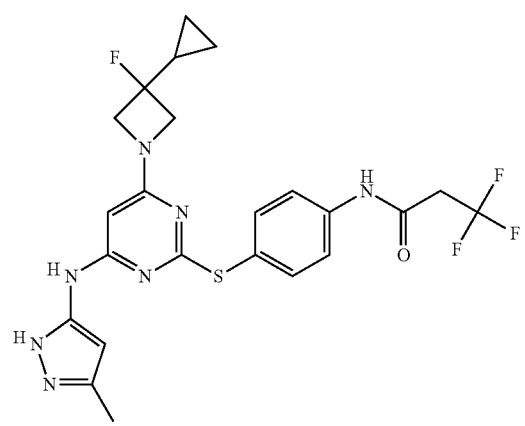
I-135
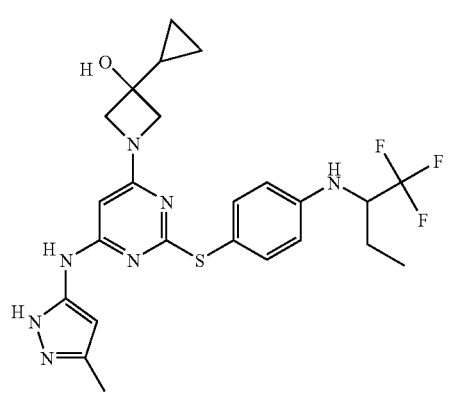
I-136
TABLE 2-continued
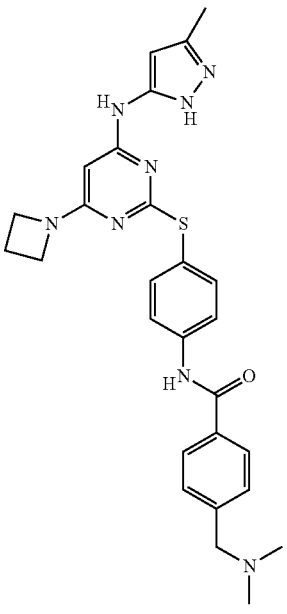
I-137
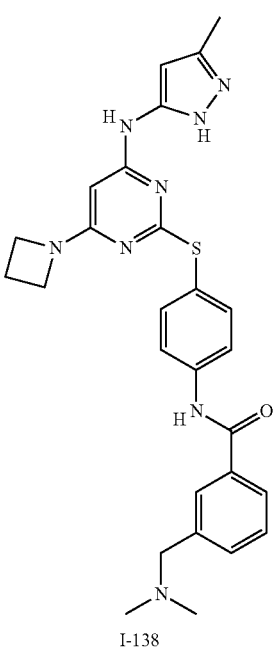
I-138

TABLE 2-continued
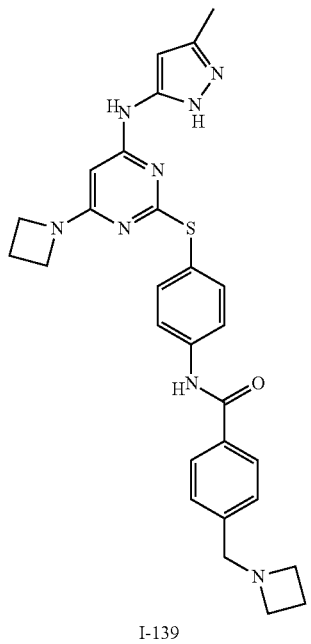
I-139
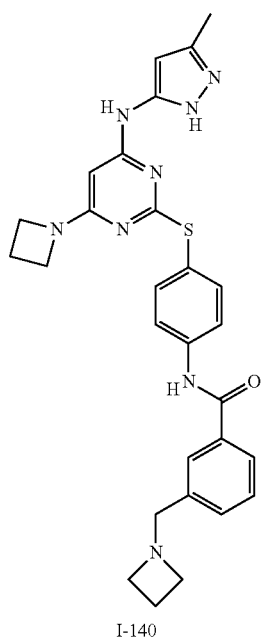
I-140
TABLE 2-continued
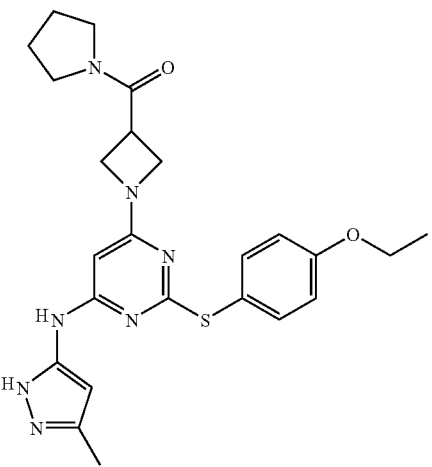
I-141
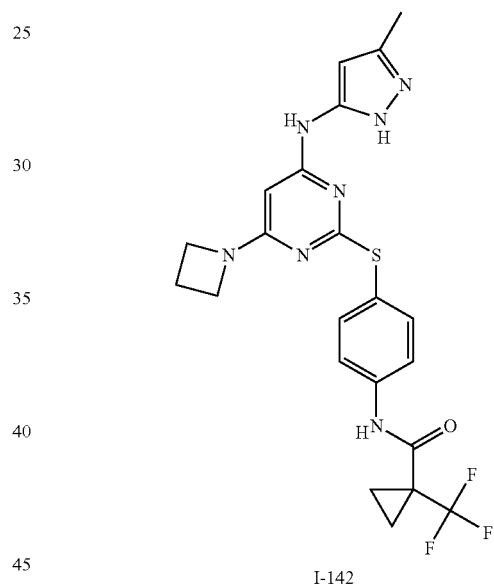
I-142
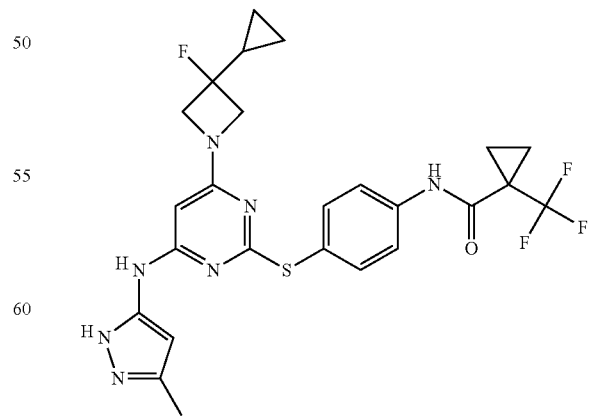
I-143

TABLE 2-continued
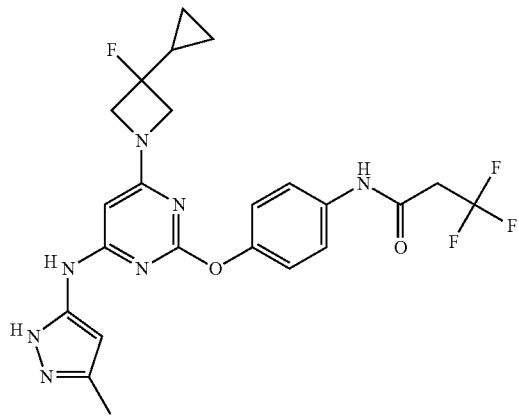
I-144
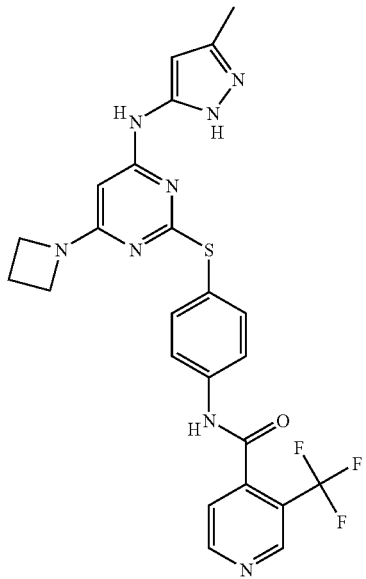
I-146
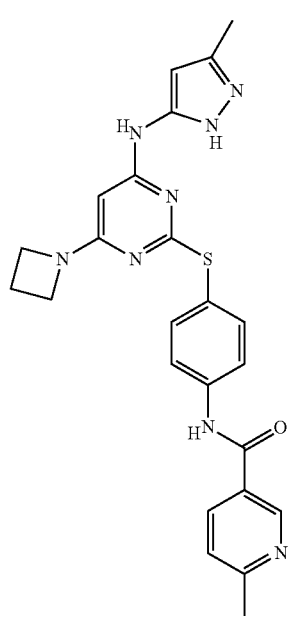
I-145
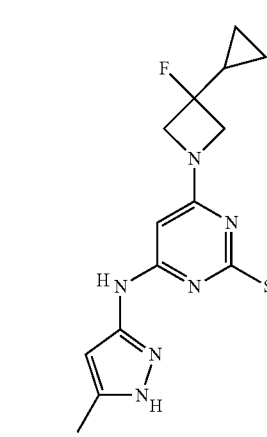
I-147
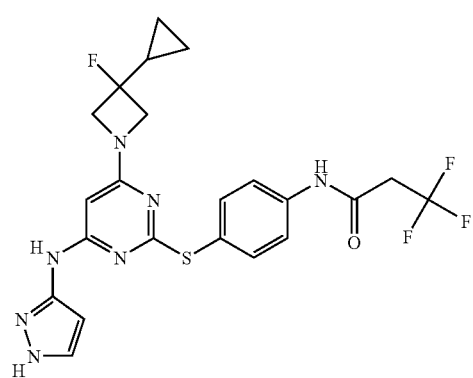
I-148

TABLE 2-continued
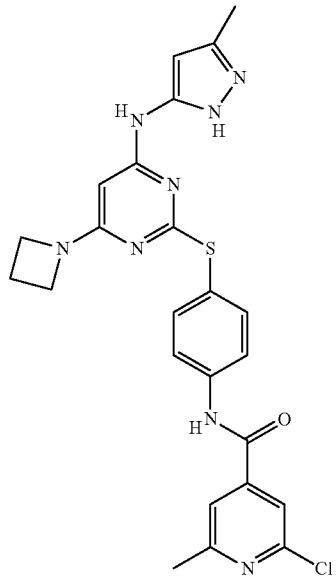
I-149
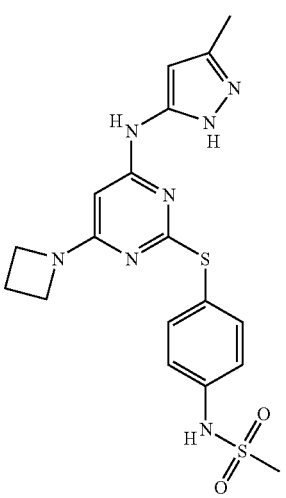
I-150
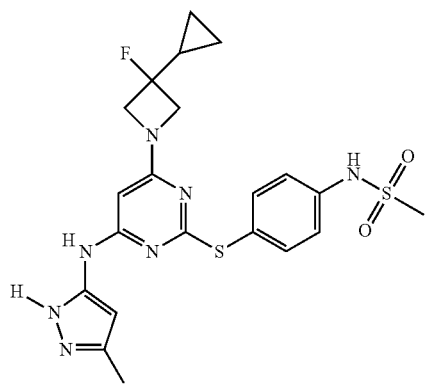
I-151
TABLE 2-continued
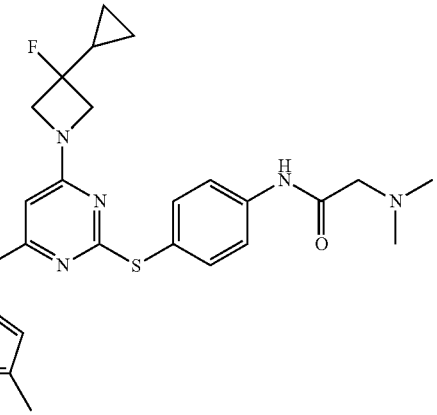
I-152
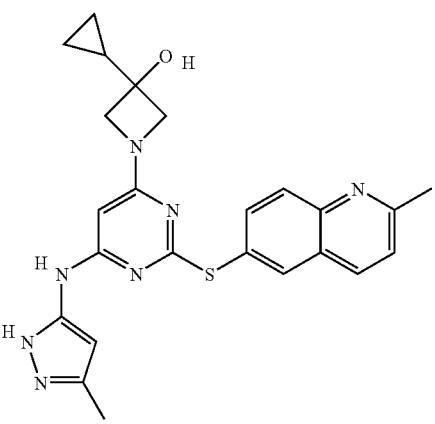
I-153
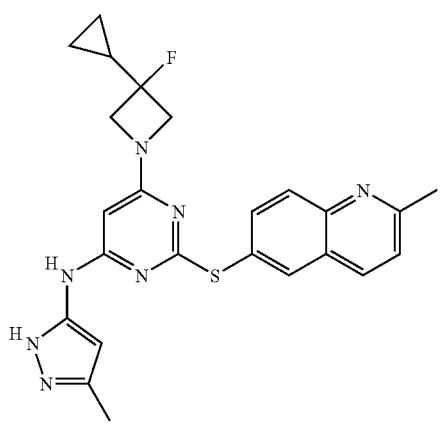
I-154

TABLE 2-continued
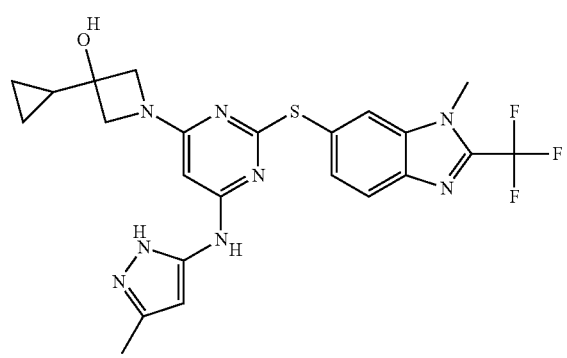
I-155
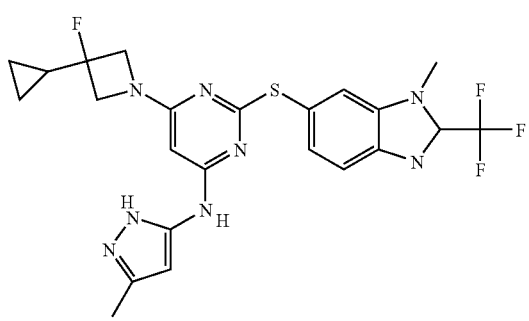
I-156
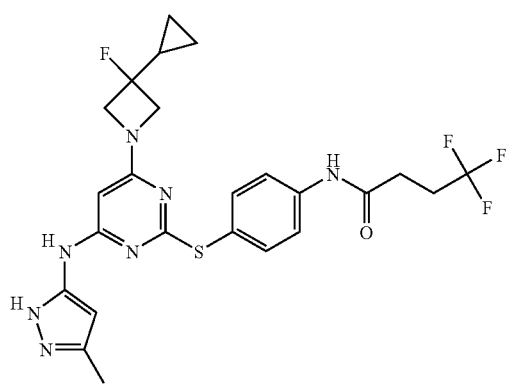
I-157
TABLE 2-continued
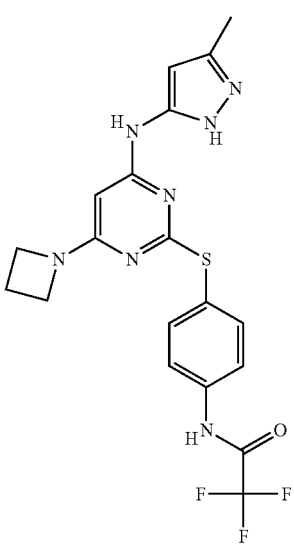
I-158
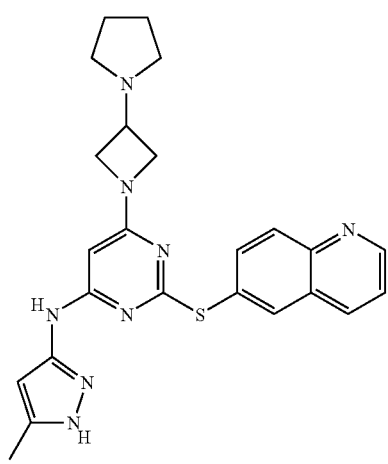
I-159
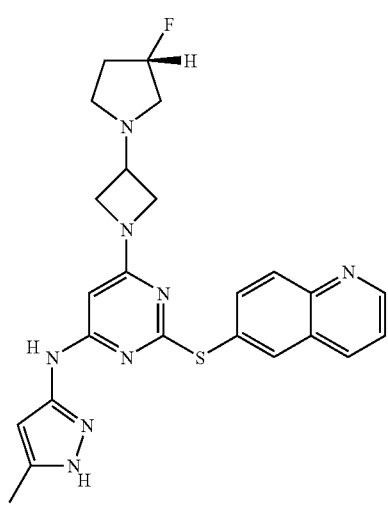
I-160

TABLE 2-continued
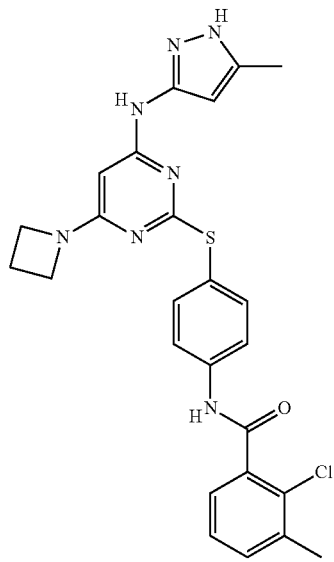
I-161
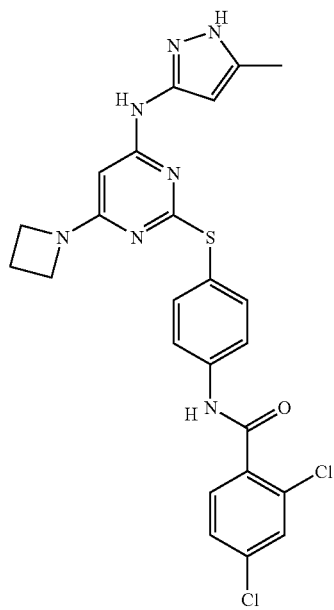
I-162
TABLE 2-continued
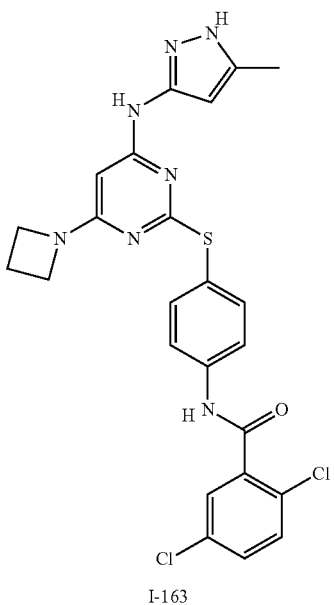
I-163
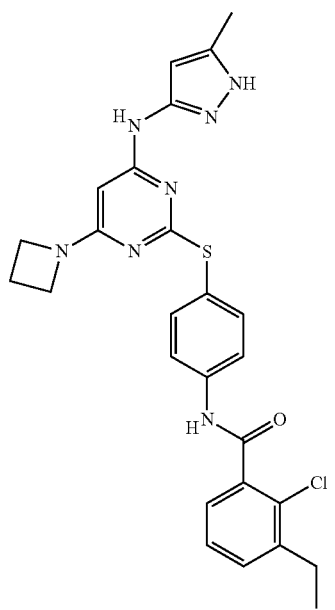
I-164

TABLE 2-continued
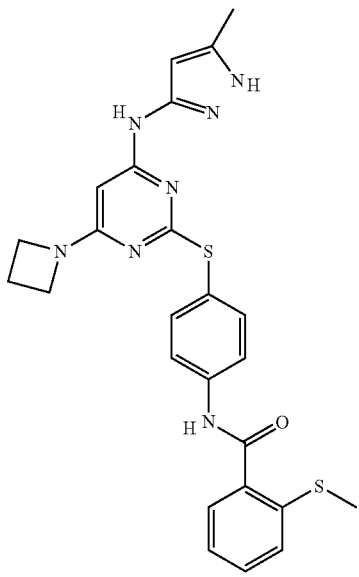
I-165
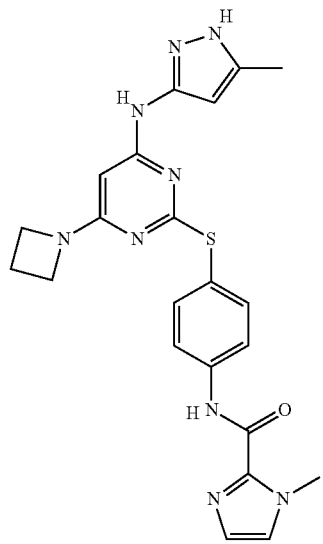
I-166
TABLE 2-continued
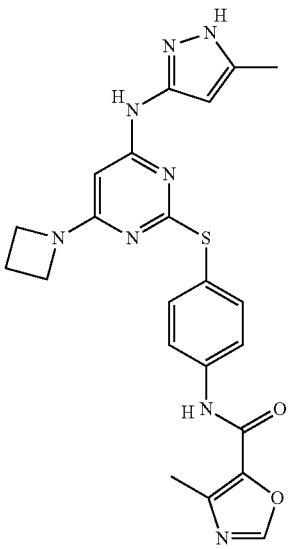
I-167
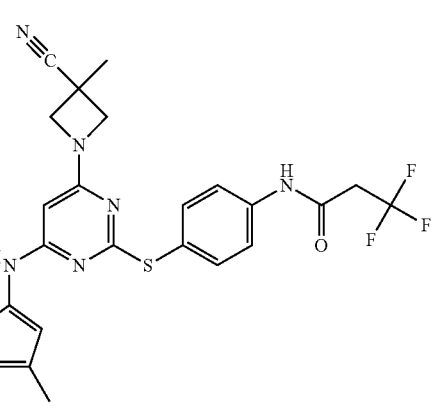
I-168
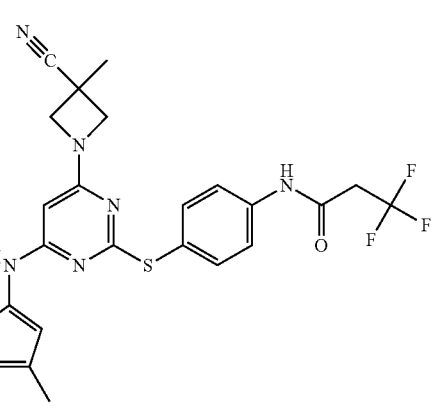
I-169

TABLE 2-continued
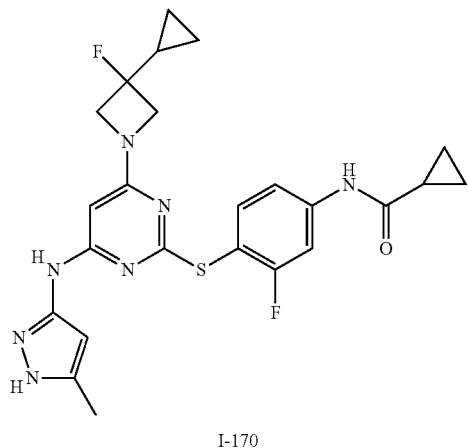
I-170
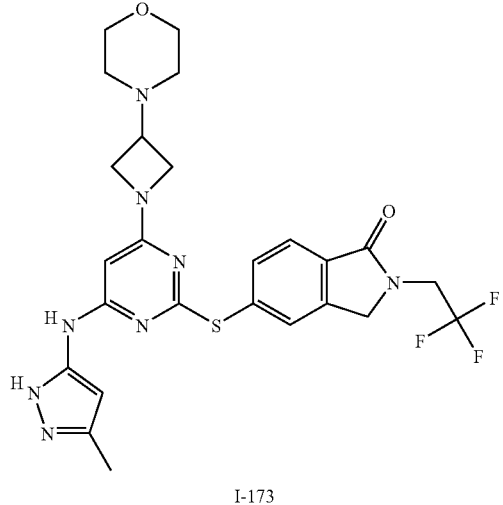
I-173
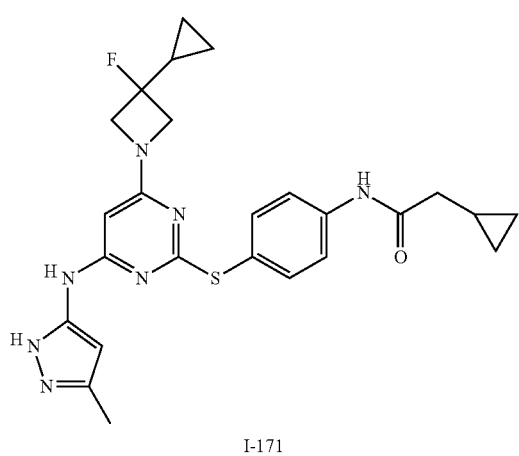
I-171
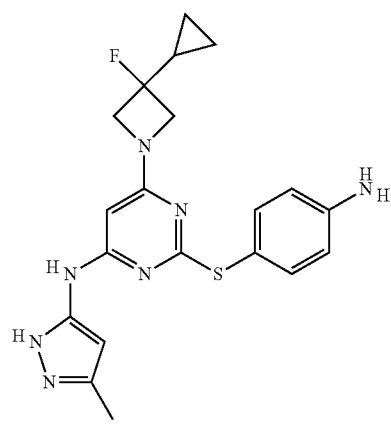
I-174
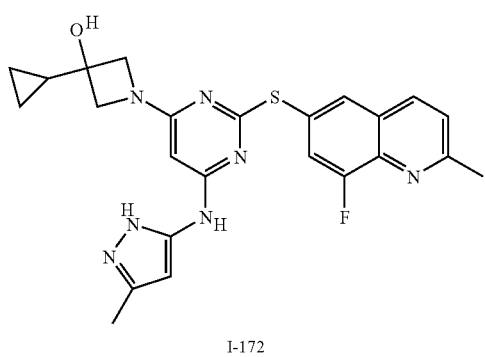
I-172
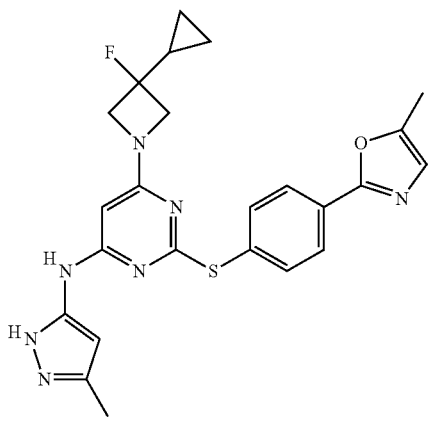
I-175

TABLE 2-continued
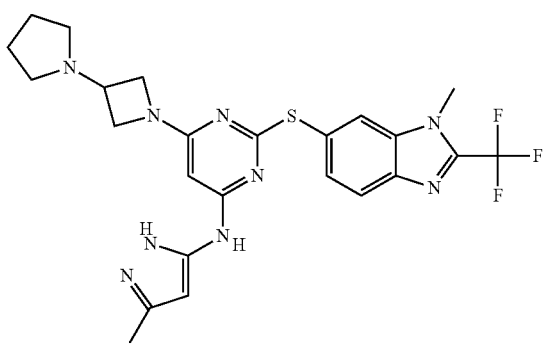
I-176
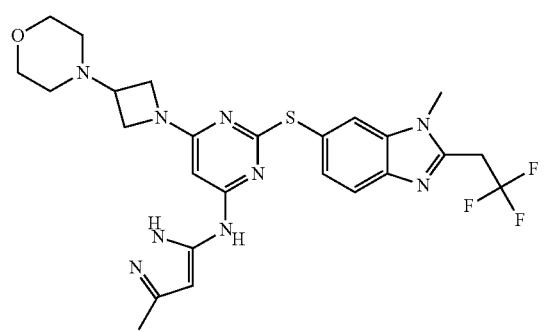
I-177
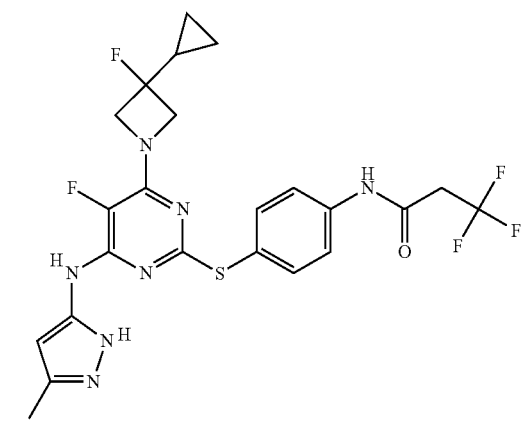
I-178
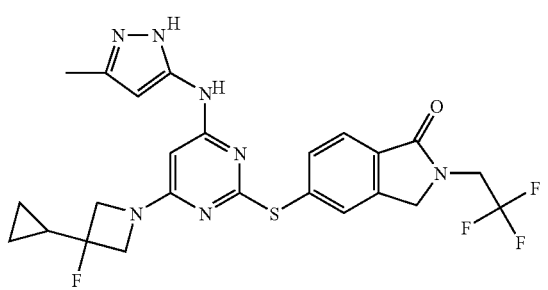
I-179
TABLE 2-continued
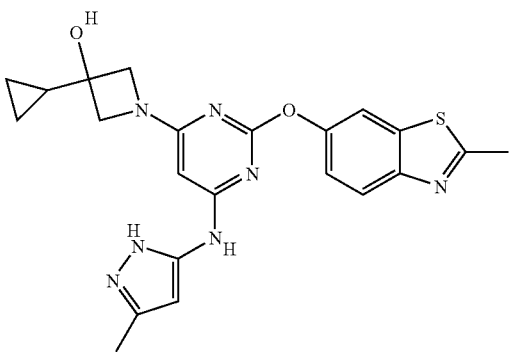
I-180
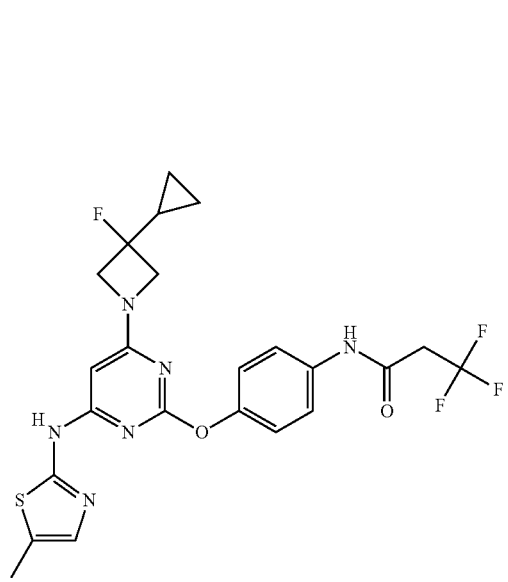
I-181
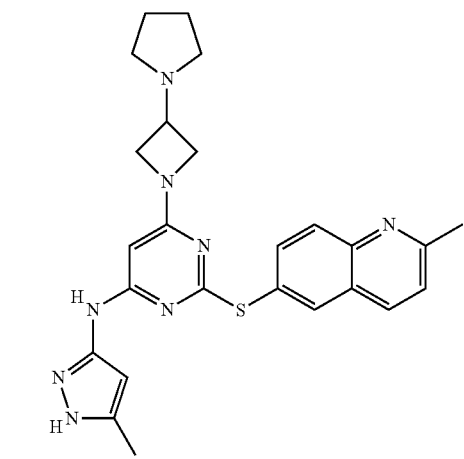
I-182

TABLE 2-continued
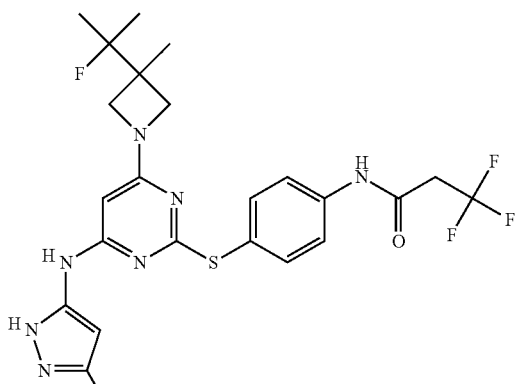
I-183
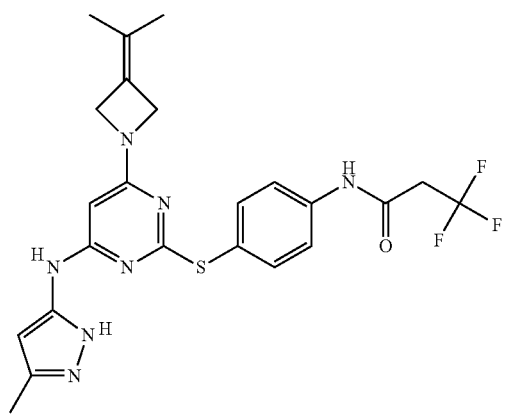
I-184
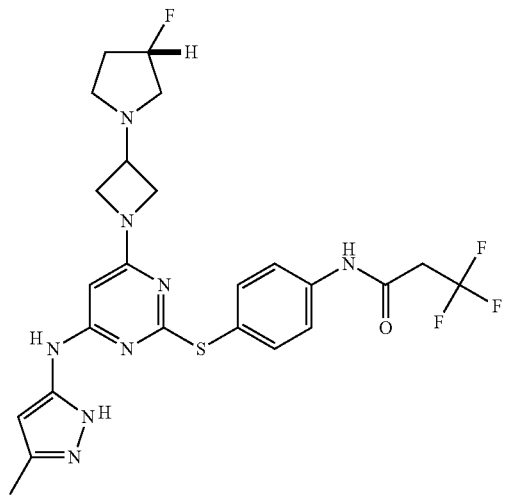
I-185
TABLE 2-continued
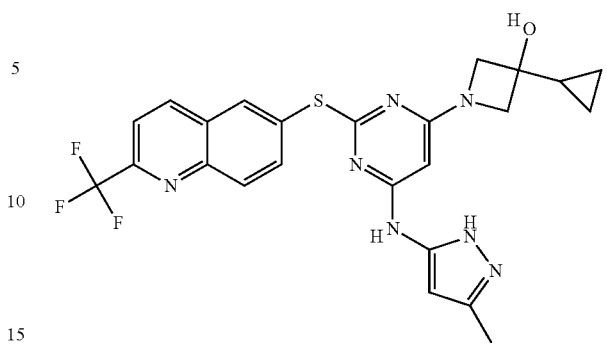
I-186
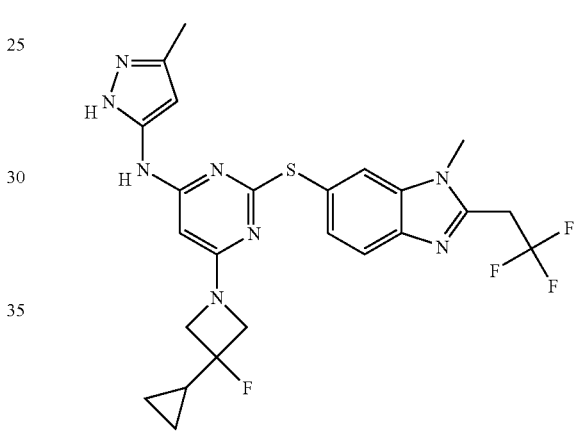
I-187
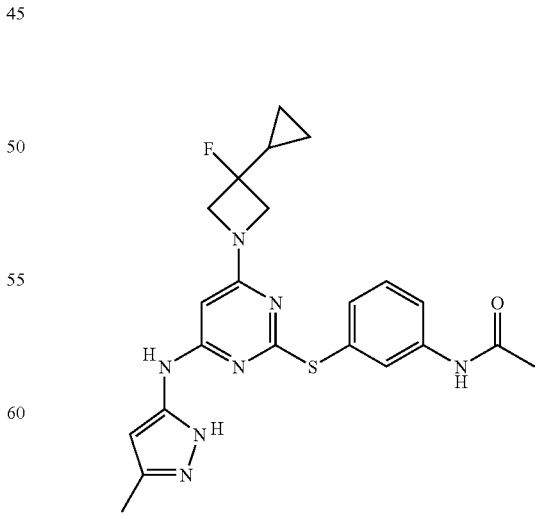
I-188

TABLE 2-continued
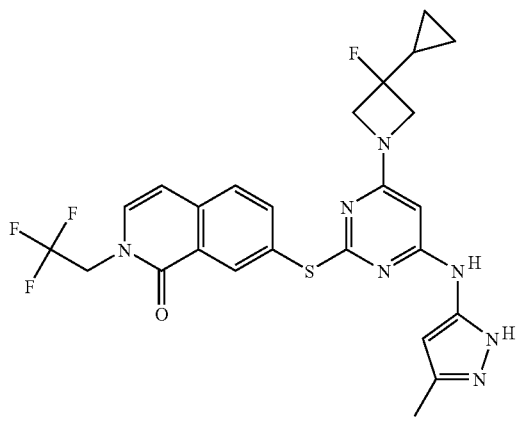
I-189
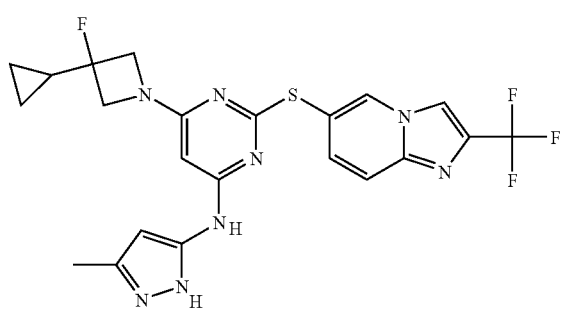
I-190
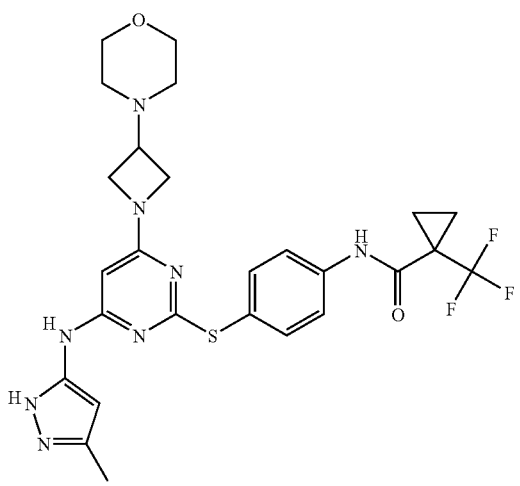
I-191
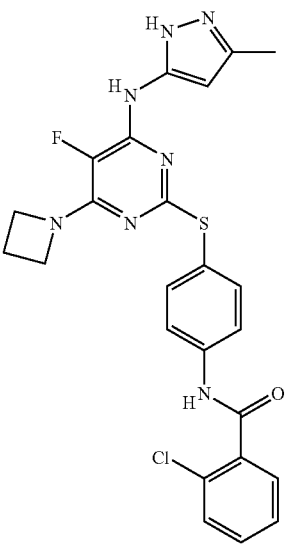
I-192
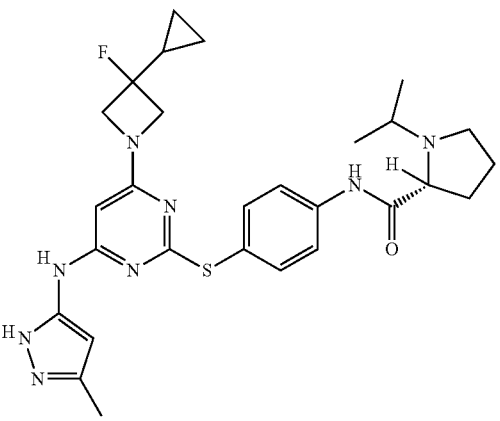
I-193
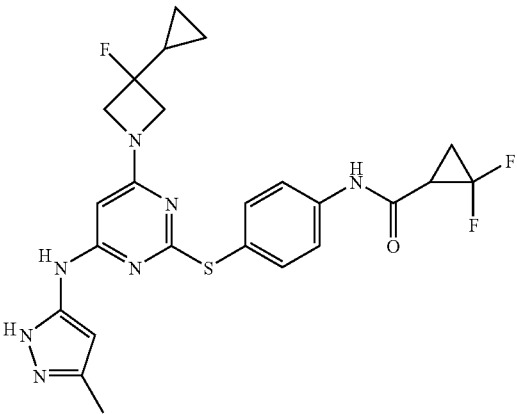
I-194

TABLE 2-continued
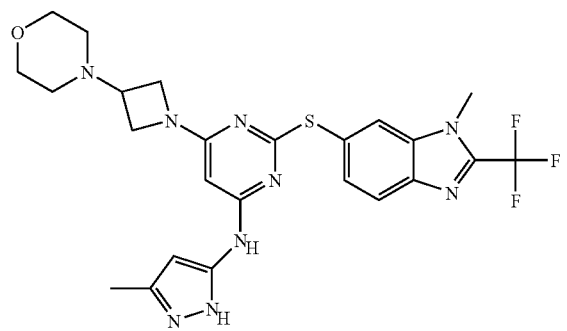
I-195
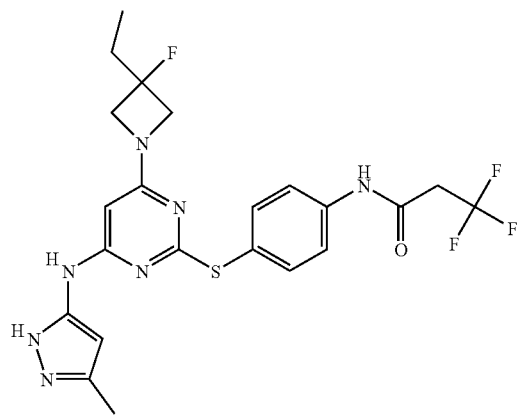
I-196
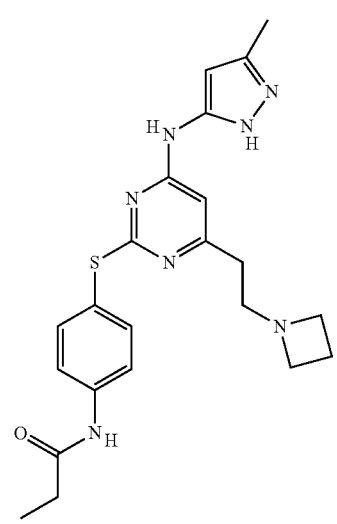
I-197
TABLE 2-continued
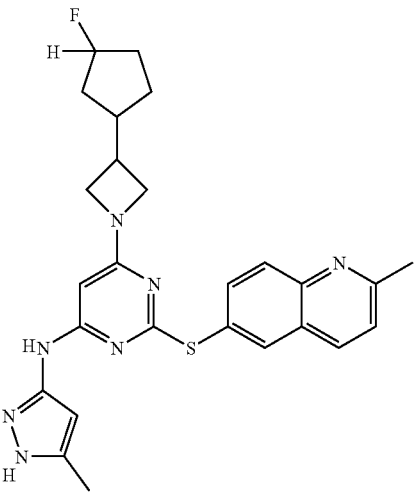
I-198
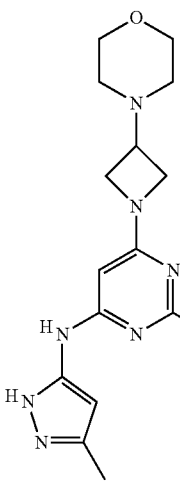
I-199
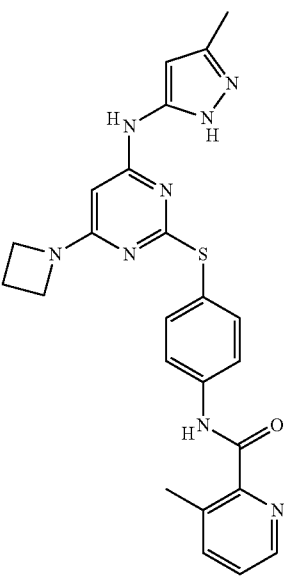
I-200

TABLE 2-continued
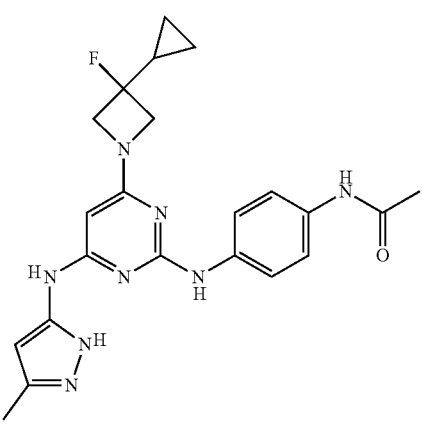
I-201
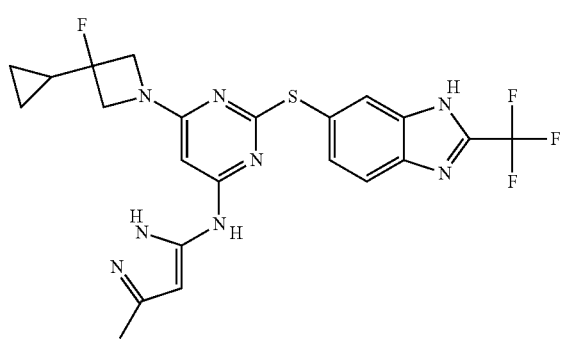
I-202
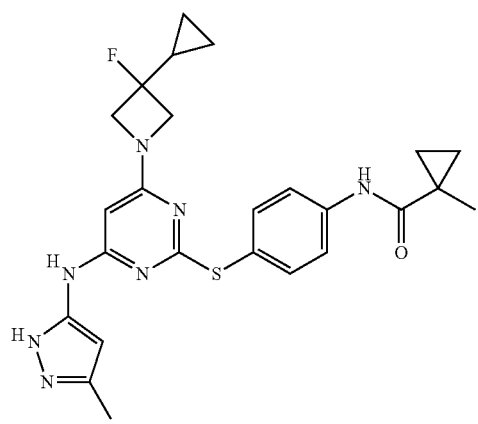
I-203
TABLE 2-continued
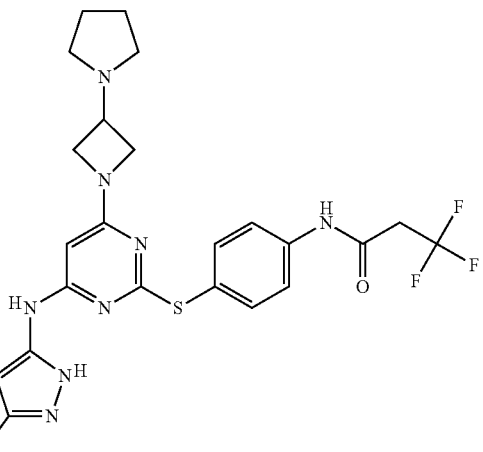
I-204
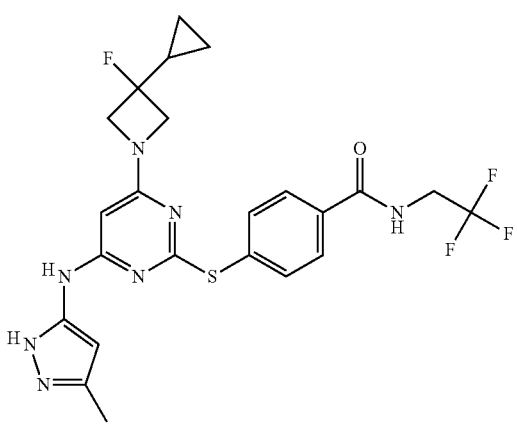
I-205
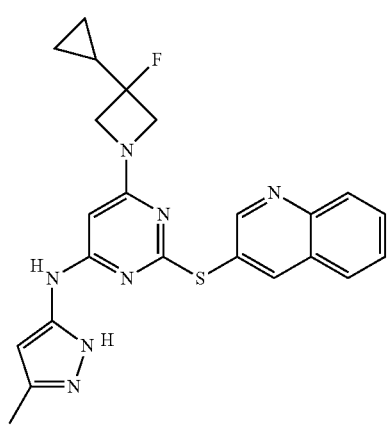
I-206

TABLE 2-continued

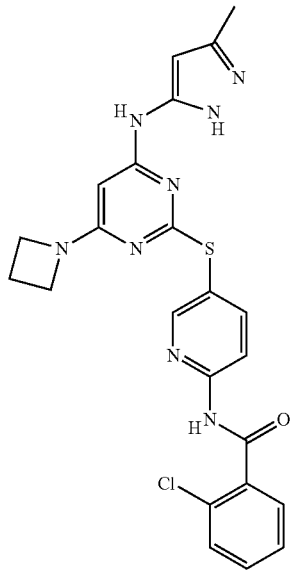

I-207

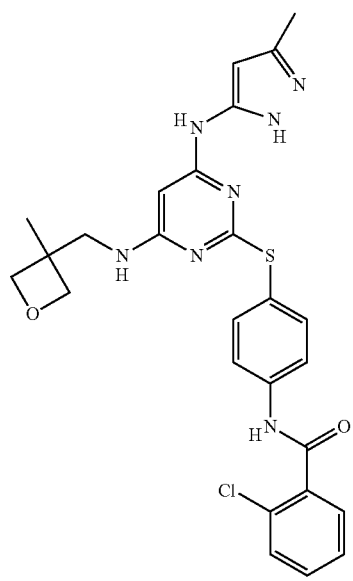

I-208

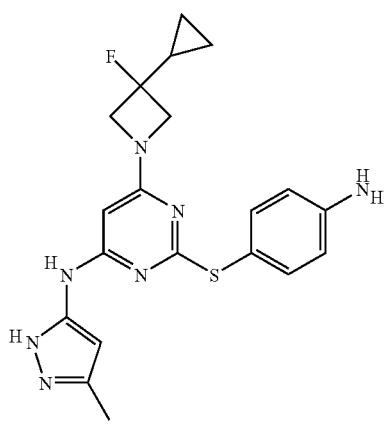

I-209

TABLE 2-continued

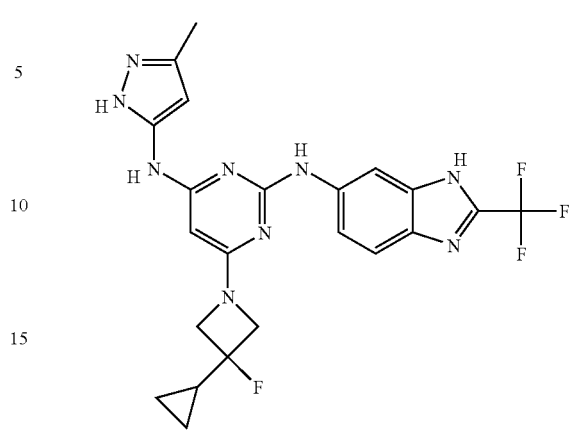

I-210

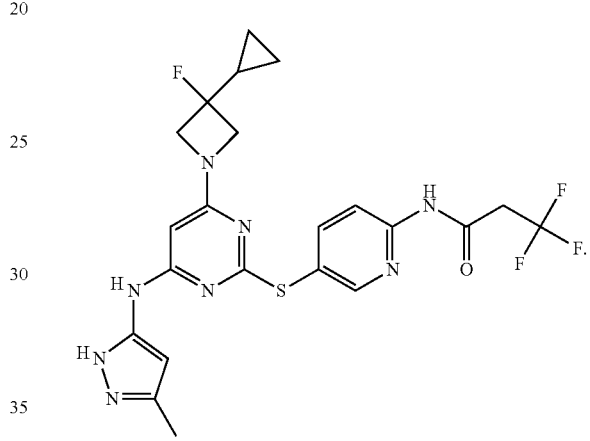

I-211

For purposes of this invention, the chemical elements are identified in accordance with the Periodic Table of the Elements, CAS version, Handbook of Chemistry and Physics, 75$^{th}$ Ed. Additionally, general principles of organic chemistry are described in texts known to those of ordinary skill in the art, including, for example, "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", and the like, as used herein, means an unbranched or branched, straight-chain or cyclic, substituted or unsubstituted hydrocarbon that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl" and the like) refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

In the compounds of this invention, rings include linearly-fused, bridged, or spirocyclic rings. Examples of bridged cycloaliphatic groups include, but are not limited to, bicyclo [3.3.2]decane, bicyclo[3.1.1]heptane, and bicyclo[3.2.2] nonane.

The term "heterocycle", "heterocyclyl", "heterocycloaliphatic", or "heterocyclic", and the like, as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members. Examples of bridged heterocycles include, but are not limited to, 7-aza-bicyclo[2.2.1]heptane and 3-aza-bicyclo[3.2.2] nonane.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

As used herein, the term "Ht" is interchangeable with "Het" and

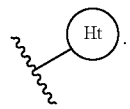

.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3, 5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; a 4-6 membered heteroaryl or heterocyclic ring optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°—, —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —C(=NH)—OR°; —P(O)$_2$R°; —PO(R°)$_2$; —OPO(R°)$_2$; or —(CH$_2$)$_{0-2}$NHC(O)R°; wherein each independent occurrence of R° is selected from hydrogen, optionally substituted C$_{1-6}$ aliphatic, an unsubstituted 4-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic group or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), =N—OH, =N—(OR*) or =NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 4-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O (halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule. Examples of alkylidine chains include, but are not limited to, —CH$_2$—CH=CH—, —CH$_2$—CH$_2$—CH$_2$—CH$_2$—, —CH$_2$—C≡C—, —C(CH$_3$)$_2$—, and =CH—CH$_2$—CH(CH$_2$—CH$_3$)—.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, two independent occurrences of a group are taken together with the atom(s) to which they are bound to form a ring. This ring is an optionally substituted 3-12 membered saturated, partially unsaturated, or fully unsaturated monocyclic or bicyclic ring having 0-4 heteroatoms independently selected from nitrogen, oxygen, or sulfur.

Examples of such rings include, but are not limited to the following: piperidin-1-yl, piperazin-1-yl, or morpholin-4-yl group.

In some embodiments, a carbon unit (or C unit) of an alkyl, alkylidene, or aliphatic chain is optionally replaced with another atom or group. Examples of such atoms or groups include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Examples of C units include —CH$_2$— and =CH—. Unless otherwise specified, the optional replacements form a chemically stable compound. Optional replacements can occur both within the chain and at either end of the chain; i.e., both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if a C unit of —CH₂CH₂CH₃ were optionally replaced with —O—, the resulting compound could be —OCH₂CH₃, —CH₂OCH₃, or —CH₂CH₂OH.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention. As would be understood by a skilled practitioner, a pyrazole group can be represented in a variety of ways. For example, a structure drawn as

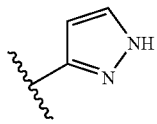 [SMILES: *c1cc[nH]n1]

also represents other possible tautomers, such as

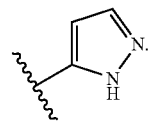 [SMILES: *c1ccn[nH]1]

Likewise, a structure drawn as

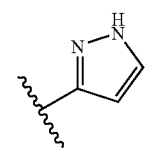

also represents other possible tautomers, such as

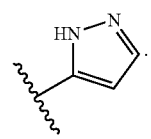 [SMILES: *c1ccn[nH]1]

Unless otherwise indicated, a substituent can freely rotate around any rotatable bonds. For example, a substituent drawn as

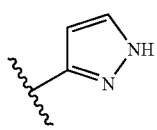 [SMILES: *c1cc[nH]n1]

also represents

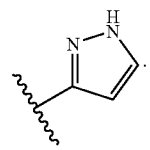 [SMILES: *c1cc[nH]n1]

Likewise, a substituent drawn as

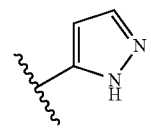

also represents

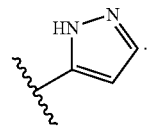

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention may be prepared in light of the specification using steps generally known to those of ordinary skill in the art. Those compounds may be analyzed by known methods, including but not limited to LCMS (liquid chromatography mass spectrometry) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

The following abbreviations are used:
BOC is t-butyloxycarbonyl
DIPEA is diisopropylethylamine
DMF is dimethylformamide
i-PrOH is isopropyl alcohol
n-BuOH is n-butanol
t-BuOH is tert-butanol
EtOH is ethanol
MeOH is methanol
EtOAc is ethyl acetate
TFA is trifluoroacetic acid
DMSO is dimethyl sulfoxide
Rt is retention time
Ph is phenyl
DCM is dichloromethane
MeCN is acetonitrile
THF is tetrahydrofuran
TBTU is 2-(1H-Benzotriazole-1-yl)-1,1,3,3-tetramethyluronium tetrafluoroborate HPLC is high performance liquid chromatography
LCMS liquid chromatography mass spectrometry
¹H NMR is nuclear magnetic resonance

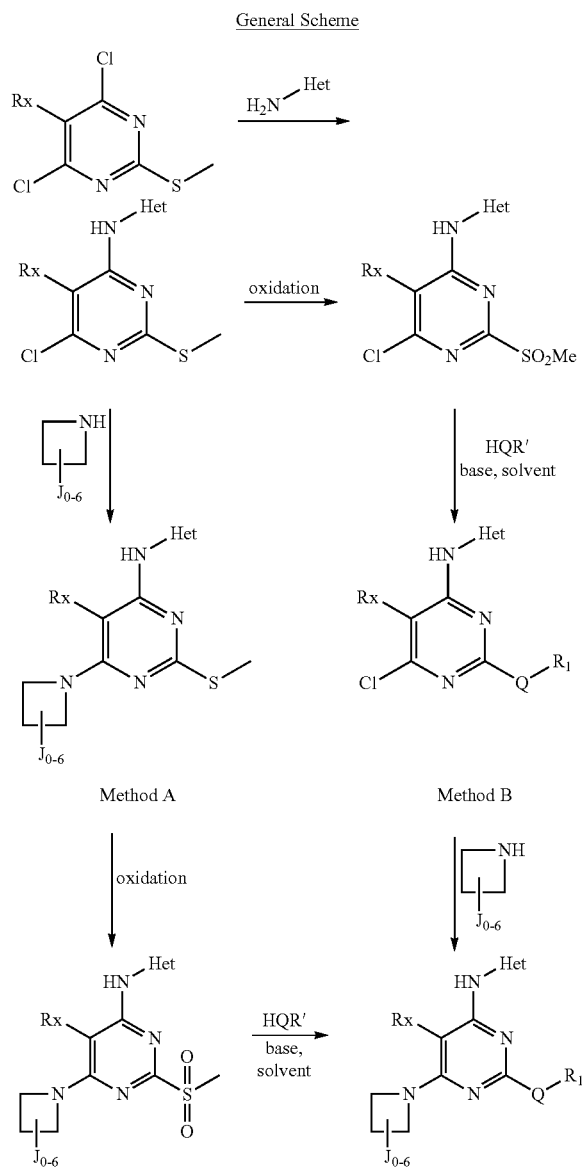

General Scheme

The general scheme above shows some methods of making compounds of this invention wherein the azetidine is directly attached via a nitrogen atom.

Scheme I

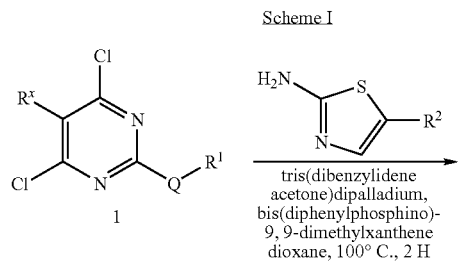

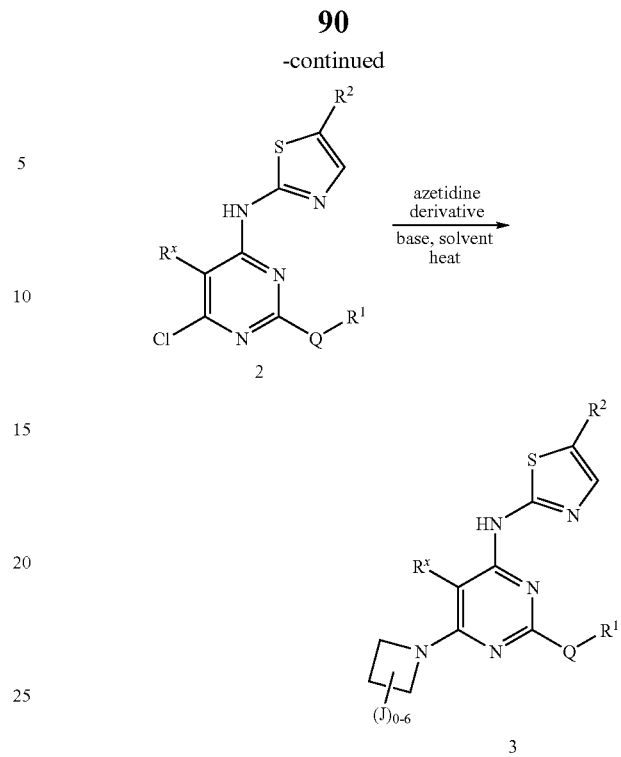

Scheme I above shows a general route for the preparation of compounds of formula 3 (of Scheme I), wherein $R^x$, $R^1$, $R^2$, and J are as defined herein and Q is —O—, —NR¹—, or —S—. In some embodiments the dichlorinated pyrimidine of formula 1 is heated in the presence of a suitable base (e.g. NaI/DIPEA) and a suitable solvent (e.g. DMF) with an optionally substituted aminothiazole to form a compound of formula 2. In other embodiments, the dichlorinated pyrimidine of formula 1 is heated in the presence of a suitable catalyst (see scheme I), a suitable solvent (e.g. dioxane), and an optionally substituted aminothiazole under coupling conditions known to one skilled in the art to form a compound of formula 2. The compound of formula 2 is then heated in the presence of a suitable base (e.g. DIPEA/NaI) and a suitable solvent, (e.g. n-BuOH), with an azetidine derivative to form a compound of formula 3.

Scheme II

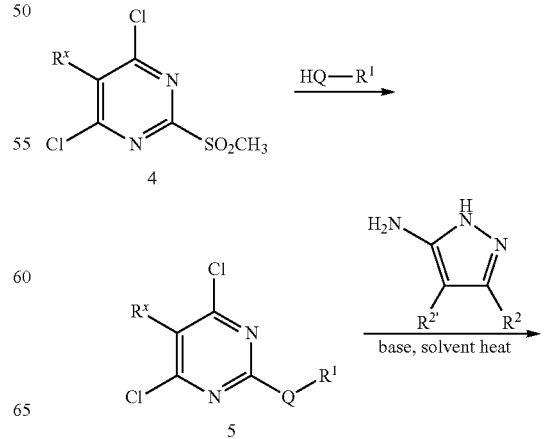

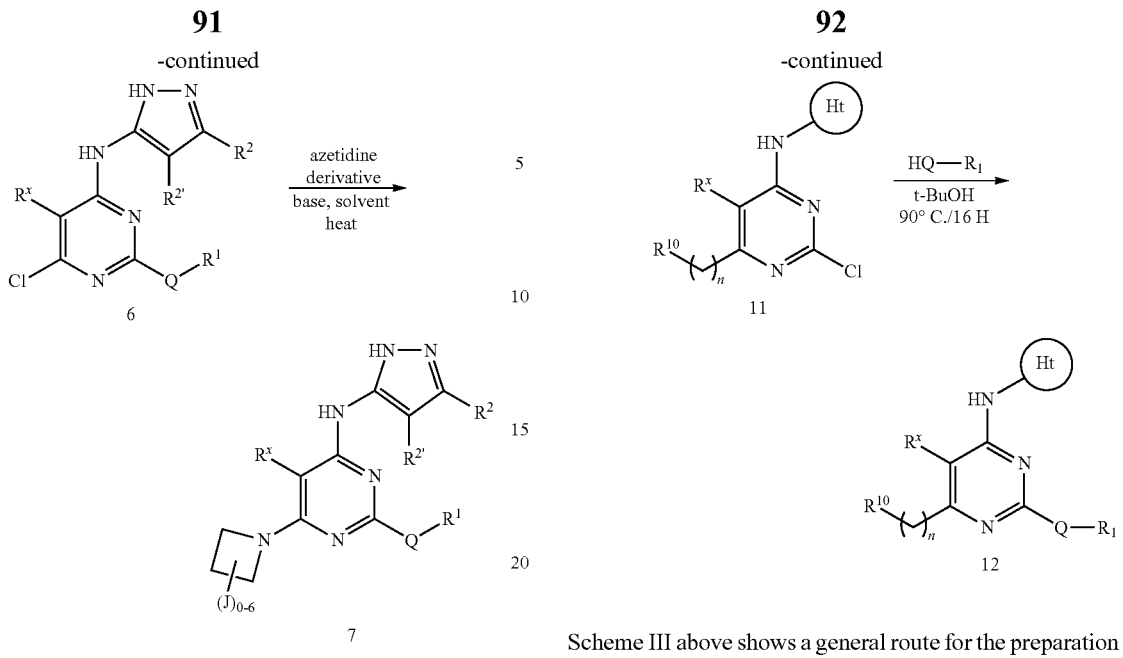

Scheme II above shows a general route for the preparation of compounds of formula 7 (of Scheme II), wherein $R^X$, $R^1$, $R^2$, $R^{2'}$, and J are as defined herein and Q is —O—, —NR'—, or —S—. The dichlorinated pyrimidine of formula 4 is combined with HQ-$R^1$ to form a compound of formula 5. In some embodiments, the two compounds are heated in the presence of a suitable solvent (e.g. t-BuOH) for 16 hours. In other embodiments, the two compounds are mixed at 0° C. in the presence of acetonitrile and triethylamine for 1 hour. The compound of formula 5 is then heated in the presence of a suitable solvent (e.g. DMF) and a suitable base (e.g. DIPEA/NaI) with an optionally substituted aminopyrazole to form a compound of formula 6, which is heated in the presence of an azetidine derivative in the presence of a suitable solvent (e.g. n-BuOH) to form a compound of formula 7.

Scheme III above shows a general route for the preparation of compounds of formula 12 (of Scheme III), wherein $R^X$, $R^1$, $R^{10}$, and Ht are as defined herein and Q is —O—, —NR'—, or —S—. The ketoester of formula 8 is cyclized in the presence of urea, a suitable solvent (e.g. NeOH, EtOH), and a suitable base (e.g. NaOMe) to form the dihydroxy pyrimidine of formula 9. The compound of formula 9 is then chlorinated under suitable chlorination conditions, such as heating in the presence of POCl₃ and DIPEA, to form a dichloropyrimidine of formula 10. The dichloropyrimidine is then heated in the presence of an appropriate amino-heteroaryl under suitable conditions known to those skilled in the art (see Scheme III for examples) to form a compound of formula 11, which is subsequently heated with HQ-$R^1$ in the presence of a suitable solvent (e.g. t-BuOH) to form a compound of formula 12.

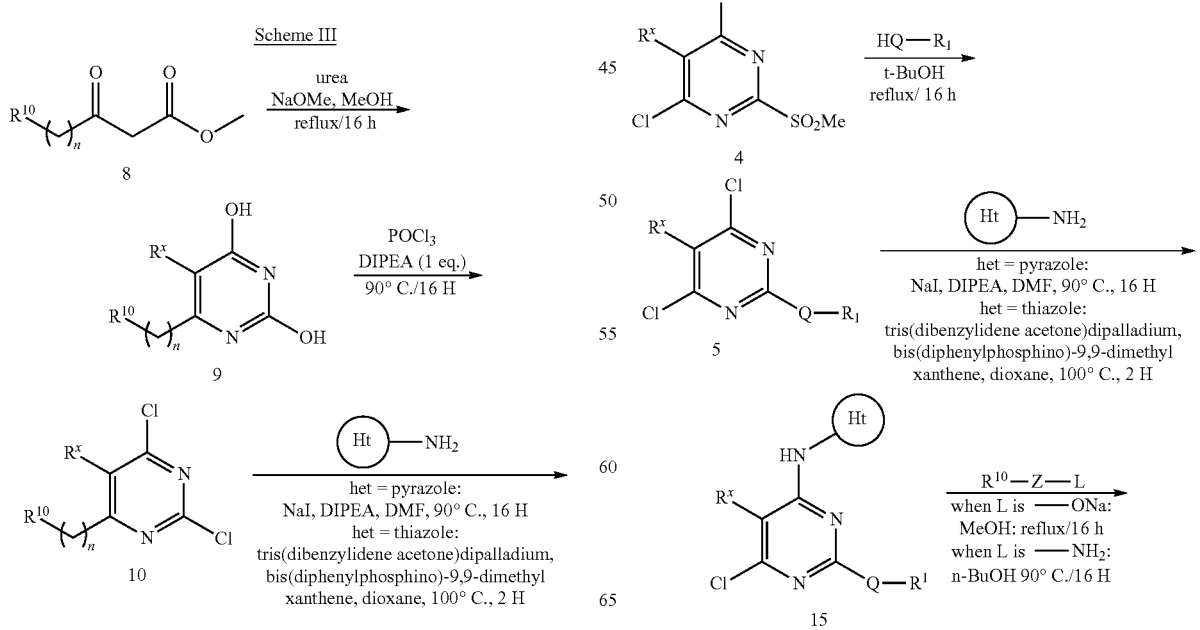

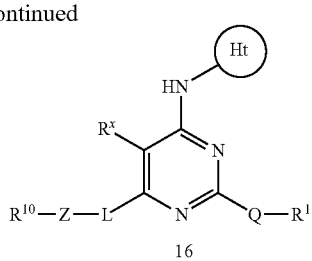

Scheme IV above shows a general route for the preparation of compounds of formula 16 (of Scheme IV), wherein L is an appropriate nucleophile (such as N, O, or S), Q is —O—, —NR'—, or —S—, and Z, $R^1$, $R^{10}$, $R^X$, and Ht are as defined herein. The dichloropyrimidine of formula 4 is heated in the presence of HQ-$R^1$ to form the substituted dichloropyrimidine of formula 5. The compound of formula 5 is then heated in the presence of an appropriate amino-heteroaryl under suitable conditions known to those skilled in the art (see Scheme IV above for examples) to form a compound of formula 15, which is heated with $R^{10}$—Z-L, wherein L is an appropriate nucleophile (such as N, O, or S), and Z and $R^{10}$ are as defined herein, to form a compound of formula 16.

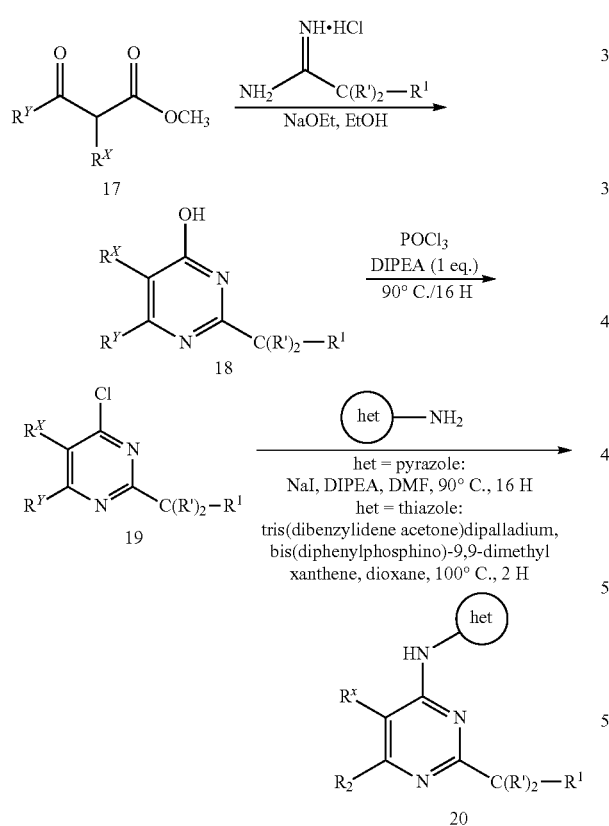

Scheme V above shows a general route for the preparation of compounds of formula 20 (of Scheme V), wherein $R^1$, $R^X$, $R^Y$, R' and Ht are as defined herein. The ketoester of formula 17, together with a substituted amidine, cyclizes to form the hydroxypyrimidine of formula 18. The compound of formula 18 is then chlorinated under suitable chlorination conditions known to those skilled in the art (e.g. $POCl_3$/DIPEA), to form the chloropyrimidine of formula 19. The chloropyrimidine is then heated in the presence of an appropriate amino-heteroaryl under suitable conditions known to those skilled in the art (see scheme V above for examples) to form a compound of formula 20.

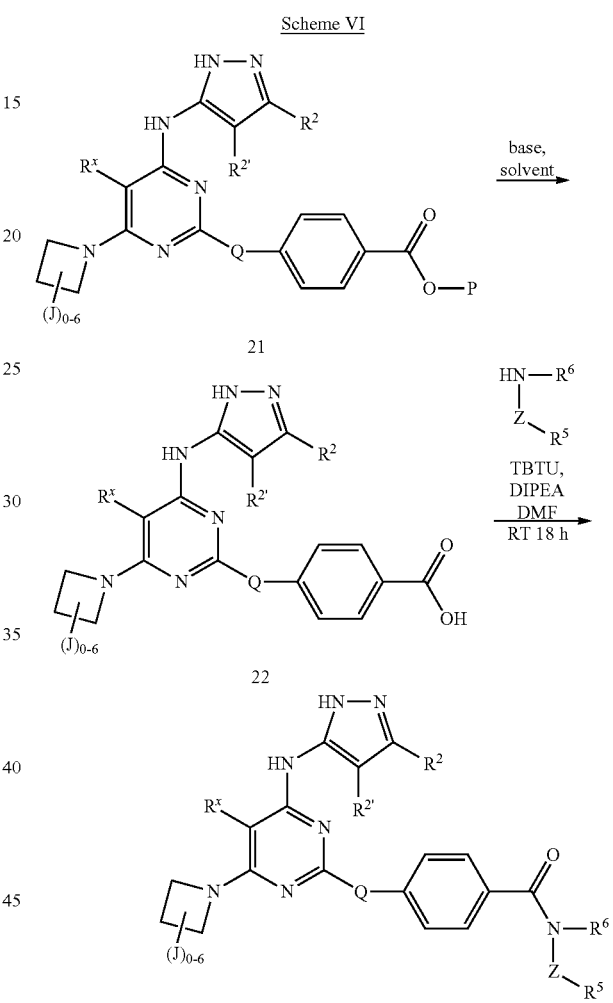

Scheme VI above shows a general route for the preparation of compounds of formula 23 (of Scheme VI), wherein $R^X$, $R^2$, $R^{2'}$, $R^5$, $R^6$, Z, J, and Ht are as defined herein. The protected acid of formula 21 is deprotected with a suitable base (e.g. NaOH) in the presence of a suitable solvent or solvents (e.g. THF/MeOH) to form the acid of formula 22. The acid of formula 22 is then combined with a suitable amine in the presence of coupling reagents known to one skilled in the art (e.g. TBTU), a suitable base (e.g. DIPEA), and a suitable solvent (e.g. DMF) to form the compound of formula 23.

Scheme VII

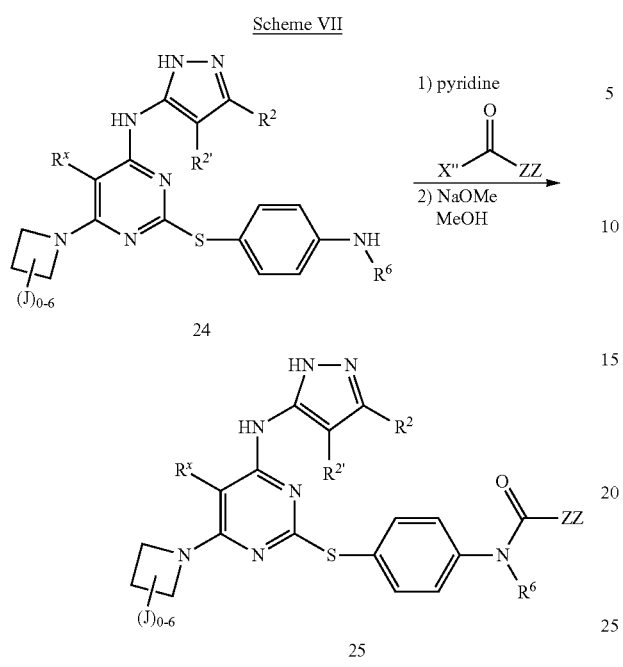

Scheme VII above shows a general route for the preparation of compounds of formula 25 (of Scheme VII), wherein $R^x$, $R^2$, $R^{2'}$, $R^6$, and J are as defined herein and ZZ is —N($R^6$)—$ZR^5$, —O—$ZR^5$, or —$ZR^5$ wherein $R^5$, $R^6$, and Z are as defined herein. The compound of 24 is combined with a suitable acid chloride (wherein X″ is Cl) in the presence of pyridine to form an intermediate compound that, upon mixing in the presence of sodium methoxide and methanol, forms the compound of formula 25. In some embodiments, X″ can be OH, in which case a suitable acid coupling reagent is used to couple the acid to the amine. Examples of suitable acid coupling reagents include, but are not limited to, EDC, DCI, and HOBT. Suitable solvents for these coupling reactions include, but are not limited to, THF, $CH_2Cl_2$, and dioxane.

Scheme VIII

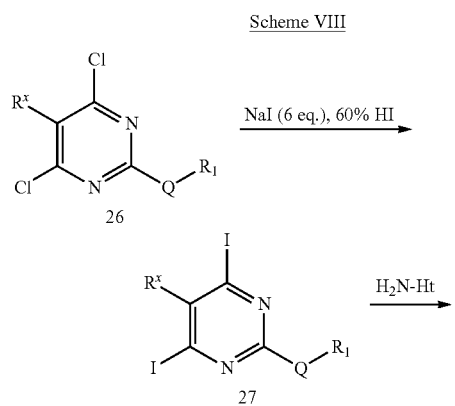

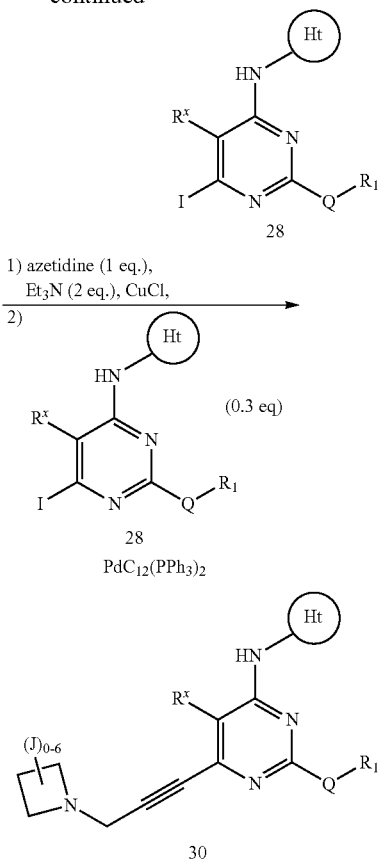

Scheme VIII above shows a general route for the preparation of compounds of formula 30 (of Scheme VIII) wherein Z is —C≡C—$CH_2$—. Dichloropyrimidine 26 is converted to di-iodinated pyrimidine 27 in the presence of NaI and HI. Compound 27 is combined with an aminoheteroaryl to form the compound 28. Compound 29 is then combined with azetidine under basic displacement conditions to form an optionally substituted propynyl-azetidine, which is combined with compound 28 under palladium coupling conditions to form a compound of formula 30.

Scheme IX

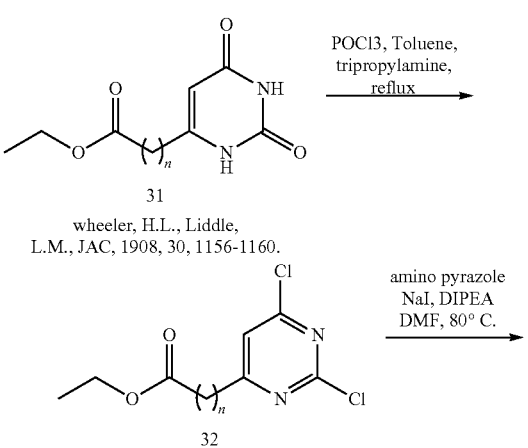

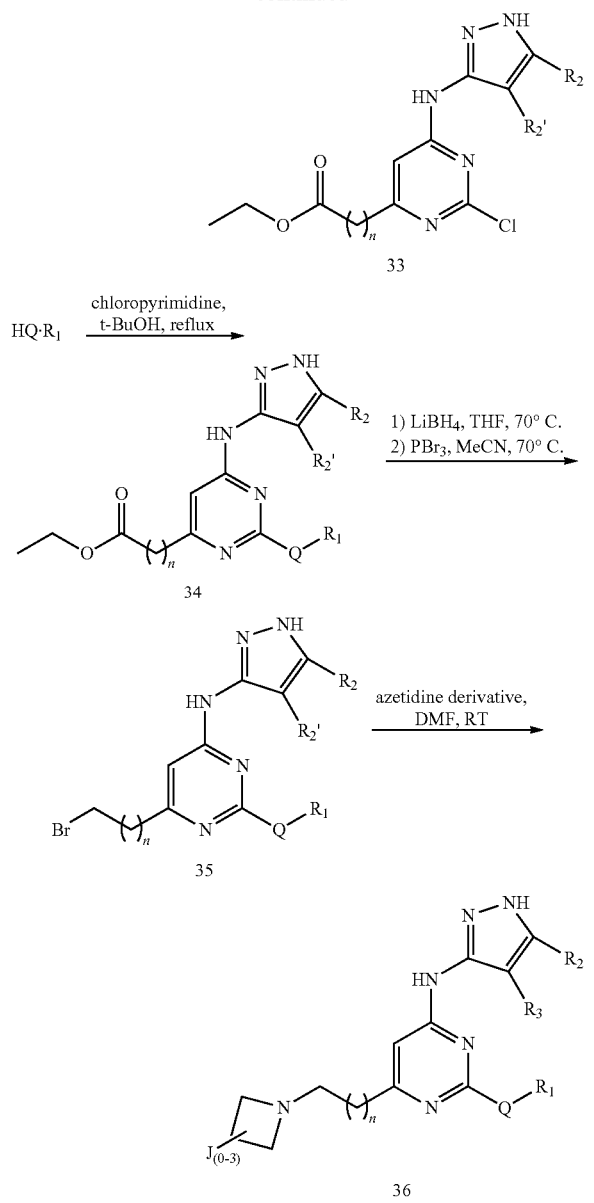

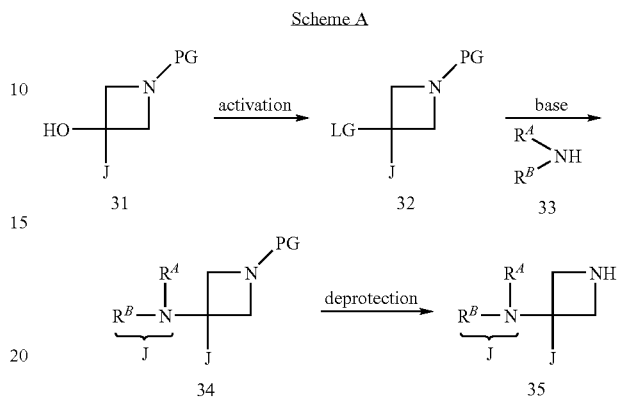

Scheme IX above shows a general route for the preparation of compounds of formula 36 (in Scheme IX) wherein $R^2$, $R^V$, $R^1$, and J are as defined herein and Q is —O—, —NR'—, or —S—. Compound 31 is converted to dichloro pyrimidine 32 by treating 31 with $POCl_3$ in the presence of a suitable solvent (e.g. toluene) and in the presence of suitable base (e.g. tripropylamine). Compound 32 is then heated in the presence of a suitable solvent (e.g. DMF) and a suitable base (e.g. DIPEA/NaI) with an optionally substituted aminopyrazole to form a compound of formula 33. The chlorinated pyrimidine of formula 33 is combined with HQ-$R^1$ to form a compound of formula 34 and the two compounds are heated in the presence of a suitable solvent (e.g. t-BuOH). Reduction of the ester and treatment of the corresponding alcohol with $PBr_3$ leads to the formation of bromoderivative 35. Bromoderivative 35 can be then treated with a variety of azetidines at room temperature in the presence of a suitable solvent (e.g. DMF) to yield the final compound 36.

The following schemes depict methods for synthesizing various types of azetidines. Theses azetidines can be used to form compounds of this invention according to the methods described herein.

Scheme A above shows a general route for the preparation of N-substituted azetidines wherein at least one J group is bonded to the azetidine via a nitrogen atom. Protected azetidine 31 is activated with a suitable leaving group under suitable conditions to form azetidine 32, which, upon treatment with $NHR^AR^B$ under basic conditions, forms the amine-substituted azetidine 34. Azetidine 34 is then deprotected under suitable nitrogen deprotection conditions to form compound 35.

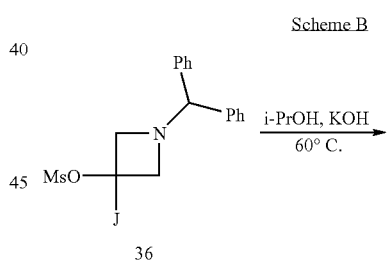

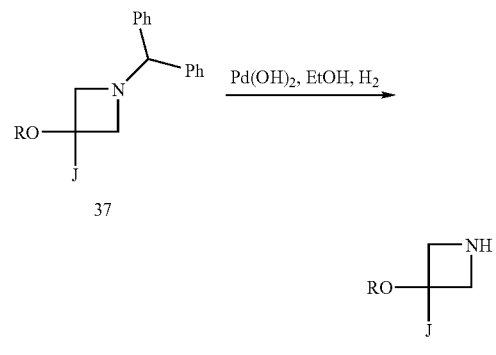

Scheme B above shows a general route for the preparation of O-substituted azetidines wherein at least one J group is OR wherein R is H or $C_{1-6}$alkyl.

Scheme C

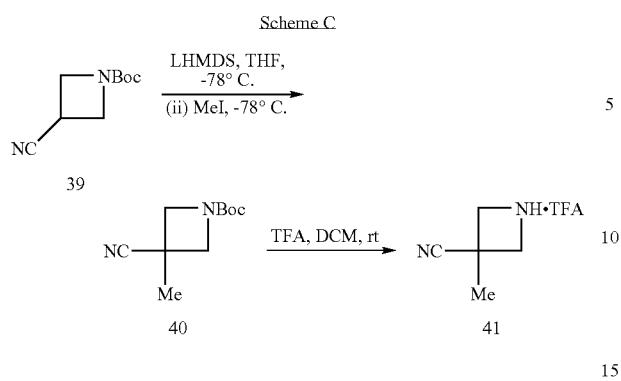

Scheme C above shows a general route for the preparation of substituted azetidines wherein J is CN and $C_{1-6}$alkyl.

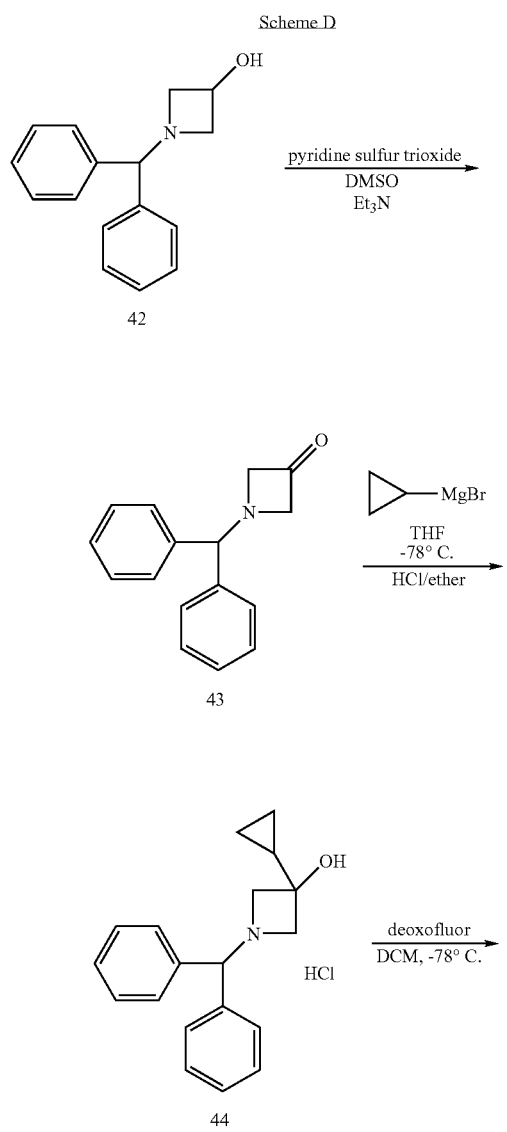

Scheme D depicts a general route for the preparation of cyclopropyl-fluoro-substituted azetidines. Compound 42 is oxidized under suitable conditions to form compound 43, which, under suitable Grignard conditions, is combined with cyclopropyl-MgBr to form the cyclopropyl-substituted azetidine 44. Compound 44 is then fluorinated under suitable fluorination conditions to form 45, which is hydrogenated under Pd/C conditions to form the deprotected free azetidine 46.

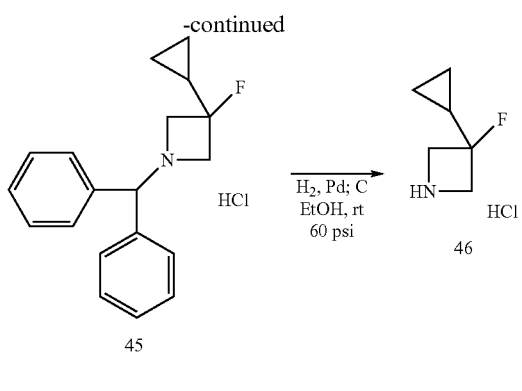

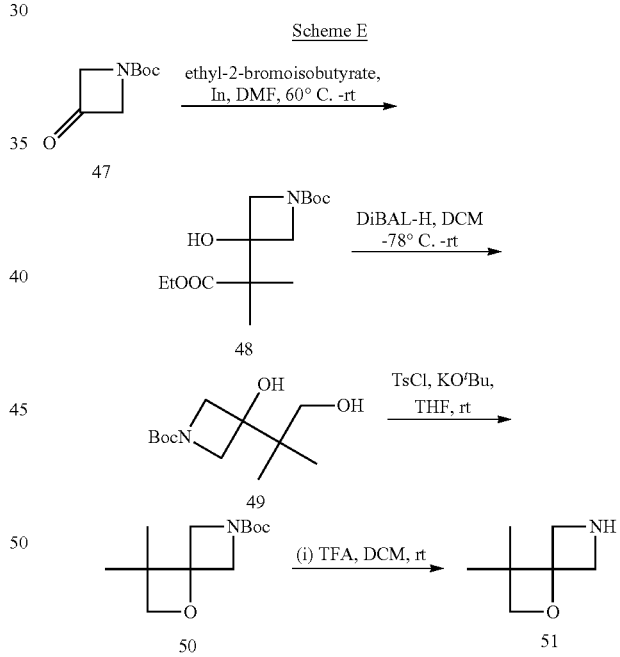

Scheme E depicts a general route for the preparation of 4-membered spirocyclic azetidines. The protected azetidinone 47 is combined with ethyl-2-bromoisobutyrate to form compound 48. Compound 48 is then deprotected with DiBAL to form compound 49. Compound 49 is then cyclized under suitable conditions to form the spirocyclic azetidine 50. Compound 50 is then deprotected under standard conditions to form compound 51.

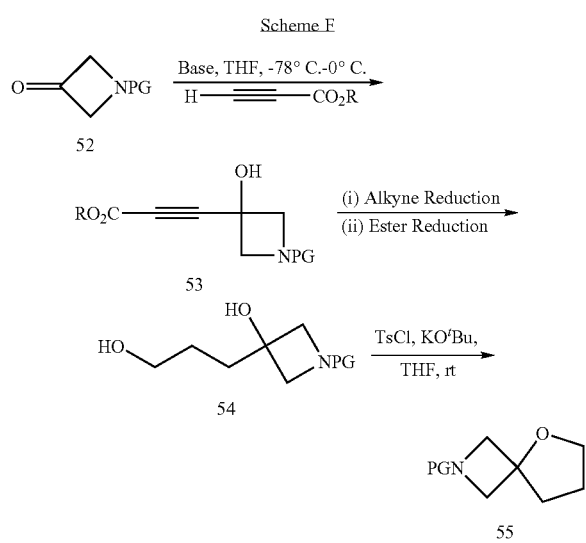

Schemes E and F above depict a general route for the preparation of 4 and 5 membered spirocyclic azetidines. In the above scheme, PG stands for nitrogen protecting groups known to one skilled in the art. R is $C_{1-6}$alkyl. The protected azetidinone 52 is combined with an alkynyl ester to form compound 53. The alkynyl group of compound 53 is then reduced, followed by the reduction of the ester in compound 53 to form compound 54, which is cyclized under appropriate conditions (e.g. TsCl, KO$^t$Bu) to form spirocycle 55. Reduction of alkynes and esters are known to those skilled in the art.

Accordingly, this invention relates to processes for making the compounds of this invention.

One aspect of this invention relates to a method for treating a disease state in patients that is alleviated by treatment with a protein kinase inhibitor, which method comprises administering to a patient in need of such a treatment a therapeutically effective amount of a compound of formula I (herein including Ia, Ib, II-a, II-b, II-c, II-d, II-e, II-f, and II-g). The method is particularly useful for treating a disease state that is alleviated by the use of an inhibitor of a kinase such as the Aurora kinases (Aurora A, Aurora B, Aurora C), FLT-3, JAK-2, JAK-3, ITK, Abl, Abl(T315I), Arg, FGFR1, MELK, MLK1, MuSK, Ret, TrkA, PLK4, Tie-2, and TrkA.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of this invention is directed towards a method of treating cancer in a subject in need thereof, comprising the sequential or co-administration of a compound of this invention or a pharmaceutically acceptable salt thereof, and another therapeutic agent. In some embodiments, said additional therapeutic agent is selected from an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxang®).

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevecm, adriamycin, dexamethasone, and cyclophosphamide.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tab®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukin®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsule®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

The protein kinase inhibitors or pharmaceutical salts thereof may be formulated into pharmaceutical compositions for administration to animals or humans. These pharmaceutical compositions, which comprise an amount of the protein inhibitor effective to treat or prevent kinase-mediated condition and a pharmaceutically acceptable carrier, are another embodiment of the present invention.

The term "protein kinase-mediated condition", as used herein, means diseases or other deleterious conditions in which a protein kinase is known to play a role. Such conditions include, without limitation, autoimmune diseases, inflammatory diseases, neurological and neurodegenerative diseases, cancer, cardiovascular diseases, allergy and asthma. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma, non-small cell lung; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, non-small cell, adenocarcinoma, alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer. The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer such as colorectal, thyroid, and breast cancer; and myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In some embodiments, the compounds of this invention are useful for treating cancer, such as colorectal, thyroid, breast, and non-small cell lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Such derivatives or prodrugs include those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Base addition salts can be prepared by 1) reacting the purified compound in its acid form with a suitable organic or inorganic base and 2) isolating the salt thus formed.

Salts derived from appropriate bases include alkali metal (e.g., sodium and potassium), alkaline earth metal (e.g., magnesium), ammonium and $N^+$ ($C_{1-4}$ alkyl)$_4$ salts. This invention also envisions the quaternization of any basic nitrogen-containing groups of the compounds disclosed herein. Water or oil-soluble or dispersible products may be obtained by such quaternization.

Base addition salts also include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraperitoneal, intrahepatic, intralesional and intracranial injection or infusion techniques.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, a bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used may include lactose and corn starch. Lubricating agents, such as magnesium stearate, may also be added. For oral administration in a capsule form, useful diluents may include lactose and dried cornstarch. When aqueous suspensions are required for oral use, the active ingredient may be combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials may include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations may be prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention may include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration, and the indication. In an embodiment, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a kinase-mediated condition comprising the step of administering to a patient one of the above-described compounds or pharmaceutical compositions. The term "patient", as used herein, means an animal, including a human.

In some embodiments, said kinase-mediated condition is a proliferative disorder or cancer. In some embodiments, said kinase-mediated condition is selected from a hematopoietic disorder, in particular, acute-myelogenous leukemia (AML), acute-promyelocytic leukemia (APL), chronic-myelogenous leukemia (CML), and acute lymphocytic leukemia (ALL).

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma, small cell lung cancer, and non-small cell lung cancer; stroke, diabetes, myeloma, hepatomegaly, cardiomegaly, Alzheimer's disease, cystic fibrosis, and viral disease, or any specific disease or disorder described above.

According to another embodiment, the invention provides methods for treating or preventing cancer, a proliferative disorder, or a myeloproliferative disorder comprising the step of administering to a patient one of the herein-described compounds or pharmaceutical compositions.

In some embodiments, said method is used to treat or prevent a hematopoietic disorder, such as acute-myelogenous leukemia (AML), acute-promyelocytic leukemia (APL), chronic-myelogenous leukemia (CML), or acute lymphocytic leukemia (ALL).

In other embodiments, said method is used to treat or prevent myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In yet other embodiments, said method is used to treat or prevent cancer, such as cancers of the breast, colon, prostate, skin, pancreas, brain, genitourinary tract, lymphatic system, stomach, larynx and lung, including lung adenocarcinoma, small cell lung cancer, and non-small cell lung cancer.

According to another embodiment, the invention provides methods for treating or preventing a kinase-mediated condition comprising the step of administering to a patient a compound of formula I or a composition comprising said compound. In some embodiments, said kinase is an Aurora kinase.

Another aspect of the invention relates to inhibiting kinase activity in a patient, which method comprises administering to the patient a compound of formula I or a composition comprising said compound. In some embodiments, said kinase is an Aurora kinase (Aurora A, Aurora B, Aurora C), FLT-3, JAK-2, JAK-3, ITK, Abl, Abl(T315I), Arg, FGFR1, MELK, MLK1, MuSK, Ret, TrkA, PLK4, Tie-2, and TrkA.

Another aspect of the invention relates to inhibiting kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, biological specimen storage, and biological assays.

Depending upon the particular conditions to be treated or prevented, additional drugs, which are normally administered to treat or prevent that condition, may be administered together with the compounds of this invention. For example, chemotherapeutic agents or other anti-proliferative agents may be combined with the compounds of this invention to treat proliferative diseases.

Examples of known chemotherapeutic agents include, but are not limited to, Gleevec®, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin. Another embodiment provides a simultaneous, separate or sequential use of a combined preparation.

Those additional agents may be administered separately, as part of a multiple dosage regimen, from the kinase inhibitor-containing compound or composition. Alternatively, those agents may be part of a single dosage form, mixed together with the kinase inhibitor in a single composition.

Methods for evaluating the activity of the compounds of this invention (e.g., kinase assays) are known in the art and are also described in the example set forth.

In order that this invention be more fully understood, the following preparative and testing examples are set forth. These examples are for the purpose of illustration only and are not to be construed as limiting the scope of the invention in any way. All documents cited herein are hereby incorporated by reference.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm

Gradient: 0-100% acetonitrile+methanol 60:40 (20 mM Tris phosphate)

Flow rate: 1.5 mL/minute

Detection: 225 nm.

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions were 5%-100% acetonitrile-methanol over 3.5 mins gradient time and 5 mins run time on an ACE C8 3.0×75 mm column. Flow rate was 1.2 ml/min.

$^1$H-NMR spectra were recorded at 400 MHz using a Bruker DPX 400 instrument. The following compounds of formula I were prepared and analyzed as follows.

Example 1

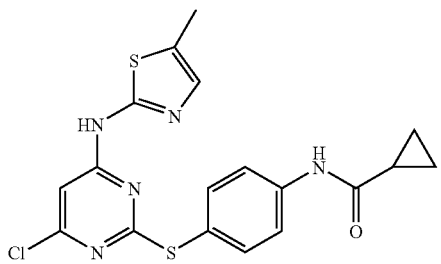 [SMILES: Cc1cnc(Nc2cc(Cl)nc(Sc3ccc(NC(=O)C4CC4)cc3)n2)s1]

N-(4-(4-(5-methylthiazol-2-ylamino)-6-chloropyrimidin-2-ylthio)phenyl)cyclopropanecarboxamide A suspension of N-(4-(4,6-dichloropyrimidin-2-ylthio)phenyl)cyclopropane-carboxamide (5.0 g, 14.7 mmol), amino-5-methylthiazole (1.85 g, 16.2 mmol), tris(dibenzylideneacetone)dipalladium (0.673 g, 0.74 mmol), 4,5-bis(diphenylphosphino)-9,9-dimethyl-xanthene (0.636 g, 1.10 mmol) and sodium carbonate (2.18 g, 20.58 mmol) in dioxane (120 ml) was heated at 100° C. for 2 h. The reaction mixture was then allowed to cool to room temperature before the tan precipitate was collected by filtration, washed with ethyl acetate (50 ml) water (3×30 ml) and then diethyl ether (50 ml) and dried to give title compound as a tan solid (4.32 g, 70%). 1H NMR (DMSO) 0.81 (4H, d), 1.83 (1H, m), 2.09 (3H, s), 6.35 (1H, br s), 6.88 (1H, s), 7.53 (2H, d), 7.74 (2H, d), 10.48 (1H, s). MS (ES+): 418.

Example 2

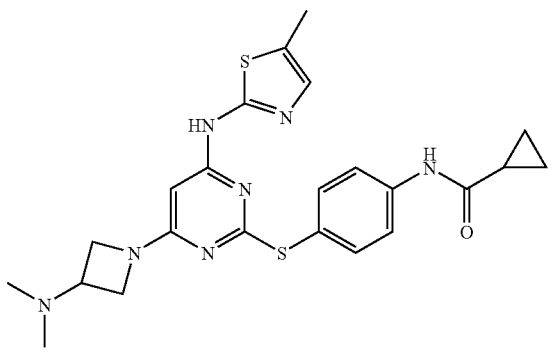 [SMILES: Cc1cnc(Nc2cc(N3CC(N(C)C)C3)nc(Sc3ccc(NC(=O)C4CC4)cc3)n2)s1]

N-(4-(4-(5-methylthiazol-2-ylamino)-6-(3-(dimethylamino) azetidin-1-yl)pyrimidin-2 ylthio)phenyl) cyclopropane carboxamide A suspension of N-(4-(4-(5-methylthiazol-2-ylamino)-6-chloropyrimidin-2-ylthio)phenyl)cyclopropanecarboxamide (138 mg, 0.33 mmol), 3-dimethylaminoazetidine dihydrochloride (178 mg, 1.0 mmol), N,N-diisopropylethylamine (0.34 ml, 1.98 mmol) in n-butanol (10 ml) was heated at 90° C. for 17 h. Reaction mixture was then allowed to cool to room temperature, concentrated in vacuo. The crude product was purified on HPLC to give the title compound as an off-white solid (106 mg, 58%). 1H NMR (DMSO) 0.82-0.81 (4H, m), 1.87-1.81 (1H, m), 2.07 (3H, s), 2.78-2.77 (6H, m), 4.20 (5H, s), 5.56 (1H, s), 6.94 (1H, s), 7.52 (2H, d), 7.76 (2H, d), 10.55 (1H, s). MS (ES+): 482.

Table 3 below depicts data for certain exemplary compounds made according to the method described in Scheme I and in Examples 1-2. Compound numbers correspond to those compounds depicted in Table 1.

TABLE 3

| Compound No | M + 1 (obs) | 1H NMR | Rt (mins) |
|---|---|---|---|
| I-1 | 482 | (DMSO-d6): 0.81 (4H, d), 1.83-1.80 (1H, m), 2.06 (3H, s), 2.11 (6H, s), 3.19-3.16 (1H, m), 3.73-3.70 (2 H, m), 3.95 (2 H, t), 5.43 (1H, s), 6.85 (1H, s), 7.51 (2H, d), 7.73 (2 H, d), 10.44 (1H, s), 10.86 (1 H, s) | |
| I-2 | 454 | (DMSO-d6): 0.80-0.82 (4 H, m), 1.83-1.91 (1 H, m), 2.08 (3 H, s), 3.95-3.98 (2 H, m), 4.13 (1 H, br m), 4.20-4.24 (2 H, m), 5.59 (1 H, s), 6.98 (1 H, s), 7.52 (2 H, d, J 8.5), 7.77 (2 H, d, J 8.5), 8.40-8.58 (2 H, m), 10.59 (1 H, s | |
| I-3 | 455 | (DMSO-d6): 0.80 (4H, m), 1.80 (1H, m), 2.06 (3H, s), 3.64 (2H, m), 4.12 (2H, m), 4.55 (1H, m), 5.39 (1H, s), 6.83 (1H, m), 7.49 (2H, m), 7.73 (2H, m), 10.44 (1H, s) | 8.07 |
| I-4 | 439 | (MeOH-d4): 0.85-1.00 (4H, m), 1.80-1.90 (1H, m), 2.10-2.15 (3H, s), 2.40-2.50 (2H, m), 4.05-4.15 (4H, m), 5.40 (1H, s), 6.85 (1H, s), 7.55-7.60 (2H, d), 7.75-7.80 (2H, d), 10.30-10.40 (1H, s). | 8.99 |

Example 3

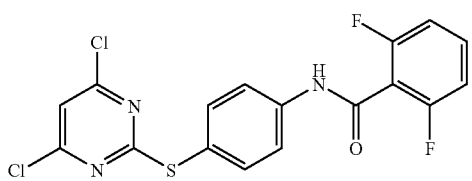 [SMILES: O=C(Nc1ccc(Sc2nc(Cl)cc(Cl)n2)cc1)c1c(F)cccc1F]

2,6-Difluoro-N-[4-(4,6-dichloro-pyrimidin-2-ylsulfanyl)-phenyl]-benzamide

A 250 ml round bottom flask equipped with a condenser was charged with 4,6-dichloro-2-methanesulfonyl pyrimidine (4.2 g, 18.8 mmol), 2,6-difluoro-N-(4-mercapto-phenyl)-benzamide (4.98 g, 18.8 mmol) and tert-butanol (75 ml) under nitrogen. The reaction mixture was degassed thoroughly and then heated at 90° C. for 2 h. The reaction mixture was allowed to cool to room temperature and concentrated in vacuo. The solid residue was taken up in ethyl acetate (50 ml) and washed with saturated sodium bicarbonate solution and brine. The organic was dried over magnesium sulfate, filtered and concentrated until the product began to precipitate. The mixture was then cooled and aged for 12 hrs. The product was collected by filtration, washed with cold ethyl acetate and dried. This gave the title compound as an off-white solid (2.7 g, 35%). 1H NMR (DMSO) 7.32 (2H, m), 7.61 (3H, m), 7.79 (1H, s), 7.82 (2H, d), 10.9 (1H, s). MS (ES+): 412.19

Example 4

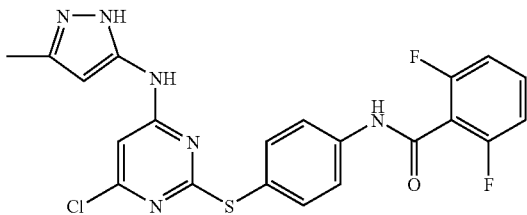 [SMILES: Cc1cc(Nc2cc(Cl)nc(Sc3ccc(NC(=O)c4c(F)cccc4F)cc3)n2)[nH]n1]

2,6-Difluoro-N-{4-[4-chloro-6-(5-methyl-2H-pyrazol-3-ylamino)-pyrimidin-2-ylsulfanyl]-phenyl}-benzamide A 50 ml round bottom flask was charged with 2,6-difluoro-N-[4-(4,6-dichloro-pyrimidin-2-ylsulfanyl)-phenyl]-benzamide (1.0 g, 2.3 mmol), 5-methyl-2H-pyrazol-3-ylamine (250 mg, 2.58 mmol), sodium iodide (351 mg, 2.34 mmol), diisopropylethyl amine (333 mg, 2.58 mmol) and dimethylformamide (5 ml) under nitrogen. The reaction mixture was stirred at 90° C. for 18 h, then allowed to cool to room temperature. The reaction mixture was diluted with ethyl acetate (25 ml), washed with saturated sodium bicarbonate solution and brine. The organic was dried over magnesium sulfate, filtered and concentrated in vacuo. The compound was purified by flash chromatography (75 to 80% ethyl acetate/petrol) to give the title compound (1.08 g, 98%). 1H NMR (DMSO) 2.00 (3H, s), 5.25 (1H, brs), 6.48 (1H, brs), 7.30-7.97 (7H, m), 10.28 (1H, s), 10.89 (1H, s), 11.90 (1H, s); MS (ES+): 473.4.

Example 5

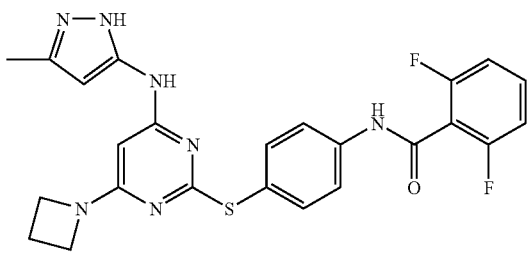 [SMILES: Cc1cc(Nc2cc(N3CCC3)nc(Sc3ccc(NC(=O)c4c(F)cccc4F)cc3)n2)[nH]n1]

N-{4-[4-Azetidin-1-yl-6-(5-methyl-2H-pyrazol-3-ylamino)-pyrimidin-2-ylsulfanyl]-phenyl}-2,6-Difluoro-benzamide A 10 ml round bottom flask was charged with 2,6-difluoro-N-{4-[4-chloro-6-(5-methyl-2H-pyrazol-3-ylamino)-pyrimidin-2-ylsulfanyl]-phenyl}-benzamide (150 mg, 0.31 mmol), azetidine (35 mg, 0.62 mmol), diisopropyl ethylamine (80 mg, 0.62 mmol) and n-butanol (1.5 ml). The reaction mixture was stirred at 80° C. for 4 h, then cooled and concentrated in vacuo. The compound was purified by preparative HPLC (MeCN/water+0.05% TFA 10/90 to 100/0 over 10 min) to give the title compound as the trifluoroacetic acid salt (54 mg, 29%). 1H NMR (DMSO) 2.05 (3H, s), 2.25-2.36 (2H, m), 3.70-3.98 (4H, m, masked), 5.31 (1H, s), 5.52 (1H, brs), 7.39 (2H, m), 7.46-7.67 (3H, m), 7.79 (2H, d), 9.35 (1H, brs), 11.04 (1H, s), 11.80 (1H, brs); MS (ES+): 494.5.

Table 4 below depicts data for certain exemplary compounds made according to the method described in Scheme II and in Examples 3-5. Compound numbers correspond to those compounds depicted in Table 1.

TABLE 4

| Compound No | M + 1 (obs) | 1H NMR | Rt (mins) |
|---|---|---|---|
| I-6 | 465 | (MeOH-d4): 2.10-2.35 (6H, m), 2.40-2.50 (2H, m), 2.70-2.75 (1H, m), 3.05 (3H, s), 3.70-3.80 (1H, m), 4.10-4.15 (4H, m), 4.25-4.30 (1H, m), 5.35 (1H, s), 5.60 (1H, s), 7.70-7.80 (4H, m) | 8.82 |
| I-7 | 494.5 | (DMSO-d6): 2.05 (3H, s), 2.25-2.36 (2H, m), 3.70-3.98 (4H, m, masked), 5.31 (1H, s), 5.52 (1H, brs), 7.39 (2H, m), 7.46-7.67 (3H, m), 7.79 (2H, d), 9.35 (1H, brs), 11.04 (1H, s), 11.80 (1H, brs) | 8.86 |
| I-8 | 532 | (DMSO-d6): 2.05 (3H, s), 2.16-2.34 (4H, m), 3.82-4.92 (8H, m), 5.48 (1H, s), 5.60 (1H, br), 6.30 (1H, d), 6.58 (1H, m), 7.25 (1H, m), 7.55 (2H, d), 7.80 (2H, d), 9.20 (1H, brs), 10.80 (1H, s), 11.69 (1H, brs) | 9.23 |
| I-9 | 476.5 | (DMSO-d6): 2.01 (3H, s), 2.32 (2H, m), 3.77-3.94 (4H, m), 5.39 (1H, s), 5.55 (1H, brs), 7.30-7.41 (2H, m), 7.45-7.70 (4H, m), 7.79-7.90 (2H, m), 9.25 (1H, brs), 10.68 (1H, s), 11.68 (1H, brs) | 8.99 |
| I-10 | 490.5 | (DMSO-d6): 2.15 (3H, s), 2.30 (2H, m), 3.20-3.50 (7H, m), 5.74 (1H, s), 5.95 (1H, brs), 6.95-7.62 (8H, m), 9.20 (1H, s), 11.84 (1H, brs) | 9.09 |
| I-11 | 508.5 | (DMSO-d6): 2.18 (3H, s), 2.30 (2H, m), 3.15-3.50 (7H, m), 5.75 (1H, s), 5.95 (1H, brs), 7.05 (2H, m), 7.26 (2H, m), 7.27-7.70 (3H, m), 9.20 (1H, s), 11.86 (1H, brs) | 9.19 |
| I-12 | 522 | (DMSO-d6): 2.04 (3H, s), 3.24 (3H, s), 3.66-3.73 (2H, m), 4.05-4.11 (2H, m), 4.27-4.33 (1H, m), 5.4 (1H, brs), 5.6 (1H, vbrs), 7.45-7.6 (6H, m), 7.80-7.87 (2H, m), 9.28 (1H, brs), 10.75 (1H, brs), 11.70 (1H, brs) | 8.88 |
| I-13 | 508 | (DMSO-d6): 2.04 (3H, s), 3.6-3.65 (2H, m), 4.05-4.13 (2H, m), 4.52-4.58 (2H, m), 5.40 (1H, brs), 5.71 (1H, d), 7.48-7.66 (6H, m), 7.83 (1H, d), 9.23 (1H, s), 10.75 (1H, s), 11.69 (1H, brs) | 8.14 |
| I-14 | 410 | (MeOH-d4): 1.20-1.30 (3H, t), 2.10-2.15 (3H, s), 2.30-2.40 (4H, m), 3.90-4.00 (4H, t), 5.30-5.40 (2H, m), 7.50-7.55 (2H, d), 7.65-7.7 (2H, d) | 8.14 |
| I-15 | 426 | (DMSO-d6): 1.08 (3H, m), 1.93 (3H, br s), 2.35 (2H, m), 3.59 (2H, m), 4.08 (2H, m), 4.52 (1H, m), 5.35 (1H, br s), 5.69 (1H, m), 7.46 (2H, m), 7.69 (2H, m), 9.21 (1H, br s), 10.08 (1H, s), 11.67 (1H, br s) | 7.05 |
| I-16 | 517 | (DMSO-d6): 2.05 (3 H, s), 3.89-3.83 (1 H, m), 4.07-4.04 (2 H, m), 4.18 (2 H, t), 5.39 (1 H, br s), 5.56 (1 H, br s), 7.61-7.47 (6 H, m), 7.48 (2 H, d), 9.39 (1 H, br s), 10.76 (1 H, s) | 8.75 |
| I-17 | 422 | (DMSO-d6): 0.82 (4H, m), 1.82 (1H, m), 1.98 (3H, s), 2.30 (2H, m), 3.83 (4H, m), 5.31 (1H, brs), 5.58 (1H, brs), 7.48 (2H, d), 7.70 (2H, d), 9.20 (1H, brs), 10.40 (1H, brs), 11.70 (1H, brs) | 8.38 |
| I-21 | 492 | (DMSO-d6): 1.90-2.00 (3H, s), 2.20-2.30 (2H, m), 3.85-3.90 (4H, t), 5.30-5.35 (1H, s), 5.60-5.70 (1H, brs), 7.37-7.42 (2H, d), 7.70-7.75 (2H, d), 7.80-7.85 (2H, d), 8.00-8.05 (2H, d), 9.20-9.25 (1H, s), 10.40-10.45 (1H, s) | 9.82 |
| I-25 | 389 | (DMSO-d6): 1.4-1.7 (3H, brs, CH3), 2.2-2.3 (2H, q, CH3), 3.8-3.95 (4H, t, alk), 5.15 (H, brs, ar), 5.6 (H, brs, ar), 7.5-7.65 (3H, m, ar), 7.9-8.0 (3H, m, ar), 8.2 (H, s, ar) and 9.35 (H, s, NH) | 9.73 |

TABLE 4-continued

| Compound No | M + 1 (obs) | 1H NMR | Rt (mins) |
|---|---|---|---|
| I-37 | 537 | (DMSO-d6): 1.14 (3H, t), 2.04 (3H, s), 3.44 (2H, q), 3.69 (2H, dd), 4.06-4.11 (2H, m), 4.35-4.40 (1H, m), 5.39 (1H, s), 7.46-7.61 (6H, m), 7.81-7.86 (2H, m), 9.27 (1H, s), 10.74 (1H, s), 11.67 (1H, s) | 9.26 |
| I-38 | 551 | (DMSO-d6): 1.1 (6H, d), 2.04 (3H, s), 3.6-3.68 (3H, m), 4.09-4.14 (2H, m), 4.44-4.49 (1H, m), 5.39 (1H, s), 7.47-7.62 (6H, m), 7.82-7.85 (2H, m), 9.27 (1H, s), 10.74 (1H, s), 11.69 (1H, s) | 9.56 |
| I-39 | 506.5 | (DMSO-d6): 1.22 (3H, t), 2.04 (3H, s), 2.73-2.79 (1H, m), 3.44 (2H, dd), 3.97-4.03 (2H, m), 5.40 (1H, s), 5.55 (1H, vbrs), 7.44-7.62 (7H, m), 7.81-7.85 (2H, m), 9.22 (1H, brs), 10.74 (1H, s), 11.67 (1H, brs) | 9.38 |

Example 6

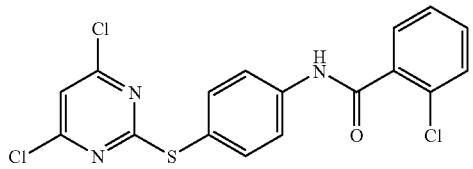 [SMILES: O=C(Nc1ccc(Sc2nc(Cl)cc(Cl)n2)cc1)c1ccccc1Cl]

2-Chloro-N-[4-(4,6-dichloro-pyrimidin-2-ylsulfanyl)-phenyl]-benzamide

A 250 mL round bottom flask was charged with 4,6-dichloro-2-methanesulfonylpyrimidine (7.00 g, 26.6 mmol), 2-chloro-N-(4-mercapto-phenyl)-benzamide (6.33 g, 27.9 mmol) and acetonitrile (100 mL) under nitrogen. Once the solid had dissolved, the reaction mixture was cooled to 0° C. and triethylamine (3.7 mL, 26.6 mmol) was added dropwise. The solution was stirred at 0° C. for 10 min and then allowed to warm to room temperature and stirred for 1 h. After this time, water (50 mL) was added and a white solid precipitated and the reaction mixture stirred for an additional 4 h. After this time, the reaction mixture was filtered and the solid washed with acetonitrile (2×10 mL) to give the title compound as a white solid (8.03 g, 74%). 1H NMR (DMSO) 7.4-7.6 (5H, m), 7.7 (1H, s), 7.80-7.85 (2H, d), 10.9 (1H, s). MS (ES+): 412

Example 7

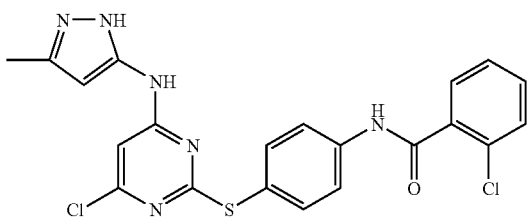 [SMILES: Cc1cc(Nc2cc(Cl)nc(Sc3ccc(NC(=O)c4ccccc4Cl)cc3)n2)[nH]n1]

2-Chloro-N-{4-[4-chloro-6-(5-methyl-2H-pyrazol-3-ylamino)-pyrimidin-2-ylsulfanyl]-phenyl}-benzamide A 250 mL round bottom flask was charged with 2-chloro-N-[4-(4,6-dichloro-pyrimidin-2-ylsulfanyl)-phenyl]-benzamide (12.5 g, 30.4 mmol), 5-methyl-2H-pyrazol-3-ylamine (3.55 g, 36.5 mmol), sodium iodide (4.56 g, 30.4 mmol), N,N-diisopropylethylamine (6.9 mL, 40.0 mmol) and N,N-dimethylformamide (125 mL) under nitrogen. The reaction mixture was stirred at 90° C. for 5 h, then allowed to cool to room temperature. Water (600 mL) was added and the resulting suspension stirred at room temperature for 2 h and the solid collected by filtration and dried. The resulting white solid was triturated with hot ethyl acetate (50 mL), filtered and washed with ethyl acetate (1×20 mL) to give the title compound as a white solid (11.76 g, 82%). 1H NMR (DMSO): 2.16 (3H, s), 5.30 (1H, s), 6.48 (1H, s), 7.49-7.62 (6H, m), 7.89 (2H, m), 10.28 (1H, s), 10.84 (1H, s), 11.93 (1H, s); MS (ES+): 471.

Example 8

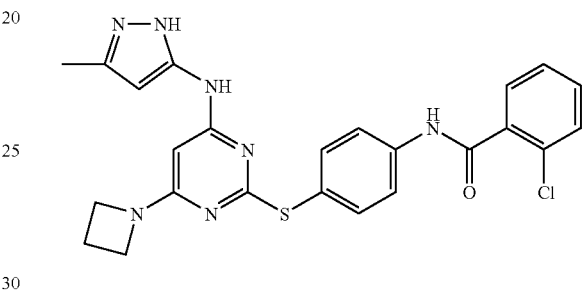

N-{4-[4-Azetidin-1-yl-6-(5-methyl-2H-pyrazol-3-ylamino)-pyrimidin-2-ylsulfanyl]-phenyl}-2-chloro-benzamide A 500 mL round bottom flask was charged with 2-chloro-N-{4-[4-chloro-6-(5-methyl-2H-pyrazol-3-ylamino)-pyrimidin-2-ylsulfanyl]-phenyl}-benzamide (16.0 g, 34.0 mmol), azetidine (3.87 g, 68.0 mmol), N,N-diisopropylethylamine (13.0 mL, 74.7 mmol) and n-butanol (250 mL). The reaction mixture was stirred at 90° C. for 5 h. The reaction mixture was cooled and concentrated in vacuo. Diethyl ether (200 mL) was added and a light brown solid precipitated. The solution was filtered and the solid recrystallized from ethanol to give the pure product as a white solid (9.42 g, 52%) 1H NMR (DMSO): 2.04 (3H, s), 2.32 (2H, m), 3.87 (4H, m), 5.39 (1H, s), 5.66 (1H, br s), 7.48-7.59 (6H, m), 7.82 (2H, m), 9.87 (1H, s), 10.74 (1H, s), 11.68 (1H, s); MS (ES+): 492.

Another method used to prepare example 8 is described below:

To a suspension of 2-chloro-N-{4-[4-chloro-6-(5-methyl-2H-pyrazol-3-ylamino)-pyrimidin-2-ylsulfanyl]-phenyl}-benzamide (169 g, 0.36 mol) in 2-propanol (1.3 L) azetidine (100 g, 1.76 mol) was added portion wise. The reaction mixture was heated to 80-82° C. After 24 hours, di-isopropylethylamine (73.4 g, 0.57 mol) was added. The progress of the reaction was monitored by HPLC. The reaction mixture was concentrated under reduce pressure to dryness, azeotroped with methanol three times (3×650 mL), stirred for 2 hours in methanol (1 L) at 40° C., and cooled to 10° C. The resulting off-white solid was filtered. The isolated material was slurried in refluxing acetonitrile for 3 hours, cooled to 20-25° C., filtered and dried in a vacuum oven overnight. The material was slurried again in refluxing acetonitrile for 3 hours, cooled to 20-25° C., and filtered. The material was allowed to dry until it was a constant weight. The desired product was isolated as an off-white solid (154 g, 86%).

Table 4 below depicts data for certain exemplary compounds made according to the method described in Scheme II and in Examples 6-8. Compound numbers correspond to those compounds depicted in Table 1.

TABLE 5

| Compound No | M + 1 (obs) | 1H NMR | Rt (mins) |
| --- | --- | --- | --- |
| I-5 | 492 | (DMSO-d6): 2.04 (3H, s), 2.32 (2H, m), 3.87 (4H, m), 5.39 (1H, s), 5.66 (1H, br s), 7.48-7.59 (6H, m), 7.82 (2H, m), 9.87 (1H, s), 10.74 (1H, s), 11.68 (1H, s) | 9.00 |
| I-26 | 454 | (DMSO-d6): 1.49 (9H, s), 1.99 (3H, brs), 2.29 (2H, qn), 3.87 (4H, t), 5.33 (1H, brs), 5.50 (1H, vbrs), 7.44 (2H, d), 7.55 (2H, d), 9.19 (1H, brs), 9.62 (1H, s), 11.66 (1H, brs) | 9.49 |
| I-27 | 508 | (DMSO-d6): 2.07 (3H, s), 2.25 (2H, qn), 2.34 (3H, s), 3.78 (4H, t), 5.48 (1H, s), 5.69 (1H, vbrs), 7.14 (2H, d), 7.35 (2H, d), 7.40 (2H, d), 7.69 (2H, d), 9.16 (1H, brs), 10.48 (1H, s), 11.72 (1H, brs) | 9.27 |
| I-31 | 473 | (DMSO-d6): 2.07 (3H, s), 2.30 (2H, m), 2.39 (3H, s), 3.91 (4H, m), 5.40 (1H, s), 5.58 (1H, brs), 7.35 (2H, m), 7.40 (2H, m), 7.55 (2H, d), 7.89 (2H, d), 9.21 (1H, brs), 10.55 (1H, brs), 11.68 (1H, s) | 9.20 |
| I-32 | 488.5 | (DMSO-d6): 2.07 (3H, s), 2.31 (2H, m), 3.82-3.94 (7H, m), 5.40 (1H, s), 5.56 (1H, brs), 7.08 (1H, m), 7.19 (1H, d), 7.42-7.61 (4H, m), 7.87 (2H, d), 9.21 (1H, brs), 10.34 (1H, brs), 11.68 (1H, brs) | 9.24 |
| I-33 | 495 | (DMSO-d6): 2.05 (3H, s), 2.35 (2H, m), 3.98 (4H, m), 5.40 (1H, s), 5.54 (1H, brs), 7.38 (1H, m), 7.49 (1H, m), 7.59 (2H, d), 7.64 (1H, m), 7.83 (2H, d), 9.50 (1H, brs), 10.80 (1H, brs), 11.6 (1H, brs) | 9.22 |
| I-34 | 543 | (DMSO-d6): 2.09 (3H, s), 2.38 (2H, m), 3.95 (4H, m), 5.46 (1H, s), 5.60 (1H, brs), 7.49-7.63 (4H, m), 7.70 (2H, m), 7.88 (2H, d), 9.49 (1H, brs), 10.75 (1H, brs), 11.6 (1H, brs) | 9.46 |
| I-35 | 472.5 | (DMSO-d6): 2.19 (3H, s), 2.30 (2H, m), 3.68 (2H, s), 3.88 (4H, m), 5.30 (1H, s), 5.54 (1H, brs), 7.20-7.40 (5H, m), 7.50 (2H, d), 7.70 (2H, d), 9.18 (1H, brs), 10.41 (1H, brs), 11.6 (1H, brs) | 8.97 |
| I-36 | 507 | (DMSO-d6): 1.91 (3H, s), 2.30 (2H, m), 3.70 (2H, s), 3.90 (4H, m), 5.31 (1H, s), 5.56 (1H, brs), 7.26-7.44 (4H, m), 7.51 (2H, d), 7.71 (2H, d), 9.36 (1H, brs), 10.45 (1H, brs), 11.6 (1H, brs) | 9.53 |
| I-40 | 464 | (DMSO-d6): 1.98 (3 H, s), 2.33-2.26 (2 H, m), 3.55 (2 H, q), 3.89 (4 H, t), 5.35 (1 H, s), 5.57 (1 H, br s), 7.54 (2 H, d), 7.68 (2 H, d), 9.37 (1 H, brs), 10.54 (1 H, s) | 8.69 |
| I-41 | 493 | (DMSO-d6): 2.01 (3 H, s), 2.34-2.27 (2 H, m), 2.55 (3 H, s), 2.68 (3 H, s), 3.90 (4 H, t), 5.38 (1 H, s), 5.58 (1 H, br s), 7.55 (2 H, d), 7.79 (2 H, d), 9.30 (1 H, br s), 10.34 (1 H, s) | 8.73 |
| I-42 | 526 | (DMSO-d6): 2.05 (3 H, s), 2.34-2.27 (2 H, m), 3.91 (4 H, t), 5.41 (1 H, s), 5.60 (1 H, br s), 7.58-7.50 (4 H, m), 7.83-7.79 (3 H, m), 9.37 (1 H, brs), 10.83 (1 H, s) | 9.55 |
| I-43 | 498 | (DMSO-d6): 2.02 (3 H, s), 2.34-2.26 (2 H, m), 3.89 (4 H, t), 5.34 (1 H, s), 5.58 (1 H, br s), 7.23 (2 H, d), 7.55 (2 H, d), 7.80 (2 H, d), 7.94 (1 H, d), 9.30 (1 H, s), 10.50 (1 H, s) | 9.43 |
| I-44 | 494 | (DMSO-d6): 2.02 (3 H, s), 2.34-2.27 (2 H, m), 3.92-3.88 (4 H, m), 5.37 (1 H, s), 5.56 (1 H, br s), 7.26 (1 H, m), 7.47 (1 H, m), 7.56 (2 H, d), 7.74 (1 H, m), 7.82 (2 H, d), 9.37 (1 H, s), 10.68 (1 H, s) | 9.22 |
| I-45 | 494 | (DMSO-d6): 2.02 (3 H, s), 2.34-2.27 (2 H, m), 3.92-3.88 (4 H, m), 5.38 (1 H, s), 5.58 (1 H, br s), 7.49-7.43 (2 H, m), 7.58-7.53 (3 H, m), 7.82 (2 H, d), 9.36 (1 H, br s), 10.75 (1 H, s) | 9.26 |
| I-46 | 526 | (DMSO-d6): 2.05 (3 H, s), 2.34-2.27 (2 H, m), 3.91 (4 H, t), 5.46 (1 H, s), 5.59 (1 H, br s), 7.62-7.51 (5 H, m), 7.79 (2 H, d), 9.38 (1 H, br s), 10.98 (1 H, s) | 9.52 |

Example 9

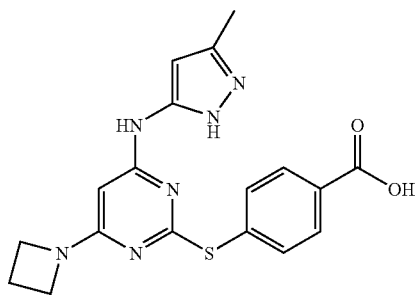 [SMILES: Cc1cc(Nc2cc(N3CCC3)nc(Sc3ccc(C(=O)O)cc3)n2)[nH]n1]

4-[4-Azetidin-1-yl-6-(5-methyl-2H-pyrazol-3-ylamino)-pyrimidin-2-ylsulfanyl]-benzoic acid A 50 ml round bottom flask equipped with a condenser was charged with 4-[4-azetidin-1-yl-6-(5-methyl-2H-pyrazol-3-ylamino)-pyrimidin-2-ylsulfanyl]-benzoic acid methyl ester (800 mg, 2.0 mmol), 2M sodium hydroxide aqueous solution (5 ml), tetrahydrofuran (30 ml) and methanol (5 ml). The reaction mixture was heated to reflux for one hour. The reaction mixture was allowed to cool to room temperature and concentrated in vacuo. The solid residue was taken up in methanol (30 ml) and concentrated hydrochloric acid (1 ml). The solvent was then removed under reduced pressure to give the title compound (0.84 g, 100%) as a mono HCl salt. 1H NMR (DMSO) 2.05-2.10 (3H, s), 2.20-2.30 (2H, m), 3.80-3.85 (2H, t), 4.05-4.10 (2H, s), 7.40-7.45 (2H, d), 7.85-7.90 (2H, d). MS (ES+): 383

Example 10

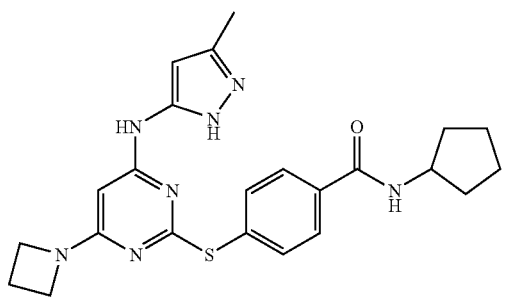 [SMILES: Cc1cc(Nc2cc(N3CCC3)nc(Sc3ccc(C(=O)NC4CCCC4)cc3)n2)[nH]n1]

4-[4-Azetidin-1-yl-6-(5-methyl-2H-pyrazol-3-ylamino)-pyrimidin-2-ylsulfanyl]-N-cyclopentyl-benzamide A 25 ml round bottom flask was charged with 4-[4-azetidin-1-yl-6-(5-methyl-2H-pyrazol-3-ylamino)-pyrimidin-2- ylsulfanyl]-benzoic acid (200 mg, 0.48 mmol), cyclopentyl amine (85 mg, 1 mmol), 2-(1H-benzotriazol-1-yl)-1,1,3,3,-tetramethyluroniumtetrafluoroborate (321 mg, 1 mmol), diisopropylethylamine (0.34 ml, 2 mmol) in dimethylformamide (5 ml), under nitrogen. The reaction mixture was stirred at room temperature for 18 hours and then was diluted with ethyl acetate (40 ml), washed with a saturated sodium hydrogen carbonate aqueous solution (40 ml) and brine (40 ml). The organic was dried over magnesium sulfate, filtered and concentrated in vacuo. The residue was triturated in dichloromethane to afford the title compound. 1H NMR (DMSO-d6): 1.60-1.65 (4H, m), 1.70-1.80 (2H, m), 1.95-2.10 (5H, m), 2.20-2.30 (2H, m), 3.90-4.00 (4H, s), 4.30-4.35 (1H, m), 5.35-5.40 (1H, s), 7.70-7.75 (2H, d), 8.00-8.05 (2H, d), 8.45-8.50 (1H, d), 9.3 (1H, s). MS (ES+): 450.

Table 6 below depicts data for certain exemplary compounds made according to the method described in Scheme VI and in Examples 9-10. Compound numbers correspond to those compounds depicted in Table 1.

TABLE 6

| Compound No | M + 1 (obs) | 1H NMR | Rt (mins) |
|---|---|---|---|
| I-18 | 422 | (DMSO-d6): 0.50-0.55 (2H, m), 0.62-0.67 (2H, m), 1.90-2.00 (3H, s), 2.20-2.30 (2H, m), 2.80-2.85 (1H, m), 3.85-3.90 (4H, t), 5.30-5.35 (1H, s), 5.60-5.70 (1H, br s), 7.63-7.68 (2H, d), 7.85-7.90 (2H, d), 8.50 (1H, s), 9.3 (1H, s) | 8.25 |
| I-19 | 472 | (DMSO-d6): 1.85-1.95 (3H, s), 2.20-2.30 (2H, m), 3.83-3.90 (4H, t), 4.45-4.50 (2H, d), 5.30-5.35 (1H, s), 5.60-5.70 (1H, br s), 7.20-7.25 (1H, m), 7.28-7.33 (4H, d), 7.63-7.68 (2H, d), 7.90-7.95 (2H, d), 9.10-9.20 (2H, m) | 9.12 |
| I-20 | 410 | (DMSO-d6): 1.08-1.13 (3H, t), 1.90-2.00 (3H, s), 2.20-2.30 (2H, m), 3.25-3.30 (2H, m), 3.85-3.90 (4H, t), 5.30-5.35 (1H, s), 5.60-5.70 (1H, br s), 7.63-7.68 (2H, d), 7.85-7.90 (2H, d), 8.50 (1H, s), 9.3 (1H, s) | 8.13 |
| I-22 | 436 | (DMSO-d6): 1.80-1.90 (4H, m), 2.05 (3H, s), 2.20-2.30 (2H, m), 3.35-3.40 (2H, t), 3.45-3.50 (2H, t), 3.80-3.85 (4H, s), 5.50-5.55 (1H, s), 7.50-7.55 (2H, d), 7.60-7.65 (2H, d), 9.15-9.20 (1H, s) | 8.59 |
| I-23 | 450 | (DMSO-d6): 1.60-1.65 (4H, m), 1.70-1.80 (2H, m), 1.95-2.10 (5H, m), 2.20-2.30 (2H, m), 3.90-4.00 (4H, s), 4.30-4.35 (1H, m), 5.35-5.40 (1H, s), 7.70-7.75 (2H, d), 8.00-8.05 (2H, d), 8.45-8.50 (1H, d), 9.3 (1H, s) | 9.07 |
| I-24 | 506 | (DMSO-d6): 1.90-2.00 (3H, s), 2.20-2.30 (2H, m), 3.83-3.90 (4H, t), 4.45-4.50 (2H, d), 5.35-5.40 (1H, s), 7.25-7.35 (3H, m), 7.40-7.45 (1H, d), 7.60-7.65 (2H, d), 7.90-7.95 (2H, d), 9.10-9.20 (2H, m) | 9.49 |

Example 11

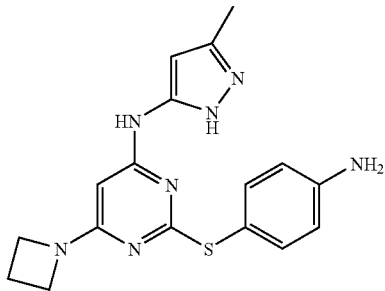 [SMILES: Cc1cc(Nc2cc(N3CCC3)nc(Sc3ccc(N)cc3)n2)[nH]n1]

2-(4-aminophenylthio)-6-(azetidin-1-yl)-N-(3-methyl-1H-pyrazol-5-yl)pyrimidin-4-amine Compound I-26 (2.53 g, 5.6 mmol) was dissolved in 1:1 TFA-DCM (20 mL) and the resulting solution allowed to stand overnight at room temperature. The solution was concentrated in vacuo. The residue was taken up in EtOAc and washed with saturated aqueous sodium bicarbonate solution (×2) then brine and dried over sodium sulfate. The resulting tan solid (1.8 g, 91%) [MS (ES+) 354] was used without further purification or characterization in the next step.

Example 12

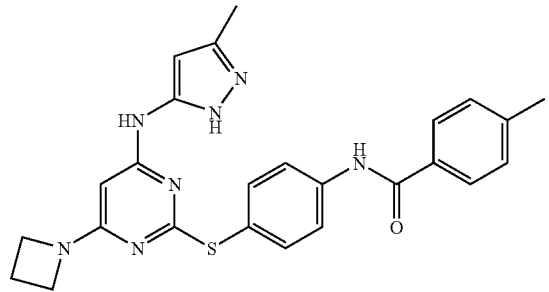 [SMILES: Cc1ccc(C(=O)Nc2ccc(Sc3nc(Nc4cc(C)n[nH]4)cc(N4CCC4)n3)cc2)cc1]

N-(4-(4-(3-methyl-1H-pyrazol-5-ylamino)-6-(azetidin-1-yl)pyrimidin-2-ylthio)phenyl)-4-methylbenzamide 2-(4-Aminophenylthio)-6-(azetidin-1-yl)-N-(3-methyl-1H-pyrazol-5-yl)pyrimidin-4-amine (200 mg, 0.57 mmol) was taken up in pyridine (2 mL) and p-toluoyl chloride (0.187 mL, 1.42 mmol) was added dropwise at room temperature. After 15 minutes the reaction mixture was concentrated in vacuo and the residue taken up in methanol (3 mL). Sodium methoxide (25% w/w solution in MeOH, 1 mL) was added and the resulting cloudy solution stirred at room temperature for 15 minutes. The reaction mixture was purified directly by chromatography (silica, 5-100% EtOAc-petrol gradient elution) to give the title compound (91 mg, 34%) as a white solid. $^1$H NMR: (400 MHz, DMSO) 1.99 (3H, brs), 2.33 (2H, qn), 2.40 (3H, s), 3.88 (4H, t), 5.38 (1H, brs), 5.59 (1H, vbrs), 7.36 (2H, d), 7.53 (2H, d), 7.87 (2H, d), 7:91 (2H, d), 9.20 (1H, brs), 10.36 (1H, s), 11.66 (1H, brs); MS (ES+) 472.

Table 7 below depicts data for certain exemplary compounds made according to the method described in Scheme VII and in Examples 11-12. Compound numbers correspond to those compounds depicted in Table 1.

TABLE 7

| Compound No | M + 1 (obs) | 1H NMR | Rt (mins) |
|---|---|---|---|
| I-28 | 472 | (DMSO-d6): 1.99 (3H, brs), 2.33 (2H, qn), 2.40 (3H, s), 3.88 (4H, t), 5.38 (1H, brs), 5.59 (1H, vbrs), 7.36 (2H, d), 7.53 (2H, d), 7.87 (2H, d), 7.91 (2H, d), 9.20 (1H, brs), 10.36 (1H, s), 11.66 (1H, brs) | 9.38 |
| I-29 | 472 | (DMSO-d6): 1.99 (3H, brs), 2.31 (2H, qn), 2.42 (3H, s), 3.88 (4H, t), 5.39 (1H, brs), 5.67 (1H, vbrs), 7.43-7.46 (2H, m), 7.54 (2H, d), 7.73-7.76 (2H, m), 7.91 (2H, d), 9.23 (1H, brs), 10.42 (1H, s), 11.67 (1H, brs) | 9.42 |
| I-30 | 464 | (DMSO-d6): 1.09-1.31 (4H, m), 1.36-1.45 (2H, m), 1.64-1.67 (1H, m), 1.75-1.85 (3H, m), 1.99 (3H, brs), 2.31-2.36 (3H, m), 3.87 (4H, t), 5.31 (1H, brs), 5.53 (1H, vbrs), 7.46 (2H, d), 7.71 (2H, d), 9.21 (1H, brs), 10.03 (1H, s), 11.64 (1H, brs) | 9.43 |

Example 13

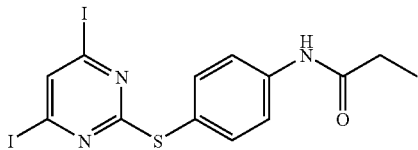 [SMILES: CCC(=O)Nc1ccc(Sc2nc(I)cc(I)n2)cc1]

N-(4-(4,6-diiodopyrimidin-2-ylthio)phenyl)propionamide

Sodium iodide (13.5 g, 90 mmol) was added to a solution of N-(4-(4,6-dichloropyrimidin-2-ylthio)phenyl)propionamide (5 g, 15 mmol) in 60% HI (50 ml). The reaction mixture was stirred at 70° C. for 10 h. The suspension was filtered. The recovered solid was taken up in saturated sodium bicarbonate aqueous solution (~200 ml). Extractions were carried out with ethyl acetate (3×100 ml). The organic was washed with saturated sodium bicarbonate solution and brine. The solid was triturated in a minimum of dichloromethane to afford the title compound as a white solid (6 g, 78%). ES+512.

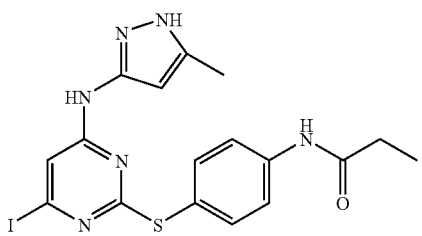 [SMILES: CCC(=O)Nc1ccc(Sc2nc(I)cc(Nc3cc(C)[nH]n3)n2)cc1]

N-(4-(4-(4,5-dimethyl-1H-pyrazol-3-ylamino)-6-iodopyrimidin-2-ylthio)phenyl)propionamide 5-methyl-1H-pyrazol-3-amine (580 mg, 6 mmol) was added to a stirred, mixture of N-4-(4.6-diiodopyrimidin-2-ylthio)phenyl)propionamide (3 g, 5.9 mmol) and diisopropylethylamine (1.4 ml, 8.3 mmol) in dimethylformamide (40 ml). The reaction mixture was stirred at 90° C. for 6 hours. The reaction mixture was diluted with ethyl acetate (200 ml) and washed with saturated sodium bicarbonate solution (~100 ml) and brine, dried over magnesium sulfate, then concentrated in vacuo. The residue was purified by flash chromatography (40 g SiO$_2$, pentane/Ethylacetate) to afford the title compound (1.8 g, 64%).

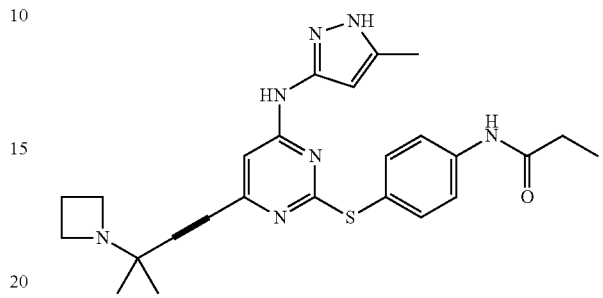

N-(4-(4-(4,5-dimethyl-1H-pyrazol-3-ylamino)-6-(3-azetidin-1-yl)-3-methylbut-1-ynyl)pyrimidin-2-ylthio)phenyl)propionamide Azetidine (57 mg, 1 mmol) was added to a stirred solution of 3-chloro-3-methylbut-1-yne (102.5 mg, 1 mmol), triethylamine (202 mg, 2 mmol) and copper chloride (I) (7.5 mg, catalyst) in dimethylformamide (5 ml) under nitrogen. The reaction mixture was stirred for 2 hours at room temperature. Then, N-(4-(4-(4,5-dimethyl-1H-pyrazol-3-ylamino)-6-iodopyrimidin-2-ylthio)phenyl)propionamide (150 mg, 0.3 mmol) and dichloro-di-(triphenylphosphino)-palladium (50 mg, catalyst) were added to the reaction mixture, which was stirred a further 18 hours. The solution was concentrated in vacuo The residue was purified on silica gel, eluting with ethyl acetate/petrol/triethylamine (0-100-0 to 98-0-2). The product was obtained as a white solid (130 mg, 90%); $^1$H NMR CD$_3$OD δ 1.20-1.25 (3H, t), 1.30-1.35 (6H, s), 2.00-2.05 (3H, s), 2.1 (2H, s), 2.35-2.40 (2H, qd), 3.60-3.75 (6H, br s), 5.35-5.45 (1H, s), 6.50-6.60 (1H, s), 7.50-7.55 (2H, d), 7.75-7.80 (2H, d); ES+476

Example 14

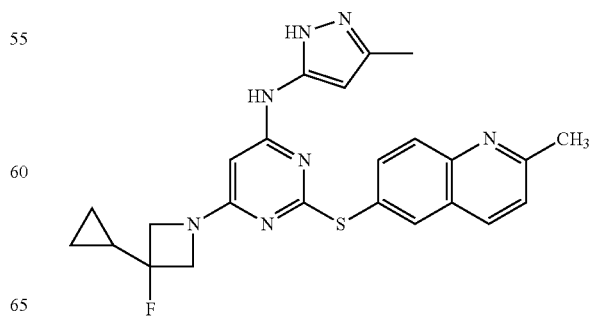

2-(2-methylquinolin-6-ylthio)-6-(3-cyclopropyl-3-fluoroazetidin-1-yl)-N-(3-methyl-1H-pyrazol-5-yl)pyrimidin-4-amine

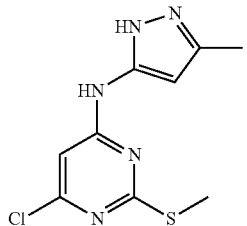 [SMILES: CSc1nc(Cl)cc(Nc2cc(C)n[nH]2)n1]

6-Chloro-N-(3-methyl-1H-pyrazol-5-yl)-2-(methylthio) pyrimidin-4-amine

To a stirred solution of 4,6-dichloro-2-(methylthio)pyrimidine (25 g, 0.128 mol) in DMF (100 ml) was added diisopropylamine (19.8 g, 0.154 mol) followed by 3-amino-5-methylpyrazole (13.7 g, 0.154 mol) portionwise over 10 minutes. The solution was heated to 50° C. for 16 hours, after which time all of the starting material had reacted (by LC/MS analysis). The mixture was cooled to ambient and poured into water (250 ml). The precipitate was filtered and the wet solid slurried in diethyl ether (300 ml). The solid was again filtered and re-slurried in methanol (100 ml). The filtered product was air dried on the sinter, then further dried under vacuum. This affords the title compound as an off-white solid (22.1 g, 66% yield). $^1$H NMR (d6-DMSO) δ 2.22 (3H, s, CH$_3$), 3.31 (3H, s, CH$_3$), 6.00-7.50 (2H, br, CH), 10.17 (1H, s, NH), 12.10 (1H, s, NH); MS ES+256.08, ES−254.25.

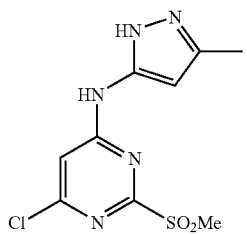 [SMILES: Cc1cc(Nc2cc(Cl)nc(S(C)(=O)=O)n2)[nH]n1]

6-chloro-N-(3-methyl-1H-pyrazol-5-yl)-2-(methylsulfonyl)pyrimidin-4-amine

To a stirred suspension of 6-chloro-N-(3-methyl-1H-pyrazol-5-yl)-2-(methylsulfinyl)pyrimidin-4-amine (8 g, 31.2 mmol) in Methanol (200 ml) at 0° C. was added a suspension of Oxone (44 g, 71.7 mmol) in water (100 ml) portionwise over 10 minutes. The mixture was stirred for 30 minutes at 0° C. then warmed to ambient and stirred for an additional 2 hours. The reaction mixture was filtered and the resulting solid slurried in aqueous sodium bicarbonate. The mixture was filtered and the solid washed with water, then diethyl ether. The solid was slurried in ethyl acetate, filtered and dried. This gave the title product as an off-white solid (7.9 g, 88%); $^1$H NMR (d6-DMSO) δ 2.24 (3H, s), 3.35 (3H, s), 5.85 (0.5H, brs), 6.50 (0.5H, brs), 6.95 (0.5H, brs), 8.00 (0.5H, brs), 10.95 (1H, s), 12.28 (1H, s); MS ES+288.07, ES−286.25.

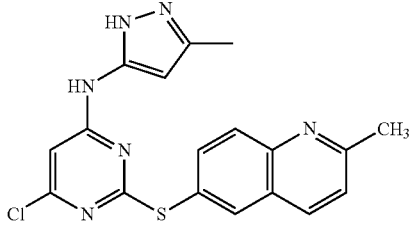 [SMILES: Cc1cc(Nc2cc(Cl)nc(Sc3ccc4nc(C)ccc4c3)n2)[nH]n1]

2-(2-methylquinolin-6-ylthio)-6-chloro-N-(3-methyl-1H-pyrazol-5-yl)pyrimidin-4-amine

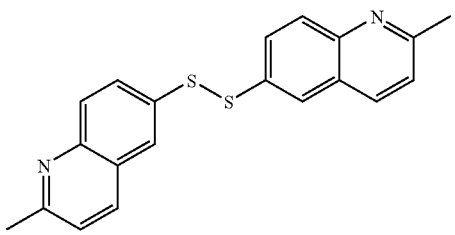

2-methyl-6-(2-(2-methylquinolin-6-yl)disulfanyl) quinoline

To a stirred slurry of 4-aminophenyl disulfide (5.0 g, 0.02 mol) in refluxing 6M HCl (65 ml) was added crotonaldehyde (4.2 g, 0.06 mol) dropwise over 90 minutes. The resulting mixture was refluxed for an additional 2 hours, then cooled to ambient. Conc aqueous ammonia was added to adjust the pH to neutral and the mixture extracted with ethyl acetate. The combined extracts were washed with water, then saturated aqueous brine, dried (MgSO$_4$), filtered and concentrated. The crude was purified on silica gel, eluting with 50 to 100% ethyl acetate/petrol. The product was an oil (2.57 g, 37%); MS ES+349.17.

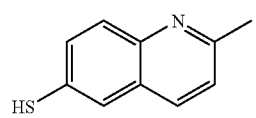

2-methylquinoline-6-thiol

To a solution of disulfide (886 mg, 2.55 mmol) in DMF (12 ml)/water (0.5 ml) was added triethylamine (284 mg) followed by tris-(2-carboxyethyl)phosphine hydrochloride (1.52 g, 5.32 mmol). The mixture was stirred for 30 minutes, then diluted with ethyl acetate/water. The organic phase was separated and the aqueous phase extracted with ethyl acetate. The combined organic extracts were washed with brine, dried (MgSO$_4$), filtered and concentrated. The crude thiol (870 mg) was used directly without further purification; MS ES+176.02, ES−174.13

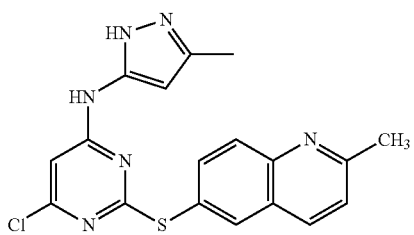 [SMILES: Cc1cc(Nc2cc(Cl)nc(Sc3ccc4nc(C)ccc4c3)n2)[nH]n1]

2-(2-methylquinolin-6-ylthio)-6-chloro-N-(3-methyl-1H-pyrazol-5-yl)pyrimidin-4-amine To a stirred suspension of 6-chloro-N-(3-methyl-1H-pyrazol-5-yl)-2-(methylsulfonyl)pyrimidin-4-amine (2.02 g, 7.03 mmol) in tert-butanol (20 ml) was added 2-methylquinoline-6-thiol (1.23 g, 7.03 mmol). The mixture was heated to 70° C. for 4 hours, then cooled to ambient and diluted with ethyl acetate/saturated aqueous potassium carbonate. The mixture was filtered to remove unreacted starting material and the organic layer removed form the filtrate. The aqueous layer was extracted with ethyl acetate and the combined organic extracts washed with brine, dried (MgSO$_4$), filtered and concentrated. The crude was purified on silica gel, eluting with 90 to 100% ethyl acetate/petrol. The title compound was further purified by trituration with dichloromethane. This gave the product as a white solid (514 mg, 19%); MS ES+383.25, ES−381.36.

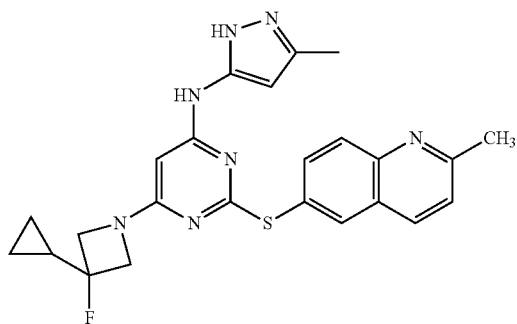 [SMILES: Cc1cc(Nc2cc(N3CC(F)(C4CC4)C3)nc(Sc3ccc4nc(C)ccc4c3)n2)[nH]n1]

2-(2-methylquinolin-6-ylthio)-6-(3-cyclopropyl-3-fluoroazetidin-1-yl)-N-(3-methyl-1H-pyrazol-5-yl)pyrimidin-4-amine 2-(2-methylquinolin-6-ylthio)-6-chloro-N-(3-methyl-1H-pyrazol-5-yl)pyrimidin-4-amine (50 mg, 0.13 mmol) was slurried in n-butanol (1 ml). Diisopropylamine was added (151 mg, 1.17 mmol) followed by 4-(1-pyrrolidinyl)-piperidine (58 mg, 0.46 mmol). The mixture was heated to 85° C. for 14 hours, then allowed to cool to ambient. The reaction mixture was purified by column chromatography (5% MeoH/95% dichloromethane) to give an off-white solid (25 mg, 21%); $^1$H NMR (400 MHz, (DMSO) δ 0.42-0.46 (2H, m), 0.59-0.63 (2H, m), 1.36-1.38 (1H, m), 1.60 (3H, brs), 2.69 (3H, s), 3.80-3.94 (4H, m), 5.10 (1H, brs), 5.76 (1H, s), 7.48 (1H, d), 7.82 (1H, dd), 7.95 (1H, d), 8.22 (1H, d), 8.30 (1H, d), 9.33 (1H, s), 11.62 (1H, s); MS ES+462, ES−460.

Example 15

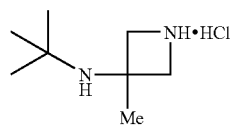

1-benzhydryl-3-methylazetidin-3-yl methanesulfonate

To a slurry of 1-benzhydryl-3-methylazetidin-3-ol hydrochloride (10.00 g, 34.54 mmol) in dichloromethane (80 ml) was added triethylamine (8.00 g, 79.20 mmol) and the mixture cooled to 0° C. Methanesulfonyl chloride (5.20 g, 45.41 mmol) was added dropwise and the reaction mixture was then allowed to warm to room temperature and stirred for 4 hrs. The reaction was diluted with water and dichloromethane and the organic layer was washed further with water, brine then dried (MgSO$_4$) and concentrated to give a pale pink solid. The solid was purified on silica gel eluting with 20% ethyl acetate/petrol to provide the title compound as a white solid (1.69 g, 64%). 1H NMR (CDCl$_3$) 1.92 (3H, s), 3.05 (3H, s), 3.33 (4H, s), 4.42 (1H, s), 7.18-7.20 (2H, m), 7.23-7.30 (4H, m), 7.39-7.52 (4H, m).

N-tert-butyl-1-benzhydryl-3-methylazetidin-3-amine hydrochloride

To a solution of 1-benzhydryl-3-methylazetidin-3-yl methanesulfonate (2.00 g, 6.23 mmol) in iso-propanol (10 ml) was added tert-butyl amine (1.36 g, 18.63 mmol). The mixture was heated at 80° C. for 3 h. The reaction mixture was then allowed to cool to room temperature and concentrated. The residue was slurried with ethyl acetate and filtered, washing with further ethyl acetate and then concentrated to give a solid. The solid was slurried in ether and hydrochloric acid (20 ml, 2M in ether) was added, then stirred for 10 mins and filtered to provide the title compound as a tan solid (1.69 g, 74%). 1H NMR (DMSO) 1.40 (9H, s), 1.99 (3H, s), 3.85 (2H, brs), 4.11 (2H, brs), 4.71 (1H, brs), 7.35-7.50 (6H, m), 7.70-7.81 (4H, m), 10.23 (1H, s).

N-tert-butyl-3-methylazetidin-3-amine hydrochloride

To a slurry of N-tert-butyl-1-benzhydryl-3-methylazetidin-3-amine hydrochloride (1.69 g, 4.91 mmol) in ethanol (30 ml) was added 10% Palladium hydroxide on carbon (160 mg) and the mixture degassed three times with nitrogen and three times with hydrogen. The mixture was then stirred under a hydrogen atmosphere 40° C. (warm water bath) for 3 h and then at room temperature for a further 12 h. The reaction was degassed with nitrogen and filtered through celite and concentrated. The compound was used crude in subsequent chemistry. $^1$H NMR (MeOH) 1.50 (9H, s), 1.99 (3H, s), 4.19 (2H, d), 4.91 (2H, d).

Example 16

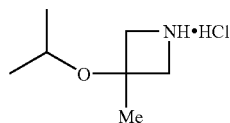

1-benzhydryl-3-isopropoxy-3-methylazetidine hydrochloride

A slurry of 1-benzhydryl-3-methylazetidin-3-yl methanesulfonate (2.75 g, 8.56 mmol) in iso-propanol (150 ml) was heated to 60° C. Freshly ground potassium hydroxide (1.40 g, 25.0 mmol) was added and stirring continued at 60° C. overnight. The reaction mixture was allowed to cool to room temperature and diluted with ethyl acetate and water. The organic phase was washed with brine, dried (MgSO$_4$) and concentrated. The residue was purified on silica gel eluting with 5 to 8% ethyl acetate/petrol to provide a colorless oil (1.29 g). The oil was dissolved in ether and hydrochloric acid (5 ml, 2M in ether) was added and stirred at room temperature for 10 mins. The resulting precipitate was filtered and washed with ether to provide the title compound as a white solid (1.23 g, 43%). 1H NMR (CDCl$_3$). 1.12 (6H, d), 1.62 (3H, s), 2.95 (2H, d), 3.15 (2H, d), 3.75 (1H, m), 4.41 (1H, s), 7.15-7.30 (6H, m), 7.41-7.50 (4H, m). ES+296.

3-isopropoxy-3-methylazetidine hydrochloride

To a slurry of 1-benzhydryl-3-isopropoxy-3-methylazetidine hydrochloride (1.23 g, 3.71 mmol) in ethanol (30 ml) was added 10% Palladium hydroxide on carbon (200 mg) and the mixture degassed three times with nitrogen and three times with hydrogen. The mixture was then stirred under a hydrogen atmosphere at room temperature for a 12 h. The reaction was degassed with nitrogen and filtered through celite and concentrated. The compound was used crude in subsequent chemistry.

Example 17

N-(4-((4-(3-methyl-1H-pyrazol-5-ylamino)-6-(3-cyano-3-methylazetidin-1-yl)pyrimidin-2-yl)sulfanyl)phenyl)propionamide

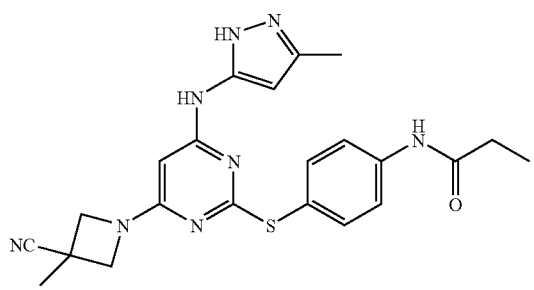

tert-butyl 3-cyano-3-methylazetidine-1-carboxylate

A solution of tert-butyl 3-cyanoazetidine-1-carboxylate (0.55 g, 3.04 mmol) in THF (10 ml) was cooled to −78° C. under a nitrogen atmosphere. LHMDS (3.34 ml, 1M THF) was added dropwise and the solution stirred at −78° C. for 1 hr. Methyl iodide was added dropwise and stirring continued for a further 2 h. The reaction was quenched with water and diluted with ethyl acetate. The organic layer was washed with brine, dried (Na2SO4) and concentrated. The residue was purified on silica gel eluting with 20% ethyl acetate/petrol provide the title compound as a pale yellow oil (0.46 g, 77%). 1H NMR (CDCl$_3$) 1.48 (9H, s), 1.71 (3H, s), 3.82 (2H, d), 4.31 (2H, d).

3-methylazetidine-3-carbonitrile trifluoro acetic acid

To a solution of tert-butyl 3-cyano-3-methylazetidine-1-carboxylate (30.0 mg, 0.15 mmol) in dichloromethane (5 ml) was added trifluoroacetic acid (2 ml) and the solution stirred at room temperature for 1 hr. The reaction was concentrated and dried under vacuum to give a viscous oil which was used crude in subsequent chemistry.

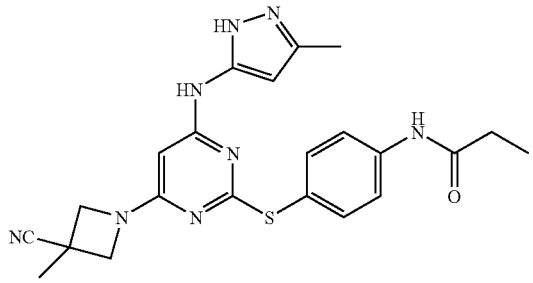

N-(4-((4-(3-methyl-1H-pyrazol-5-ylamino)-6-(3-cyano-3-methylazetidin-1-yl)pyrimidin-2-yl)sulfinyl)phenyl)propionamide To a suspension of N-(4-(4-(3-methyl-1H-pyrazol-5-ylamino)-6-chloropyrimidin-2-ylthio)phenyl)propionamide (150 mg, 0.387 mmol) in n-butanol (4 ml) was added diispropylamine (500 mg, 3.87 mmol) followed by 3-methylazetidine-3-carbonitrile hydrochloride (255 mg, 1.94 mmol). The mixture was heated at 85° C. for 18 hours then concentrated and the residue purified by mass directed HPLC. This gave the title compound as a TFA salt (72 mg, 41%); 1H NMR (DMSO) 1.05 (3H, t), 1.65 (3H, s), 2.03 (3H, s), 2.37 (2H, q), 3.88 (2H, d), 4.18 (2H, d), 5.37 (1H, s), 5.60 (1H, brs), 7.50 (2H, d), 7.71 (2H, d), 9.50 (1H, brs), 10.11 (1H, brs); MS ES+449.4, ES−447.6.

Example 18

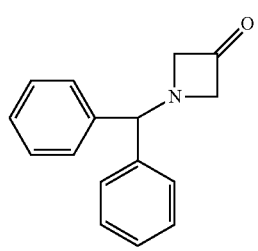 [SMILES: O=C1CN(C(c2ccccc2)c2ccccc2)C1]

N-Benzhydrylazetidin-3-one

To a stirred slurry of 1-(diphenylmethyl)-3-hydroxyazetidine (30 g, 0.126 mol) in triethylamine (63 g, 0.628 mol) was added a solution of sulfur trioxide pyridine complex (60 g, 0.376 mol) in anhydrous DMSO (300 ml) dropwise over 30 minutes. The resulting mixture was warmed to 50° C. for 30 minutes. The reaction mixture was then cooled to ambient and poured into a mixture of water (1 L) and ethyl acetate (800 ml). The organic layer was separated and the aqueous layer extracted with ethyl acetate (3×200 ml). The combined organic solutions were then washed with water (3×200 ml), then saturated brine (200 ml), dried (magnesium sulfate), filtered and concentrated. The residue was purified on silica gel, eluting with 5-10% ethyl acetate/petrol. The product was obtained as a white solid (26.2 g, 86%); $^1$H NMR CDCl$_3$ δ 4.07 (4H, s), 4.62 (1H, s), 7.20-7.39 (6H, m), 7.53 (4H, d).

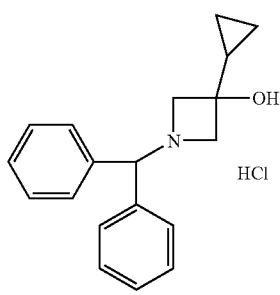 [SMILES: OC1(C2CC2)CN(C(c2ccccc2)c2ccccc2)C1 ; Cl]

1-Benzhydryl-3-cyclopropylazetidin-3-ol hydrochloride

A solution of cyclopropylmagnesium bromide in THF (0.5M, 600 ml, 0.5 mol) was cooled to −78° C. under a nitrogen atmosphere. Precipitation appeared to occur at this temperature. A solution of N-benzhydrylazetidin-3-one (24.2 g, 0.102 mol) in anhydrous THF (130 ml) was added dropwise over 30 minutes. The mixture was stirred for an additional 90 minutes at −78° C. after which time saturated sodium bicarbonate solution (400 ml) and water (100 ml) were added slowly. The mixture was then diluted with ethyl acetate (1 L) and allowed to warm to ambient. The organic phase was then separated (the aqueous layer was an emulsion of magnesium salts but was easily separable from the organic layer) and the aqueous phase extracted with ethyl acetate (3×300 ml). The combined organic solutions were then washed with brine saturated (300 ml), dried (magnesium sulfate), filtered and concentrated to give a pale yellow oil. The crude was purified on silica gel, eluting with 20-30% ethyl acetate/petrol. The resulting alcohol (28.3 g) was dissolved in ether (350 ml) and the solution cooled to 0° C. A solution of HCl in ether (2M, 130 ml) was then added dropwise over 15 minutes. The HCl salt precipitated from solution. The resulting slurry was stirred at 0° C. for an additional 10 minutes then filtered. The filter cake was washed with ether (2×100 ml) and the solid dried under vacuum. This furnished the product as a white solid (28.2 g, 88%); $^1$H NMR d$_6$-DMSO δ 0.31-0.50 (4H, m), 1.35 (0.3H, m), 0.51 (0.7H, m), 3.41-4.10 (5H, m), 5.88 (0.3H, d), 6.05 (0.7H, d), 6.35 (1H, brs), 7.30-7.50 (6H, m), 7.61-7.82 (4H, m); ES+280.71.

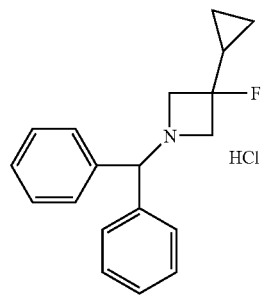 [SMILES: FC1(C2CC2)CN(C(c2ccccc2)c2ccccc2)C1 ; Cl]

1-Benzhydryl-3-cyclopropyl-3-fluoroazetidine hydrochloride

Saturated NaHCO$_3$ (100 ml) was added to a suspension of 1-Benzhydryl-3-cyclopropylazetidin-3-ol hydrochloride (7.78 g, 24.50 mmol) in ethyl acetate (100 ml). The mixture was transferred to a separating funnel and shaken vigorously until all of the solid had dissolved. The organic layer was separated and the aqueous layer extracted further with ethyl acetate (50 ml). The combined organic extracts were dried (Na$_2$SO$_4$) and concentrated to an oil. The oil was dissolved in dichloromethane (100 ml) and cooled to −78° C. [bis(2-methoxyethyl)amino]sulfur trifluoride (5.98 g, 27.05 mmol, 5.0 ml) was added dropwise and the solution stirred for 30 mins at −78° C. and then warmed to 0° C. and stirred for a further 1 hr. Reaction was quenched with Saturated NaHCO$_3$ (50 ml) and brine (50 ml) and the aqueous layer extracted with dichloromethane (50 ml). The combined organic extracts were dried (Na$_2$SO$_4$) and concentrated to give a yellow oil. The crude was purified on silica gel, eluting with 5% ethyl acetate/petrol. The resulting alcohol was dissolved in ether (100 ml) and the solution cooled to 0° C. A solution of HCl in ether (2M, 25 ml) was then added dropwise over 5 minutes. The HCl salt precipitated from solution. The resulting slurry was stirred at 0° C. for an additional 10 minutes then filtered. The filter cake was washed with ether (20 ml) and the solid dried under vacuum. This furnished the product as a white solid (4.71 g, 61%). $^1$H NMR d$_4$-MeOH δ 0.30-0.52 (4H, m), 1.22 (1H, brs), 4.01-4.23 (4H, m), 5.50-5.60 (1H, brs), 7.13-7.46 (10H, m); ES+282.

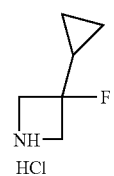

3-cyclopropyl-3-fluoroazetidine hydrochloride

To wet 10% palladium on carbon (Degussa catalyst) under nitrogen was added ethanol (100 ml). A solution of 1-Benzhydryl-3-cyclopropyl-3-fluoroazetidine hydrochloride (6.74 g, 21.23 mmol) in ethanol (50 ml) was added to the catalyst and the mixture hydrogenated at 60 psi on the Parr shaker hydrogenation apparatus for 5 hrs. The reaction was filtered through celite and concentrated to an oil. Ether (50 ml) was added and the mixture cooled to 0° C. and stirred until a precipitate formed. The suspension was filtered and the filter cake was washed with ether (20 ml) and the solid dried under vacuum. This furnished the product as an off white solid (3.00 g, 93%). $^1$H NMR d$_6$-DMSO δ 0.52-0.56 (2H, m), 0.59-0.64 (2H, m), 1.35-1.40 (1H, m), 3.91-4.10 (4H, m), 4.01-4.23 (4H, m), 9.50 (1H, brs), 9.63 (1H, brs).

Example 19

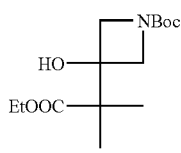

tert-butyl-(2-(ethoxycarbonyl)propan-2-yl)-3-hydroxyazetidine-1-carboxylate

Indium powder was added to a solution of ethyl-2-bromoisobutyrate (1.71 g, 8.76 mmol) and tert-butyl 3-oxoazetidine-1-carboxylate in dry DMF (5 ml). The suspension was warmed to 60° C. for 2 mins and the heat source was removed (the internal temperature remained at 60° C. for a sustained period after removal of the heat source). The reaction was stirred at room temperature for 90 mins and quenched with ice. The aqueous phase was extracted with ethyl acetate (2×50 ml), dried (Na$_2$SO$_4$) and concentrated to give an oil. The oil was purified by flash column chromatography eluting with 30% ethylacetate/hexanes to give the title compound as a white solid 1.40 g, 84%. $^1$H NMR (CDCl$_3$, 400 Mhz) 1.29-1.33 (9H, m), 1.48 (9H, s), 3.55 (1H, s), 3.79 (2H, d), 4.03 (2H, d), 4.18 (2H, q).

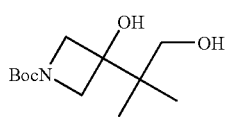

tert-butyl 3-hydroxy-3-(1-hydroxy-2-methylpropan-2-yl)azetidine-1-carboxylate

A solution of tert-butyl 3-(2-(ethoxycarbonyl)propan-2-yl)-3-hydroxyazetidine-1-carboxylate (0.50 g, 1.74 mmol) in DCM (5 ml) was cooled to −78° C. A solution of DIBAL-H in DCM (5.23 mmol, 5.23 ml, 1M) was added dropwise and the solution allowed to warm to 0° C. and stirred for 4 hrs. Sat NH$_4$Cl (20 ml) and ethyl acetate (40 ml) was added. The organic layer washed with brine (30 ml), dried (Na$_2$SO$_4$), and concentrated to give an oil. The oil was purified by flash column chromatography eluting with 30 to 70% ethylacetate/ hexanes to give the title compound as a colorless oil 0.20 g, 47%. $^1$H NMR (CDCl$_3$, 400 Mhz) 1.01 (6H, s), 1.43 (9H, s), 3.58 (2H, s), 3.75 (2H, d), 4.03 (2H, d).

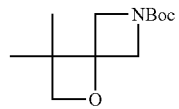

3,3-Dimethyl-1-oxa-6-aza-spiro[3.3]heptane-6-carboxylic acid tert-butyl ester

To a solution of tert-butyl 3-hydroxy-3-(1-hydroxy-2-methylpropan-2-yl)azetidine-1-carboxylate (0.20 g, 0.82 mmol) in THF (4 ml) was added in rapid succession, KO$^t$Bu (0.19 g, 1.72 mmol) and p-toluenesulfonylchloride (0.16 g, 0.82 mmol) and the solution stirred at room temperature for 90 mins. Water (10 ml) was added and extracted with ethyl acetate. The organic layer was dried (Na$_2$SO$_4$) and concentrated to give an oil. The oil was purified by flash column chromatography eluting with 30 to 70% ethylacetate/hexanes to give the title compound as a colorless oil 0.13 g, 70%. $^1$H NMR (CDCl$_3$, 400 Mhz) 1.25 (6H, s), 1.45 (9H, s), 3.89 (2H, d), 4.12 (2H, d), 4.20 (2H, s).

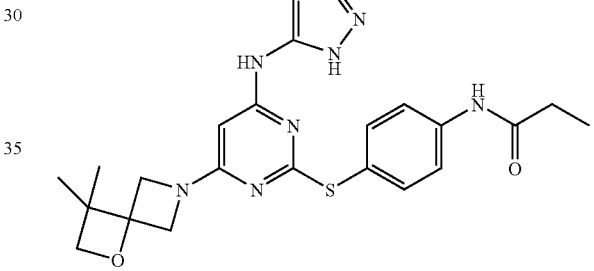

N-{4-[4-(3,3-Dimethyl-1-oxa-6-aza-spiro[3.3]hept-6-yl)-6-(5-methyl-2H-pyrazol-3-ylamino)-pyrimidin-2-ylsulfanyl]-phenyl}-propionamide To a solution of 3,3-Dimethyl-1-oxa-6-aza-spiro[3.3]heptane-6-carboxylic acid tert-butyl ester (60 mg, 0.27 mmol) in DCM (3 ml) at 0° C. was added trifluoroacetic acid and the reaction stirred at room temperature for 1 hr. The reaction was concentrated to give an oil which was used crude in the next step. The oily residue was dissolved in n-BuOH (3 ml) and diisopropylethylamine (171 mg, 1.35 mmol, 0.24 ml) and N-{4-[4-Chloro-6-(5-methyl-2H-pyrazol-3-ylamino)-pyrimidin-2-ylsulfanyl]-phenyl}-propionamide (93 mg, 0.24 mmol) was added. The mixture was heated to 100° C. and stirred for 18 hrs. The reaction was allowed to cool to room temperature and diluted with brine (20 ml) and ethyl acetate (20 ml). The organic layer was dried (Na$_2$SO$_4$) and concentrated to give an oil. The oil was purified by flash column chromatography eluting with 2.5% MeOH in ethyl acetate to give the title compound as a pale orange solid 25 mg, 20%. $^1$H NMR (d6-DMSO, 400 MHz) 1.08 (3H, m), 1.20 (6H, s), 1.98 (3H, s), 2.34 (2H, q), 3.78 (2H, d), 4.14-4.15 (4H, m), 5.35 (1H, s), 5.61 (1H, brs), 7.47 (2H, d), 7.70 (2H, d), 9.24 (1H, s), 10.07 (1H, s), 11.43 (1H, s). ES+480.

Example 20

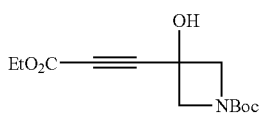

tert-butyl 3-(2-(ethoxycarbonyl)ethynyl)-3-hydroxyazetidine-1-carboxylate n-butyl lithium (1.17 mmol, 0.47 ml, 2.5 M) was added dropwise to a solution of diisopropylamine (130 mg, 1.29 mmol, 0.18 ml) in THF (8 ml) at −78° C. The solution was warmed to 0° C., stirred for 15 mins, and cooled back to −78° C. Ethyl propiolate (126 mg, 1.29 mmol, 0.13 ml) was added dropwise and the solution stirred for 1 hr at −78° C. A solution of tert-butyl 3-oxoazetidine-1-carboxylate (200 mg, 1.17° mmol) in THF (2 ml) was added dropwise, stirring continued for 30 mins, and the solution warmed to 0° C. and stirred for a further 15 mins. The reaction was quenched with Sat NH4Cl (20 ml) and extracted into ethyl acetate (20 ml), dried (Na$_2$SO$_4$), and concentrated to give a brown oil. The oil was purified by flash column chromatography eluting with 30% ethylacetate/hexanes to give the title compound as a colorless oil 0.20 g, 64%. $^1$H NMR (CDCl$_3$, 400 MHz) 1.33 (3H, t), 1.48 (9H, s), 2.92 (1H, s), 4.04 (2H, d), 4.22-4.31 (4H, m).

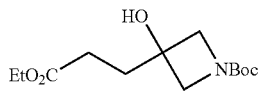

tert-butyl 3-(2-(ethoxycarbonyl)ethyl)-3-hydroxyazetidine-1-carboxylate

To palladium on carbon (10%, 75 mg) under a nitrogen atmosphere was added a solution of tert-butyl 3-(2-(ethoxycarbonyl)ethynyl)-3-hydroxyazetidine-1-carboxylate (0.20 g, 0.74 mmol) in ethanol (10 ml). The suspension was subjected to hydrogen (Parr hydrogenation apparatus) at 45 Psi for 3 hr. The reaction was filtered and concentrated to give an oil. The oil was purified by flash column chromatography eluting with 30 to 50% ethyl acetate/hexanes to give the title compound as a colorless oil 0.11 g, 50%. 1H NMR (CDCl$_3$, 400 MHz) 1.28 (3H, t), 1.43 (9H, s), 2.15 (2H, t), 2.50 (2H, t), 3.32 (1H, s), 3.83 (4H, dd), 4.18 (2H, q).

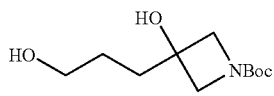

tert-butyl 3-hydroxy-3-(3-hydroxypropyl)azetidine-1-carboxylate

Diisobutyl aluminium hydride (1.48 mmol, 1.48 ml, 1 M DCM) was added dropwise to a solution of tert-butyl 3-(2-(ethoxycarbonyl)ethyl)-3-hydroxyazetidine-1-carboxylate (0.10 g, 0.37 mmol) in DCM (3 ml) at −78° C. The solution was allowed to warm to 0° C. and stirred for a further 5 hrs. The reaction was quenched with Sat NH4Cl (10 ml) and extracted into ethyl acetate (10 ml), dried (Na2SO4), and concentrated to give an oil. The oil was purified by flash column chromatography eluting with 60% ethylacetate/hexanes to give the title compound as a colorless oil 27 mg, 32%. 1H NMR (CDCl$_3$, 400 MHz) 1.48 (9H, s), 1.69-1.75 (2H, m), 1.93 (2H, t), 3.76 (2H, t), 3.82 (4H, s).

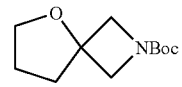 [SMILES: CC(C)(C)OC(=O)N1CC2(CCCO2)C1]

1-oxa-7-aza-spiro[4.3]octane-7-carboxylic acid tert-butyl ester

To a solution of tert-butyl 3-hydroxy-3-(3-hydroxypropyl)azetidine-1-carboxylate (27 mg, 0.13 mmol) in THF (2 ml) was added in rapid succession, KOtBu (31 mg, 0.27 mmol) and p-toluenesulfonylchloride (25 mg, 0.13 mmol) and the solution stirred at room temperature for 90 mins. Water (10 ml) was added and extracted with ethyl acetate. The organic layer was dried (Na$_2$SO$_4$) and concentrated to give an oil. The oil was used crude in the next step.

Example 21

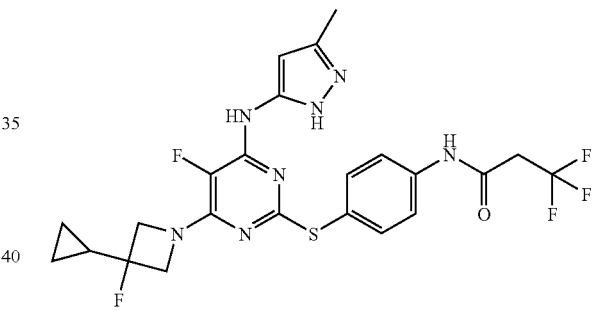

N-(4-(4-(3-methyl-1H-pyrazol-5-ylamino)-6-(3-cyclopropyl-3-fluoroazetidin-1-yl)-5-fluoropyrimidin-2-ylthio)phenyl)-3,3,3-trifluoropropanamide

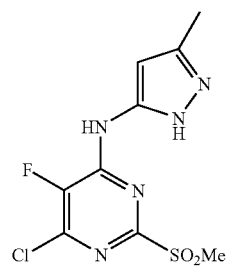 [SMILES: Cc1cc(Nc2nc(S(C)(=O)=O)nc(Cl)c2F)[nH]n1]

6-chloro-5-fluoro-N-(3-methyl-1H-pyrazol-5-yl)-2-(methylsulfonyl)pyrimidin-4-amine To a solution of 4,6-dichloro-5-fluoro-2-(methylsulfonyl) pyrimidine in THF (25 ml) was added diisopropylamine (1.32 g, 10.20 mmol, 1.82 ml) and 3-methyl-1H-pyrazol-5-amine (1.04 g, 10.71 mmol) and the mixture stirred at room temperature for 30 mins. The reaction was diluted with ethyl acetate (100 ml) and water (100 ml), the organic layer was washed with brine (50 ml), dried (Na2SO4), and partially concentrated until a solid started to precipitate. The suspension was cooled in an ice bath for 1 hr and filtered to give the title compound as a pale yellow solid. A second crop was obtained by leaving the filtrate to stand overnight (total 1.55 g, 50%). 1H NMR (DMSO, 400 MHz) 2.26 (3H, s), 3.32 (3H, s), 6.48 (1H, s), 11.03 (1H, s), 12.35 (1H, s) ES+306.

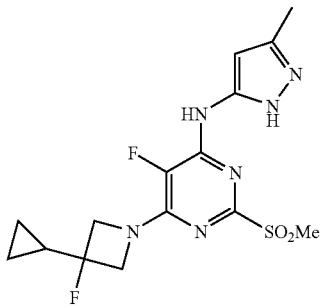 [SMILES: Cc1cc(Nc2nc(S(C)(=O)=O)nc(N3CC(F)(C4CC4)C3)c2F)[nH]n1]

6-(3-cyclopropyl-3-fluoroazetidin-1-yl)-5-fluoro-N-(3-methyl-1H-pyrazol-5-yl)-2-(methylsulfonyl)pyrimidin-4-amine A suspension of 6-chloro-5-fluoro-N-(3-methyl-1H-pyrazol-5-yl)-2-(methylsulfonyl)pyrimidin-4-amine (100 mg, 0.33 mmol) and 3-cyclopropyl-3-fluoroazetidine (50 mg, 0.33 mmol) in acetonitrile (5 ml) was heated to 50° C. and stirred for 1 hr. The mixture was allowed to cool and diluted with ethylacetate (20 ml) and water (20 ml). The organic layer was dried (Na2SO4) and concentrated to give a solid. Purification by flash column chromatography eluting with 40% ethylacetate/hexanes and ethyl acetate gave the title compound as an off white solid (64 mg, 51%). 1H NMR (DMSO, 400 MHz) 0.51-0.52 (2H, m), 0.68-0.76 (2H, m), 1.42-1.59 (1H, m), 2.29 (3H, s), 3.31 (3H, s), 4.20-4.36 (4H, m), 6.41 (1H, s), 9.98 (1H, s), 12.13 (1H, s). ES+385.

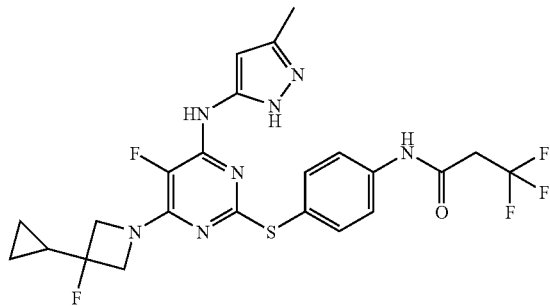 [SMILES: Cc1cc(Nc2nc(Sc3ccc(NC(=O)CC(F)(F)F)cc3)nc(N3CC(F)(C4CC4)C3)c2F)[nH]n1]

N-(4-(4-(3-methyl-1H-pyrazol-5-ylamino)-6-(3-cyclopropyl-3-fluoroazetidin-1-yl)-5-fluoropyrimidin-2-ylthio)phenyl)-3,3,3-trifluoropropanamide A solution of 6-(3-cyclopropyl-3-fluoroazetidin-1-yl)-5-fluoro-N-(3-methyl-1H-pyrazol-5-yl)-2-(methylsulfonyl)pyrimidin-4-amine (64 mg, 0.17 mmol) and 3,3,3-trifluoro-N-(4-mercaptophenyl)propanamide (47 mg, 0.20 mmol) in DMF (3 ml) was heated to 80° C. and stirred for 6 hrs. The reaction was diluted with ethylacetate (20 ml) and Sat. NaHCO3 (20 ml) and the organic layer washed with brine (20 ml), dried (Na2SO4) and concentrated to give an oil. Compound was purified by mass directed preparative HPLC, eluted with acetonitrile/water/TFA to give the title compound as a white solid (TFA salt, 41.2 mg, 37%). 1H NMR (DMSO, 400 MHz) 0.46-0.50 (2H, m), 0.61-0.64 (2H, m), 1.38-1.45 (1H, m), 1.93 (3H, s), 3.55 (2H, q), 4.00-4.18 (4H, m), 5.27 (1H, s), 7.54 (2H, d), 7.71 (2H, d), 9.39 (1H, s), 10.57 (1H, s). ES+540.

Example 22

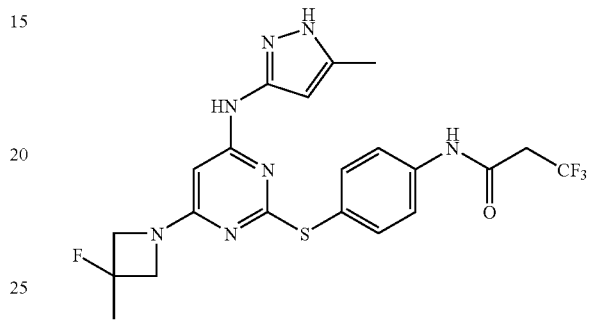

N-(4-(4-(5-methyl-1H-pyrazol-3-ylamino)-6-(3-fluoro-3-methylazetidin-1-yl)pyrimidin-2-ylthio)phenyl)-3,3,3-trifluoropropanamide (I-168)

The alcohol N-(4-((4-(5-methyl-1H-pyrazol-3-ylamino)-6-(3-hydroxy-3-methylazetidin-1-yl)pyrimidin-2-yl)sulfanyl)phenyl)-3,3,3-trifluoropropanamide (24 mg, 0.05 mmol) was dissolved with dry dichloromethane (3 mL) under nitrogen. The mixture was sonicated for 10 minutes and the resulting pale pink cloudy suspension cooled on an ice bath. Deoxofluor (11 μL, 0.06 mmol) was added dropwise. After 10 minutes, LC-MS of the resulting clear solution showed complete and clean conversion to the title compound. The reaction mixture was diluted with DCM and washed with saturated sodium bicarbonate solution, then brine. The organic phase was dried over sodium sulfate and concentrated in vacuo. The residue was taken up in ethyl acetate and purified by column chromatography (silica, 0-100% EtOAc-petroleum ether 40-60 gradient elution) to give the product as a white solid after freeze drying (14 mg, 60%).

Example 23

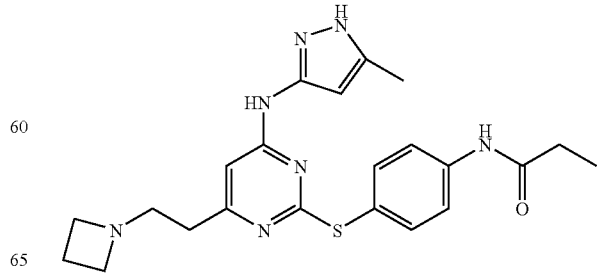

N-(4-(4-(5-methyl-1H-pyrazol-3-ylamino)-6-(2-(azetidin-1-yl)ethyl)pyrimidin-2-ylthio)phenyl)propionamide

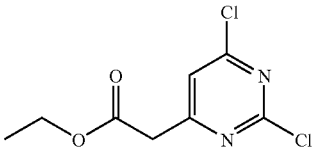

Ethyl 2-(2,6-dichloropyrimidin-4-yl)acetate

To a solution of ethyl 2-(1,2,3,6-tetrahydro-2,6-dioxopyrimidine-4-yl)acetate (10 g, 50.5 mmol) in toluene (150 ml) and POCl$_3$ (14.1 ml, 151.5 mmol) was added tripropylamine (9 ml) dropwise (exothermic reaction occurs). On complete addition, the reaction mixture was heated under reflux for 3 h. Reaction mixture was then cooled to room temperature then poured onto crushed ice and water with rapid stirring. Mixture stirred for 30 mins, then basified with sodium carbonate and extracted with ethyl acetate (3×150 ml). Organics were combined, washed with water, brine, dried (MgSO4), filtered and evaporated in vacuo to leave a dark red oil. Crude product purified by flash chromatography (120 g SiO$_2$, 0 to 35% EtOAc/petrol) to afford the title compound as a red oil (8.95 g, 75%). 1H NMR (CDCl$_3$) 1.31 (3H, t), 3.83 (2H, s), 4.24 (2H, q), 7.41 (1H, s); ES+235.

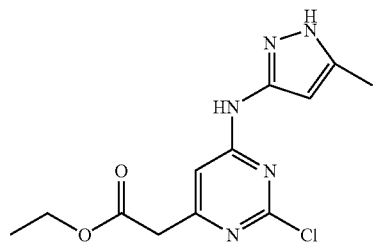 [SMILES: CCOC(=O)Cc1cc(Nc2cc(C)[nH]n2)nc(Cl)n1]

Ethyl 2-(6-(5-methyl-1H-pyrazol-3-ylamino)-2-chloropyrimidin-4-yl)acetate

A solution of ethyl 2-(2,6-dichloropyrimidin-4-yl)acetate (1.0 g, 4.25 mmol), sodium iodide (0.637 g, 4.25 mmol), 3-amino-5-methylpyrazole (0.413 g, 4.25 mmol), and N,N-diisopropylethylamine (0.96 ml, 5.53 mmol) was heated at 90° C. until reaction was complete (~3 h). Reaction mixture was then cooled to room temperature, diluted with ethyl acetate (100 ml), washed with sat. sodium hydrogen carbonate solution (1×30 ml), water (3×30 ml), brine (30 ml), dried (MgSO4), filtered and evaporated in vacuo to leave an orange oil. Crude product was purified by flash chromatography (SiO2, 60-100% EtOAc/Petrol) to give title compound as a red sticky oil (0.520 g, 41%). 1H NMR (CDCl$_3$) 1.29 (3H, t), 2.41 (3H, s), 3.52 (2H, s), 4.23 (2H, q), 5.20-4.60 (2H, very broad signal); ES+296.

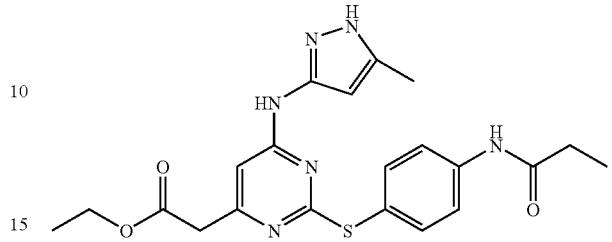

Ethyl 2-(6-(5-methyl-1H-pyrazol-3-ylamino)-2-((4-(propionamido)phenyl)sulfanyl)pyrimidin-4-yl)acetate A suspension of Ethyl 2-(6-(5-methyl-1H-pyrazol-3-ylamino)-2-chloropyrimidin-4-yl)acetate (0.676 g, 2.29 mmol) and N-(4-mercaptophenyl)propionamide (0.415 g, 2.29 mmol) in t-butanol (10 ml) was heated under reflux overnight. Reaction mixture was then cooled to room temperature, ethyl acetate (20 ml) added causing precipitation of product. Solid was collected by filtration, washed with sat. sodium hydrogen carbonate solution, water, diethyl ether then dried by suction to leave title compound as a yellow solid (0.425 g, 43%). 1H NMR (DMSO) 1.12 (3H, t), 1.20 (3H, t), 2.00 (3H, s), 2.40 (2H, q), 3.66 (2'H, s), 4.11 (2H, q), 5.05 (1H, br s), 5.30 (1H, br s), 7.53 (2H, d), 7.79 (2H, d), 10.20 (1H, s); ES+441.

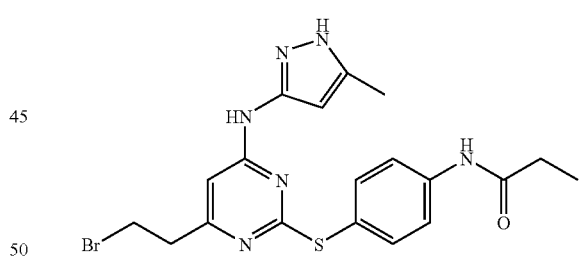

N-(4-(4-(5-methyl-1H-pyrazol-3-ylamino)-6-(2-bromoethyl)pyrimidin-2-ylthio)phenyl)propionamide A 2M solution of lithium borohydride in tetrahydrofuran (3.5 ml, 6.8 mmol) was added to a suspension of Ethyl 2-(6-(5-methyl-1H-pyrazol-3-ylamino)-2-((4-(propionamido)phenyl)sulfanyl)pyrimidin-4-yl)acetate (1 g, 2.3 mmol) in tetrahydrofuran (10 ml) under a nitrogen atmosphere. The suspension was stirred at 70° C. for one hour. The reaction mixture was hydrolysed with a saturated solution of sodium bicarbonate (15 ml). Extractions were carried out with ethyl acetate (3×25 ml). The organic was backwashed with brine then dried over magnesium sulfate. The residue was taken up in acetonitrile (25 ml). Potassium tribromide (1.3 ml) was added to the reaction mixture which was then stirred at 70° C. for one hour. The reaction mixture was hydrolysed with a saturated solution of sodium bicarbonate (15 ml). Extractions were carried out with ethyl acetate (3×25 ml). The organic was backwashed with brine then dried over magnesium sulfate to afford the title compound without any further purification (300 mg, 30%). ES+462

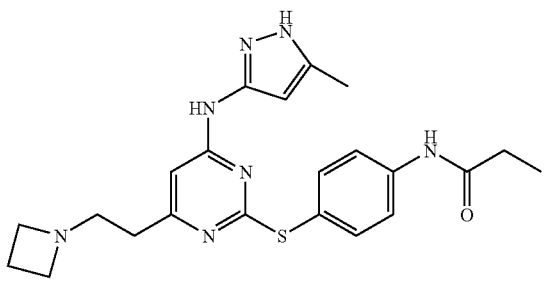 [SMILES: CCC(=O)Nc1ccc(Sc2nc(CCN3CCC3)cc(Nc3cc(C)[nH]n3)n2)cc1]

N-(4-(4-(5-methyl-1H-pyrazol-3-ylamino)-6-(2-(azetidin-1-yl)ethyl)pyrimidin-2-ylthio)phenyl)propionamide A mixture of N-(4-(4-(5-methyl-1H-pyrazol-3-ylamino)-6-(2-bromoethyl)pyrimidin-2-ylthio)phenyl)propionamide (100 mg, 0.21 mmol) and azetidine (36 mg, 0.63 mmol) in dimethylformamide (2 ml) was stirred at room temperature under a nitrogen atmosphere for 24 hours. The reaction mixture was diluted with ethyl acetate (40 ml). The organic layer was washed with a saturated solution of sodium bicarbonate (10 ml) and brine (10 ml), then dried over magnesium sulfate. The residue was purified by Gilson HPLC to afford the title compound as a bis-trifluoro acetic acid salt (0.5 mg, 1%). 1H NMR (CD$_3$OD): 1.30-1.37 (3H, m), 2.15-2.20 (3H, s), 2.40-2.50 (4H, m), 2.80-2.90 (2H, t), 3.50-3.55 (2H, t), 4.00-4.15 (4H, s), 6.50-6.55 (1H, s), 7.55-7.65 (2H, m), 7.75-7.80 (2H, m). ES+438

Example 24

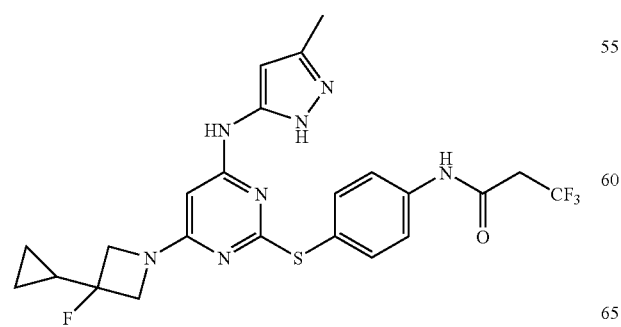

N-(4-(4-(3-methyl-1H-pyrazol-5-ylamino)-6-(3-cyclopropyl-3-fluoroazetidin-1-yl)pyrimidin-2-ylthio)phenyl)-3,3,3-trifluoropropanamide

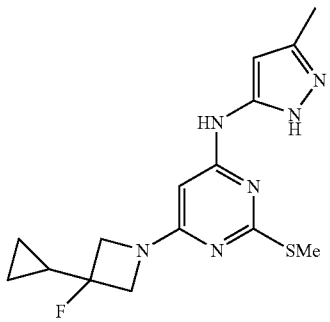 [SMILES: CSc1nc(Nc2cc(C)n[nH]2)cc(N2CC(F)(C3CC3)C2)n1]

6-(3-cyclopropyl-3-fluoroazetidin-1-yl)-N-(3-methyl-1H-pyrazol-5-yl)-2-(methylthio)pyrimidin-4-amine To a mixture of 6-chloro-N-(3-methyl-1H-pyrazol-5-yl)-2-(methylthio)pyrimidin-4-amine (150 g, 0.58 mol) and 3-cyclopropyl-3-fluoroazetidine hydrochloride (132.2 g, 0.87 mol) was added diisopropylethylamine (208 g, 1.61 mol) and isopropanol (1.125 L). The mixture was heated to reflux for 23 hours. The reaction was then cooled to 85° C. (a slightly hazy solution) and filtered. The homogeneous solution was concentrated to a minimal volume. EtOAc was then added (1 L) and the solution was concentrated to a minimal volume. EtOAc (1 L) and H$_2$O (1 L) were then added and the layers were separated. Crystallized product began to crystallize out of the organic layer during the extraction. The aqueous layer was further extracted with EtOAc (500 ml). The 1st organic layer was concentrated to dryness to give a white solid. Hexane (750 ml) was added to the second organic extract and the slurry was stirred at ambient temperature, and then cooled to 0° C. for 30 min. The slurry was filtered and washed with copious Heptane. The filter cake was dried under vacuum. The filter cake and the white solid from the 1$^{st}$ extraction were combined to afford 155.1 g of the desired product. (155.1 g, 77%). 1H NMR (DMSO, 400 MHz) 0.44 (2H; m), 0.60 (2H, m), 1.38-1.43 (1H, m), 2.18 (3H, s), 2.42 (3H, s), 3.89-3.97 (4H, m), 5.92 (1H, br s), 6.04 (1H, br s), 9.23 (1H, s), 11.86 (1H, s). ES+335

(155.1 g, 77%). 1H NMR (DMSO, 400 MHz) 0.44 (2H, m), 0.60 (2H, m), 1.38-1.43 (1H, m), 2.18 (3H, s), 2.42 (3H, s), 3.89-3.97 (4H, m), 5.92 (1H, br s), 6.04 (1H, br s), 9.23 (1H, s), 11.86 (1H, s). ES+335

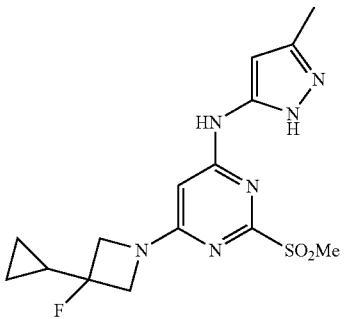 [SMILES: Cc1cc(Nc2cc(N3CC(F)(C4CC4)C3)nc(S(C)(=O)=O)n2)[nH]n1]

6-(3-cyclopropyl-3-fluoroazetidin-1-yl)-N-(3-methyl-1H-pyrazol-5-yl)-2-(methylsulfonyl)pyrimidin-4-amine A solution of 6-(3-cyclopropyl-3-fluoroazetidin-1-yl)-N-(3-methyl-1H-pyrazol-5-yl)-2-(methylthio)pyrimidin-4-amine (130 g, 389 mmol) in MeOH (5.2 L) was cooled to 0° C. A solution of oxone (526 g, 855 mmol) in H$_2$O (5.2 L) was slowly added to the slurry keeping the temperature below 5° C. After addition the reaction was allowed to warm to room temperature overnight. A 10% solution of NaHSO$_3$ (325 ml) and a 10% solution of K$_2$CO$_3$ (2.6 L) was then added to neutralize the reaction mixture, the solution filtered and the filter cake washed with H$_2$O (3.3 L). The solid was slurried in H$_2$O (2.6 L), the solution filtered and the filter cake washed with H$_2$O (3.3 L). The solid was dried under vacuum (72.3 g, 51%). 1H NMR (DMSO): 0.47 (2H, m), 0.60 (2H, m), 1.43-1.46 (1H, m), 2.20 (3H, s), 3.25 (3H, s), 3.97-4.11 (4H, m), 5.93 (1H, br s), 6.47 (1H, br s). 9.88 (1H, s), 12.01 (1H, br s). ES+367

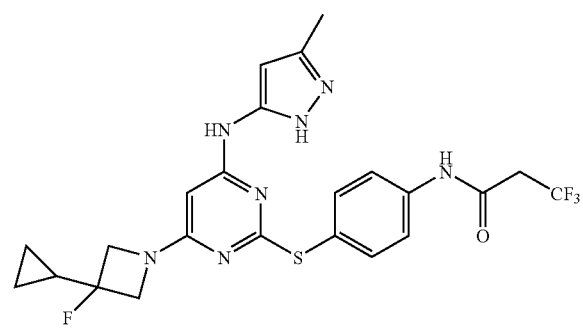 [SMILES: Cc1cc(Nc2cc(N3CC(F)(C4CC4)C3)nc(Sc3ccc(NC(=O)CC(F)(F)F)cc3)n2)[nH]n1]

N-(4-(4-(3-methyl-1H-pyrazol-5-ylamino)-6-(3-cyclopropyl-3-fluoroazetidin-1-yl)pyrimidin-2-ylthio)phenyl)-3,3,3-trifluoropropanamide (Compound I-13)

A slurry of 6-(3-cyclopropyl-3-fluoroazetidin-1-yl)-N-(3-methyl-1H-pyrazol-5-yl)-2-(methylsulfonyl)pyrimidin-4-amine (61 g, 170 mmol) and 3,3,3-trifluoro-N-(4-mercaptophenyl)propanamide (41 g, 175 mmol) in CH$_3$CN (1300 mL) was heated to reflux for 1.5 hours. During this time, the slurry transformed from thin and yellowish to thick and brilliant white. The mixture was then cooled to 0° C. and stirred at this temperature for 15 min. The mixture was then filtered and washed with cold CH$_3$CN (650 mL). The resulting solid was dried for 20 hours at 38° C. under house vacuum. The white solid was charged to a suitable reactor with EtOAc (1300 mL) and NaHCO$_3$(sat) (1300 mL). The mixture was stirred until no more solid remained. Then, the aqueous and organic layers were separated and the aqueous layer was washed with EtOAc (390 mL). The combined organic layers were dried over MgSO$_4$, filtered, washed with EtOAc (130 mL) and concentrated to a minimal volume on rotavap. The resulting mixture was re-crystallized out of EtOAc and hexane to give the desired product as a white solid (56.2 g, 72%) 1H NMR (MeOD, 400 MHz): 0.40-0.45 (2H, m), 0.60-0.65 (2H, m), 1.3-1.4 (1H, m), 2.05 (2H, s), 3.25-3.40 (2H, m), 3.85-3.40 (4H, m), 5.40-5.50 (2H, m), 7.50-7.55 (2H, d), 7.65-7.70 (2H, d). ES+522.

Example 25

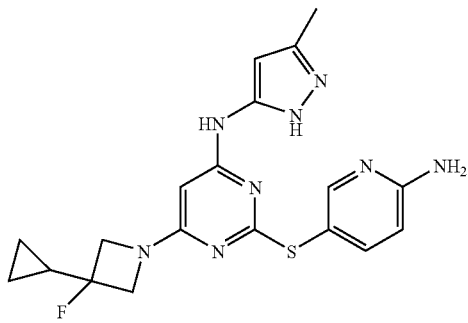 [SMILES: Cc1cc(Nc2cc(N3CC(F)(C4CC4)C3)nc(Sc3ccc(N)nc3)n2)[nH]n1]

2-(6-aminopyridin-3-ylthio)-6-(3-cyclopropyl-3-fluoroazetidin-1-yl)-N-(3-methyl-1H-pyrazol-5-yl)pyrimidin-4-amine A solution of 6-(3-cyclopropyl-3-fluoroazetidin-1-yl)-N-(3-methyl-1H-pyrazol-5-yl)-2-(methylsulfonyl)pyrimidin-4-amine (880 mg, 2.4 mmol) and 6-aminopyridine-3-thiol) (300 mg, 2.4 mmol) in DMF (10 ml) was heated to 80° C. and stirred for 2 hrs. The reaction was diluted with ethylacetate (150 ml) and Sat. NaHCO3 (50 ml) and the organic layer washed with brine (50 ml), dried (MgSO$_4$) and concentrated to give an oil. The residue was purified by flash column chromatography eluting with Pentane/EtOAc (5% MeOH) 0 to 100%. The resulting compound was triturated in 10:1 DCM:MeOH and filtered to give the title compound as a white solid (300 mg, 30%). 1H NMR (DMSO, 400 MHz) 0.42-0.44 (2H, m), 0.55-0.60 (2H, m), 1.35-1.45 (1H, m), 2.11 (3H, s), 3.81-3.90 (4H, m), 5.55-5.80 (2H, m), 6.35 (2H, s), 6.49-6.52 (1H, d), 7.46-7.49 (1H, d), 7.97 (1H, s), 9.30-9.35 (1H, s). ES+413

Example 26

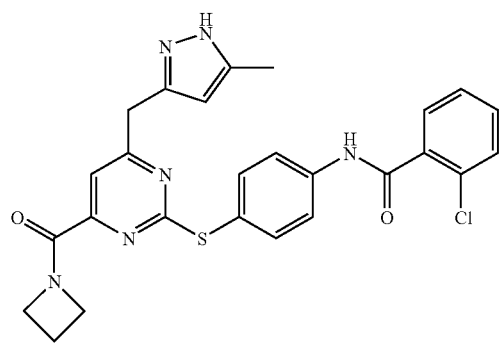 [SMILES: Cc1cc(Cc2cc(C(=O)N3CCC3)nc(Sc3ccc(NC(=O)c4ccccc4Cl)cc3)n2)n[nH]1]

2-((4-(2-chlorobenzamido)phenyl)sulfanyl)-6-(5-methyl-1H-pyrazol-3-ylamino)-(azetidin-1-yl)pyrimidine-4-carboxamide To a suspension of methyl 2-((4-(2-chlorobenzamido) phenyl)sulfanyl)-6-(5-methyl-1H-pyrazol-3-ylamino)pyrimidine-4-carboxylate (235 mg, 0.46 mmol) in ethyl alcohol was added a large excess of azetine (0.5 ml, 7.4 mmol). The tube was then sealed and heated to 90° C. for 16 hours, then allowed to cool to room temperature. The volatile components were then removed in vacuo and the residue purified by mass directed preparative HPLC, eluted with acetonitrile/water/TFA to give the product as a white solid after freeze drying (3.5 mg, 1.2%). 1H NMR (DMSO-d$^6$): 2.16 (5H, m), 3.24 (2H, m), 3.98 (2H, m), 4.18 (1H, s), 5.62 (1H, br s), 6.94 (1H, br s), 7.54 (6H, m), 7.87 (2H, d), 10.25 (1H, s), 10.78 (1H, s), 11.92 (1H, s). ES+520

Example 27

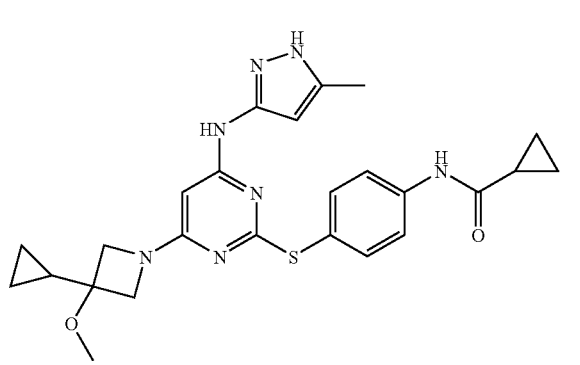 [SMILES: COC1(C2CC2)CN(c2cc(Nc3cc(C)[nH]n3)nc(Sc3ccc(NC(=O)C4CC4)cc3)n2)C1]

N-(4-(4-(5-methyl-1H-pyrazol-3-ylamino)-6-(3-cyclopropyl-3-methoxyazetidin-1-yl)pyrimidin-2-ylthio)phenyl)cyclo propanecarboxamide 3-Cyclopropylazetidin-3-yl diethyl phosphate (103 mg, 0.36 mmol) was added to a solution of N-(4-(4-(5-methyl-1H-pyrazol-3-ylamino)-6-chloropyrimidin-2-ylthio)phenyl) cyclopropanecarboxamide (96 mg, 0.24 mmol) and DIPEA (0.40 ml, 2.32 mmol) in methanol (5 ml), and the mixture was heated to 65° C. for 16 hours. The volatile components of the mixture were then removed in vacuo and the residue purified mass directed preparative HPLC, eluted with Acetonitrile/water/TFA to give the product as a white solid after freeze drying (6.3 mg, 5.3%). DMSO-d6: 0.34 (2H, m), 0.55 (2H, m), 0.81 (4H, d), 1.14 (1H, m), 1.81 (1H, m), 1.99 (3H, s), 3.26 (3H, s), 3.79 (4H, m), 5.37 (1H, s), 5.71 (1H, br s), 7.49 (2H, d), 7.71 (2H, d), 9.34 (1H, s), 10.39 (1H, s). ES+492

The experimentals shown below describe the preparation of some of the compounds used in the examples described herein.

Compound a

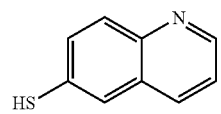

Quinoline-6-thiol

To a solution of 6-bromoquinoline (700 mg) in dimethylacetamide (3 ml) was added sodium thiomethoxide (1.9 g, 26.96 mmol). The mixture was heated at 150° C. for 2 hours, then cooled to ambient and diluted with 1M HCl/ethyl acetate. The organic layer was removed and the aqueous layer extracted with further ethyl acetate. The combined extracts were washed with water, then brine, dried (MgSO$_4$), filtered and concentrated. The crude thiol (500 mg) was used directly without further purification; MS ES+, ES−174.13

Compound b

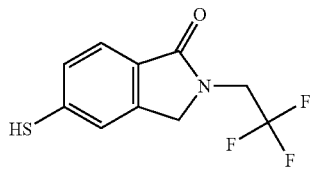

2-(2,2,2-trifluoroethyl)-5-mercaptoisoindolin-1-one

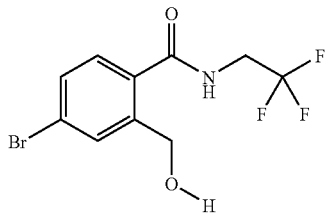 [SMILES: O=C(NCC(F)(F)F)c1ccc(Br)cc1CO]

4-bromo-N-(2,2,2-trifluoroethyl)-2-(hydroxymethyl) benzamide

To a stirred suspension of aluminium trichloride (4.07 g, 30.5 mmol) in dichloroethane (60 ml) cooled to 5° C. under a nitrogen atmosphere was added the solution of trifluoro ethyl amine (5.84 g, 38.7 mmol) at a rate to keep the temperature of the reaction mixture below 10° C. After complete addition the reaction mixture was allowed to warm up to room temperature and stirred at this temperature for 4 hours. After this time bromophthalide powder (5 g, 23.5 mmol) was added in one portion and the reaction mixture was then heated to 80° C. for 18 hours. TLC showed complete conversion from starting material to product and the reaction was carefully quenched with iced water (100 ml) and stirred for 30 minutes until all the ice melted. Dichloromethane was added and the mixture was filtered through a pad of silica and washed with copious amounts of DCM to remove the aluminium residues. The filtrate was separated and the aqueous layer was further extracted with DCM (2×100 ml). The organic layers were combined and dried over Magnesium sulfate powder, filtered and concentrated under reduced pressure to leave an off-white powder. Crude product 3.37 g (46% yield). NMR (DMSO 400 MHz) 4.02-4.11 (2H, m, alk), 4.60-4.61 (2H, m, alk), 5.43-5.46 (H, m, alk), 7.36-7.39 (H, d, ar), 7.55-7.57 (H, m, alk), 7.76 (H, s, ar) and 9.09-9.12 (H, m, NH). F19 NMR (DMSO 400 Mhz) −70.59. ES+312

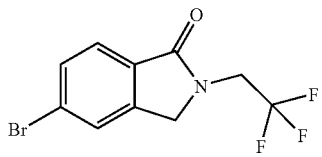 [SMILES: O=C1c2ccc(Br)cc2CN1CC(F)(F)F]

5-bromo-2-(2,2,2-trifluoroethyl)isoindolin-1-one

To a stirred solution of 4-bromo-2-hydroxymethyl-N-(2,2,2-trifluoro-ethyl)-benzamide (3.37 g, 10.8 mmol) in anhydrous tetrahydrofuran (50 ml), N-methyl-2-pyrrolinone (20 mL), cooled to 5° C. under a nitrogen atmosphere was added a solution of 2M isopropyl magnesium chloride in anhydrous THF (25 ml) at a rate to keep the temperature of the reaction mixture under 10° C., After complete addition, approximately 45 minutes the reaction was stirred at this temperature for an additional 60 minutes, and then at room temperature for 60 minutes. After that time the reaction mixture was re-cooled to 5° C. and a solution of bis(dimethyl amino)phosphoryl chloride (1.85 g, 14.1 mmol) was added dropwise. No exotherm was observed and the reaction was heated at reflux for 72 hours once the addition was completed. After this time no starting material was observed by both TLC and LCMS and the reaction mixture was carefully quenched with water, and acidified with 1M aqueous hydrochloric acid. The aqueous layer was extracted with ethyl acetate (3×100 ml) and the organic layers were combined and dried over Magnesium sulfate powder, filtered and concentrated under reduced pressure. Purification by column chromatography eluting with 25% ethyl acetate 75% petroleum ether gave product as a white powder 2.81 g (88% yield). NMR (DMSO 400 MHz) 4.36-4.43 (2H, m, alk), 4.62 (2H, s, alk), 7.68-7.74 (2H, m, ar) and 7.93 (H, s, ar). F19 NMR (DMSO 400 Mhz) −69.03. ES+296

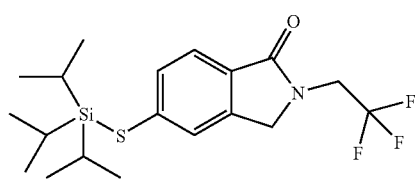 [SMILES: CC(C)[Si](Sc1ccc2c(c1)CN(CC(F)(F)F)C2=O)(C(C)C)C(C)C]

2-(2,2,2-trifluoroethyl)-5-((triisopropylsilyl)sulfanyl)isoindolin-1-one

To a stirred solution of triisopropylsilane thiol (648 mg, 3.4 mmol in anhydrous THF (10 ml), cooled to 5° C. under nitrogen atmosphere was added 60% sodium hydride powder 143 mg, 3.57 mmol) portion wise over 10 minutes. The resulting yellow solution was stirred for 20 minutes and then a solution of 5-bromo-2-(2,2,2-trifluoro-ethyl)-2,3-dihydro-isoindol-1-one (1 g, 3.4 mmol) in anhydrous THF (10 ml) and tetrakis palladium triphenylphosphine (393 mg 0.34 mmol) was added. The reaction mixture was degassed with nitrogen and heated at 90° C. for 2 hours. The mixture was concentrated and the reside was purified using column chromatography eluting with 30% ethyl acetate 70% petroleum ether to isolate both the protected (406 mg, 30% yield based on FW) and non-protected thiol (171 mg, 20% yield based on FW). ES+248.14

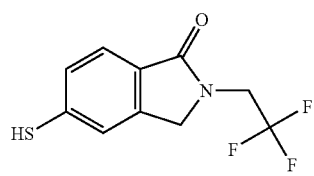 [SMILES: O=C1c2ccc(S)cc2CN1CC(F)(F)F]

2-(2,2,2-trifluoroethyl)-5-mercaptoisoindolin-1-one 2-(2,2,2-trifluoroethyl)-5-((triisopropylsilyl)sulfanyl)isoindolin-1-one was dissolved in a solution of hydrochloric acid in methanol (2 ml) and tetrahydrofuran (2 ml) and stirred at room temperature for 2 hours or until disappearance of starting material. Reaction mixture concentrated to give desired material (quant yield). ES+248

Compound c

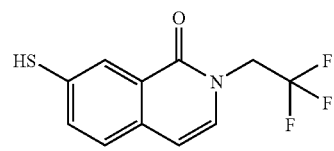 [SMILES: O=c1c2cc(S)ccc2ccn1CC(F)(F)F]

2-(2,2,2-trifluoroethyl)-7-mercaptoisoquinolin-1(2H)-one

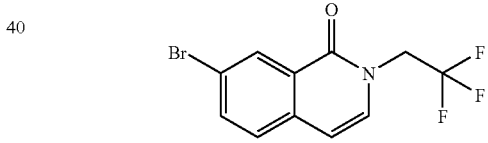

7-bromo-2-(2,2,2-trifluoroethyl)isoquinolin-1(2H)-one

To a stirred solution of 7-bromoisoquinolin-1(2H)-one (5 g, 22.3 mmol) and iodotrifluoroethane (4.9 g, 23.4 mmol) in dimethylacetimide cooled to 5° C. was added sodium hydride 60% wt (0.89 g 22.3 mmol) portion wise over 5 minutes. After complete addition reaction mixture allowed to warm up to room temperature over 2 hours and then heated at 50° C. for 24 hours. Reaction mixture was evaporated to leave a residue, which was diluted with ethyl acetate (200 ml) and water (200 ml). The aqueous layer was further extracted with ethyl acetate (2×50 ml) and organic layers were combined and washed with saturated aqueous bicarbonate (200 ml), brine (200 ml) and dried over Magnesium sulfate powder, filtered and concentrated under reduced pressure to leave a residue and purified using column chromatography eluting with 50% ethyl acetate/petrol ether to give a yellow solid which was still impure by LCMS (1.53 g, 22% yield)

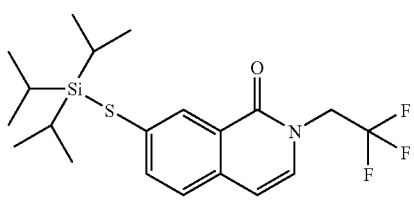

2-(2,2,2-trifluoroethyl)-7-((triisopropylsilyl)sulfanyl)
isoquinolin-1(2H)-one 7-bromo-2-(2,2,2-trifluoroethyl)isoquinolin-1(2H)-one (0.5 g, 1.63 mmol), cesium carbonate (0.693 g 2.1 mmol), Palladium acetate (0.018 g, 0.08 mmol) and triphenylphoshine (0.094 g, 0.36 mmol) in anhydrous toluene in a microwave vessel was degassed with nitrogen, trisiopropylsilane thiol (0.404 g 0.36 mmol) was added to the vessel and the vessel was then subjected to heating at 100° C. in a microwave reactor for 2 hours. The reaction mixture was diluted with petroleum ether and the solid precipitate was removed by filtration and the filtrate was evaporated and the residue was purified by column chromatography eluting with ethyl acetate/petroleum (3:7) ether to give an oil (1.05 g, 50% yield).

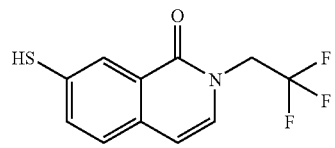 [SMILES: O=c1c2cc(Br)ccc2ccn1CC(F)(F)F]

2-(2,2,2-trifluoroethyl)-7-mercaptoisoquinolin-1(2H)-one 2-(2,2,2-trifluoroethyl)-7-((triisopropylsilyl)sulfanyl)isoquinolin-1(2H)-one was dissolved in a solution of hydrochloric acid in methanol (2 ml) and tetrahydrofuran (2 ml) and stirred at room temperature for 2 hours or until disappearance of starting material. Reaction mixture was concentrated to give the desired material (quant yield).

Compound d

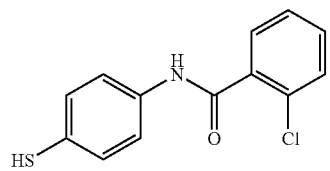 [SMILES: O=C(Nc1ccc(S)cc1)c1ccccc1Cl]

2-chloro-N-(4-mercaptophenyl)benzamide

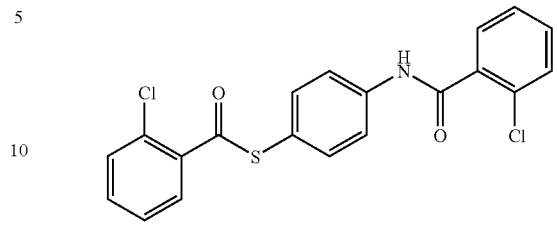

S-4-(2-chlorobenzamido)phenyl
2-chlorobenzothioate

Degassed EtOAc (3.2 L) is charged in a flask. The solvent is cooled to 0° C. under nitrogen. 4-aminobenzenethiol (435 g, 3.48 mol) is melted and added directly to the flask. Triethylamine (773 g, 7.65 mol) is added over 30 minutes forming a precipitate. Then, 2-chlorobenzoyl chloride (1340 g, 7.65 mol) is added neat keeping the temperature below 5° C. After complete addition, the mixture is heated to 20° C. for one hour. The slurry is filtered and the cake washed with EtOAc (780 mL). The material is dried at 50° C. under vacuum with a nitrogen sweep until a constant weight is obtained and carried to the next reaction without further purification.

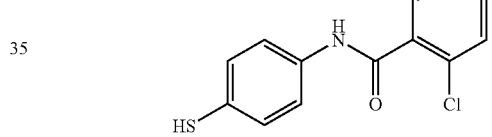

2-chloro-N-(4-mercaptophenyl)benzamide

S-4-(2-chlorobenzamido)phenyl 2-chlorobenzothioate (305 g, 0.76 mol), EtOAc (325 mL), and water (65 mL) are charged to a flask fitted with reflux condenser. A solution of NaOH (3 eq., 50% aq.) is added and the mixture heated to 70° C. for 30-40 minutes. EtOAc was removed by distillation at 100 mm Hg and the mixture cooled to 5° C. The mixture was acidified with 6N HCl to pH 2. The solid is collected by vacuum filtration and washed with water (390 mL). The solid is taken up in CH2Cl2 (520 mL) and washed with saturated aqueous NaHCO3. The organic layer is dried over Na2SO4, filtered, and concentrated to give the desired material (174 g, 87%).

Compound e

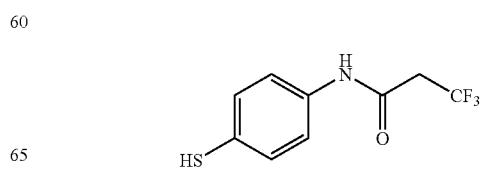

3,3,3-trifluoro-N-(4-mercaptophenyl)propanamide

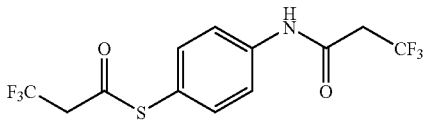 [SMILES: O=C(CC(F)(F)F)Nc1ccc(SC(=O)CC(F)(F)F)cc1]

S-4-(3,3,3-trifluoropropanamido)phenyl
3,3,3-trifluoropropanethioate

4-Aminothiophenol is melted and charged to a flask. Degassed EtOAc (1950 mL) was added. A solution of $K_2CO_3$ (92 g, 670 mmol) in degassed $H_2O$ (1300 vol) was then added. The solution was cooled to 0° C. and the 3,3,3-trifluoropropanoyl chloride (55.2 g, 600 mmol) was slowly added to keep the temperature below 10° C.). The reaction was then warmed to room temperature. The organic layer was separated and washed with brine (1300 mL). The organic layer was then concentrated on the rotary evaporator. The solid was slurried in Heptane/EtOAc (390 mL/390 mL) for 30 min. Heptane (780 mL) was then added and the slurry was cooled to 0° C. for 30 min. The slurry was filtered and the filter cake was dried under vacuum to give the desired compound (51.3 g, 87.2%).

3,3,3-trifluoro-N-(4-mercaptophenyl)propanamide

S-4-(3,3,3-trifluoropropanamido)phenyl 3,3,3-trifluoropropanethioate (44.8 g, 189 mmol) and EtOH (70 mL) are charged to a flask. Concentrated HCl (22.5 mL) is slowly added to keep the temp below 30° C. The reaction is then heated to 50° C. for 17.5 h. The reaction mixture is reduced to 41 mL by vacuum distillation at 50° C. Cool the reaction to room temperature and H2O (51 mL) is added. The slurry is filtered and the filter cake is washed with H2O (3×35 mL). The solid is dried under vacuum to produce the desired compound (19.9 g, 58%).

Table 8 depicts data for additional exemplary compounds of this invention.

Compounds 47, 48, 49, 50, 51, 52, 53, 54, 55, 56, 57, 58, 59, 60, 61, 63, 64, 65, 66, 67, 69, 71, 75, 76, 78, 80, 81, 82, 84, 85, 86, 88, 89, 90, 91, 93, 94, 95, 97, 98, 99, 101, 102, 103, 104, 105, 106, 107, 109, 111, 115, 122, 123, 124, 125, 126, 127, 128, 129, 130, 131, 133, 134, 135, 136, 142, 143, 144, 145, 146, 147, 148, 149, 150, 151, 153, 155, 156, 157, 159, 160, 169, 174, 176, 178, 180, 182, 184, 185, 187, 191, 193, 198, 199, 200, 203, 204 and 208 were made according to the method described in Scheme II and in Examples 6-8.

Compounds 68, 70, 96, 100, 110, 112, 113, 119, 141, 170, 172, 173, 175, 177, 186, 194, 195 and 202 were made according to the method described in General Scheme (method B) and in example 14.

Compounds 171, 179, 188, 189, 190, 201, 206 and 210 were made according to the method described in General Scheme (method A) and in example 24.

Compounds 72, 73, 74, 83, 87, 108, 114, 116, 117, 120, 121, 137, 138, 139, 140, 152, 158, 161, 162, 163, 164, 165, 166, 167, 207 and 211 were made according to the method described in Scheme VII and in Example 11.

Compound 181 was made according to the method described in Scheme I and in Example 1-2.

Compound 132 was made according to the method described in Scheme IX and in Example 23.

Compound 192 was made according to the method described in Scheme II and in Example 21.

Compounds 183, 196 were made according to the method described in Example 22.

Compound 205 was made according to the method described in Example 9-10.

TABLE 8

| Compound No | M + 1 (obs) | 1H NMR | Rt (mins) |
|---|---|---|---|
| I-47 | 432.40 | (DMSO-d6) 2.09 (3H, s), 2.30 (2H, m), 3.91 (4H, masked signal), 5.68 (1H, s), 5.81 (1H, brs), 6.38 (1H, t), 6.54 (1H, d), 7.45-7.60 (3H, m), 7.64-7.81 (3H, m), 9.50 (1H, brs). | 8.16 |
| I-48 | 492.00 | (DMSO-d6): 2.00-2.05 (3H, s), 2.25-2.35 (2H, m), 3.85-3.90 (4H, t), 5.40-5.45 (1H, s), 7.30-7.35 (1H, m), 7.40-7.45 (1H, t), 7.55-7.60 (2H, t), 7.70-7.75 (2H, d), 8.00-8.05 (2H, d), 9.25-9.30 (1H, s), 10.15 (1H, s). | 9.528 |
| I-49 | 492.00 | (DMSO-d6): 2.05-2.10 (3H, s), 2.25-2.35 (2H, m), 3.85-3.90 (4H, t), 5.35-5.40 (1H, s), 5.60-5.80 (1H, br s), 7.30-7.35 (1H, d), 7.40-7.60 (5H, m), 7.85-7.90 (1H, m), 7.95 (1H, s), 9.20-9.25 (1H, s), 10.60-10.65 (1H, s). | 9.004 |
| I-50 | 522.60 | (DMSO-d6) 1.41 (3H, s), 2.05 (3H, s), 3.69-3.77 (4H, m), 5.41 (1H, brs), 5.60 (1H, vbrs), 7.47-7.85 (6H, m), 7.82-7.85 (2H, m), 9.24 (1H, brs), 10.74 (1H, brs), 11.69 (1H, brs) | 8.45 |
| I-51 | 536.60 | (DMSO-d6) 1.44 (3H, s), 2.06 (3H, s), 3.19 (3H, s), 3.69 (2H, d), 3.83 (2H, d), 5.41 (1H, brs), 5.60 (1H, vbrs), 7.45-7.61 (6H, m), 7.82-7.87 (2H, m), 9.28 (1H, brs), 10.75 (1H, brs), 11.69 (1H, brs) | 9.1 |
| I-52 | 458.50 | (DMSO-d6): 1.99 (3H, s), 2.29 (2H, m), 3.89 (4H, m), 5.31 (1H, s), 5.51 (1H, br s), 7.62 (5H, m), 7.93 (4H, m), 9.21 (1H, s), 10.54 (1H, s), 11.91 (1H, s) | 8.965 |
| I-53 | 492.52 | (DMSO-d6): 1.99 (3H, s), 2.33 (2H, m), 3.89 (4H, m), 5.39 (1H, s), 5.60 (1H, br s), 7.58 (3H, m), 7.69 (1H, d), 7.91 (3H, m), 8.00 (1H, d), 9.24 (1H, s), 10.56 (1H, s), 11.77 (1H, s) | 9.598 |
| I-54 | 492.52 | (DMSO-d6): 1.99 (3H, s), 2.33 (2H, m), 3.90 (4H, m), 5.39 (1H, s), 5.60 (1H, br s), 7.56 (2H, d), 7.65 (2H, d), 7.92 (2H, d), 7.99 (2H, d), 9.38 (1H, s), 10.54 (1H, s) | 9.540 |
| I-55 | 544.59 | (DMSO-d6): 2.03 (3H, s), 2.34 (2H, m), 3.89 (4H, m), 5.37 (1H, s), 5.56 (1H, br s), 7.57 (3H, m), 7.82 (2H, s), 7.99 (2H, m), 9.42 (1H, s), 10.90 (1H, s), 11.90 (1H, s) | 9.636 |
| I-56 | 526.61; | (DMSO-d6) 2.05 (3H, s), 2.33 (2H, m), 3.96 (4H, m), 5.48 (1H, s), 5.60 (1H, brs), 7.58 (2H, d), 7.62-7.92 (6H, m), 9.54 (1H, brs), 10.84 (1H, brs). | 9.16 |
| I-57 | 506.58 | (DMSO-d6) 2.00 (3H, s), 2.30 (2H, m), 3.81-3.91 (6H, m), 5.37 (1H, s), 5.56 (1H, brs), 7.28-7.38 (2H, m), 7.40-7.55 (4H, m), 7.71 (2H, d), 9.20 (1H, brs), 10.41 (1H, brs), 11.66 (1H, s). | 9.20 |
| I-58 | 506.54 | (DMSO-d6) 1.90 (3H, s), 2.30 (2H, m), 3.68 (2H, s), 3.95 (4H, m), 5.37 (1H, s), 5.55 (1H, brs), 7.28-7.58 (6H, m), 7.75 (2H, d), 9.45 (1H, brs), 10.50 (1H, s). | 9.41 |

TABLE 8-continued

| Compound No | M + 1 (obs) | 1H NMR | Rt (mins) |
|---|---|---|---|
| I-59 | 527.00; | (DMSO-d6) 2.04 (3 H, s), 2.34-2.27 (2 H, m), 3.92-3.89 (4 H, m), 5.45 (1 H, s), 5.59 (1 H, br s), 7.59 (2 H, d), 7.80 (2 H, d), 7.94 (1 H, d), 9.0 (2 H, m), 9.37 (1 H, br s), 11.01 (1 H, s). | 8.837; |
| I-60 | 510.50 | DMSO 2.05 (3H, s), 3.9-4.01 (2H, m), 4.17-4.26 (2H, m), 5.38-5.42 (2H, m), 5.52-5.54 (0.5H, m), 7.45-7.61 (6H, m), 7.86 (2H, d), 9.34 (1H, brs), 10.76 (1H, s), 11.70 (1H, brs) | 8.99 |
| I-61 | — | (DMSO-d6): 2.02 (3H, s), 2.33 (2H, m), 3.90 (4H, m), 5.36 (1H, s), 5.55 (1H, br s), 7.41 (1H, t), 7.58 (2H, d), 7.62 (1H, m), 7.78 (1H, m), 9.35 (1H, s), 10.67 (1H, s), 11.83 (1H, s) | 9.451 |
| I-62 | 520.52 | (DMSO-d6): 2.16 (5H, m), 3.24 (2H, m), 3.98 (2H, m), 4.18 (1H, s), 5.62 (1H, br s), 6.94 (1H, br s), 7.54 (6H, m), 7.87 (2H, d), 10.25 (1H, s), 10.78 (1H, s), 11.92 (1H, s) | 9.232 |
| I-63 | 473.00 | (DMSO-d6) 2.05 (3 H, s), 2.36-2.27 (2 H, m), 2.62 (3 H, s), 3.91 (4 H, t), 5.42 (1 H, s), 5.58 (1 H, br s), 7.52-7.49 (1 H, m), 7.58 (2 H, d), 7.85 (2 H, d), 8.01 (1 H, d), 8.66-8.64 (1 H, m), 9.41 (1 H, s), 10.76 (1 H, s). | 8.274 |
| I-64 | 506.55 | (DMSO-d6): 107 (3H, t), 2.29 (2H, m), 2.42 (2H, m), 3.17 (3H, s), 3.88 (4H, m), 4.11 (1H, m), 5.47 (1H, s), 5.66 (1H, br s), 7.56 (6H, m), 7.81 (2H, d), 9.23 (1H, s), 10.71 (1H, s), 11.74 (1H, s) | 9.232 |
| I-65 | 518.64 | (DMSO-d6): 0.54 (2H, m), 0.84 (2H, m), 1.71 (1H, m), 2.31 (2H, m), 3.17 (3H, d), 3.87 (4H, m), 4.12 (1H, m), 5.49 (1H, s), 5.72 (1H, br s), 7.54 (6H, m), 7.83 (2H, d), 9.20 (1H, s), 10.70 (1H, s), 11.74 (1H, s) | 9.316 |
| I-66 | 564.70 | DMSO 1.16 (9H, s), 2.06 (3H, s), 3.59-3.64 (2H, m), 4.09-4.17 92H, m), 4.58-4.64 (1H, m), 5.39 (1H, s), 5.55-5.68 (1H, vbrs), 7.45-7.62 (6H, m), 7.82-7.86 (2H, m), 9.26 (1H, brs), 10.74 (1H, brs), 11.68 (1H, brs) | 9.71 |
| I-67 | 482.60 | DMSO 1.09 (3H, t), 1.14 (9H, s), 1.98 (3H, s), 2.34 (2H, q), 3.51-3.62 (2H, m), 4.02-4.12 (2H, m), 5.34 (1H, brs), 5.55 (1H, vbrs), 7.47 (2H, d), 7.71 (2H, d), 9.22 (1H, brs). 10.09 (1H, s), 11.67 (1H, brs) | 9.11 |
| I-68 | 495.00 | (CD3OD): 1.20-1.25 (3H, t), 2.15-2.20 (3H, s), 2.40-2.50 (2H, qd), 3.05-3.15 (4H, m), 3.80-3.90 (4H, br s), 4.00-4.05 (1H, m), 4.20-4.25 (2H, m), 4.30-4.38 (2H, m), 5.45 (1H, s), 5.75 (1H, s), 7.60-7.64 (2H, d), 7.66-7.70 (2H, d). | 7.656 |
| I-69 | 534.00 | (400 MHz, DMSO) 1.17 (9H, s), 2.23-2.36 (2H, m), 3.80-3.93 (4H, m), 5.66 (1H, s), 6.00 (1H, brs), 7.40-7.65 (6H, m), 7.75-7.85 (2H, m), 9.22 (1H, brs), 10.67 (1H, s), 11.89 (1H, brs). | 9.69 |
| I-70 | 465.00 | (CD3OD): 1.20-1.25 (3H, t), 2.15-2.20 (3H, s), 2.45-2.65 (4H, m), 4.05-4.10 (2H, m), 4.15-4.30 (4H, br s), 4.35-4.45 (3H, m), 5.45 (1H, s), 5.60 (1H, s), 7.60-7.70 (4H, m) | 7.975 |
| I-71 | 440.37 | (DMSO-d6) 1.05-1.15 (3H, t, CH3), 1.4 (3H, s, CH3), 2.0 (3H, s, CH3), 2.3-2.4 (2H, q, CH2), 3.7-3.9 (4H, m, alk), 5.45 (H, s, ar), 5.6 (H, s, ar), 7.5-7.55 (2H, d, ar), 7.7-7.75 (2H, d, ar), 9.85 (H, brs, NH) and 10.2 (H, s, NH). | 7.165 |
| I-72 | 453.48 | CD$_3$OD: 1.23 (6H, s), 2.12 (3H, s), 2.39 (2H, m), 3.46 (4H, q), 4.01 (4H, br s), 5.42 (1 H, s), 5.52 (4H, m) | 8.642 |
| I-73 | 439.47 | (DMSO-d6) 0.83 (3H, t), 1.49 (2H, m), 2.31 (2H, m), 3.14 (2H, q), 4.04 (4H, s), 5.55 (4H, s), 6.65 (2H, d), 7.18 (2H, d), 8.27 (1H, t), 10.04 (1H, s) | 9.513 |
| I-74 | 487.51 | (DMSO-d6): 2.28 (3H, s), 2.33 (2H, m), 3.92 (4H, m), 4.36 (2H, d), 5.56 (4H, s), 6.65 (2H, d), 7.19 (2H, d), 7.25 (5H, m), 8.87 (1H, s), 9.95 (1H, s) | 10.081 |
| I-75 | 508.00 | (DMSO-d6) 2.22-2.38 (2H, m), 3.80-3.96 (4H, m), 4.28-4.39 (2H, m), 5.10-5.22 (1H, m), 5.55-5.80 (2H, m), 7.41-7.67 (6H, m), 7.75-7.90 (2H, m), 9.23 91H, s), 10.71 (1H, s), 11.94 (1H, brs). | 8.33 |
| I-76 | 466.41 | NMR (DMSO-d6) 0.5-0.6 (2H, m, (alk), 0.8-0.9 (2H, m, alk), 1.05-.15 (3H, t, CH3), 1.45 (3H, s, CH3), 1.7 (H, m, CH), 2.3-2.4 (2H, q, Ch2), 3.15 (H, brs, OH), 3.75-3.9 (4H, m, alk), 5.5 (H, s, ar), 5.7 (H, brs, ar), 7.5-7.6 (2H, d, ar), 7.7-7.8 (2H, d, ar), 9.8 (H, brs, NH) and 10.2 (H, s, NH) | 7.58 |
| I-77 | 476.00 | (CD3OD): 1.20-1.25 (3H, t), 1.30-1.35 (6H, s), 2.00-2.05 (3H, s), 2.1 (2H, s), 2.35-2.40 (2H, qd), 3.60-3.75 (6H, br s), 5.35-5.45 (1H, s), 6.50-6.60 (1H, s), 7.50-7.55 (2H, d), 7.75-7.80 (2H, d). | 8.487 |
| I-78 | 521.00 | (CD3OD): 0.65-0.70 (2H, m), 0.95-1.00 (2H, m), 1.20-1.25 (3H, t), 1.70-1.75 (1H, s), 2.45-2.50 (2H, qd), 2.95-3.05 (4H, m), 3.80-3.95 (5H, m), 4.10-4.2 (2H, m), 4.30-4.35 (2H, m), 5.45-5.55 (2H, m), 7.60-7.70 (4H, d*d). | 7.754 |
| I-79 | 449.40 | (DMSO-d6) 1.05 (3H, t), 1.65 (3H, s), 2.03 (3H, s), 2.37 (2H, q), 3.88 (2H, d), 4.18 (2H, d), 5.37 (1H, s), 5.60 (1H, brs), 7.50 (2H, d), 7.71 (2H, d), 9.50 (1H, brs), 10.11 (1 H, brs). | 7.93 |
| I-80 | 495.54 | (DMSO-d6) 1.11 (3H, t), 1.35 (9H, s), 1.80 (3H, s), 2.00 (3H, s), 2.35 (2H, q), 3.88 (2H, d), 4.08 (2H, d), 5.36 (1H, brs), 5.67 (1H, brs), 7.45 (2H, d), 7.73 (2H, d), 9.00 (2H, brs), 9.40 (1H, brs), 10.10 (1H, brs). | 8.27 |
| I-81 | 482.00 | (DMSO-d6) 0.90 (9H, s), 1.10 (3H, t), 1.99 (3H, s), 2.33 (2H, q), 3.57 (2H, d), 3.98 (2H, d), 5.36 (1H, brs), 5.61 (1H, brs), 7.49 (2H, d), 7.71 (2H, d), 9.38 (1H, brs), 10.10 (1H, s) | 8.386 |
| I-82 | 522.00 | (DMSO-d6) 2.25-2.38 (2H, m), 3.17 (3H, s), 3.86-3.96 (4H, m), 5.55-5.80 (2H, m), 7.40-7.66 (6H, m), 7.82 (2H, d), 9.33 (1H, s), 10.75 (1H, s), 12.11 (1H, brs). | 8.67 |
| I-83 | 568.50 | (DMSO-d6) 2.07 (3H, s), 2.31 (2H, quintet), 3.92 (4H, t), 5.42 (1H, s), 5.57 (1H, bs), 7.43-7.48 (1H, m), 7.51-7.58 (4H, m), 7.66 (1H, d), 7.75-7.80 (3H, m), 7.82-7.90 (3H, m), 9.40 (1H, bs), 10.80 (1H, s). | 9.69 |
| I-84 | 496.00 | (DMSO-d6) 0.98 (9H, s), 1.10 (3H, t), 1.66 (2H, m), 1.98 (3H, m), 2.34 (2H, q), 3.69 (2H, d), 3.83 (2H, d), 5.35 (1H, brs), 5.70 (1H, s), 5.75 (1H, vbrs), 7.46 (2H, d), 7.70 (2H, d), 9.18 (1H, brs), 10.08 (1H, s), 11.68 (1H, brs). | 8.93 |
| I-85 | 466.00 | (DMSO-d6) 0.29-0.33 (2H, m), 0.40-0.49 (2H, m), 1.10 (3H, t), 1.18-1.21 (1H, m), 1.99 (3H, brs), 2.34 (2H, q), 3.63 (2H, d), 3.68 (2H, d), 5.36 (1H, s), 5.60 (1H, s), 7.47 (2H, d), 7.70 (2H, d), 9.21 (1H, brs), 10.08 (1H, s), 11.67 (1H, brs). | 7.63; |
| I-86 | 502.50 | (DMSO-d6) 1.12 (3H, t), 2.04 (3H, s), 2.42 (2H, q), 4.03-4.2 (4H, m), 5.45 (1H, brs), 5.7 (1H, brs), 6.45 (1H, s), 7.31-7.34 (1H, m), 7.42-7.47 (2H, m), 7.62-7.72 (4H, m), 7.73-7.75 (2H, m), 9.35 (1H, brs), 10.15 (1H, s), 11.7 (1H, s) | 8.39 |
| I-87 | 584.50 | (DMSO-d6) 2.04 (3H, s), 2.25-2.34 (2H, m), 3.90 (4H, t), 5.39 (1H, s), 5.55 (1H, vbs), 7.05 (1H, dd), 7.14 (2H, dd), 7.18 (1H, d), 7.27 (1H, t), 7.47-7.52 (2H, m), 7.55 (2H, d), 7.59 (1H, d), 7.83 (2H, d), 9.34 (1H, bs), 10.71 (1H, s). | 9.63 |
| I-88 | 509.52 | (DMSO-d6) 1.12 (3H, t), 1.65 (3H, s), 1.99 (3H, s), 2.38 (2H, q), 3.17 (2H, m), 3.37 (2H, m), 3.60 (4H, m), 4.05 (2H, m), 4.20 (2H, brd), 5.35 (1H, s), 5.63 (1H, brs), 7.48 | 7.81 |

TABLE 8-continued

| Compound No | M + 1 (obs) | 1H NMR | Rt (mins) |
|---|---|---|---|
| | | (2H, d), 7.72 (2H, d), 9.48 (1H, s), 10.13 (1H, s), 10.50 (1H, brs). | |
| I-89 | 493.50 | (DMSO-d6) 1.08 (3H, t), 1.63 (3H, s), 1.80-2.13 (7H, m), 2.37 (2H, q), 3.21 (2H, m), 3.58 (2H, m), 3.90 (2H, d), 4.15 (2H, d), 5.32 (1H, s), 5.61 (1H, brs), 7.48 (2H, d), 7.75 (2H, d), 9.45 (1H, s), 10.12 (1H, s), 10.57 (1H, s). | 8.14 |
| I-90 | 496.00 | (DMSO-d6) 0.89 (9H, s), 1.10 (3H, t), 1.99 (3H, s), 2.34 (2H, q), 3.37 (3H, s), 3.82 (2H, d), 4.00 (2H, d), 5.35 (1H, s), 5.67 (1H, brs), 7.49 (2H, d), 7.71 (2H, d), 9.43 (1H, s), 10.11 (1H, s) | 9.282 |
| I-91 | 542.00 | (DMSO-d6) 2.22-2.36 (2H, m), 3.81-3.95 (4H, m), 4.31 (2H, d), 5.2 (1H, brs), 5.50-5.90 (2H, m), 7.48-7.65 (4H, m), 7.72-7.85 (3H, m), 9.25 (1H, brs), 10.80 (1H, s), 11.95 (1H, brs). | 8.74 |
| I-92 | 480.00 | (DMSO-d6) 1.08 (3H, m), 1.20 (6H, s), 1.98 (3H, s), 2.34 (2H, q), 3.78 (2H, d), 4.14-4.15 (4H, m), 5.35 (1H, s), 5.61 (1H, brs), 7.47 (2H, d), 7.70 (2H, d), 9.24 (1H, s), 10.07 (1H, s), 11.43 (1H, s) | 8.307 |
| I-93 | 516.46 | (DMSO-d6) 1.10 (3H, m), 1.98 (3H, s), 2.34-2.43 (5H, m), 4.05 (2H, m), 4.38 (2H, m), 5.35 (1H, s), 6.15 (1H, br s), 7.18 (1H, m), 7.35 (1H, m), 7.47 (2H, m), 7.70 (2H, m), 9.21 (1H, br s), 10.07 (1H, s) | 8.540 |
| I-94 | 494.41 | (DMSO-d6) 1.10 (3 H, t), 2.02 (3 H, s), 2.35 (2 H, q), 3.14 (1 H, br s), 3.90 (2 H, d), 4.14 (2 H, d), 5.43 (1 H, s), 5.68 (1 H, br s), 7.49 (2 H, d), 7.72 (2 H, d), 9.54 (1 H, br s), 10.09 (1 H, s). | 8.162 |
| I-95 | 482.46 | (DMSO-d6) 1.11 (9H, m), 1.51 (1H, s), 2.06 (3H, s), 2.40 (2H, q), 3.71-3.90 (5H, m), 5.45 (1H, s), 5.62 (1H, brs), 7.51 (2H, d), 7.78 (2H, d), 9.89 (1H, brs), 10.20 (1H, s). | 9.03 |
| I-96 | 496.51 | (DMSO-d6) 1.11 (3H, t), 1.25 (9H, s), 1.60 (3H, s), 2.03 (3H, s), 2.38 (2H, q), 3.72-3.87 (4H, m), 5.42 (1H, s), 5.65 (1H, brs), 7.51 (2H, d), 7.74 (2H, d), 9.68 91H, brs), 10.12 (1H, s). | 9.42 |
| I-97 | 494.50 | (DMSO-d6) 1.15 (3H, t), 1.3-1.4 (2H, m), 1.5-1.8 (6H, m), 2.02 (3H, s), 2.17-2.23 (1H, m), 2.42 (2H, q), 3.68 (2H, d), 3.82 (2H, d), 5.5 (1H, s), 5.65 (1H, s), 5.72 (1H, brs), 7.52 (2H, d), 7.78 (2H, d), 9.22 (1H, brs), 10.12 (1H, s), 11.7 (1H, brs) | 8.9 |
| I-98 | 454.00 | (DMSO-d6) 0.89 (3H, t), 1.10 (3H, t), 1.65 (2H, brq), 1.99 (3H, brs), 2.35 (2H, q), 3.64 (2H, d), 3.75 (2H, d), 5.38 (1H, brs), 5.51 (1H, s), 5.62 (1H, vbrs), 7.47 (2H, d), 7.70 (2H, d), 9.16 (1H, brs), 10.05 (1H, brs), 11.65 (1H, brs). | 7.87 |
| I-99 | 468.00 | (DMSO-d6) 0.87 (6H, d), 1.10 (3H, t), 1.81 (1H, sep), 1.99 (3H, brs), 2.34 (2H, q), 3.61 (2h, d), 3.81 (2H, d), 5.37 (1H, brs), 5.47 (1H, brs), 5.63 (1H, vbrs), 7.47 (2H, d), 7.70 (2H, d), 9.17 (1H, brs), 10.05 (1H, s), 11.65 (1H, brs). | 8.35 |
| I-100 | 482.49 | (DMSO-d6) 0.90-0.83 (6 H, m), 1.12-1.08 (4 H, m), 1.54-1.46 (2 H, m), 2.02 (3 H, s), 2.35 (2 H, q), 3.14 (1 H, br m), 3.68 (2 H, t), 3.88 (2 H, t), 5.40 (1 H, s), 5.61 (1 H, br s), 7.50 (2 H, d), 7.72 (2 H, d), 9.63 (1 H, br s), 10.14 (1 H, s). | 8.830 |
| I-101 | 508.00 | (DMSO-d6) 1.05-1.30 (8H, m), 1.45 (1H, brt), 1.61-1.71 (3H, m), 1.75-1.82 (2H, m), 1.99 (3H, brs), 2.34 (2H, q), 3.59 (2H, d), 3.83 (2H, d), 5.37 (1H, brs), 5.44 (1H, s), 5.65 (1H, vbrs), 7.47 (2H, d), 7.69 (2H, d), 9.16 (1H, brs), 10.05 (1H, s), 11.65 (1H, brs). | 9.34 |
| I-102 | 492.84 | (DMSO-d6) 0.32 (2H, d), 0.41 (2H, d), 0.53 (2H, m), 0.82 (2H, d), 1.08 (3H, t), 1.20 (1H, m), 1.70 (1H, m), 2.34 (2H, q), 3.65 (4H, q), 5.34 (1H, s), 5.68 (1H, br s), 7.52 (2H, d), 7.71 (2H, d), 9.33 (1H, s), 10.04 (1H, s) | 8.402 |
| I-103 | 478.78 | (DMSO-d6) 0.34 (2H, d), 0.40 (2H, d), 0.81 (4H, d), 1.19 (1H, m), 1.81 (1H, m), 2.01 (3H, s), 3.66 (4H, q), 5.40 (1H, s), 5.61 (1H, br s), 7.48 (2H, d), 7.71 (2H, d), 9.37 (1H, s), 10.39 (1H, s) | 8.229 |
| I-104 | 506.00 | (DMSO-d6) 0.30-0.35 (2H, m), 0.39-0.44 (2H, m), 1.16-1.21 (1H, m), 1.56-1.75 (6H, m), 1.83-1.90 (2H, m), 2.00 (3H, s), 2.76-2.82 (1H, m), 3.65 (4H, dd), 5.35 (1H, s), 5.58 (1H, s), 7.47 (2H, d), 7.72 (2H, d), 9.19 (1H, s), 10.06 (1H, s), 11.65 (1H, s). | 8.938 |
| I-105 | 504.83 | (DMSO-d6) 0.32 (2H, d), 0.42 (2H, d), 0.55 (2H, m), 0.82 (6H, d), 1.19 (1H, m), 1.70 (1H, m), 1.80 (1H, m), 3.65 (4H, q), 5.43 (1H, s), 5.65 (1H, br s), 7.47 (2H, d), 7.69 (2H, d), 9.68 (1H, s), 10.42 (1H, s) | 8.544 |
| I-106 | 479.78 | (DMSO-d6) 0.32 (2H, d), 0.40 (2H, d), 0.49 (2H, d), 0.81 (2H, d), 1.19 (1H, m), 1.74 (1H, m), 3.63 (4H, m), 3.87 (3H, s), 5.44 (1H, s), 5.81 (1H, br s), 7.75 (1H, m), 8.00 (2H, d), 9.29 (1H, s) | 9.321 |
| I-107 | 520.00 | (DMSO-d6) 0.44-0.47 (2H, m), 0.57-0.61 (1H, m), 0.82-0.89 (4H, m), 1.54-1.60 (1H, m), 1.79-1.85 (1H, m), 2.02-2.05 (3H, m), 2.06-2.07 (3H, m), 3.76-3.80 (2H, m), 3.85-3.90 (2H, m), 5.38 (1H, s), 5.64 (1H, brs), 7.47-7.51 (2H, m), 7.70-7.74 (2H, m), 9.28 (1H, s), 10.39-10.41 (1H, m), 11.69 (1H, s) | 9.198 |
| I-108 | 354.68 | (DMSO-d6) 2.1 (3H, s, Ch3), 2.3-2.4 (2H, m, alk), 3.9-4.0 (4H, m, alk), 5.65-5.7 (3H, m, NH2, ar), 6.65-6.75 (2H, m, ar), 7.2-7.3 (2H, m, ar) and 9.6 (1H, brs, NH) | 7.81 |
| I-109 | 496.90 | (DMSO-d6) 1.33-1.36 (2H, m), 1.48-1.52 (2H, m), 1.82-1.86 (4H, m), 1.18-1.23 (2H, m), 2.08 (3H, m), 2.10-2.15 (1H, m), 3.68-3.75 (4H, m), 5.5 (1H, brs), 5.67 (1H, s), 5.8 (1H, brs), 7.42 (1H, d), 7.58 (1H, d), 8.11-8.17 (1H, m), 9.27 (1H, s), 10.15 (1H, s), 11.9 (1H, brs) | 8.6 |
| I-110 | 496.90 | (DMSO-d6) 0.33-0.36 (2H, m), 0.42-0.48 (2H, m), 0.82-0.86 (4H, m), 1.21-1.24 (2H, m), 1.85-1.89 (1H, m), 2.08 (3H, m), 2.10-2.15 (1H, m), 3.66-3.75 (4H, m), 5.42 (1H, brs), 5.67 (1H, s), 5.8 (1H, brs), 7.42 (1H, d), 7.52-7.58 (1H, m), 7.75 (1H, d), 9.27 (1H, s), 10.65 (1H, s), 11.9 (1H, brs) | 8.52 |
| I-111 | 534.00 | (DMSO-d6) 0.32-0.36 (2H, m), 0.54-0.57 (2H, m), 0.80-0.86 (4H, m), 0.88-0.91 (3H, t), 1.15-1.24 (1H, m), 1.32-1.40 (2H, m), 1.46-1.53 (2H, m), 1.80-1.84 (1H, m), 1.99 (3H, s), 3.47 (2H, t), 3.51 (2H, d), 3.64 (2H, d), 5.37 (1H, s), 5.59 (1H, brs), 7.47 (2H, d), 7.69 (2H, d), 9.21 (1H, s), 10.37 (1H, s), 11.66 (1H, s) | 10.237 |
| I-112 | 458.70 | (DMSO-d6) 1.12 (3H, s), 2.02-2.15 (5H, m), 2.3-2.4 (2H, m), 2.8-2.9 (1H, m), 3.85-3.92 (4H, m), 5.42 (1H, s), 5.65 (1H, brs), 7.55 (2H, d), 7.75 (2H, d), 9.2 (1H, brs), 10.7 (1H, s), 11.7 (1H, brs) | 8.34 |
| I-113 | 514.80 | (DMSO-d6) 0.35-0.41 (2H, m), 0.45-0.51 (2H, m), 1.2-1.28 (2H, s), 2.1-2.15 (5H, m), 2.8-2.9 (1H, m), 3.68-3.75 (4H, m), 5.45 (1H, s), 5.65 (1H, brs), 7.58 (2H, d), 7.78 (2H, d), 9.23 (1H, brs), 10.7 (1H, s), 11.7 (1H, brs) | 8.18 |
| I-114 | 438.00 | (CD3OD): 1.30 (9H, s), 2.07 (3H, s), 2.35-2.40 (2H, m), 3.95-4.02 (4H, m), 5.35-5.40 (1H, br s), 5.47 (1H, s), 7.55-7.60 (2H, d), 7.70-7.75 (2H, d). | 9.119 |
| I-115 | 556.00 | (DMSO-d6) 1.41 (3H, s), 2.05 (3H, s), 3.73 (4H, q), 5.47 (1H, s), 5.60 (1H, s), 7.55 (2H, d), 7.68-7.89 (6H, m), 9.20 (1H, s), 10.77 (1H, s), 11.67 (1H, s) | 8.761 |

TABLE 8-continued

| Compound No | M + 1 (obs) | 1H NMR | Rt (mins) |
|---|---|---|---|
| I-116 | 488.24 | (DMSO-d6) 2.0 (3H, s, Me), 2.27-2.32 (2H, m, alk), 3.85-3.90 (6H, m, alk and Me), 5.41 (H, s, ar), 5.65 (H, brs, ar), 7.18 (1H, m, ar), 7.45-7.56 (5H, m, ar), 7.90-7.91 (2H, d, ar), 9.17 (H, s, NH), 10.40 (H, s, NH) and 11.65 (H, s, NH). | 9.24 |
| I-117 | 488.24 | (DMSO-d6) 1.99 (3H, s, Me), 2.28-2.31 (2H, m, alk), 3.85-3.90 (6H, m, alk and Me), 5.41 (H, s, ar), 5.65 (H, brs, ar), 7.08-7.10 (2H, d, ar), 7.52-7.54 (2H, d, ar), 7.89-7.92 (2H, d, ar), 7.96-7.98 (2H, d, ar), 9.17 (H, s, NH), 10.27 (H, s, NH) and 11.65 (H, s, NH). | 9.126 |
| I-118 | 492.27 | (DMSO-d6) 0.34 (2H, m), 0.55 (2H, m), 0.81 (4H, d), 1.14 (1H, m), 1.81 (1H, m), 1.99 (3H, s), 3.26 (3H, s), 3.79 (4H, m), 5.37 (1H, s), 5.71 (1H, br s), 7.49 (2H, d), 7.71 (2H, d), 9.34 (1H, s), 10.39 (1H, s). | 9.106 |
| I-119 | 563.00 | (DMSO-d6) 0.46-0.48 (2H, m), 0.57-0.60 (2H, m), 0.81 (4H, d), 1.55-1.60 (1H, m), 1.77-1.82 (1H, m), 1.99 (3H, brs), 2.25 (6H, s), 3.19 (3H, s), 3.79 (2H, d), 3.86 (2H, d), 5.37 (1H, brs), 6.52 (1H, s), 7.47 (2H, d), 7.69 (2H, d), 9.27 (1H, brs), 10.38 (1H, s), 11.67 (1H, brs). | 9.15 |
| I-120 | 508.21 | (DMSO-d6) 2.04 (3H, s, CH3), 2.28-2.32 (2H, m, alk), 3.17 (3H, s, CH3), 3.87-3.91 (4H, t, alk), 4.08 (H, m, alk), 5.4 (H, brs, ar), 5.6 (H, brs, ar), 7.19-7.49 (H, t, CHF2), 7.55-7.57 (2H, d, ar), 7.70-7.80 (4H, m, ar), 7.84-7.86 (2H, d, ar), 9.2 (H, s, NH), 10.75 (H, s, NH) and 11.65 (H, brs, NH) | 9.214 |
| I-121 | 478.00 | (DMSO-d6) 1.9-5-2.00 (3H, s), 2.20-2.30 (3H, m), 2.30-2.40 (2H, m), 2.50-2.60 (3H, m), 5.35-5.40 (1H, s), 5.50-5.65 (1H, br s), 7.40-7.45 (2H, d), 7.60-7.65 (2H, d), 9.10-9.15 (1H, s), 10.25-10.30 (1H, s). | 8.883 |
| I-122 | 565.00 | (DMSO-d6) 1.64 (3H, s), 2.05 (3H, s), 3.87 (2H, d), 4.20 (2H, d), 5.46 (1H, s), 7.56 (2H, d), 7.68 (1H, d), 7.72-7.85 (4H, m), 7.88 (1H, d), 9.36 (1h, s), 10.78 (1H, s), 11.72 (1H, s) | 9.086 |
| I-123 | 478.00 | (DMSO-d6) 0.80-0.82 (4H, m), 1.80-1.90 (2H, m), 2.06 (3H, s), 2.08 (2H, t), 3.76 (2H, t), 3.80 (2H, d), 3.89 (2H, d), 5.38 (1H, s), 5.61 (1H, brs), 7.47 (2H, d), 7.69 (2H, d), 9.20 (1H, s), 10.37 (1H, s), 11.66 (1H, brs) | 8.441 |
| I-124 | 501.34 | (DMSO-d6) 2.02 (3H, s, alk), 2.29-2.33 (2H, m, alK), 2.83 (6H, s, (CH3)2N), 3.89-3.92 (4H, m, alk), 5.5 (H, s, ar), 5.6 (H, brs, ar), 7.16 (H, t, ar), 7.31-7.33 (H, m, ar), 7.5 (H, t, ar), 7.55-7.57 (2H, d, ar), 7.70-7.72 (H, d, ar), 7.84-7.86 (2H, d, ar), 9.3 (H, s, NH) and 11.5 (H, s, NH) | 9.589 |
| I-125 | 480.31 | (DMSO-d6) 0.31 (2H, d), 0.40 (2H, d), 1.16 (4H, m), 2.11 (3H, s), 2.96 (3H, d), 3.35 (1H, s), 3.61 (1H, s), 3.68 (4H, m), 5.66 (1H, br s), 5.82 (1H, br s), 7.50 (2H, s), 7.66 (2H, d), 9.35 (1H, s), 11.93 (1H, br s) | 8.305 |
| I-126 | 556.30 | (DMSO-d6) 2.07 (3H, s), 3.25 (3H, s), 3.7-3.73 (2H, m), 4.1-4.14 (2H, m), 4.3-4.34 (1H, m), 5.5 (1H, brs), 5.7 (1H, vbrs), 7.62 (2H, d), 7.68-7.92 (6H, m), 9.28 (1H, brs), 10.8 (1H, s), 11.7 (1H, brs) | 8.96 |
| I-127 | 492.00 | (MeOD): 1.25-1.30 (3H, s), 2.05-2.10 (3H, s), 2.30-2.40 (2H, m), 2.65-2.80 (2H, m), 2.85-2.95 (1H, m), 3.95-4.05 (4H, m), 5.35-5.40 (1H, s), 5.45-5.50 (1H, s), 7.50-7.55 (2H, d), 7.65-7.70 (2H, d). | 8.985 |
| I-128 | 480.00 | (MeOD): 0.40-0.45 (2H, m), 0.57-0.62 (2H, m), 0.80-0.85 (2H, m), 0.90-0.95 (2H, m), 1.30-1.40 (1H, m), 1.80-1.85 (1H, m), 2.05-2.10 (1H, s), 3.80-4.00 (4H, m), 5.40-5.50 (2H, m), 7.50-7.55 (2H, d), 7.65-7.70 (2H, d). | 9.148 |
| I-129 | 664.00 | (DMSO-d6) 1.20 (3H, t), 1.67 (3H, s), 2.05 (3H, s), 3.85 (2H, d), 3.95 (2H, q), 4.08 (2H, d), 5.47 (1H, s), 5.60 (1H, brs), 7.55 (2H, d), 7.68 (1H, d), 7.72-7.76 (1H, m), 7.79-7.84 (3H, m), 7.87 (1H, d), 9.30 (1H, s), 10.78 (1H, s), 11.81 (1H, brs) | 7.826 |
| I-130 | 500.21 | (DMSO-d6) 2.00 (3H, s), 3.56 (2H, q), 4.44 (4H, m), 5.36 (1H, s), 5.80 (1H, br s), 7.51 (2H, d), 7.70 (2H, d), 9.45 (1H, s), 10.51 (1H, s) | 8.989 |
| I-131 | 445.00 | (DMSO-d6) 0.30-0.35 (2H, m), 0.37-0.43 (2H, m), 1.15-1.22 (1H, m), 1.59 (3H, brs), 3.66 (4H, q), 5.21 (1H, s), 5.58 (1H, s), 5.69 (1H, brs), 7.55-7.65 (3H, m), 7.96-8.00 (3H, m), 8.21 (1H, s), 9.19 (1H, s), 11.58 (1H, brs) | |
| I-132 | 540.20 | (DMSO-d6) 2.05-2.11 (3H, m), 4.0-4.13 (4H, m), 4.32-4.37 (2H, m), 5.5 (1H, brs), 6.5 (1H, brs), 7.62 (2H, d), 7.67-7.8 (2H, m), 7.8-7.95 (4H, m), 10.15-10.3 (2H, m), 10.8 (1H, brs), 11.7 (1H, brs) | 8.5 |
| I-133 | 478.00 | (DMSO-d6) 0.30-0.34 (1H, m), 0.39-0.44 (2H, m), 1.15-1.21 (1H, m), 2.00 (3H, s), 2.09 (2H, q), 3.66 (4H, q), 3.88 (2H, t), 5.42 (1H, s), 5.58 (1H, s) 5.60 (1H, brs), 7.55 (2H, d), 7.78 (2H, d), 9.18 (1H, s), 11.68 (1H, s). 2 hydrogens masked by solvent | 8.063 |
| I-134 | 510.16 | (DMSO-d6) 2.08 (3 H, s), 2.36-2.29 (2 H, m), 3.93 (4 H, t), 5.61 (1H, s), 5.81 (1 H, br s), 7.12 (2 H, d), 7.88-7.65 (6 H, m), 9.16 (1 H, br s), 10.59 (1 H, s), 11.73 (1 H, br s). | 8.476 |
| I-135 | 522.00 | (MeOD): 0.40-0.45 (2H, m), 0.60-0.65 (2H, m), 1.3-1.4 (1H, m), 2.05 (2H, s), 3.25-3.40 (2H, m), 3.85-3.40 (4H, m), 5.40-5.50 (2H, m), 7.50-7.55 (2H, d), 7.65-7.70 (2H, d). | 9.235; |
| I-136 | 520.00 | (MeOD): 0.30-0.40 (2H, m), 0.45-0.50 (2H, m), 1.00-1.05 (3H, t), 1.15-1.20 (1H, m), 1.60-1.70 (1H, m), 1.80-1.90 (1H, m), 2.05-2.10 (3H, s), 3.65-3.80 (4H, m), 3.90-4.00 (1H, m), 5.45-5.50 (1H, m), 5.60-5.65 (1H, m), 6.75-6.85 (2H, d), 7.30-7.40 (2H, d). | 9.454 |
| I-137 | 515.33 | (DMSO-d6) 2.00 (3H, s), 2.31 (2H, m), 2.78 (6H, s), 3.89 (4H, m), 4.39 (2H, d), 5.41 (1H, s), 5.60 (1H, br s), 7.58 (2H, d), 7.63 (2H, d), 7.90 (2H, d), 8.06 (2H, d), 9.31 (1H, s), 9.84 (1H, s), 10.54 (1H, s) | 8.505 |
| I-138 | 515.33 | (DMSO-d6) 2.00 (3H, s), 2.31 (2H, m), 2.77 (6H, s), 3.88 (4H, m), 4.40 (2H, d), 5.41 (1H, s), 5.58 (1H, br s), 7.58 (2H, d), 7.69 (2H, m), 7.89 (2H, d), 8.12 (2H, d), 9.28 (1H, s), 9.71 (1H, s), 10.54 (1H, s) | 8.510 |
| I-139 | 527.36 | (DMSO-d6) 1.99 (4H, m), 2.33 (4H, m), 3.88 (4H, m), 4.02 (4H, m), 4.45 (2H, d), 5.40 (1H, s), 5.77 (1H, br s), 7.56 (2H, d), 7.63 (2H, m), 7.92 (2H, d), 8.03 (2H, d), 9.30 (1H, s), 10.21 (1H, s), 10.57 (1H, s) | 8.154 |
| I-140 | 527.36 | (DMSO-d6) 2.00 (3H, s), 2.33 (4H, m), 4.00 (4H, m), 4.12 (4H, m), 4.47 (2H, d), 5.48 (1H, s), 5.69 (1H, br s), 7.58 (2H, d), 7.68 (2H, m), 7.89 (2H, d), 8.03 (2H, d), 9.27 (1H, s), 10.02 (1H, s), 10.53 (1H, s) | 8.167 |
| I-141 | 480.00 | (DMSO-d6) 1.35 (3H, t), 1.74-1.81 (2H, m), 1.84-1.89 (2H, m), 2.02 (3H, brs), 3.66-3.71 (1H, m), 3.93 (1H, t), 4.01-4.09 (4H, m), 5.34 (1H, brs), 5.60 (1H, vbrs), 6.99 (2H, d), 7.46 (2H, d), 9.24 (1H, brs), 11.68 (1H, brs). | 9.00 |
| I-142 | 490.00 | (DMSO-d6) 1.28-1.33 (2H, m), 1.40-1.45 (2H, m), 1.85-1.95 (3H, s), 2.20-2.30 (2H, m), 3.80-3.85 (4H, m), 5.25-5.30 (1H, s), 5.50-5.70 (1H, s), 7.40-7.50 (2H, d), 7.70-7.55 (2H, d), 9.15-9.20 (1H, s), 9.95-10.00 (1H, s), 11.6-11.7 (1H, s). | 9.058 |

TABLE 8-continued

| Compound No | M + 1 (obs) | 1H NMR | Rt (mins) |
|---|---|---|---|
| I-143 | 548.00 | (MeOD): 0.35-0.40 (2H, m), 0.55-0.60 (2H, m), 1.25-1.35 (6H, m), 2.0 (3H, m), 3.80-3.90 (4H, m), 5.35-5.40 (2H, m), 7.45-7.50 (2H, d), 7.60-7.65 (2H, d).; | 9.715; |
| I-144 | 506.00 | (DMSO-d6) 0.43-0.47 (2H, m), 0.61-0.64 (2H, m), 1.40-1.46 (2H, m), 2.01 (3H, s), 3.50 (2H, q), 3.85-3.98 (4H, m), 5.54 (1H, s), 7.11 (2H, d), 7.60 (2H, d), 9.32 (1H, brs), 10.37 (1H, s), 11.74 (1H, brs) | 8.727 |
| I-145 | 473.38 | (DMSO-d6) 1.99 (3 H, s), 2.33-2.27 (2 H, m), 3.88 (4 H, t), 5.39 (1 H, br s), 5.66 (1 H, br s), 7.45 (1 H, d), 7.56 (2 H, d), 7.90 (2 H, d), 8.20 (1 H, dd), 9.00 (1 H, d), 9.21 (1 H, br s), 10.55 (1 H, s), 11.68 (1 H, br s). | 8.434 |
| I-146 | 527.29 | (DMSO-d6) 2.04 (3 H, s), 2.33-2.26 (2 H, m), 3.88 (4 H, t), 5.45 (1 H, s), 5.66 (1 H, br s), 7.58 (2 H, d), 7.77 (2 H, d), 9.06 (1 H, d), 9.13 (1 H, s), 9.23 (1 H, br s), 10.98 (1 H, s), 11.70 (1 H, br s). | 8.794 |
| I-147 | 468.40 | CD3OD: 0.80 (2H, m), 1.10 (2H, d), 1.65 (3H, t), 1.90 (1H, m), 2.50 (3H, s), 2.88 (2H, q), 4.40 (4H, m), 5.94 (2H, m), 7.49 (2H, d), 8.10 (2H, d). | 9.035 |
| I-148 | 508.34 | (DMSO-d6) 0.43 (2H, d), 0.62 (2H, d), 1.39 (1H, m), 3.55 (2H, q), 3.88 (4H, m), 5.66 (1H, s), 5.79 (1H, br s), 7.29 (1H, s), 7.55 (2H, d), 7.65 (2H, d), 9.45 (1H, s), 10.49 (1H, s) | 9.272 |
| I-149 | 508.64 | (DMSO-d6) 2.00 (3 H, s), 2.33-2.25 (2 H, m), 2.57 (3H, s), 3.87 (4 H, t), 5.25 (1 H, s), 5.63 (1 H, br s), 7.58 (2 H, d), 7.76 (2 H, d), 7.88 (2 H, d), 9.22 (1 H, br s), 10.71 (1 H, s), 11.69 (1 H, br s). | 9.277 |
| I-150 | 432.00 | (DMSO-d6): 2.00-2.05 (3H, s), 2.20-2.30 (2H, m), 3.00-3.05 (3H, s), 3.80-3.85 (4H, m), 5.40-5.45 (1H, s), 5.50-5.70 (1H, s), 7.20-7.25 (2H, d), 7.50-7.55 (2H, d), 9.15-9.20 (1H, s), 10.00-10.05 (1H, s), 11.65-11.70 (1H, s). | 7.947 |
| I-151 | 490.00 | (MeOD): 0.45-0.50 (1H, d), 0.60-0.70 (2H, d), 1.30-1.40 (1H, m), 2.05-2.20 (3H, s), 3.00-3.10 (3H, s), 3.80-4.00 (4H, m), 5.50-5.60 (2H, m), 7.25-7.35 (2H, d), 7.50-7.55 (2H, d). | 8.849 |
| I-152 | 497.00 | (DMSO-d6): 0.41-0.45 (2H, m), 0.58-0.63 (2H, m), 1.39-1.41 (11H, m), 2.01-2.08 (3H, s), 2.89 (6H, s), 3.79-3.93 (4H, m), 4.18 (2H, s), 5.40-5.45 (1H, s), 5.50-5.70 (1H, s), 7.57-7.64 (2H, d), 7.69-7.71 (2H, d), 9.39 (1H, s), 9.87 (1H, s), 10.79 (1H, s). | 9.112 |
| I-153 | 460.00 | (DMSO-d6) 0.35-0.38 (2H, m), 0.43-0.49 (2H, m), 1.21-1.30 (1H, m), 1.66 (3H, brs), 2.74 (3H, s), 3.71 (4H, q), 5.20 (1H, brs), 5.76 (1H, s), 7.54 (1H, d), 7.87 (1H, dd), 8.00 (1H, d), 8.27 (1H, d), 8.36 (1H, d), 9.29 (1H, s), 11.69 (1H, s) | 8.487 |
| I-154 | 462.00 | (DMSO-d6) 0.42-0.46 (2H, m), 0.59-0.63 (2H, m), 1.36-1.38 (1H, m), 1.60 (3H, brs), 2.69 (3H, s), 3.80-3.94 (4H, m), 5.10 (1H, brs), 5.76 (1H, s), 7.48 (1H, d), 7.82 (1H, dd), 7.95 (1H, d), 8.22 (1H, d), 8.30 (1H, d), 9.33 (1H, s), 11.62 (1H, s) | 9.530 |
| I-155 | 517.00 | (DMSO-d6) 0.30-0.33 (2H, m), 0.39-0.43 (2H, m), 1.16-1.24 (1H, m), 1.70 (3H, brs), 3.66 (4H, q), 4.02 (3H, s), 5.12 (1H, brs), 5.65 (1H, s), 7.55 (1H, dd), 7.87 (1H, d), 8.14 (1H, d), 9.23 (1h, s), 11.64 (1H, s), | 9.475 |
| I-156 | 519.00 | (DMSO-d6) 0.42-0.46 (2H, m), 0.60-0.62 (2H, m), 1.37-1.44 (1H, m), 1.68 (3H, brs), 3.81-4.00 (4H, m), 4.04 (3H, s), 5.10 (1H, brs), 5.61 (1H, brs), 7.56 (1H, dd), 7.88 (1H, d), 8.15 (1H, s), 9.35 (1H, s), 11.65 (1H, s), | 9.596 |
| I-157 | 536.36 | (DMSO-d6) 0.42-0.46 (2H, m, alk), 0.60-0.63 (2H, m, alK), 1.4 (1H, m, alK), 1.98 (3H, s, CH3), 2.59-2.68 (4H, m, alk), 3.80-3.93 (4H, m, alk), 5.36 (H, brs, ar), 5.75 (H, brs, ar), 7.50-7.52 (2H, d, ar), 7.69-7.71 (2H, d, ar), 9.37 (H, s, NH), 10.31 (H, s, NH) and 11.75 (H, brs, NH) | 9.579 |
| I-158 | 450.00 | (MeOD): 2.00-2.20 (3H, s), 2.400-2.50 (2H, m), 3.80-3.90 (4H, m), 5.30-5.35 (1H, m), 5.50-5.70 (1H, br s), 7.55-7.60 (2H, d), 7.75-7.80 (2H, d). | 9.041 |
| I-159 | 459.30 | DMSO 1.5-1.65 (2H, m), 1.72-1.76 (5H, m), 2.4-2.45 (4H, m), 3.74-3.78 (2H, m), 3.93-39.8 (2H, m), 5.65 (1H, brs), 5.7 (1H, brs), 7.6-7.63 (1H, m), 7.9 (1H, d), 8.05 (1H, d), 8.3 (1H, s), 8.43 (1H, d), 9.0 (1H, s), 9.28 (1H, brs), 11.7 (1H, brs) | 8.34 |
| I-160 | 477.30 | (DMSO-d6) 1.5-1.65 (1H, m), 1.85-1.95 (1H, m), 2.02-2.2 (1H, m), 2.38-2.43 (1H, m), 2.6-2.72 (1H, m), 2.8-2.92 (1H, m), 3.4-3.45 (1H, m), 3.72-3.78 (2H, m), 3.93-3.96 (2H, m), 5.12-5.16 (1.5H, m), 5.32-5.34 (1H, m) 5.5 (1H, brs), 5.7 91H, brs), 7.6-7.63 (1H, m), 7.9 (1H, d), 8.05 (1H, d), 8.34 (1H, s), 8.43 (1H, d), 9.0 (1H, s), 9.28 (1H, brs), 11.7 (1H, brs) | 8.24 |
| I-161 | 506.00 | (DMSO-d6) 2.04 (3H, brs), 2.30 (2H, qn), 2.41 (3H, s), 3.88 (4H, t), 5.40 (1H, brs), 5.59 (1H, vbrs), 7.36-7.40 (2H, m), 7.49-7.55 (3H, m), 7.82 (2H, d), 9.22 (1H, brs), 10.71 (1H, s), 11.68 (1H, brs). | 9.31 |
| I-162 | 526.00 | (DMSO-d6) 2.03 (3H, brs), 2.30 (2H, qn), 3.88 (4H, t), 5.40 (1H, brs), 5.60 (1H, vbrs), 7.55-7.63 (4H, m), 7.78-7.82 (3H, m), 9.22 (1H, brs), 10.78 (1H, s), 11.69 (1H, brs). | 9.54 |
| I-163 | 526.00 | (DMSO-d6) 2.04 (3H, brs), 2.30 (2H, qn), 3.88 (4H, t), 5.41 (1H, brs), 5.58 (1H, vbrs), 7.56 (1H, d), 7.60-7.66 (2H, m), 7.71 (1H, s), 7.81 (2H, d), 9.22 (1H, brs), 10.81 (1H, s), 11.68 (1H, brs). | 9.51 |
| I-164 | 520.00 | (DMSO-d6) 1.22 (3H, t), 2.05 (3H, brs), 2.28 (2H, qn), 2.79 (2H, q), 3.88 (4H, t), 5.40 (1H, brs), 5.50 (1H, vbrs), 7.36-7.43 (2H, m), 7.48-7.51 (1H, m), 7.54 (1H, d), 7.83 (2H, d), 9.22 (1H, brs), 10.72 (1H, s), 11.68 (1H, brs). | 9.64 |
| I-165 | 504.00 | (DMSO-d6) 2.05 (3H, brs), 2.30 (2H, qn), 2.46 (3H, s), 3.88 (4H, t), 5.40 (1H, brs), 5.60 (1H, vbrs), 7.29 (1H, t), 7.44 (1H, d), 7.48-7.54 (2H, m), 8.84 (2H, d), 9.21 (1H, brs),, 10.56 (1H, s), 11.68 (1H, brs). | 9.01 |
| I-166 | 462.00 | (DMSO-d6) 1.98 (3H, brs), 2.29 (2H, qn), 3.87 (4H, t), 4.00 (3H, s), 5.40 (1H, brs), 5.50 (1H, vbrs), 7.11 (2H, d), 7.47 (1H, s), 7.51 (2H, d), 7.96 (2H, d), 9.20 (1H, brs), 10.56 (1H, s), 11.67 (1H, brs). | 8.67 |
| I-167 | 463.00 | (DMSO-d6) 1.98 (3H, brs), 2.89 (2H, qn), 2.45 (3H, s), 3.87 (4H, t), 5.41 (1H, brs), 5.60 (1H, vbrs), 7.53 (2H, d), 7.88 (2H, d), 8.57 (1H, s), 9.20 (1H, brs), 10.49 (1H, s), 11.69 (1H, brs). | 8.45 |
| I-168 | 496.00 | (DMSO-d6) 1.60 (3H, d), 1.97 (3H, brs), 3.55 (2H, q), 3.91-4.03 (4H, m), 5.35 (1H, brs), 5.60 (1H, vbrs), 7.54 (2H, d), 7.68 (2H, d), 9.32 (1H, brs), 10.53 (1H, s), 11.70 (1H, brs). | 8.91 |
| I-169 | 503.00 | (DMSO-d6): 1.63 (3H, s), 1.93-1.98 (3H, s), 3.50-3.55 (2H, m), 3.85-3.87 (2H, d), 4.18-4.20 (1H, d), 5.35-5.40 (1H, s), 5.60-5.75 (1H, br s), 7.50-7.55 (2H, d), 7.67-7.69 (2H, d), 9.25-9.30 (1H, s), 10.49 (1H, s). | 8.587 |
| I-170 | 498.70 | (DMSO-d6) 0.45-0.48 (2H, m), 0.6-0.63 (2H, m), 0.87-0.92 (4H, m), 1.45 (1H, brs), 1.82-1.85 (1H, m), 2.02 (3H, s), 3.8-3.95 (4H, m), 5.3 (1H, vbrs), 5.75 (1H, brs), 7.4 (1H, d), 7.52-7.55 (1H, m), 7.8 (1H, d), 9.4 (1H, brs), 10.7 (1H, brs), 11.7 (1H, brs) | 9.2 |
| I-171 | 494.58 | (DMSO-d6) 0.20 (2H, m), 0.42-0.51 (4H, m), 0.59 (2H, ), 1.07 (1H, m), 1.40 (1H, | 9.304 |

TABLE 8-continued

| Compound No | M + 1 (obs) | 1H NMR | Rt (mins) |
|---|---|---|---|
| | | m), 1.99 (3H, m), 2.24 (2H, m), 3.81-3.94 (4H, m), 5.36 (1H, s), 5.70 (1H, br s), 7.47 (2H, m), 7.72 (2H, m), 9.27 (1H, s), 9.99 (1H, s), 11.65 (1H, br s) | |
| I-172 | 478.42 | (DMSO-d6) 0.30 (2H, m), 0.39 (2H, m), 1.12 (1H, m), 1.68 (4H, m), 2.70 (3H, s), 3.63 (4H, m), 5.25 (1H, brs), 5.60 (1H, s), 7.57 (1H, d), 7.69 (1H, d), 8.06 (1H, s), 8.35 (1H, m), 9.30 (1H, brs), 11.65 (1H, s). | 8.50 |
| I-173 | 561.37 | (DMSO-d6) 1.92 (3H, s, CH3), 2.33-2.34 (4H, m, alk), 3.27 (H, m, CH), 3.59-3.61 (4H, m, alk), 3.75 (2H, m, alk), 3.92 (2H, m, alk), 4.42-4.44 (2H, m, alk), 4.64 (2H, m, alk), 5.35 (1H, brs, ar), 5.7 (H, brs, ar), 7.79 (2H, m, ar), 7.92 (H, s, ar), 9.25 (H, brs, NH) and 11.7 (H, brs, NH). | 8.185 |
| I-174 | 412.28 | (DMSO-d6) 0.23-0.19 (2 H, m), 0.41-0.36 (2 H, m), 1.20-1.16 (1 H, m), 1.88 (3 H, s), 3.73-3.59 (4 H, m), 5.31 (1 H, s), 5.39 (1 H, br s), 6.49 (2 H, d), 7.01 (2 H, d), 9.25 (1 H, s) | 8.733 |
| I-175 | 478.00 | (DMSO-d6) 0.42-0.46 (2H, m), 0.59-0.63 (2H, m), 0.81-0.88 (1H, m), 1.91 (3H, s), 2.41 (3H, s), 3.82-4.07 (4H, m), 5.43 (1H, s), 5.75 (1H, brs), 7.04 (1H, s), 7.72 (2H, dd), 7.98 (2H, dd), 9.35 (1H, s) | 9.964 |
| I-176 | 530.00 | (DMSO-d6) 1.29-1.41 (2H, m), 1.62-1.98 (7H, m), 3.88 (1H, brs), 4.02-4.10 (7H, m), 5.13 (1H, brs), 7.61 (1H, dd), 7.93 (1H, d), 8.21 (1H, d), 9.35 (1H, brs), 11.68 (1H, brs) | 8.863 |
| I-177 | 560.40 | (DMSO-d6) 1.69 (3 H, br s), 4.28-3.18 (13 H, masked signals), 4.15 (3 H, s (slightly masked signal)), 4.24 (2 H, q (slightly masked signal)), 5.13 (1 H, br s), 5.67 (1 H, br s), 7.41 (1 H, dd), 7.71 (1 H, d), 7.87 (1 H, d), 9.38 (1 H, s). | 7.853 |
| I-178 | 540.00 | (DMSO-d6) 0.46-0.50 (2H, m), 0.61-0.64 (2H, m), 1.38-1.45 (1H, m), 1.93 (3H, s), 3.55 (2H, q), 4.00-4.18 (4H, m), 5.27 (1H, s), 7.54 (2H, d), 7.71 (2H, d), 9.39 (1H, s), 10.57 (1H, s), | 9.643 |
| I-179 | 534.31 | (DMSO-d6) 0.4-0.5 (2H, m, CyP), 0.5-0.65 (2H, m, CyP), 1.35-1.5 (2H, m, alk), 1.9 (2H, m, CH3), 3.3 (3H, s, CH3), 3.8-4.0 (4H, m, alk), 4.4-4.5 (2H, m, alk), 4.65 (3H, s, CH3), 5.25 (1H, brs, ar), 5.85 (H, brs, ar), 7.7 (H, d, ar), 7.8 (H, d, ar), 7.9 (H, s, ar), 9.4 (H, brs, NH) and 11.8 (H, brs, NH). | 9.456 |
| I-180 | 450.26 | (DMSO-d6) 0.23-0.12 (4 H, m), 1.02-0.96 (1 H, m), 1.68 (3 H, s), 2.58 (3 H, s), 3.50 (4 H, q), 5.22 (1 H, s), 5.56 (1 H, br s), 7.04 (1 H, dd), 7.64 (1 H, d), 7.69 (1 H, d), 9.10 (1 H, br s) | 7.898 |
| I-181 | 523.25 | (DMSO-d6) 0.49-0.45 (2 H, m), 0.64-0.61 (2 H, m), 1.49-1.39 (1 H, m), 2.07 (3 H, s), 3.49 (2 H, q), 4.04-3.91 (4 H, m), 5.56 (1 H, s), 6.90 (1 H, s), 7.14 (2 H, d), 7.64 (2 H, d), 10.37 (1 H, s), 11.0 (1 H, br s). | 9.184 |
| I-182 | 473.40 | (DMSO-d6) 1.5-1.65 (2H, m), 1.72-1.76 (5H, m), 2.4-2.45 (4H, m), 2.65 (3H, s), 3.70-3.78 (2H, m), 3.92-3.96 (2H, m), 5.65 (1H, brs), 5.7 (1H, brs), 7.6 (1H, s), 7.9 (1H, d), 7.97 (1H, d), 8.25 (1H, d), 8.33 (1H, d), 9.28 (1H, brs), 11.7 (1H, brs) | 8.63 |
| I-183 | 538.00 | (DMSO-d6) 1.19 (3H, s), 1.24 (6H, s), 1.91 (3H, brs), 3.38-3.42 (2H, m), 3.47 (2H, q), 3.83 (2H, brd), 5.30 (1H, brs), 5.55 (1H, vbrs), 7.47 (2H, d), 7.61 (2H, d), 9.12 (1H, brs), 10.42 (1H, s), 11.57 (1H, s) | 9.34 |
| I-184 | 504.00 | (DMSO-d6) 1.56 (6H, s), 1.99 (3H, s), 4.39 (4H, brs), 5.38 (1H, brs), 5.67 (1H, vbrs), 7.54 (2H, d), 7.68 (2H, d), 9.23 (1H, brs), 10.49 (1H, s), 11.66 (1H, vbrs). NB water peak obscures some signals | 9.68 |
| I-185 | 551.30 | (DMSO-d6) 2.07 (3H, s), 2.4-2.5 (1H, m), 2.8-2.9 (1H, m), 3.6-3.7 (2H, q), 3.8-3.9 (1H, m), 4.02-4.07 (1H, m), 4.2-4.33 (1H, m), 5.28-5.33 (0.5H, m), 5.4-5.5 (1.5H, m), 5.7 (1H, vbrs), 6.65 (1H, brs), 7.73 (2H, d), 7.83 (2H, d), 9.36 (1H, brs), 10.65 (1H, brs), 11.7 (1H, brs) | 8.4 |
| I-186 | 514.44 | (DMSO-d6) 0.30 (2H, m), 0.40 (2H, m), 1.16 (1H, m), 1.55 (4H, m), 3.65 (4H, m), 5.10 (1H, brs), 5.60 (1H, s), 8.04 (2H, m), 8.18 (1H, d), 8.47 (1H, s), 8.76 (1H, m), 9.30 (1H, brs), 11.65 (1H, brs). | 9.53 |
| I-187 | 533.53 | (DMSO-d6) 0.46-0.42 (2 H, m), 0.63-0.60 (3 H, m), 1.42-1.38 (1 H, m), 1.67 (3 H, br s), 3.85 (3H, s), 3.95-3.81 (4 H, m), 4.25 (2 H, q), 5.11 (1 H, br s), 5.621 (1 H, br s), 7.42 (1 H, dd), 7.72 (1 H, d), 7.91 (1 H, d), 9.40 (1 H, br s). | 9.204; |
| I-188 | 454.00 | (DMSO-d6): 0.40-0.45 (2H, m), 0.55-0.60 (2H, m), 1.30-1.40 (1H, m), 2.05-2.10 (6H, s), 3.75-3.90 (4H, m), 3.40-3.45 (1H, s), 5.65-5.80 (1H, br s), 7.20-7.25 (1H, d), 7.35-7.40 (1H, t), 7.70-7.75 (1H, d), 7.80 (1H, s), 9.25-9.30 (1H, s), 10.0 (1H, s). | 8.819 |
| I-189 | 546.38 | (DMSO-d6) 0.43 (2H, m), 0.61 (2H, m), 1.42 (1H, m), 1.82 (3H, brs), 3.81-3.98 (4H, m), 4.97 (2H, m), 5.26 (1H, brs), 5.76 (1H, s), 6.81 (1H, d), 7.55 (1H, d), 7.78 (1H, d), 7.90 (1H, d), 8.42 (1H, s), 9.31 (1H, m), 11.68 (1H, s). | 9.60 |
| I-190 | 505.37 | (DMSO-d6) 0.41 (2H, m), 0.61 (2H, m), 1.20 (1H, m), 1.67 (3H, m), 3.80-3.99 (4H, m), 5.30 (1H, s), 5.64 (1H, s), 7.49 (1H, d), 7.71 (1H, d), 8.51 (1H, s), 8.91 (1H, s), 9.32 (1H, s), 11.68 (1H, s). | 9.46 |
| I-191 | 575.00 | (DMSO-d6) 1.31-1.34 (2H, m), 1.38-1.46 (2H, m), 1.96 (3H, s), 2.34 (4H, brs), 3.18-3.22 (1H, m), 3.60 (4H, t), 3.70-3.73 (2H, m), 3.91 (2H, t), 5.36 (1H, s), 5.60 (1H, brs), 7.52 (2H, d), 7.74 (2H, d), 9.20 (1H, s), 10.00 (1H, s), 11.64 (1H, s) | 8.609 |
| I-192 | 510.00 | (DMSO-d6) 2.03 (3H, s), 2.29-2.36 (2H, m), 4.10 (4H, t), 5.34 (1H, s), 7.47-7.61 (6H, m), 9.24 (1H, s), 10.78 (1H, s) | 9.524 |
| I-193 | 551.00 | (MeOD-d4): 0.53-0.55 (2H, m), 0.71-0.73 (2H, m), 1.40-1.48 (7H, m), 2.10-2.18 (1H, m), 2.20-2.35 (5H, m), 2.65-2.75 (1H, m), 3.40-3.50 (1H, m), 3.70-3.85 (2H, m), 4.00-4.15 (4H, m), 4.40-4.50 (1H, m), 5.57 (1H, s), 5.70 (1H, m), 7.70-7.75 (2H, d), 7.80-7.85 (2H, d). | 10.188 |
| I-194 | 516.60 | (DMSO-d6) 0.22-0.25 (2H, m), 0.42-0.45 (2H, m), 1.20-1.26 (1H, m), 1.75-1.9 (5H, m), 2.6-2.7 (1H, m), 3.65-3.8 (4H, m), 5.1 (1H, brs), 5.4 (1H, vbrs), 7.3 (2H, d), 7.52 (2H, d), 9.1 (1H, brs), 10.4 (1H, s), 11.5 (1H, brs) | 9.34 |
| I-195 | 546.70 | (DMSO-d6) 1.6-1.75 (4H, m), 3.0-3.15 (4H, m), 4.1 93H, s), 4.1-4.3 (4H, m), 5.1 (1H, vbrs), 5.6 (1H, brs), 7.6 (1H, d), 7.9 (2H, d), 8.2 (1H, s), 9.5 (1H, brs), 10.6 (1H, brs) | 8.1 |
| I-196 | 510.00 | (DMSO-d6) 0.93 (3H, t), 1.83-1.99 (5H, m), 3.55 (2H, q), 3.89-4.01 (4H, m), 5.34 (1H, brs), 5.65 (1H, vbrs), 7.54 (2H, d), 7.68 (2H, d), 9.33 (1H, brs), 10.54 (1H, s), 11.69 (1H, brs). | 9.29 |
| I-197 | 438.00 | (CD3OD): 1.30-1.37 (3H, m), 2.15-2.20 (3H, m), 2.40-2.50 (4H, m), 2.80-2.90 (2H, t), 3.50-3.55 (2H, t), 4.00-4.15 (4H, s), 6.50-6.55 (1H, s), 7.55-7.65 (2H, m), 7.75-7.80 (2H, m). | 6.991 |
| I-198 | 491.30 | (DMSO-d6) 1.5-1.65 (3H, m), 1.85-1.95 (1H, m), 2.02-2.2 (1H, m), 2.38-2.43 (1H, m), 2.6-2.68 (1H, m), 2.7 (3H, m), 2.8-2.92 (2H, m), 3.4-3.45 (1H, m), 3.72-3.78 (2H, m), 3.93-3.96 (2H, m), 5.12-5.16 (1.5H, | 8.48 |

TABLE 8-continued

| Compound No | M + 1 (obs) | 1H NMR | Rt (mins) |
|---|---|---|---|
| | | m), 5.32-5.34 (1H, m) 5.5 (1H, brs), 5.7 (1H, brs), 7.5 (1H, d), 7.75 (1H, d), 7.95 (1H, d), 8.24 (1H, s), 8.33 (1H, d), 9.3 (1H, s), 11.7 (1H, brs) | |
| I-199 | 549.30 | (DMSO-d6) 1.95 (3H, s), 2.33-2.37 (4H, m), 3.2-3.25 (1H, m), 3.55 (2H, q), 3.55-3.6 (4H, m), 3.7-3.73 (2H, m), 3.9-3.93 (2H, m), 5.37 (1H, brs), 5.7 (1H, vbrs), 7.55 (2H, d), 7.67 (2H, d), 9.23 (1H, brs), 10.45 (1H, s), 11.7 (1H, brs) | 8.05 |
| I-200 | 473.27 | (DMSO-d6) 2.02 (3 H, s), 2.33-2.29 (2 H, m), 2.58 (3 H, s), 3.91 (4 H, t), 5.45 (1 H, s), 5.62 (1H, br s), 7.57-7.52 (3 H, m), 7.84 (1H, d), 7.96 (2H, d), 8.56-8.55 (1 H, m), 9.36 (1 H, s), 10.72 (1 H, s). | 9.256 |
| I-201 | 437.00 | (DMSO-d6): 0.45-0.50 (2H, m), 0.60-0.65 (2H, m), 1.40-1.50 (1H, m), 2.05-2.10 (3H, s), 2.20-2.23 (3H, s), 4.00-4.15 (4H, m), 5.40-5.50 (1H, s), 5.80-5.90 (1H, s), 7.50-7.60 (4H, m), 9.50-10.0 (2H, m). | |
| I-202 | 505.60 | (DMSO-d6) 0.43-0.47 (2H, m), 0.61-0.63 (2H, m), 1.4-1.5 (1H, m), 1.6-1.7 (3H, m), 3.8-4.0 (4H, m), 5.0 (1H, brs), 5.6 (1H, vbrs), 7.55-7.6 (1H, m), 7.7-8.0 (2H, m), 9.4 (1H, s), 11.7 (1H, s), 14.2 (1H, s) | 9.1 |
| I-203 | 494.29 | (DMSO-d6) 0.46-0.44 (2 H, m), 0.67-0.60 (4 H, m), 1.11-1.10 (2 H, m), 1.43 (4 H, m), 2.00 (3 H, s), 3.95-3.82 (4 H, m), 5.39 (1 H, s), 5.65 (1H, br s), 7.48 (2 H, d), 7.78 (2 H, d), 9.36 (1H, S), 9.39 (1 H, s). | 9.494 |
| I-204 | 533.40 | (DMSO-d6) 1.7-1.75 (4H, m), 1.95 (3H, s), 2.4-2.43 (1H, m), 3.55 (2H, q), 3.7-3.74 (2H, m), 3.93-3.96 (2H, m), 5.35 (1H, brs), 5.7 (1H, vbrs), 7.55 (2H, d), 7.72 (2H, d), 9.26 (1H, brs), 10.55 (1H, brs), 11.8 (1H, brs) | 8.56 |
| I-205 | 522.00 | (DMSO-d6): 0.25-0.30 (2H, m), 0.45-0.50 (2H, m), 1.20-1.30 (1H, m), 1.80-1.85 (3H, s), 3.65-3.80 (4H, m), 3.90-4.00 (2H, m), 5.20-5.25 (1H, s), 5.50-5.70 (1H, br s), 7.52-7.57 (2H, d), 7.75-7.80 (2H, d), 9.0-9.05 (1H, s), 9.15-9.20 (1H, s). | 9.407 |
| I-206 | 448.60 | (DMSO-d6) 0.45-0.48 (2H, m), 0.62-0.65 (2H, m), 1.42-1.48 (1H, m), 1.6-1.7 (3H, brs), 3.82-3.96 (4H, m), 5.15 (1H, brs), 5.7 (1H, brs), 7.7-7.3 (1H, m), 7.75-7.78 (1H, m), 8.1-8.2 (2H, m), 8.7 (1H, s), 8.9 (1H, s), 9.4 (1H, brs), 11.7 (1H, brs) | 9.6 |
| I-207 | 493.00 | (CDCl$_3$): 2.15-2.20 (3H, s), 2.30-2.40 (2H, m), 4.00-4.10 (4H, t), 5.57 (1H, s), 5.85 (1H, s), 7.35-7.45 (3H, m), 7.65-7.70 (1H, d), 8.10-8.15 (1H, d), 8.35-8.40 (1H, s), 8.49 (1H, s), 9.60-9.70 (1H, br s). | 9.021 |
| I-208 | 536.00 | (DMSO-d6): 1.21 (3H, s), 2.05-2.09 (3H, s), 3.38 (2H, s), 3.72-3.74 (4H, d), 7.40-7.60 (6H, m), 7.80-7.85 (2H, d), 9.30-9.35 (1H, s), 10.75 (1H, s). | 8.538 |
| I-209 | 413.00 | (DMSO-d6): 0.42-0.44 (2H, m), 0.55-0.60 (2H, m), 1.35-1.45 (1H, m), 2.11 (3H, s), 3.81-3.90 (4H, m), 5.55-5.80 (2H, m), 6.35 (2H, s), 6.49-6.52 (1H, d), 7.46-7.49 (1H, d), 7.97 (1H, s), 9.30-9.35 (1H, s). | 8.313 |
| I-210 | 488.39 | (DMSO-d6) 0.53-0.50 (2 H, m), 0.67-0.65 (2 H, m), 2.08 (1 H, s), 2.22 (3 H, s), 4.20-4.06 (4 H, m), 5.45 (1 H, br s), 5.92 (1 H, br s), 7.45 (1 H, br m), 7.69 (1 H, d), 8.33 (1 H, br m), 10.16 (1 H, br s). | 8.996 |
| I-211 | 523.00 | (DMSO-d6): 0.20-0.21 (2H, m), 0.36-0.38 (2H, m), 1.15-1.20 (1H, m), 1.77 (3H, s), 3.40-3.50 (2H, m), 3.57-3.72 (4H, m), 5.10-5.15 (1H, s), 5.40-5.55 (12H, s), 7.75-7.80 (1H, d), 7.92-7.97 (1H, d), 8.22 (1H, s), 9.20 (1H, s) 10.91 (1H, s). | 9.316 |

Example 28

Aurora-2 (Aurora A) Inhibition Assay

Compounds were screened for their ability to inhibit Aurora-2 using a standard coupled enzyme assay (Fox et al., Protein Sci., (1998) 7, 2249). Assays were carried out in a mixture of 100 mM Hepes (pH7.5), 10 mM MgCl$_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay are 400 µM ATP (Sigma Chemicals) and 570 µM peptide (Kemptide, American Peptide, Sunnyvale, Calif.). Assays were carried out at 30° C. and in the presence of 40 nM Aurora-2.

An assay stock buffer solution was prepared containing all of the reagents listed above, with the exception of Aurora-2 and the test compound of interest. 55 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 10 µl of Aurora-2. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Compounds 1-15, 16-17, 19, 21-22, 23-48, 50-68, 70-72, 76-90, 92-136, 141-165, 167-211 were found to have Aurora A kinase activity at <25 nM Ki.

Compounds 1, 2, 6, 10, 11, 18-24, 26, 41, 47, 49, 52, 63, 69, 72-75, 82, 91, 108, 124, 132, 137-140, 145, 150, 166, 167, 174-175, 188, 197, 200-201, and 209 were found to inhibit Aurora A kinase at a Ki value of between 0.005 uM and 0.2 uM.

Compounds 3, 4, 7-9, 14-15, 17, 25, 27-30, 32-33, 35, 39, 43-45, 48, 53-54, 58-60, 62, 70-71, 76-77, 79-80, 94-96, 98-99, 112, 114, 117, 120-121, 123, 125, 127-128, 130, 134, 141-142, 147-149, 158-159, 165, 176, 182, 189, 190, 192-193, 195, 198, 202, 207, and 210 were found to inhibit Aurora A kinase at a Ki value of between 0.001 uM and 0.005 uM.

Compounds 5, 12-13, 16, 31, 34, 36-38, 40, 42, 46, 50-51, 55-57, 61, 64-68, 78, 81, 83-90, 92-93, 97, 100-107, 109-111, 113, 115-116, 118-119, 122, 126, 129, 131, 133, 135, 136, 143-144, 146, 151-157, 160-164, 168-173, 177-181, 183-187, 191, 194, 196, 199, 203-206, 208, and 211 were found to inhibit Aurora A kinase at a Ki value of ≤0.001 uM.

Example 29

Aurora-1 (Aurora B) Inhibition Assay (Radiometric)

An assay buffer solution was prepared which consisted of 25 mM HEPES (pH 7.5), 10 mM MgCl$_2$, 0.1% BSA and 10% glycerol. A 22 nM Aurora-B solution, also containing 1.7 mM DTT and 1.5 mM Kemptide (LRRASLG), was prepared in assay buffer. To 22 µL of the Aurora-B solution, in a 96-well plate, was added 2 µl of a compound stock solution in DMSO and the mixture allowed to equilibrate for 10 minutes at 25° C. The enzyme reaction was initiated by the addition of 16 µl stock [γ-$^{33}$P]-ATP solution (~20 nCi/µL) prepared in assay buffer, to a final assay concentration of 800 µM. The reaction was stopped after 3 hours by the addition of 16 µL 500 mM phosphoric acid and the levels of $^{33}$P incorporation into the peptide substrate were determined by the following method.

A phosphocellulose 96-well plate (Millipore, Cat no. MAPHNOB50) was pre-treated with 100 μL of a 100 mM phosphoric acid prior to the addition of the enzyme reaction mixture (40 μL). The solution was left to soak on to the phosphocellulose membrane for 30 minutes and the plate subsequently washed four times with 200 μL of a 100 mM phosphoric acid. To each well of the dry plate was added 30 μL of Optiphase 'SuperMix' liquid scintillation cocktail (Perkin Elmer) prior to scintillation counting (1450 Microbeta Liquid Scintillation Counter, Wallac). Levels of non-enzyme catalyzed background radioactivity were determined by adding 16 μL of the 500 mM phosphoric acid to control wells, containing all assay components (which acts to denature the enzyme), prior to the addition of the [γ-$^{33}$P]-ATP solution. Levels of enzyme catalyzed. $^{33}$P incorporation were calculated by subtracting mean background counts from those measured at each inhibitor concentration. For each Ki determination 8 data points, typically covering the concentration range 0-10 μM compound, were obtained in duplicate (DMSO stocks were prepared from an initial compound stock of 10 mM with subsequent 1:2.5 serial dilutions). Ki values were calculated from initial rate data by non-linear regression using the Prism software package (Prism 3.0, Graphpad Software, San Diego, Calif.).

Compounds 2, 4, 10-11, 21-27, 41, 47, 49, 52, 54, 62, 67-70, 72-75, 77, 82, 93, 108, 124-125, 131, 136-141, 145, 148, 150-151, 166-167, 174-175, 189, 193, 197, 200-201, 203, 209-210 were found to inhibit Aurora B kinase at a Ki value of between 0.05 uM and 2.0 uM.

Compounds 1, 6, 14-15, 17-18, 20, 28-32, 34-36, 39, 43-45, 53, 58, 60, 63, 71, 79-80, 92, 94-96, 98-99, 107, 109, 112, 114, 117, 120-121, 127-128, 130, 132-134, 144, 147, 149, 154, 156-157, 162, 170-171, 173, 176, 178, 180-182, 184, 188, 190, 192, 194, 198, 202, and 205-207 were found to inhibit Aurora B kinase at a Ki value of between 0.01 uM and 0.05 uM.

Compounds 3, 5, 7-9, 12-13, 16, 19, 33, 37-38, 40, 42, 46, 48, 50-51, 55-57, 59, 61, 64-66, 76, 78, 81, 83-90, 97, 100-106, 110-111, 113, 115-116, 118-119, 122-123, 126, 129, 135, 142-143, 146, 152-153, 155, 158-161, 163-165, 168-169, 172, 177, 179, 183, 185-187, 191, 195-196, 199, 204, 208, and 211 were found to inhibit Aurora B kinase at a Ki value of ≤0.01 uM.

Compounds 3, 5-9, 12-16, 18-19, 29, 31, 33-34, 36-40, 42, 46, 48, 50-51, 53, 55-59, 61, 64-66, 76, 78-79, 81, 83-90, 94-106, 110-113, 115-116, 118-123, 126-130, 133-135, 142-144, 146-147, 152-165, 168-173, 176-177, 179, 182-187, 191, 194-196, 198-199, 202, 204-205, 207-208, and 211 were found to inhibit Aurora B kinase at a Ki value of <0.025 uM.

Example 30

Itk Inhibition Assay

The compounds of the present invention were evaluated as inhibitors of human Itk kinase using a radioactivity-based assay. These compounds can also be evaluated using a spectrophotometric or alphascreen assay.

Itk Inhibition Assay: Radioactivity-Based Assay

Assays were carried out in a mixture of 20 mM MOPS (pH 7.0), 10 mM MgCl$_2$, 0.1% BSA and 1 mM DTT. Final substrate concentrations in the assay were 7.5 μM [γ-$^{33}$P]ATP (400 μCi $^{33}$P ATP/μmol ATP, Amersham Pharmacia Biotech/Sigma Chemicals) and 3 μM peptide (SAM68 protein Δ332-443). Assays were carried out at 25° C. in the presence of 50 nM Itk. An assay stock buffer solution was prepared containing all of the reagents listed above, with the exception of ATP and the test compound of interest. 50 μL of the stock solution was placed in a 96 well plate followed by addition of 2 μL of DMSO stock containing serial dilutions of the test compound (typically starting from a final concentration of 50 μM with 2-fold serial dilutions) in duplicate (final DMSO concentration 2%). The plate was pre-incubated for 10 minutes at 25° C. and the reaction initiated by addition of 50 μL [γ-$^{33}$P]ATP (final concentration 7.5 μM).

The reaction was stopped after 10 minutes by the addition of 100 μL 0.2M phosphoric acid+0.01% TWEEN 20. A multiscreen phosphocellulose filter 96-well plate (Millipore, Cat no. MAPHNOB50) was pretreated with 100 μL 0.2M phosphoric acid+0.01% TWEEN 20 prior to the addition of 170 μL of the stopped assay mixture. The plate was washed with 4×200 μL 0.2M phosphoric acid+0.01% TWEEN 20. After drying, 30 μL Optiphase 'SuperMix' liquid scintillation cocktail (Perkin Elmer) was added to the well prior to scintillation counting (1450 Microbeta Liquid Scintillation Counter, Wallac).

Ki(app) data were calculated from non-linear regression analysis of the initial rate data using the Prism software package (GraphPad Prism version 3.0cx for Macintosh, GraphPad Software, San Diego Calif., USA).

Compounds 7, 12-13, 16, 37-39, 46, 50-51, 60-61, 64-65, 76, and 81 were found to have a Ki value of ≤0.1 uM.

Compounds 1-6, 8-9, 14-15, 17, 20, 28-35, 40, 44, 52-59, 66-68, 71, 77, 79-80, 82, and 161-164 were found to have a Ki value of >0.1 uM and ≤1.0 uM.

Compounds 10, 25-27, 49, 69, 75, 166, and 167 were found to have a Ki value of >1.0 uM and ≤2.0 uM.

Example 31

Itk Inhibition Assay: Alphascreen Assay

Assays are carried out in a mixture of 20 mM MOPS (pH 7.0), 10 mM MgCl$_2$, 0.1% BSA and 1 mM DTT. Final substrate concentrations in the assay are 100 μM ATP (Sigma Chemicals) and 2 μM peptide (Biotinylated SAM68 γ332-443). Assays are carried out at 25° C. and in the presence of 10 nM Itk. An assay stock buffer solution is prepared containing all of the reagents listed above, with the exception of ATP and the test compound of interest. 25 μL of the stock solution is placed in each well of a 96 well plate followed by 1 μL of DMSO containing serial dilutions of the test compound (typically starting from a final concentration of 15 μM) in duplicate (final DMSO concentration 2%). The plate is preincubated for 10 minutes at 25° C. and the reaction initiated by addition of 25 μL ATP (final concentration 100 μM). Background counts are determined by the addition of 5 μL 500 mM EDTA to control wells containing assay stock buffer and DMSO prior to initiation with ATP.

The reaction is stopped after 30 minutes by diluting the reaction 225-fold into MOPS buffer (20 mM MOPS (pH 7.0), 1 mM DTT, 10 mM MgCl$_2$, 0.1% BSA) containing 50 mM EDTA to bring the final concentration of peptide to 9 nM.

AlphaScreen™ reagents are prepared according to the manufacturers instructions (AlphaScreen™ phosphotyrosine (P-Tyr-100) assay kit, PerkinElmer catalogue number 6760620C). Under subdued lighting, 20 μL of AlphaScreen™ reagents are placed in each well of a white half area 96 well plate (Corning Inc.—COSTAR 3693) with 30 μL of the stopped, diluted kinase reactions. Plates are incubated in the dark for 60 minutes prior to reading on a Fusion Alpha plate reader (PerkinElmer).

After removing mean background values for all of the data points, Ki(app) data are calculated from non-linear regression analysis using the Prism software package (GraphPad Prism version 3.0cx for Macintosh, GraphPad Software, San Diego Calif., USA).

Example 32

Itk Inhibition Assay: Spectrophotometric Assay

Compounds are screened for their ability to inhibit Itk using a standard coupled enzyme assay (Fox et al., Protein Sci., (1998) 7, 2249).

Assays are carried out in a mixture of 20 mM MOPS (pH 7.0), 10 mM $MgCl_2$, 0.1% BSA, 1 mM DTT, 2.5 mM phosphoenolpyruvate, 300 µM NADH, 30 µg/ml pyruvate kinase and 10 µg/ml lactate dehydrogenase. Final substrate concentrations in the assay are 100 µM ATP (Sigma Chemicals) and 3 µM peptide (Biotinylated SAM68 0332-443). Assays are carried out at 25° C. and in the presence of 100 nM Itk.

An assay stock buffer solution is prepared containing all of the reagents listed above, with the exception of ATP and the test compound of interest. 60 µl of the stock solution is placed in a 96 well plate followed by addition of 2 µl of DMSO stock containing serial dilutions of the test compound (typically starting from a final concentration of 15 µM). The plate is preincubated for 10 minutes at 25° C. and the reaction initiated by addition of 5 µl of ATP. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA).

Example 33

JAK3 Inhibition Assay

Compounds were screened for their ability to inhibit JAK using the assay shown below. Reactions were carried out in a kinase buffer containing 100 mM HEPES (pH 7.4), 1 mM DTT, 10 mM $MgCl_2$, 25 mM NaCl, and 0.01% BSA. Substrate concentrations in the assay were 5 µM ATP (200 uCi/µmole ATP) and 1 µM poly(Glu)$_4$Tyr. Reactions were carried out at 25° C. and 1 nM JAK3.

To each well of a 96 well polycarbonate plate was added 1.5 µl of a candidate JAK3 inhibitor along with 50 µl of kinase buffer containing 2 µM poly(Glu)$_4$Tyr and 10 µM ATP. This was then mixed and 50 µl of kinase buffer containing 2 nM JAK3 enzyme was added to start the reaction. After 20 minutes at room temperature (25 C), the reaction was stopped with 50 µl of 20% trichloroacetic acid (TCA) that also contained 0.4 mM ATP. The entire contents of each well were then transferred to a 96 well glass fiber filter plate using a TomTek Cell Harvester. After washing, 60 µl of scintillation fluid was added and $^{33}P$ incorporation detected on a Perkin Elmer TopCount.

Compounds 12-13, 21, 25, 37, 50, 65, 76, 78, 81, 88, 92, 99, 102, 105, 108, 110, 112-113, 115, 131, 135, 150-151, 158-161, 164, 172-173, 180-181, 183, 185, 199, 202, 206, 209, and 211 were found to have a Ki value of ≤0.01 uM.

Compounds 1, 3, 5, 7-11, 14-17, 19-20, 22, 28-31, 33, 38-40, 44, 46, 48-49, 51-57, 60-61, 64, 66-68, 71, 74, 79, 80, 83, 85, 89-90, 94-97, 100, 103-104, 109, 116-117, 119-121, 126, 128, 134, 144-146, 148-149, 155, 162-163, 166-170, 175, 177, 179, 182, 184, 186, 188-191, 194-195, 198, 204-205, and 207 were found to have a Ki value of >0.01 uM and ≤0.5 uM.

Compounds 2, 4, 23-24, 26-27, 32, 34-35, 58, 69, 73, 77, 82, 87, 114, 124, 127, 132, 137-138, 152, 171, 178, 192, and 203 were found to have a Ki value of >0.5 uM and ≤2.0 uM.

Example 34

JAK2 Inhibition Assay

The assays are as described above in Example 33 except that JAK-2 enzyme was used, the final poly(Glu)$_4$Tyr concentration was 15 µM, and final ATP concentration was 12 µM.

Example 35

FLT-3 Inhibition Assay

Compounds were screened for their ability to inhibit FLT-3 activity using a radiometric filter-binding assay. This assay monitors the 33P incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/ml pE4Y (both from Sigma Chemicals, St. Louis, Mo.). The final concentration of a compound of the present invention was generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 180 mM ATP (containing 0.3 mCi of [γ-33$^P$]ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay was run on a 96 well plate by mixing 50 µl each of Solution 1 and 2.5 ml of the compounds of the present invention. The reaction was initiated with Solution 2. After incubation for 20 minutes at room temperature, the reaction was stopped with 50 µl of 20% TCA containing 0.4 mM of ATP. All of the reaction volume was then transferred to a filter plate and washed with 5% TCA by a Harvester 9600 from TOMTEC (Hamden, Conn.). The amount of $^{33}P$ incorporation into pE4y was analyzed by a Packard Top Count Microplate Scintillation Counter (Meriden, Conn.). The data was fitted using Prism software to get an IC50 or Ki.

Compounds 2, 3, 25, 50, 76, 78-79, 81, 85, 88-90, 92, 94, 97, 99-100, 102-103, 105, 108-110, 112-113, 119, 128, 131, 144, 150-151, 159-160, 168-169, 173, 181, 183, 199, 202, 206, and 209 were found to have a Ki value of ≤0.05 uM.

Compounds 1, 4-5, 8, 10, 12, 14-17, 20, 22, 26-27, 31-32, 35, 37, 39-40, 46, 51, 60, 64-65, 67, 68, 71, 73-74, 80, 95-96, 104, 115, 121, 126, 134-135, 137, 148, 155, 158, 171-172, 182, 184-186, 188-189, 194, 198, 204-205, and 211 were found to have a Ki value >0.05 uM and ≤0.15 uM.

Compounds 6-7, 9, 11, 19, 23-24, 28-30, 33-34, 38, 44, 48-49, 52-59, 61, 66, 69, 77, 82-83, 114, 117, 120, 124, 127, 132, 139, 142, 145-146, 149, 152, 161-164, 166-167, 170, 175, 177-178, 190-191, 193, 195, 203, and 207 were found to have a Ki >0.15 uM and ≤1.0 uM.

Example 36

Microsomal Stability Assay

Microsomal stability was monitored by generation of depletion-time profiles in microsomes from a range of species (male CD-1 mouse, male Sprague-Dawley rat, male Beagle dog, male Cynomolgus monkey and pooled mixed gender human). Compound spiking solutions were made up by diluting down the compound stock solution in DMSO (typically 10 mM) to give a solution in acetonitrile (0.5 mM). Compound (to give final concentration of 5 µM) was incubated with a final reaction mixture (1000 µL) consisting of liver microsome protein (1 mg/mL) and a β-nicotinamide adenine dinucleotide phosphate, reduced form (NADPH)-regenerating system (RGS) [consisting of 2 mM β-nicotinamide adenine dinucleotide phosphate (NADP), 20.5 mM isocitric acid, 0.5 U of isocitrate dehydrogenase/mL, 30 mM magnesium chloride, and 0.1 M phosphate buffer (PB) pH 7.4] in the presence of 0.1 M PB (pH 7.4).

The reaction was initiated by the addition (250 µL) of the pre-incubated RGS to the pre-incubated microsome/VRT/PB mixture (pre-incubation in both instances was for 10 minutes at 37° C.). Samples were incubated within Eppendorf vials (1.5 ml) on a heater shaker (DPC Micromix 5 (settings; form 20, amplitude 4) modified to be heated, to 37° C., by two plate heaters fixed to the deck and controlled by a Packard Manual Heater) attached to a Multiprobe II HT Ex automated liquid handler. The liquid handler was programmed (WinPREP software) to sample the microsomal incubation mixture after 0, 2, 10, 30 and 60 minutes of incubation and transfer an aliquot (100 µL) to a stop block (96-well block) containing 100 µL of chilled methanol. The % organic in the stop mixture was optimized for analysis by addition of appropriate volumes of aqueous/organic (typically 100 µL of 50:50 methanol:water).

Prior to analysis the stop block was placed on a shaker (DPC Micromix 5; 10 min, form 20, amplitude 5) to precipitate out proteins. The block was then centrifuged (Jouan GR412; 2000 rpm, 15 min, 4° C.). A sample aliquot (200 µL) was then transferred to an analysis block and the block was centrifuged again (Jouan GR412; 2000 rpm, 5 min, 4° C.) prior to being sent for analysis. Depletion profiles were determined by monitoring the disappearance of VRT by liquid chromatography-tandem mass spectrometry (LC-MS/MS). Samples were injected (20 µL; Agilent 1100 liquid chromatographic system equipped with autosampler) onto an analytical column. Mobile phase consisted of Water+0.05% (v/v) formic acid (A) and methanol+0.05% (v/v) formic acid (B).

Running a gradient method optimized for the compound of interest carried, out the compound elution from analytical column. The total run time was 6 minutes with a flow rate of 0.35 mL/min. The entire column effluent entered the electrospray ionization source (positive mode) of a Micromass Quattro LC tandem mass spectrometer between 0.5 and 5.9 min of the run. The mass spectrometry was optimized for the compound of interest. All incubations were conducted in duplicate and results were expressed as % parent remaining at either 30 minutes or 60 minutes relative to 0 minutes sample.

Compounds 5, 7, 9-17, 20-22, 25-35, 37-40, 44, 48-50, 52-61, 64-66, 68-69, 71, 75-76, 78-80, 82, 83, 85, 87-99, 94, 97, 99-100, 102-105, 108-110, 112-117, 120-121, 126-128, 132, 134-135, 137-139, 142, 144-146, 148-153, 155, 159-163, 166-173, 175, 177-178, 180-181, 183-184, 186, 188, 190-192, 194-195, 199-200, 202, 205-206, 209, and 211 were found to have stability to human liver microsomes at >50% remaining after 30 minutes.

Compounds 5, 7, 9, 12-14, 16, 18, 31, 33, 36, 37, 39, 40, 42, 46, 50, 52, 55, 56, 59, 61, 63, 64, 68, 71, 76, 79, 80, 84, 85, 94, 98, 102, 103, 105, 109, 112-117, 120-122, 126-128, 130, 132, 134-136, 142-145, 147, 150-157, 168-171, 194, and 202 were found to have stability to human liver microsomes at >50% remaining after 60 minutes.

Example 37

Analysis of Cell Proliferation and Viability

Compounds were screened for their ability to inhibit cell proliferation and their effects on cell viability using Colo205 cells obtained from ECACC and using the assay shown below.

Colo205 cells were seeded in 96 well plates and serially diluted compound was added to the wells in duplicate. Control groups included untreated cells, the compound diluent (0.1% DMSO alone) and culture medium without cells. The cells were then incubated for 72 or 96 hrs at 37 C in an atmosphere of 5% CO2/95% humidity.

To measure proliferation, 3 h prior to the end of the experiment 0.5 µCi of 3H thymidine was added to each well. Cells were then harvested and the incorporated radioactivity counted on a Wallac microplate beta-counter. Cell viability was assessed using Promega CellTiter 96AQ to measure MTS conversion. Dose response curves were calculated using either Prism 3.0 (GraphPad) or SoftMax Pro 4.3.1 LS (Molecular Devices) software.

72 Hours Incubation

The following compounds were incubated for 72 hours and were found to have an IC50 value of ≤0.03 uM: Compounds 50-51, 81, 85, 89, 97, 113, 118, 133, 135, 143-144, 146, 157, 159-160, 170, 172, 176, 182-183, 185, 187, 191, 194, 196, 198-199, 204-205, and 211.

The following compounds were incubated for 72 hours and were found to have an IC50 value >0.03 uM and ≤0.20 uM: Compounds 5, 16, 40, 56, 83, 87, 103, 115, 119, 121-123, 126-128, 130, 134, 142, 147, 151-152, 156, 168-169, 171, 173, 177-181, 184, 186, 190, 195, 202-203, and 208.

The following compounds were incubated for 72 hours and were found to have an IC50 value >0.20 uM: Compounds 59, 112, 114, 116-117, 120, 124-125, 129, 131-132, 136, 141, 145, 148-150, 158, 174-175, 188-189, 192-193, 197, 200, 206-207, 209-210.

96 Hours Incubation

The following compounds were incubated for 96 hours and were found to have an IC50 value of ≤0.05 uM: Compounds 7, 12, 38, 50-51, 56, 70-71, 78, 80-81, 84-85, 88-90, 92, 95-96, 99-105, 107, 110-111, 128, 135, 153, 155, 157, and 164.

The following compounds were incubated for 96 hours and were found to have an IC50 value of >0.05 uM and ≤1.0 uM: Compounds 1-2, 4-6, 8-9, 11, 13-18, 20, 28-37, 39-46, 48, 52-55, 57-61, 64-68, 76-77, 79, 86, 93-94, 98, 106, 109, 132, 137-140, 154, 156, 161-163, 165, and 201.

The following compounds were incubated for 96 hours and were found to have an IC50 value of >1.0 uM: Compounds 3, 19, 21-27, 47, 49, 62-63, 72-74, 97, 108, 166, and 167.

Example 38

Abl Kinase Activity Inhibition Assay and Determination of the Inhibition Constant Ki Compounds were screened for their ability to inhibit N-terminally truncated (Δ27) Abl kinase activity using a standard coupled enzyme system (Fox et al., *Protein Sci.,* 7, pp. 2249 (1998)). Reactions were carried out in a solution containing 100 mM HEPES (pH 7.5), 10 mM MgCl₂, 25 mM NaCl, 300 μM NADH, 1 mM DTT and 3% DMSO. Final substrate concentrations in the assay were 110 μM ATP (Sigma Chemicals, St Louis, Mo.) and 70 μM peptide (EAIYAAPFAKKK, American Peptide, Sunnyvale, Calif.). Reactions were carried out at 30° C. and 21 nM Abl kinase. Final concentrations of the components of the coupled enzyme system were 2.5 mM phosphoenolpyruvate, 200 μM NADH, 60 μg/ml pyruvate kinase and 20 μg/ml lactate dehydrogenase.

An assay stock buffer solution was prepared containing all of the reagents listed above with the exception of ATP and the test compound of interest. The assay stock buffer solution (60 μl) was incubated in a 96 well plate with 2 μl of the test compound of interest at final concentrations typically spanning 0.002 μM to 30 μM at 30° C. for 10 min. Typically, a 12 point titration was prepared by serial dilutions (from 1 mM compound stocks) with DMSO of the test compounds in daughter plates. The reaction was initiated by the addition of 5 μl of ATP (final concentration 110 μM). Rates of reaction were obtained using a Molecular Devices Spectramax plate reader (Sunnyvale, Calif.) over 10 min at 30° C. The Ki values were-determined from the residual rate data as a function of inhibitor concentration using nonlinear regression (Prism 3.0, Graphpad Software, San Diego, Calif.).

Example 39

Mutant Abl Kinase (T315I) Activity Inhibition Assay and Determination of the Inhibition Constant IC50

Compounds were screened for their ability to inhibit the T315I mutant form of human Abl at Upstate Cell Signaling Solutions (Dundee, UK). In a final reaction volume of 25 μl, the T315I mutant of human Abl (5-10 mU) was incubated with 8 mM MOPS pH 7.0, 0.2 mM EDTA, 50 μM EAIYAAP-FAKKK, 10 mM Mg Acetate, [γ-³³P-ATP] (specific activity approx. 500 cpm/pmol, 10 mM final assay concentration) and the test compound of interest at final concentrations over the range 0-4 μnM. The reaction was initiated by the addition of the MgATP mix. After incubation for 40 minutes at room temperature, the reaction was stopped by the addition of 5 μl of a 3% phosphoric acid solution. 10 μl of the reaction was then spotted onto a P30 filtermat and washed three times for 5 minutes in 75 mM phosphoric acid and once in methanol prior to drying and scintillation counting. Inhibition IC50 values were determined from non-linear regression analysis of the residual enzyme activities as a function of inhibitor concentration (Prism 3.0, Graphpad Software, San Diego, Calif.).

Example 40

Plk4 Inhibition Assay

Compounds were screened for their ability to inhibit Plk4 using a radioactive-phosphate incorporation assay. Assays were carried out in a mixture of 8 mM MOPS (pH 7.5), 10 mM MgCl₂, 0.1% BSA and 2 mM DTT. Final substrate concentrations were 15 μM [γ-³³P]ATP (227 mCi 33P ATP/mmol ATP, Amersham Pharmacia Biotech/Sigma Chemicals) and 300 μM peptide (KKKMDATFADQ). Assays were carried out at 25° C. in the presence of 25 nM Plk4. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 15 μM). The reaction was stopped after 180 minutes by the addition of 100 μL 0.14M phosphoric acid. A multiscreen phosphocellulose filter 96-well plate (Millipore, Cat no. MAPHNOB50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac). After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:

1. A method of inhibiting Aurora-A or Aurora-B protein kinase activity in an in vitro biological sample comprising contacting said biological sample with a compound of any one of the following:

I-1

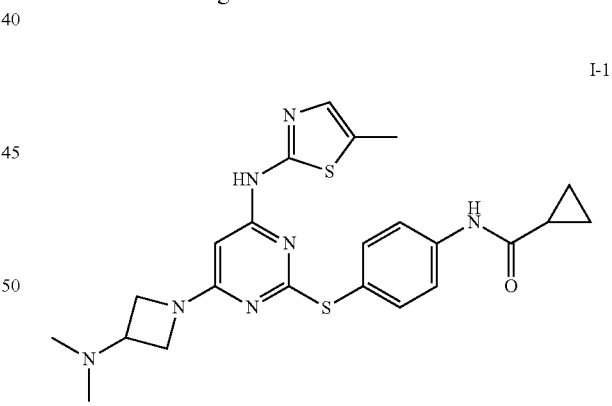

I-2

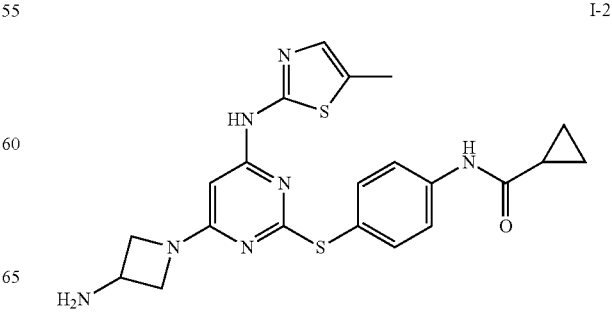

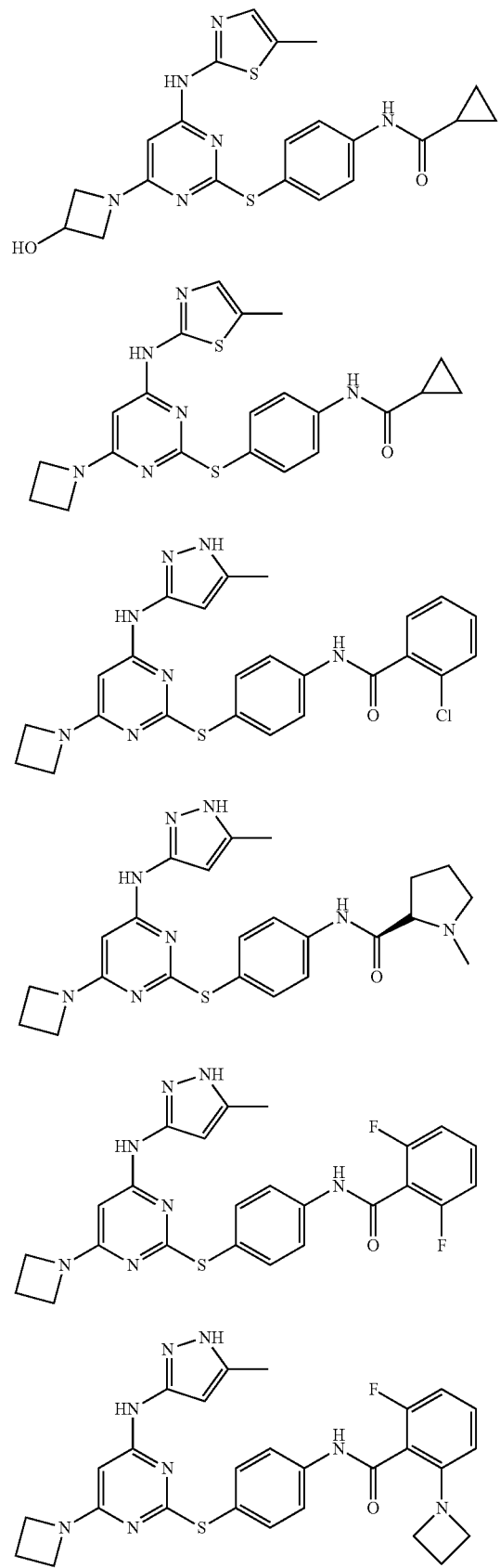
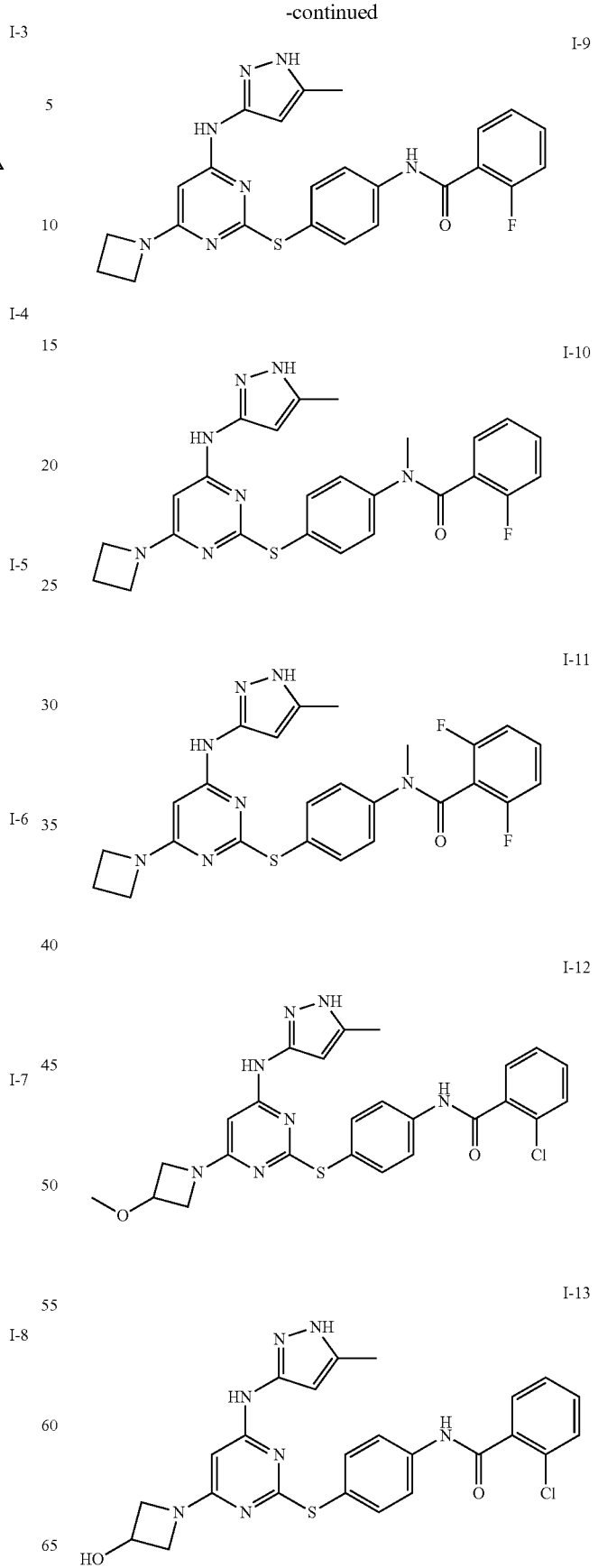

| | |
|---|---|
| I-14 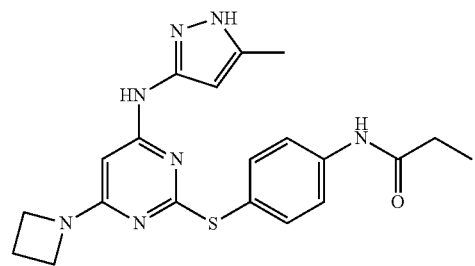 | I-19 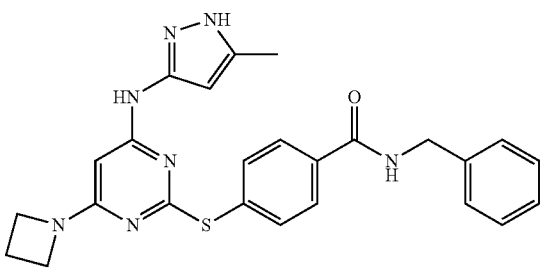 |
| I-15 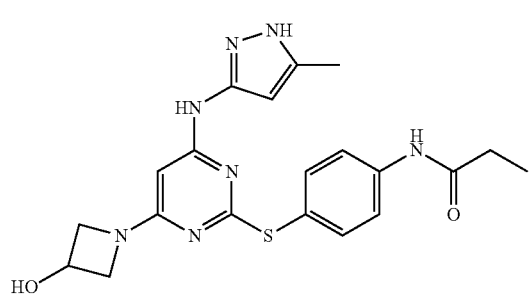 | I-20 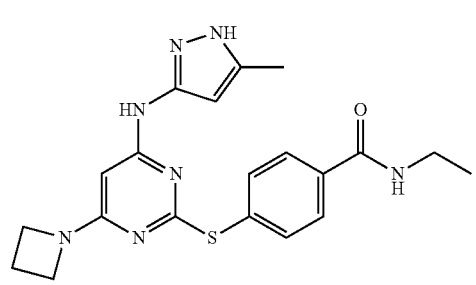 |
| I-16 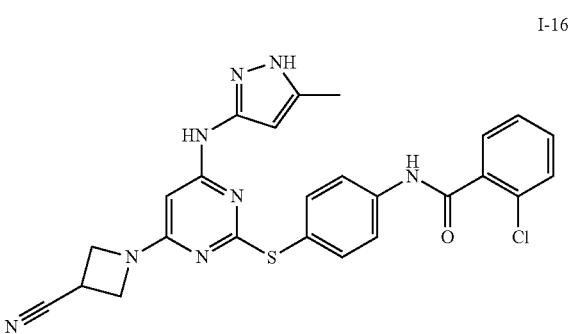 | I-21 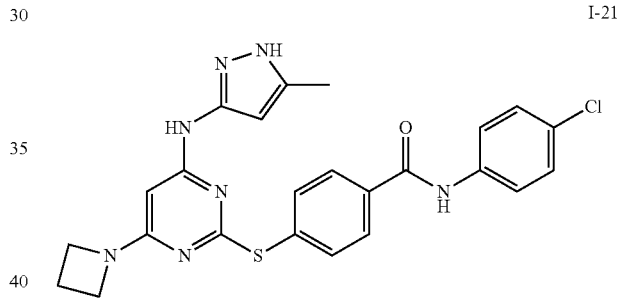 |
| I-17 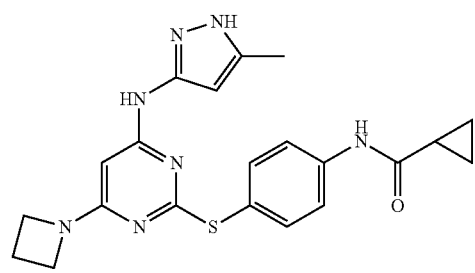 | I-22 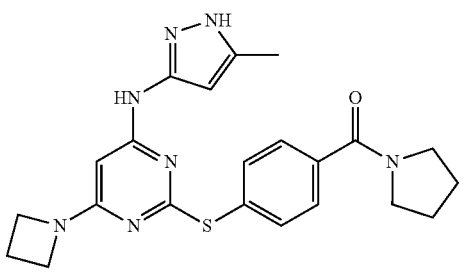 |
| I-18 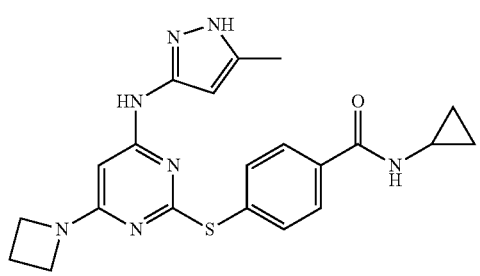 | I-23 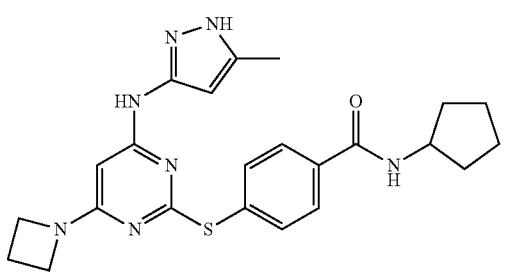 |

I-24
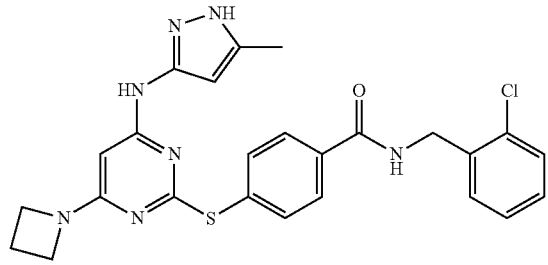
I-25
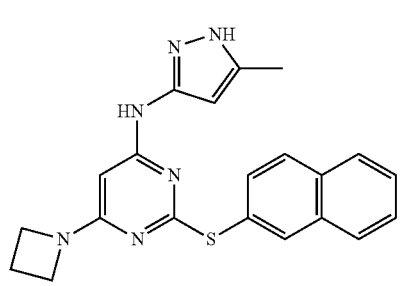
I-26
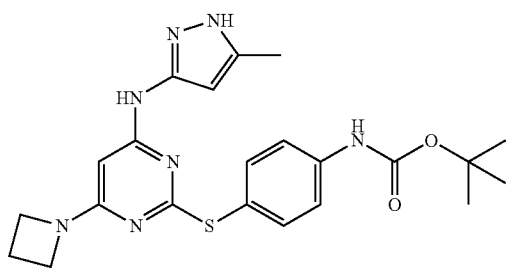
I-27
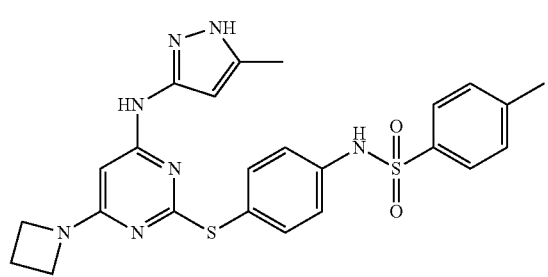
I-28
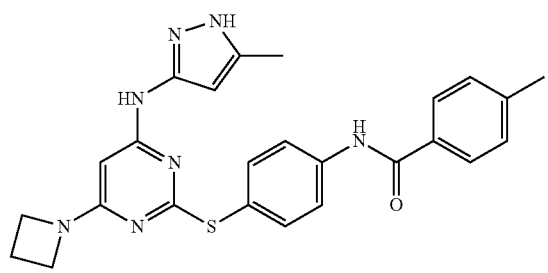
I-29
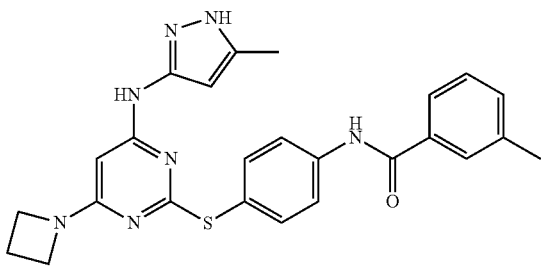
I-30
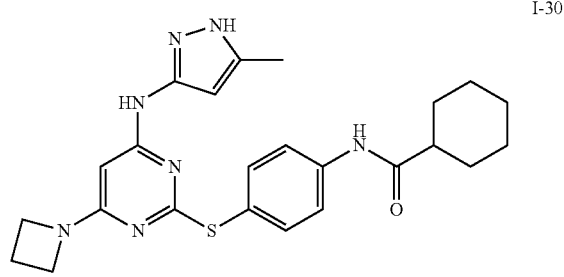
I-31
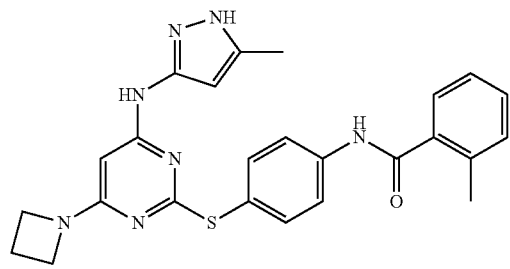
I-32
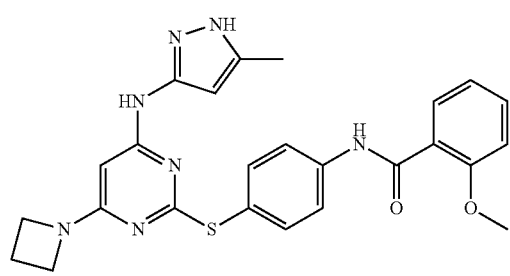
I-33
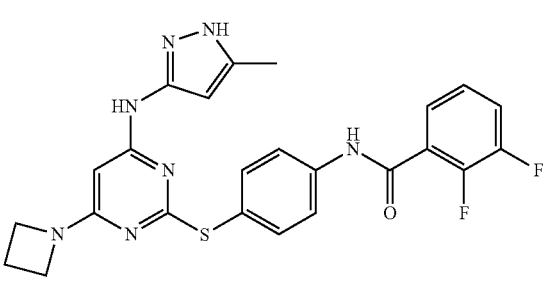

I-34
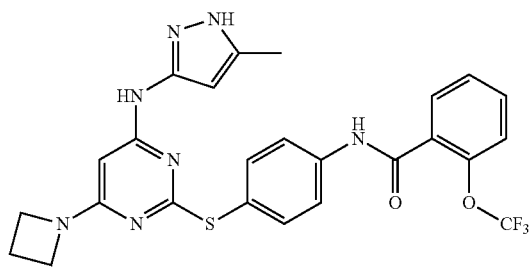
I-35
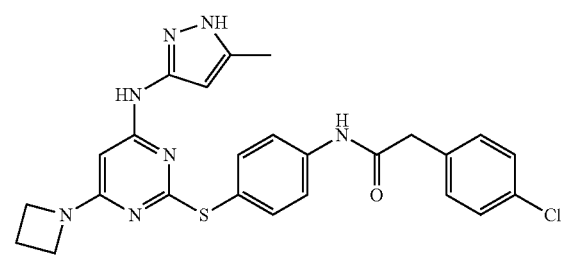
I-36
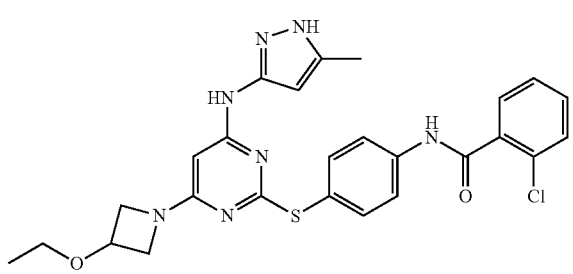
I-37
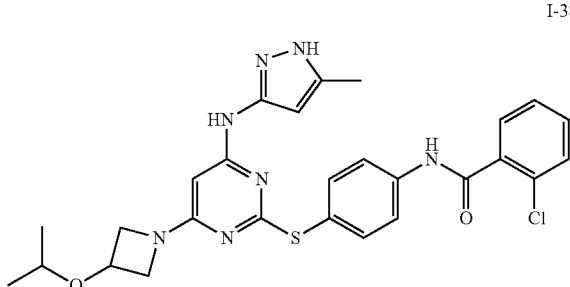
I-38
I-39
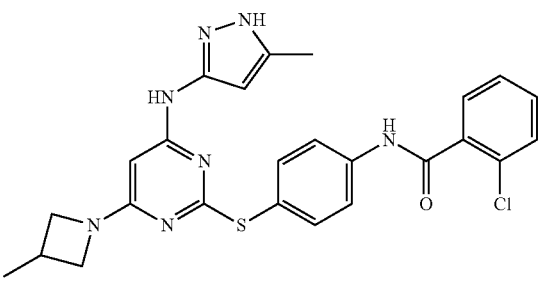
I-40
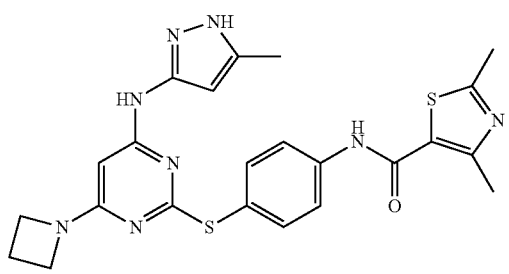
I-41
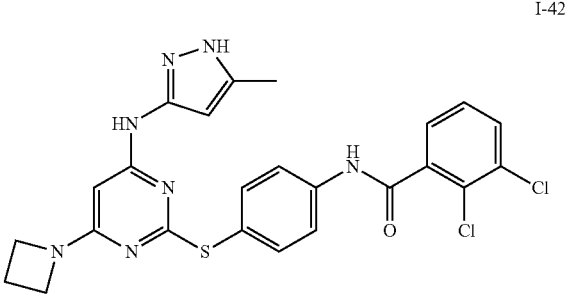
I-42
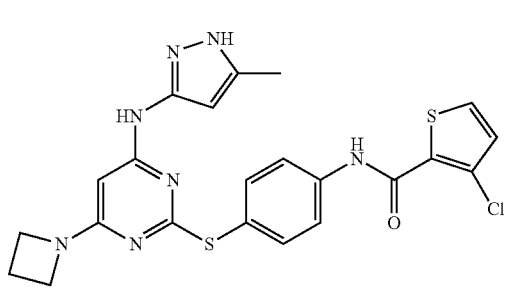
I-43

I-44
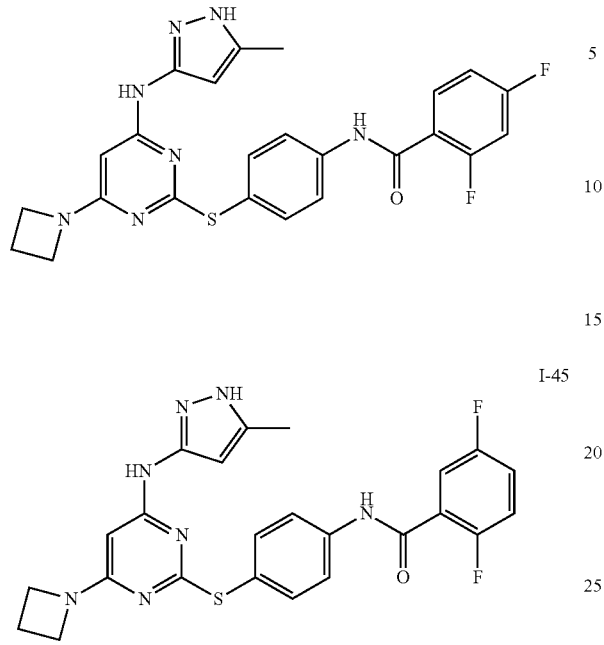
I-45
I-46
I-47
I-48
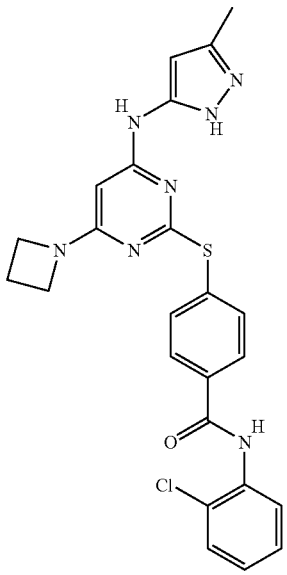
I-49
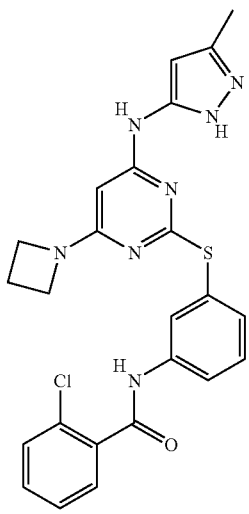
I-50
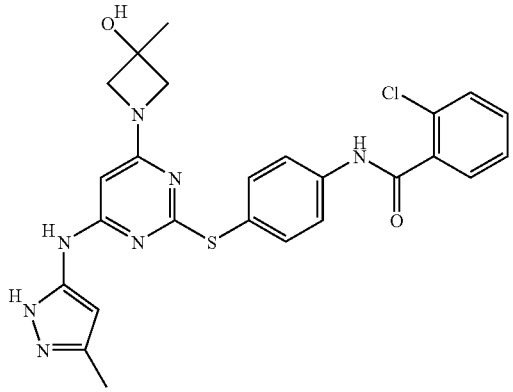

I-51
I-52
I-53
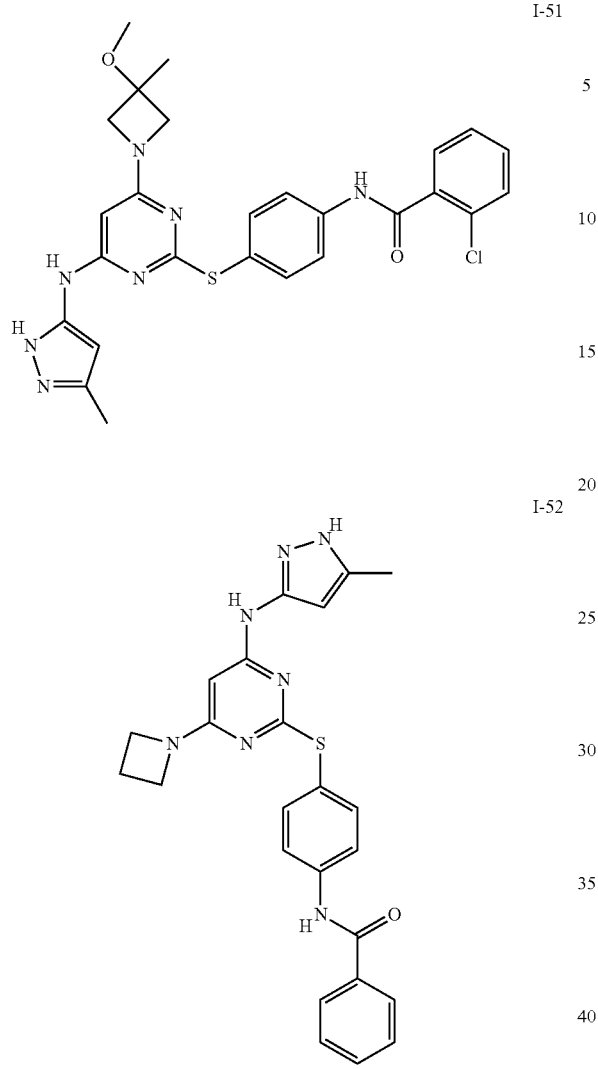
I-54
I-55
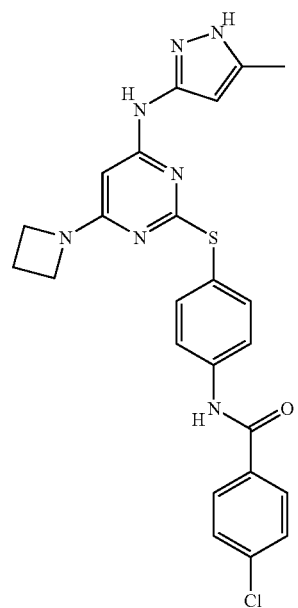
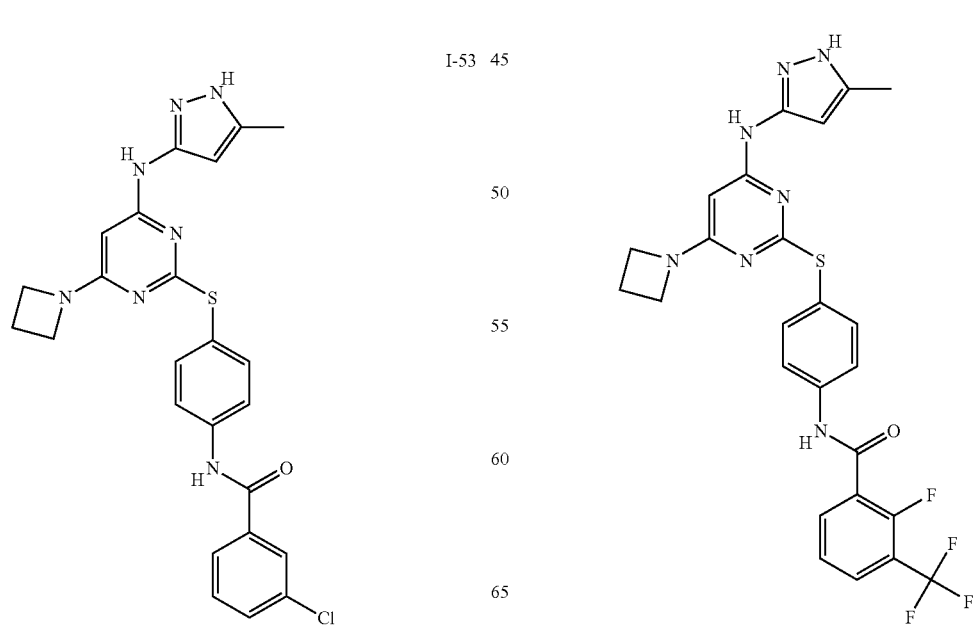

-continued
I-56
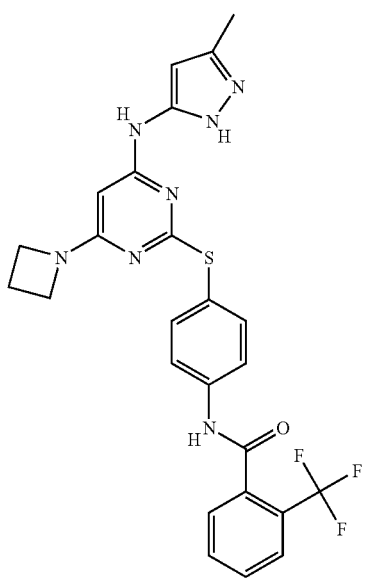
I-57
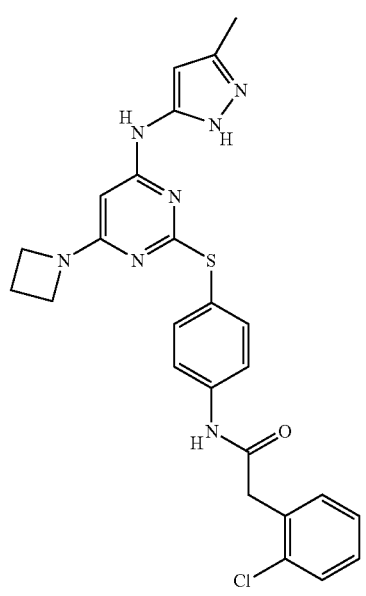
I-58
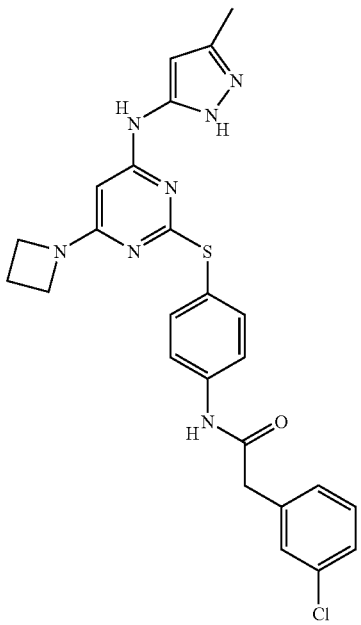
I-59
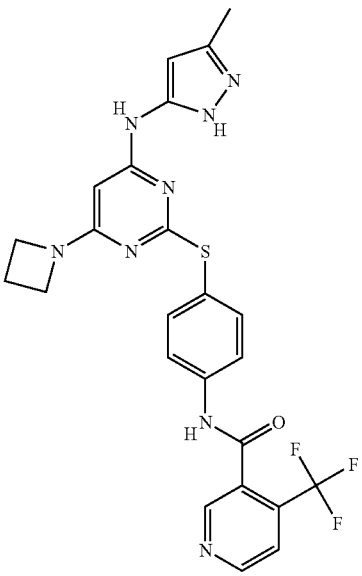
I-60

-continued
I-61
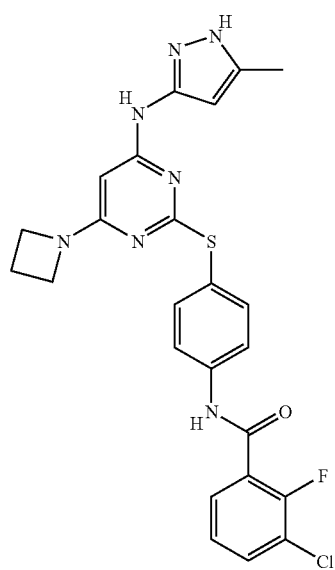
I-62
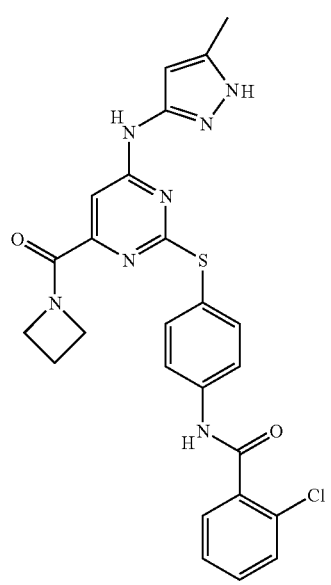
-continued
I-63
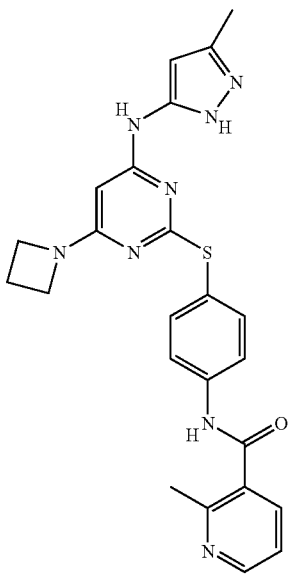
I-64
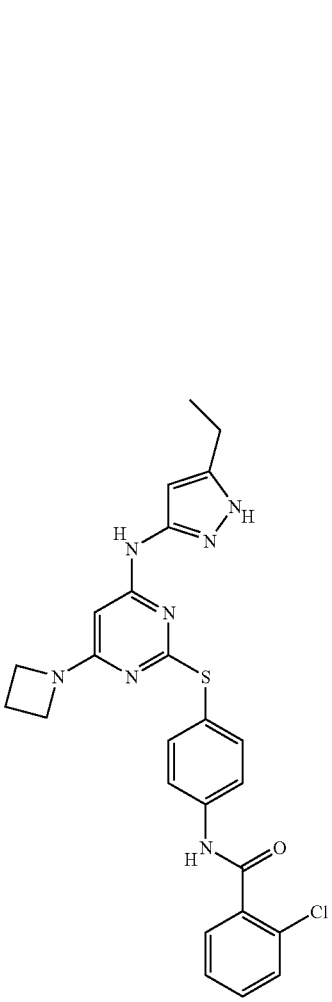

| 187 -continued | 188 -continued |
|---|---|
| I-65 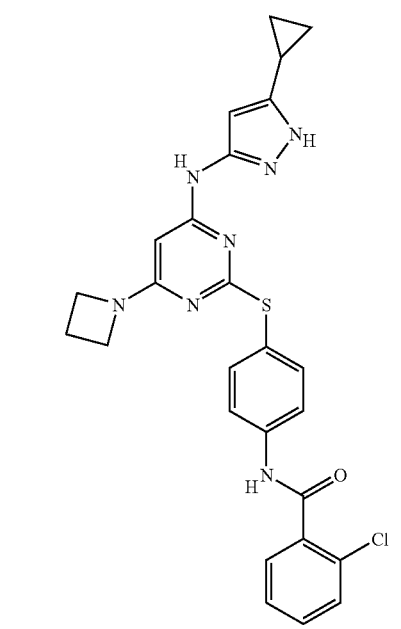 | I-68 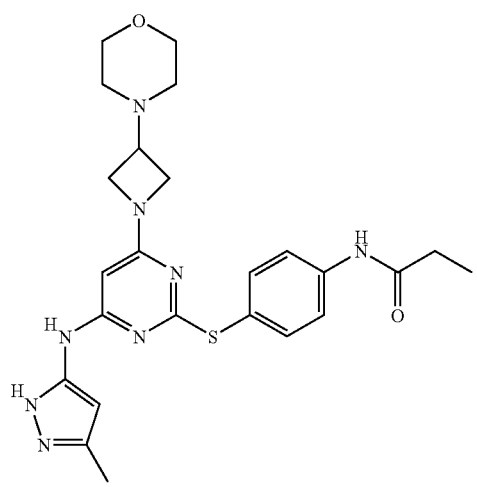 |
| I-66 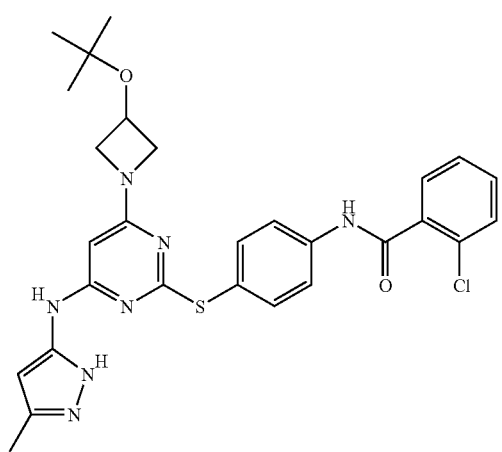 | I-69 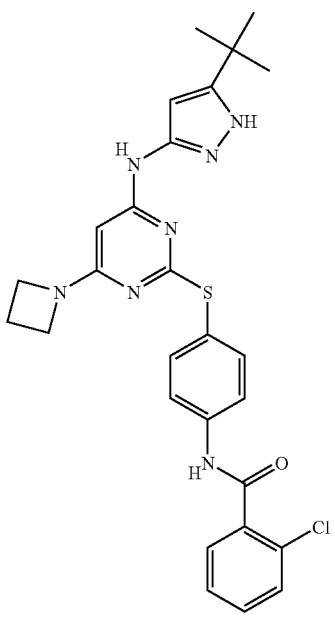 |
| I-67 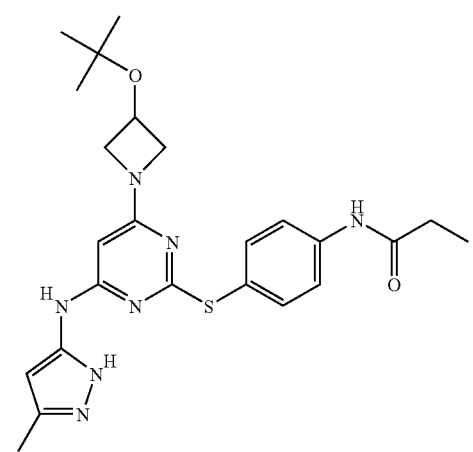 | I-70 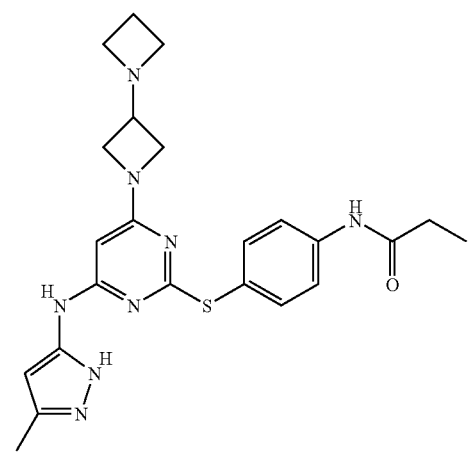 |

I-71
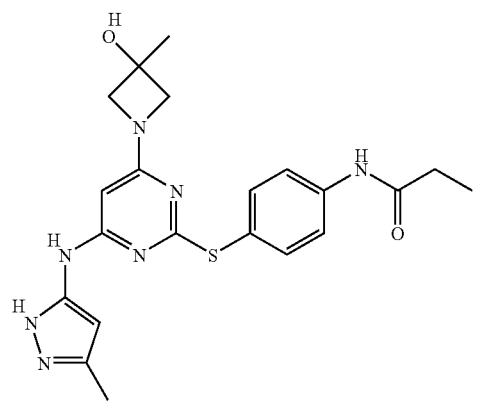
I-74
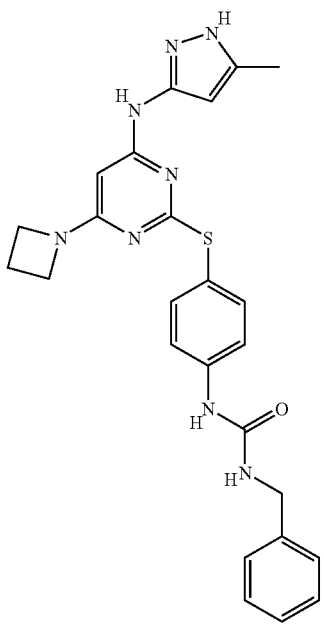
I-72
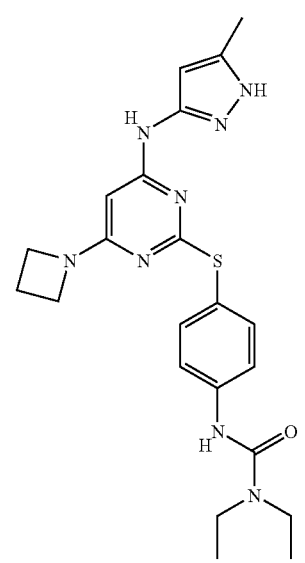
I-73
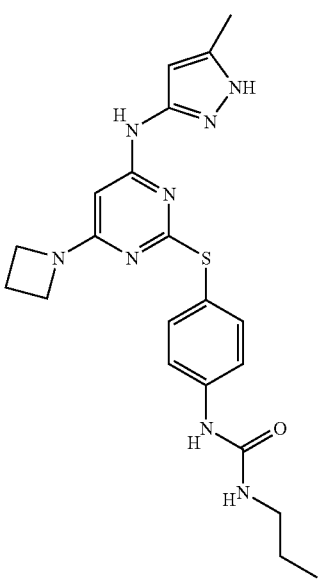
I-75
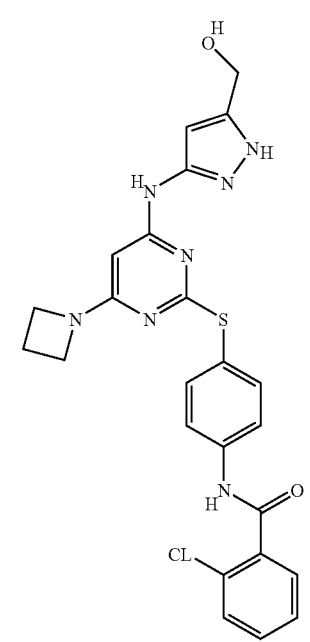

I-76
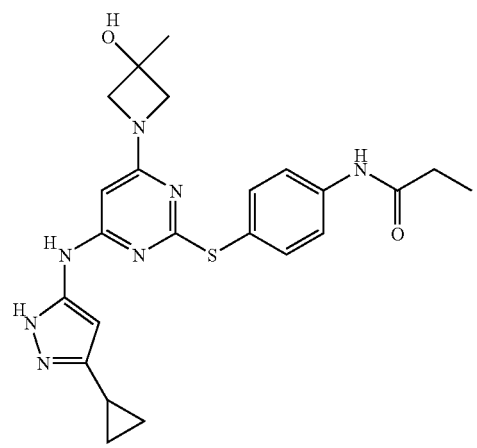
I-77
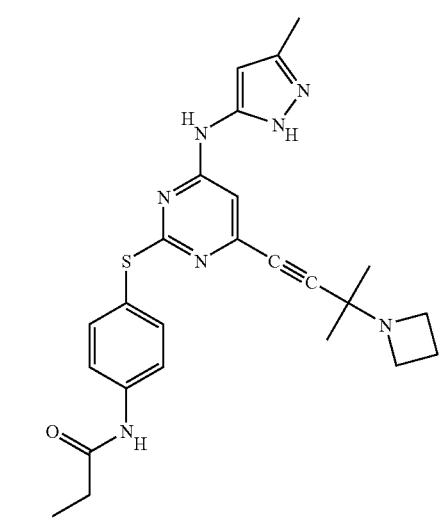
I-78
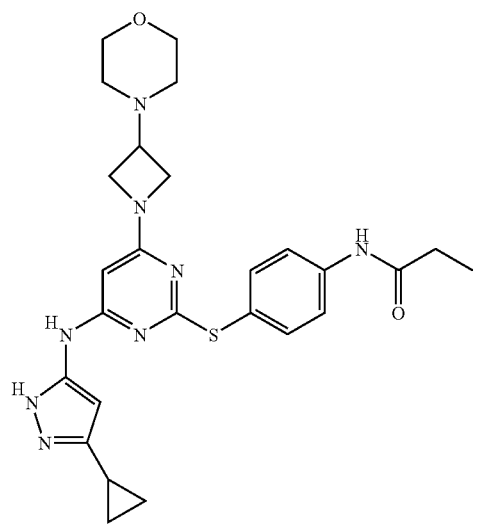
I-79
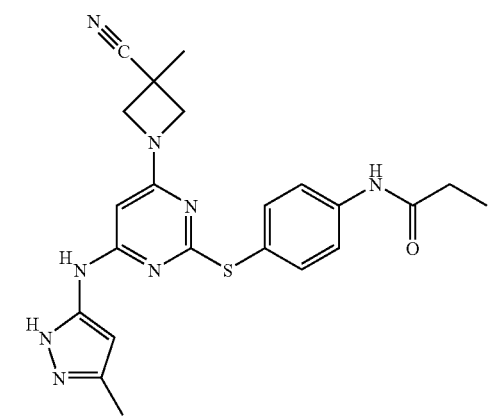
I-80
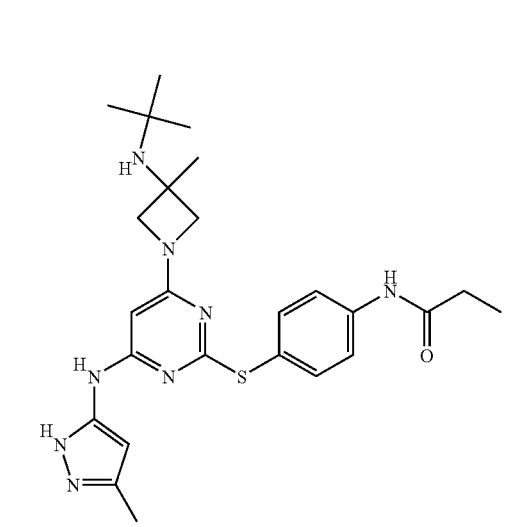
I-81
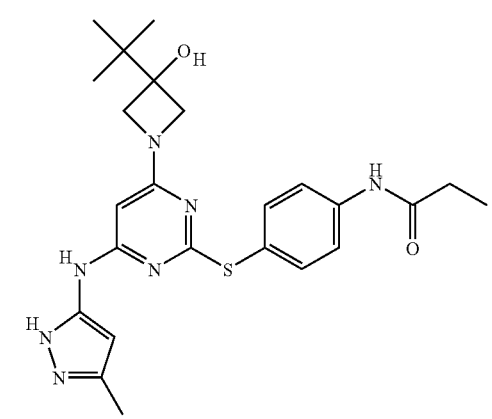

-continued
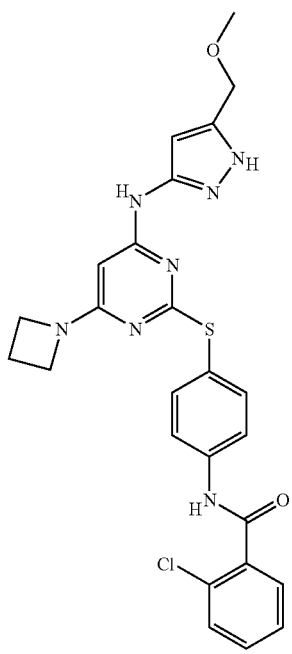
I-82
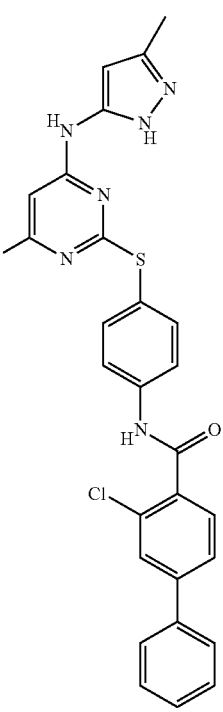
I-83
-continued
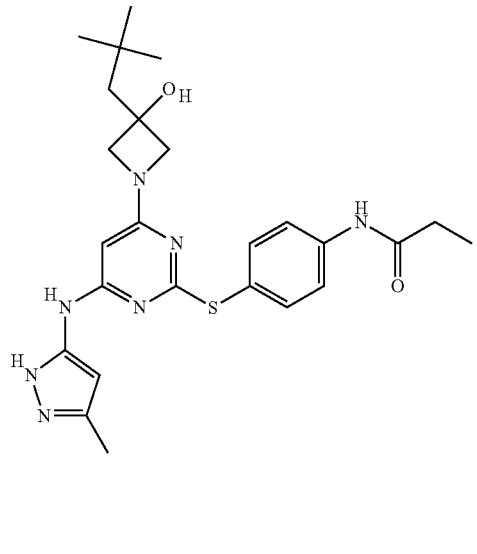
I-84
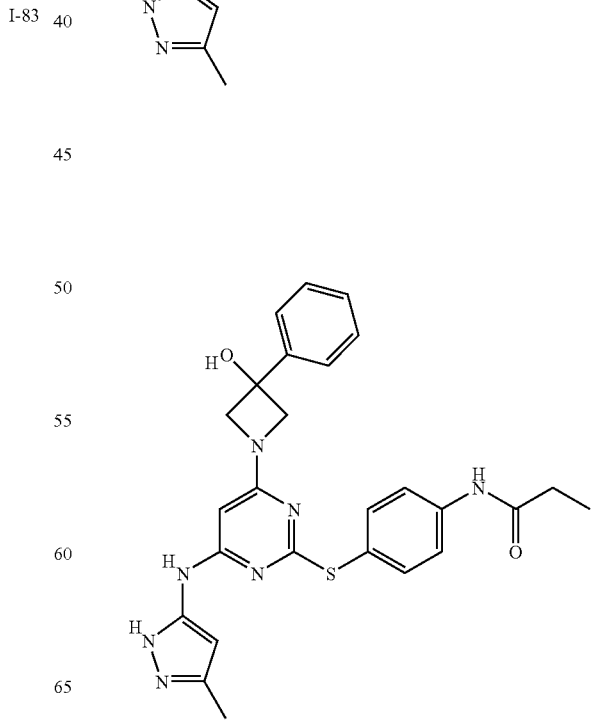
I-85
I-86

I-87
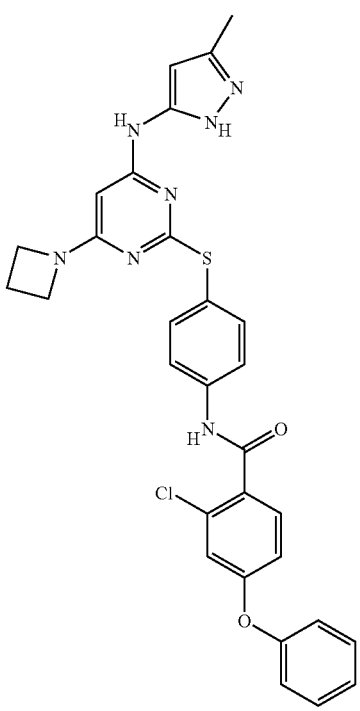
I-88
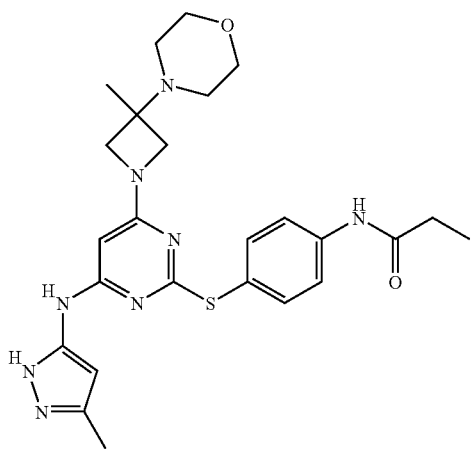
I-89
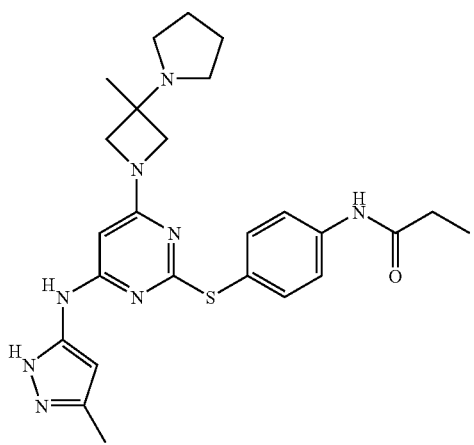
I-90
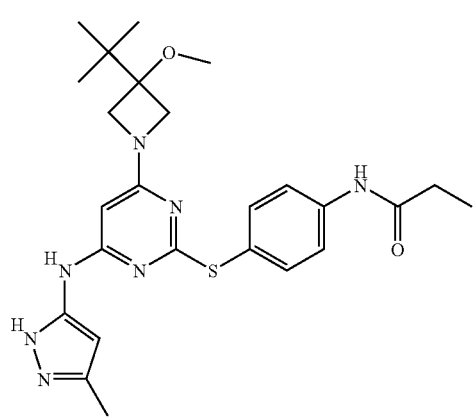
I-91
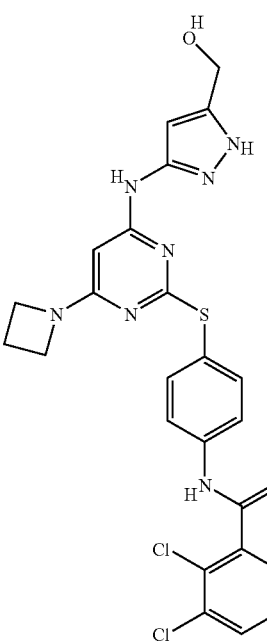
I-92
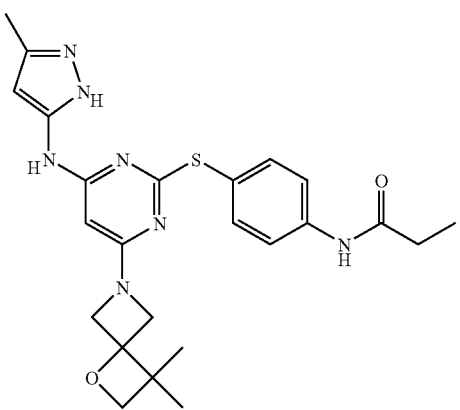

I-93
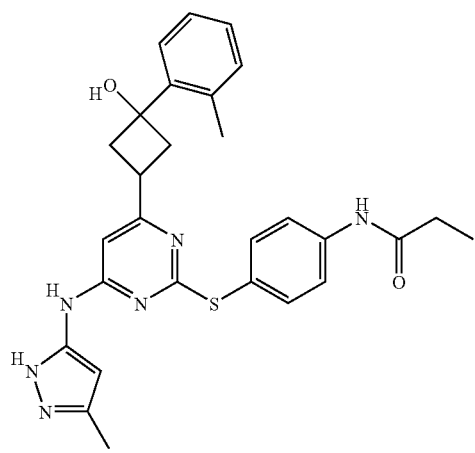
I-96
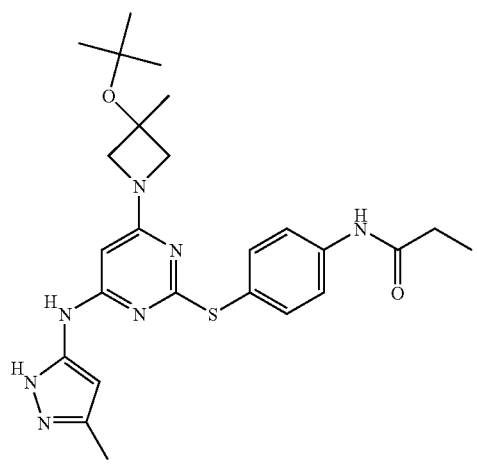
I-94
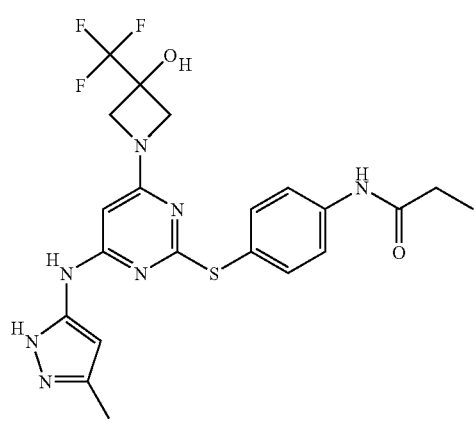
I-97
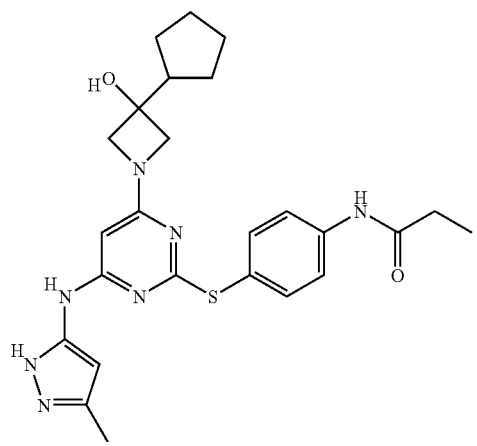
I-95
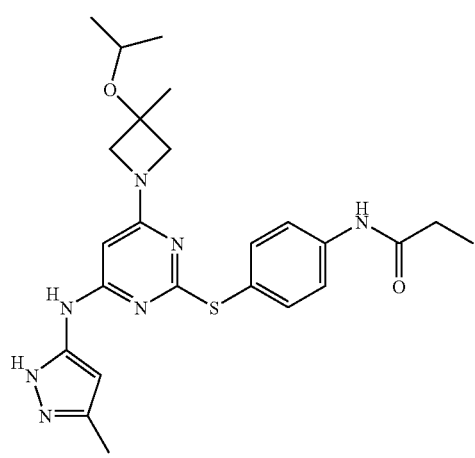
I-98
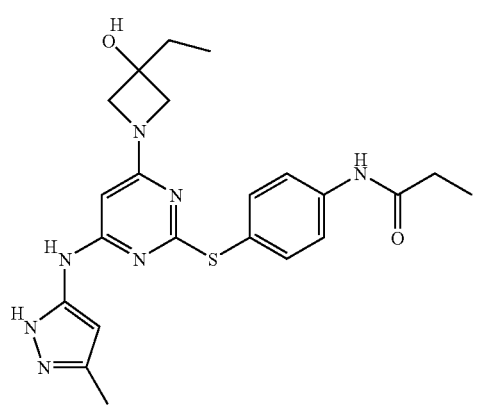

I-99
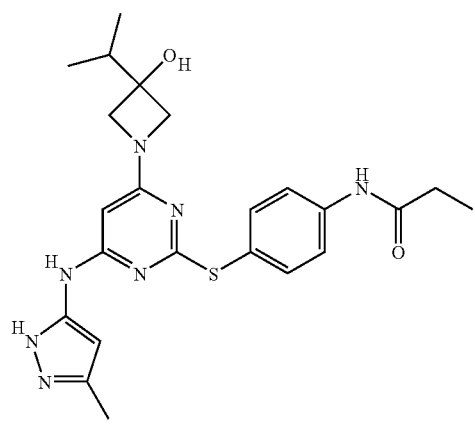
I-100
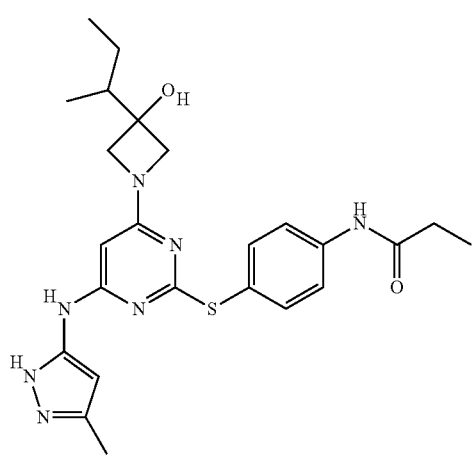
I-101
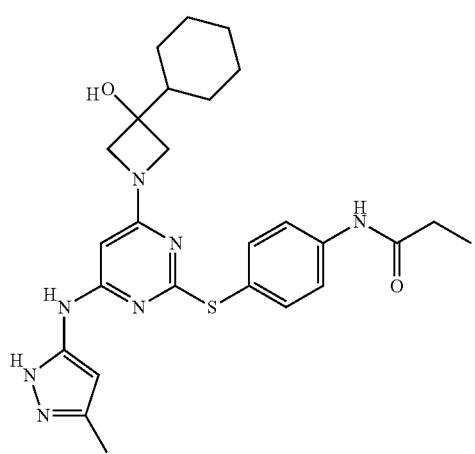
I-102
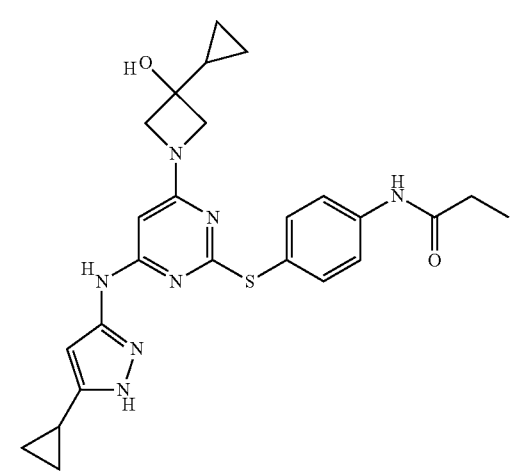
I-103
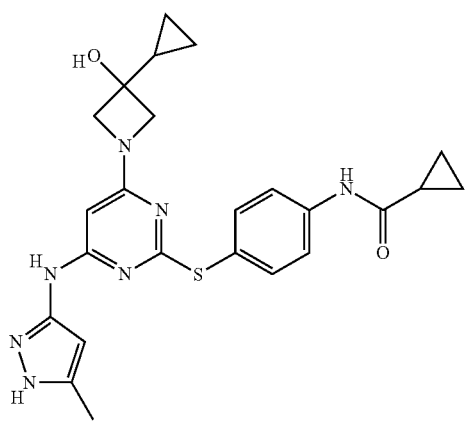
I-104
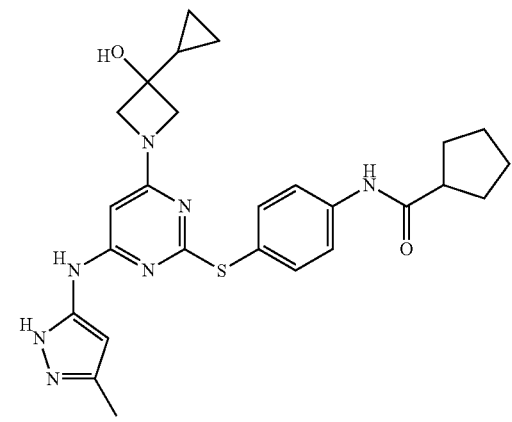

I-105
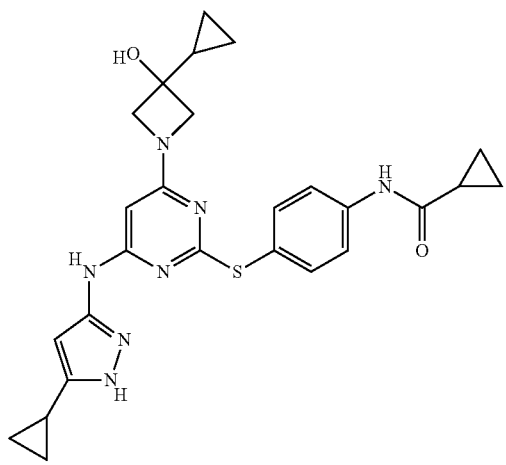
I-108
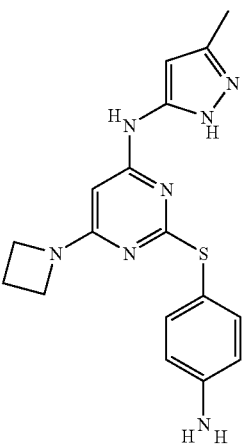
I-106
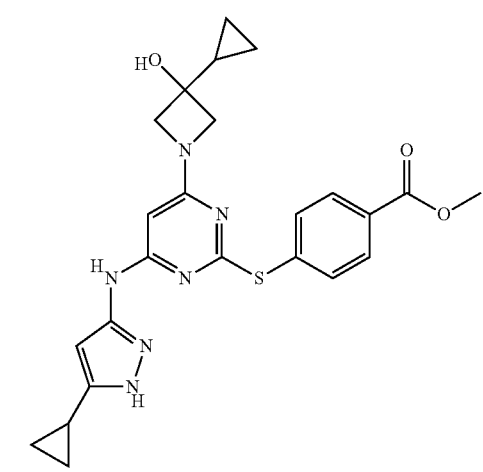
I-109
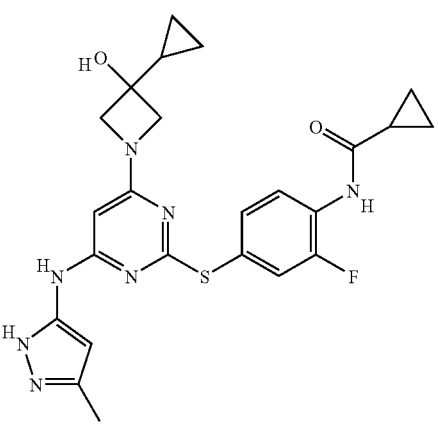
I-107
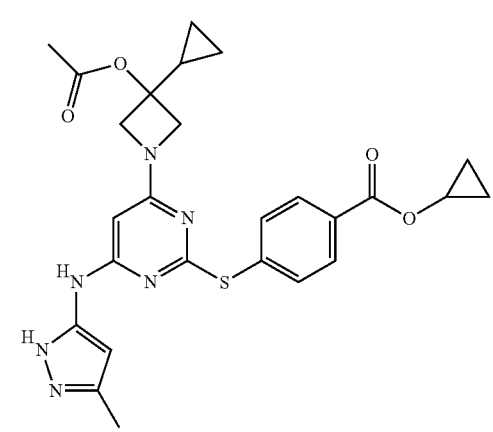
I-110
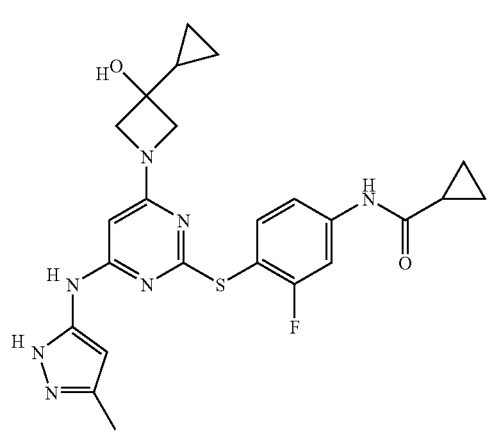

I-111
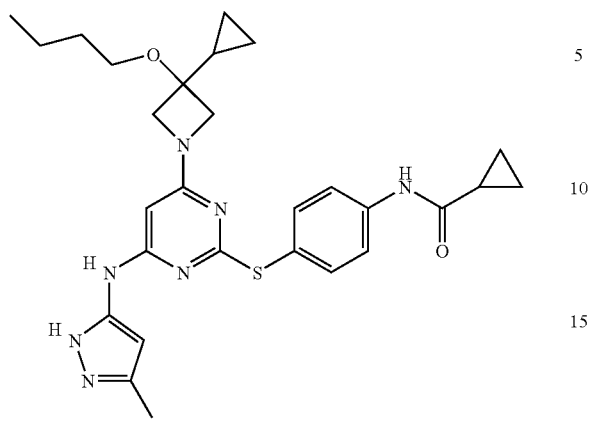
I-114
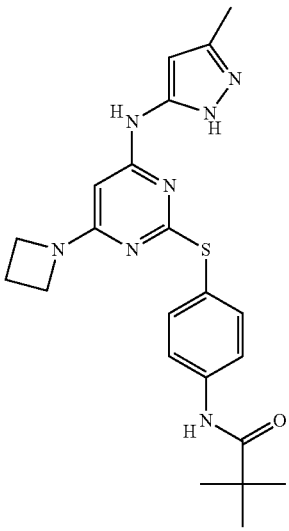
I-112
I-115
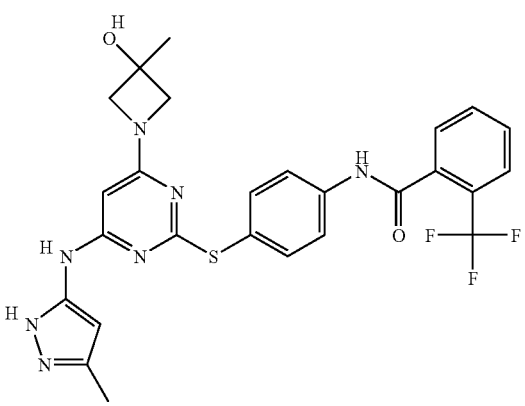
I-113
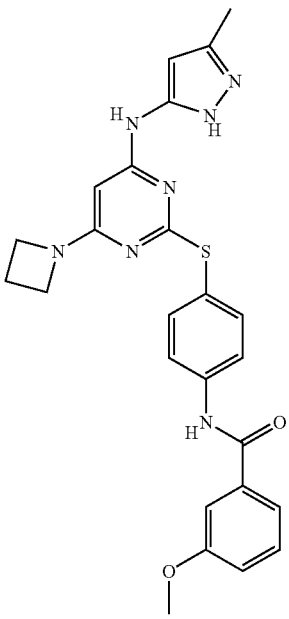
I-116

I-117
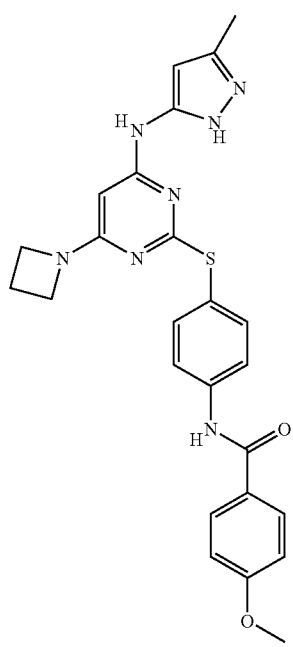
I-118
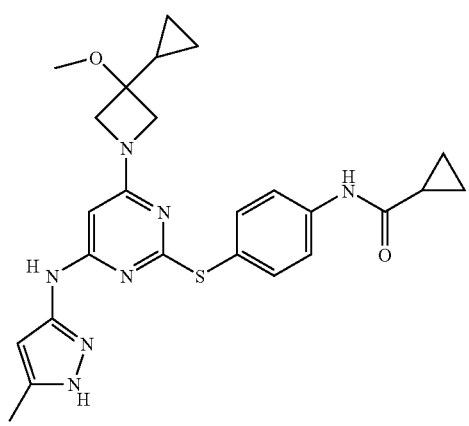
I-119
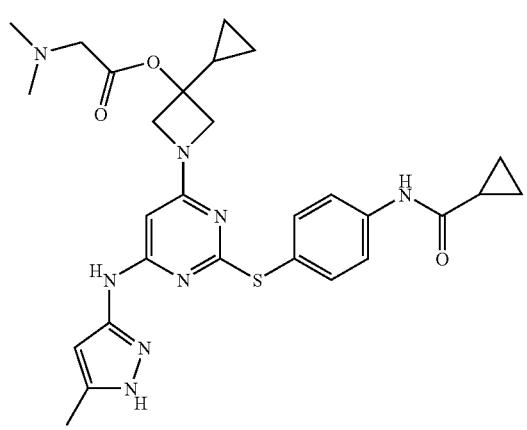
I-120
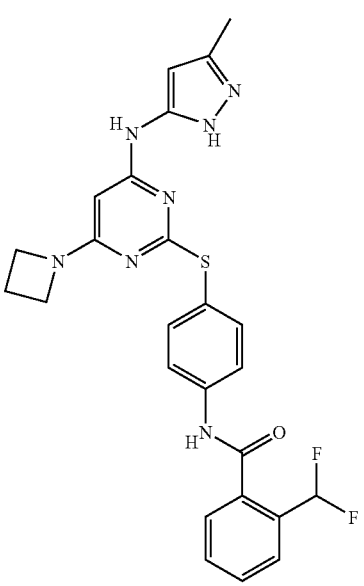
I-121
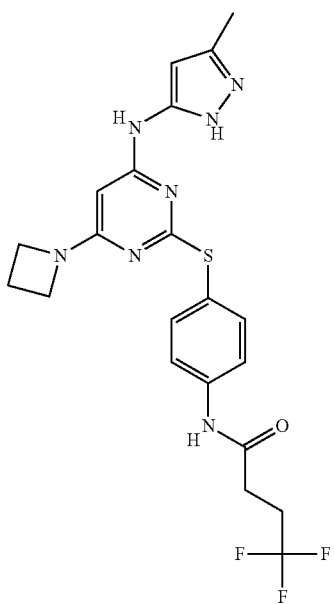
I-122
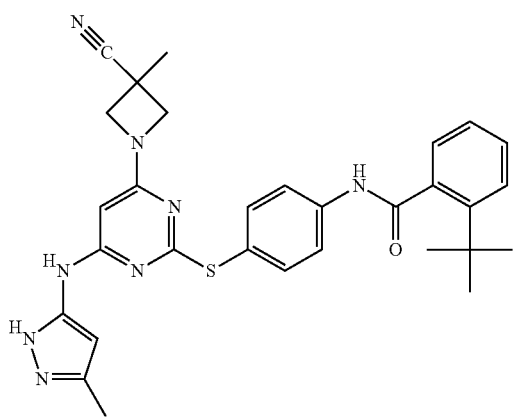

I-123
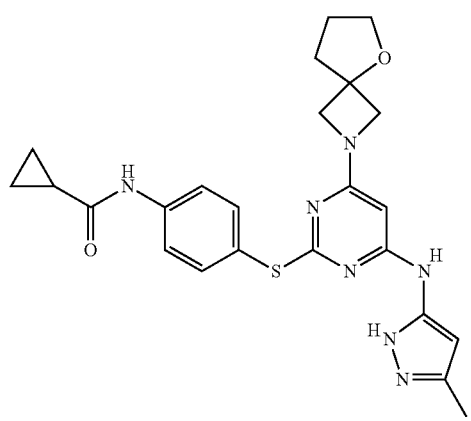
I-126
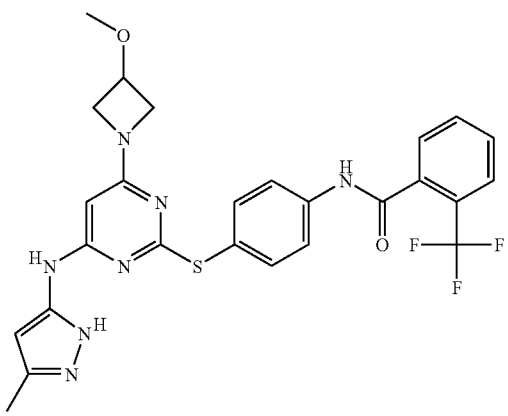
I-124
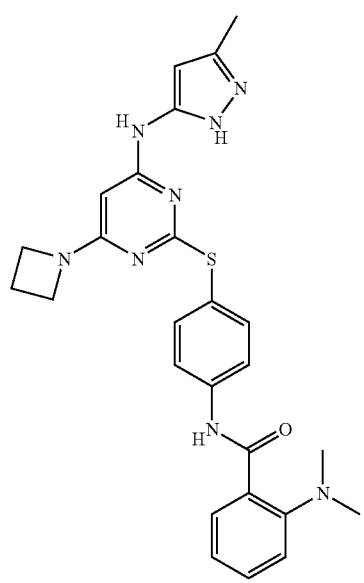
I-127
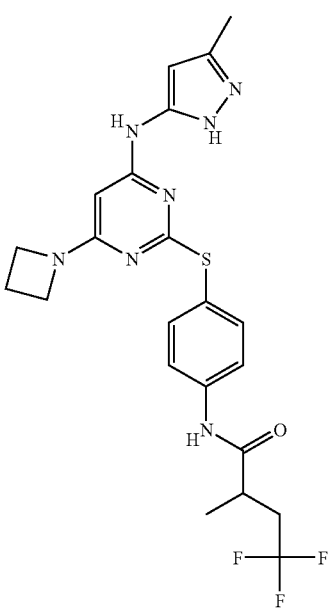
I-125
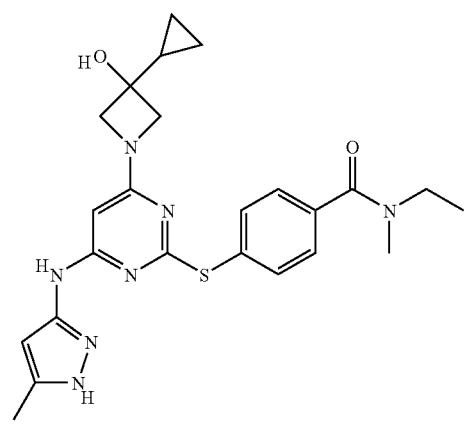
I-128
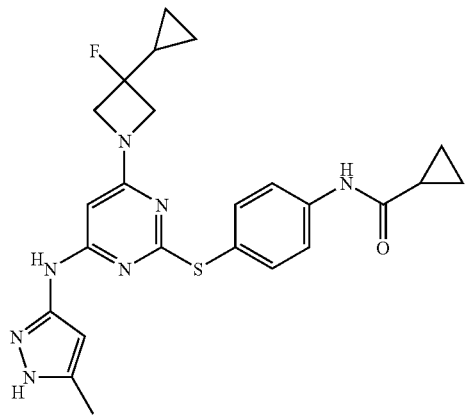

I-129
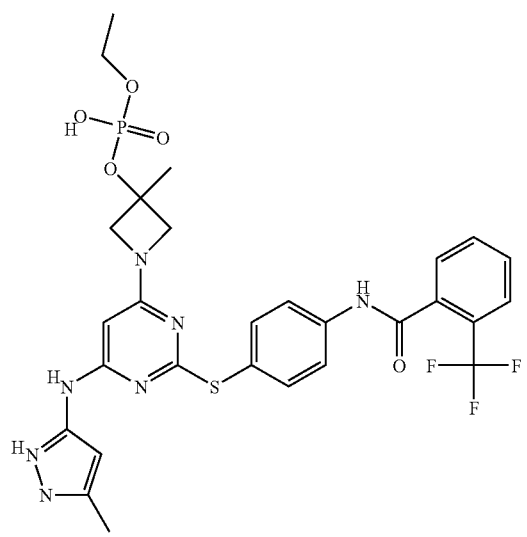
I-132
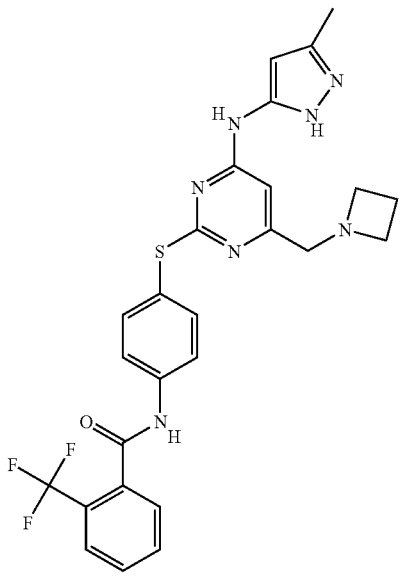
I-130
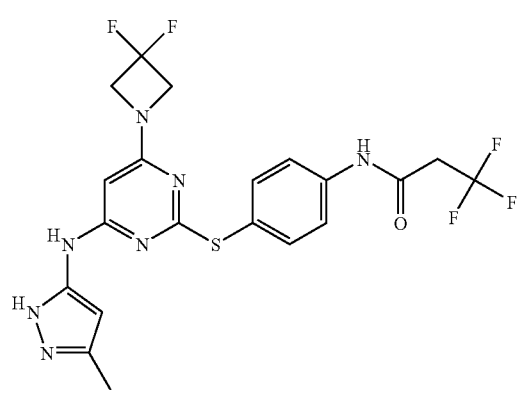
I-133
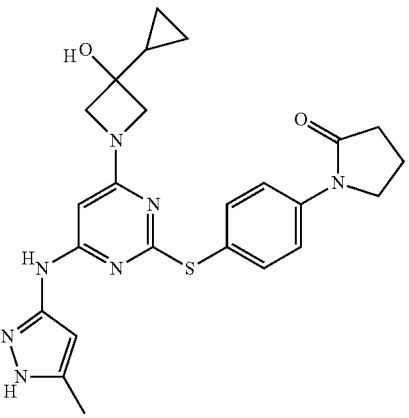
I-131
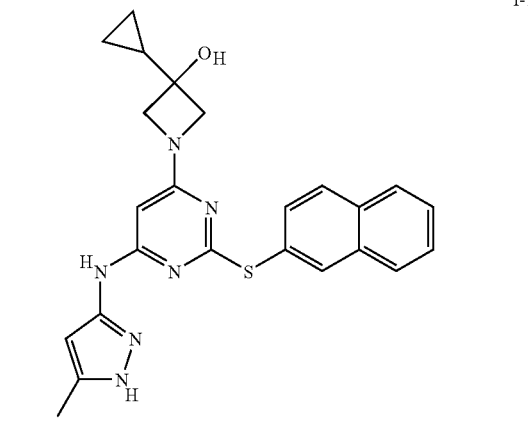
I-134
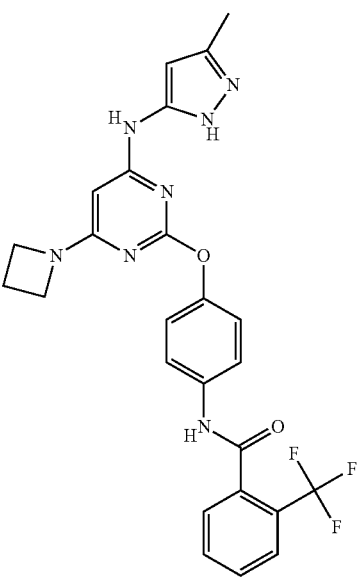

I-135
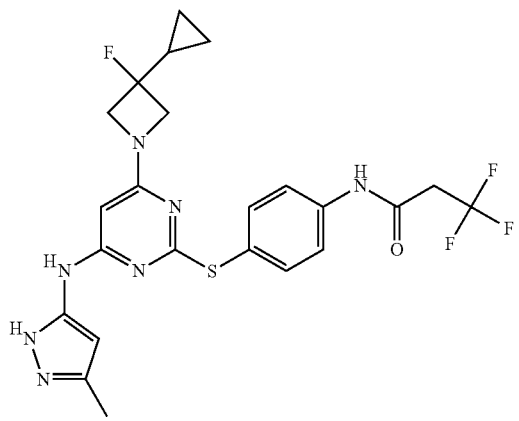
I-136
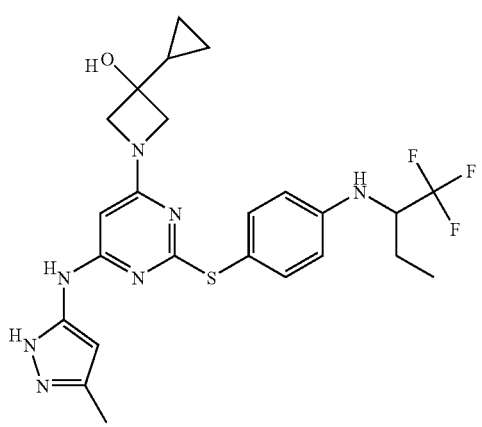
I-138
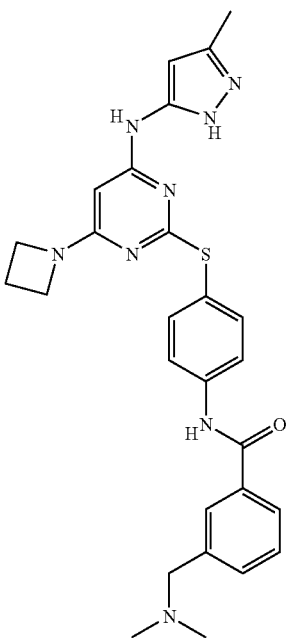
I-137
I-139
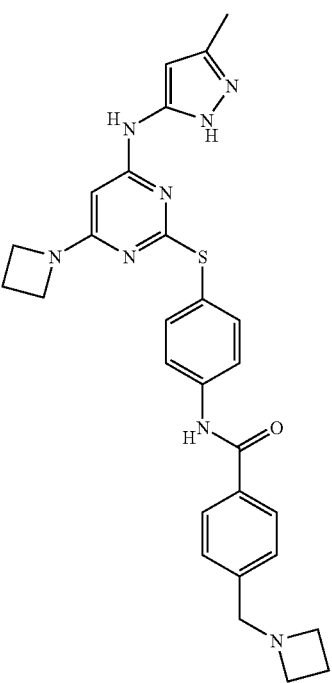

I-140
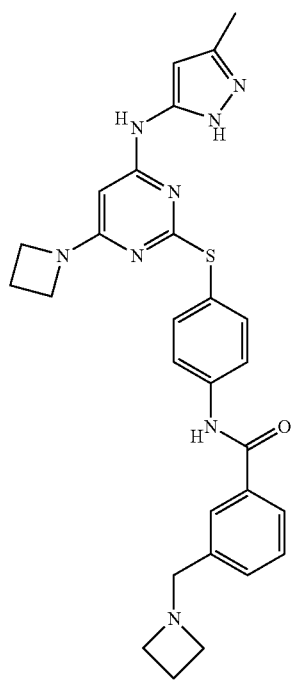
I-141
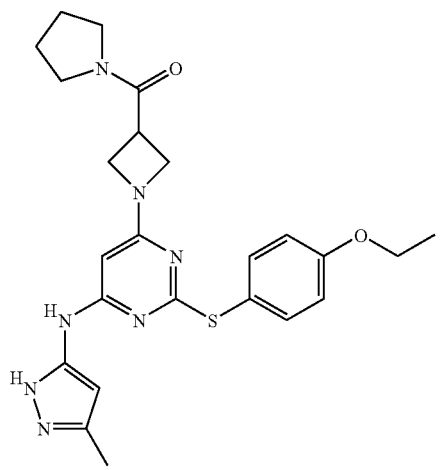
I-142
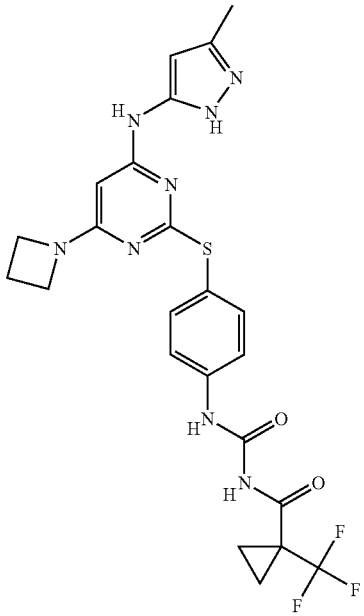
I-143
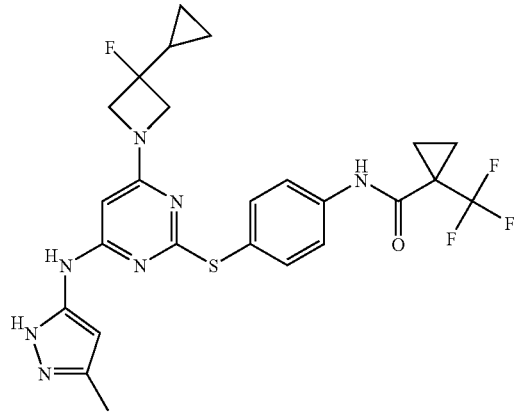
I-144
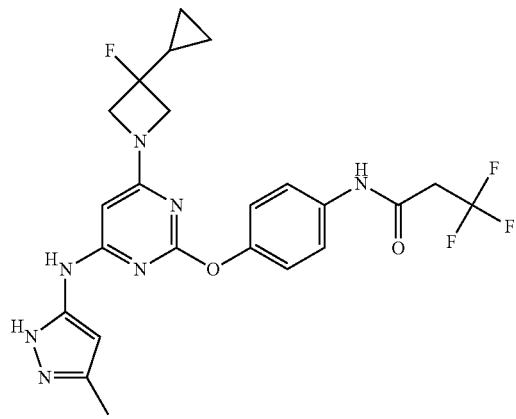

I-145
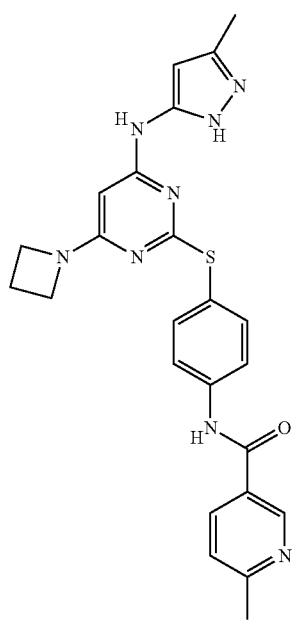
I-148
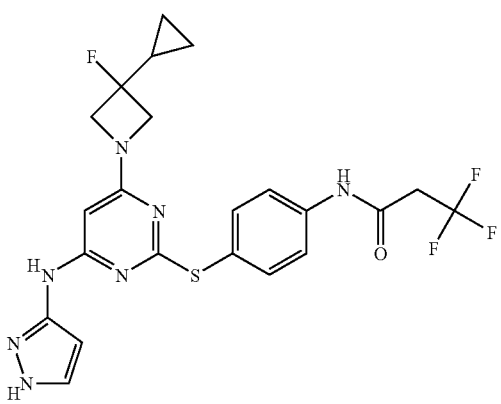
I-146
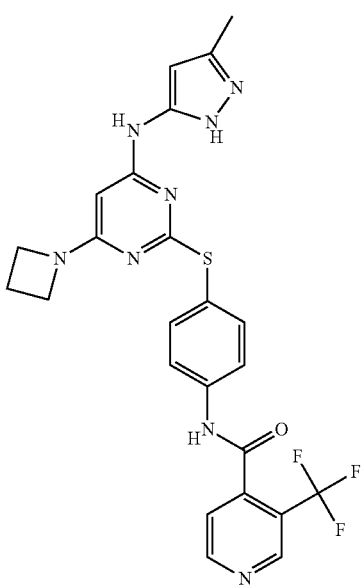
I-149
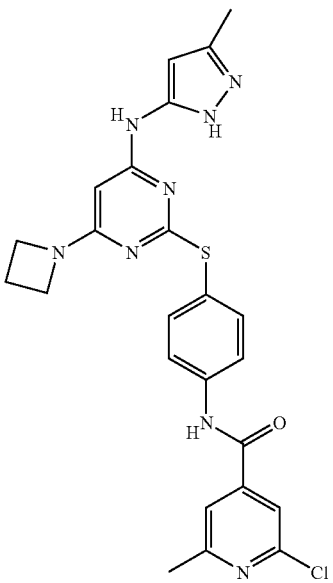
I-147
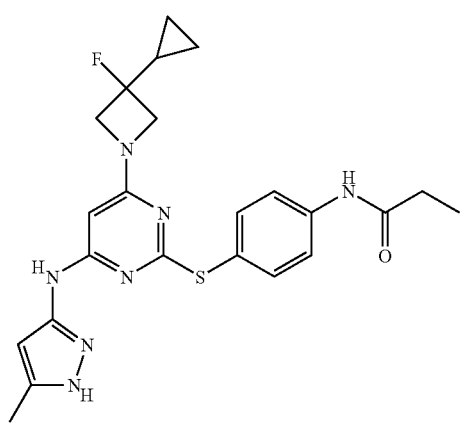
I-150
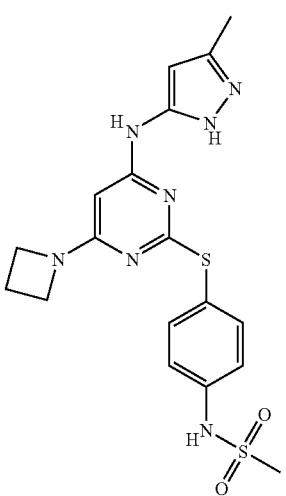

I-151
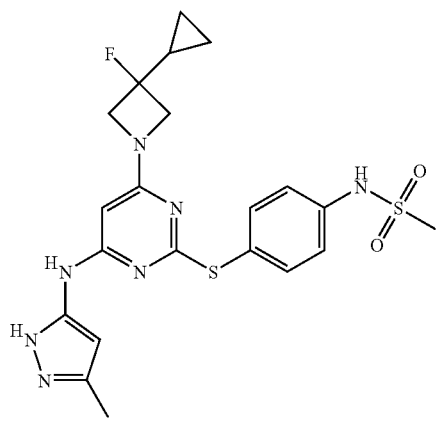
I-152
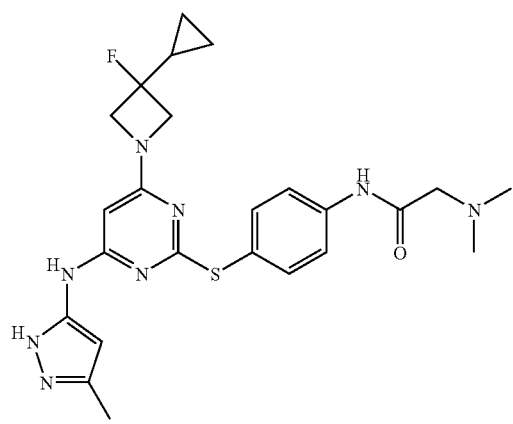
I-153
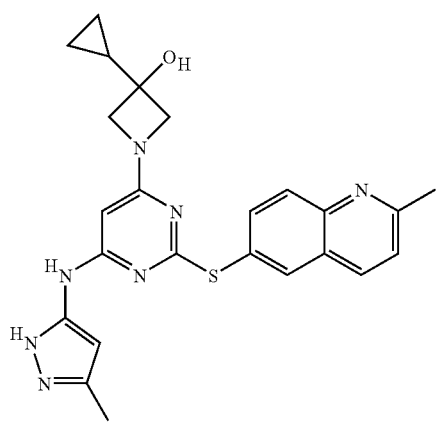
I-154
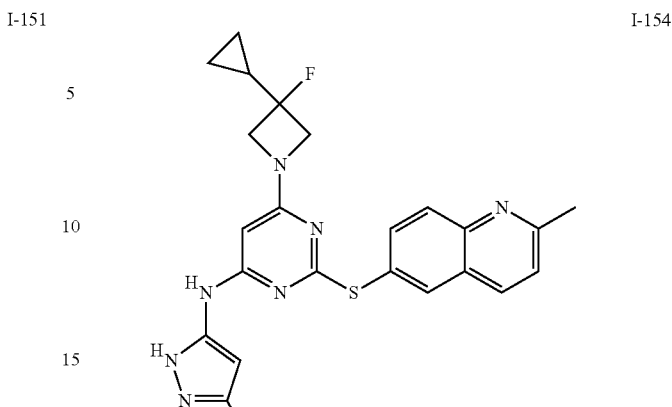
I-155
I-156
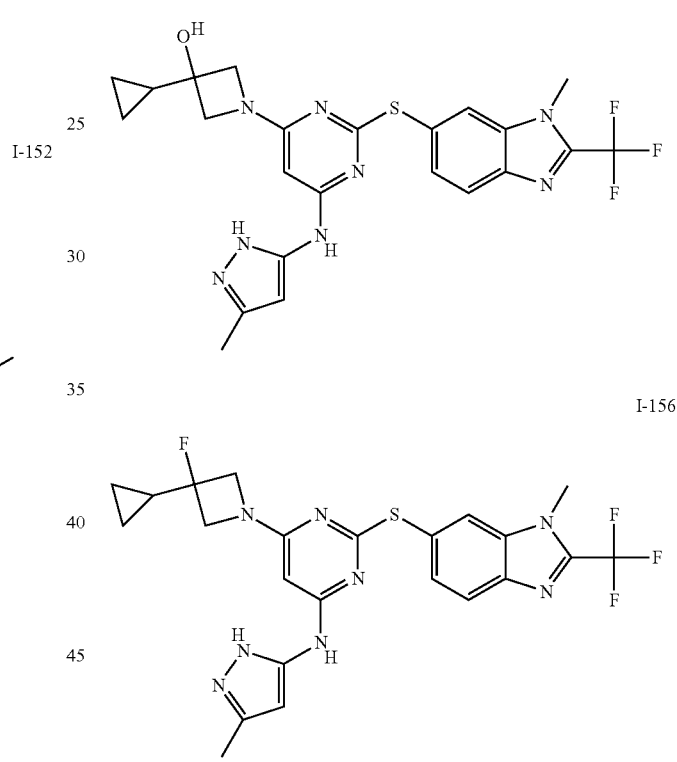
I-157

I-158 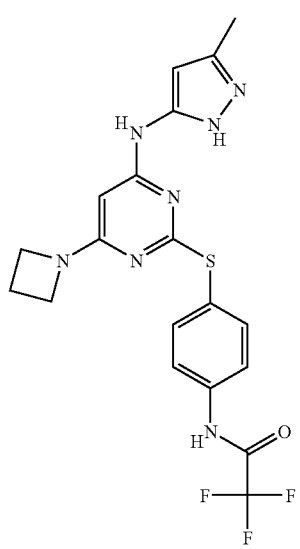
I-161 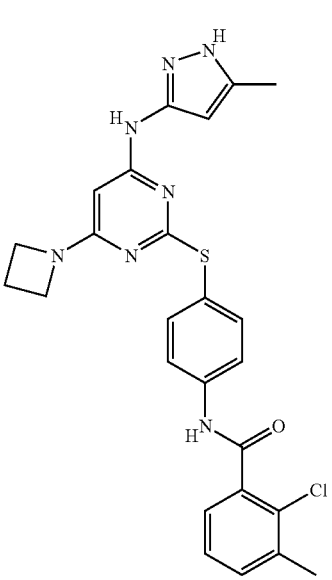
I-159 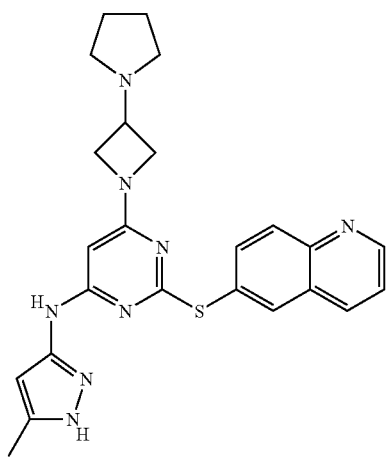
I-160 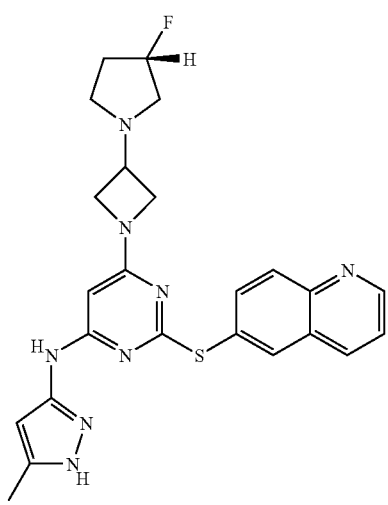
I-162 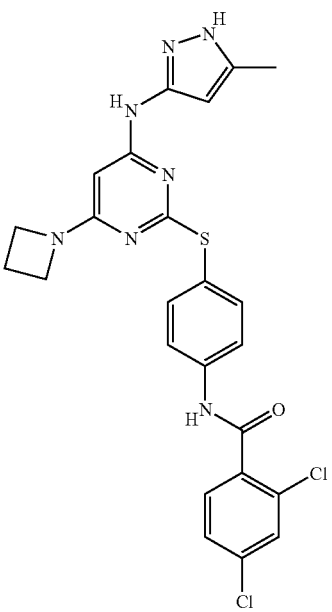

I-163
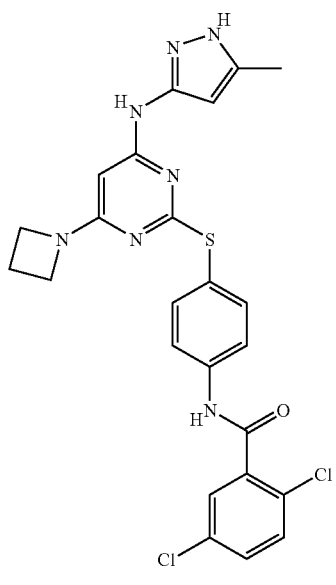
I-164
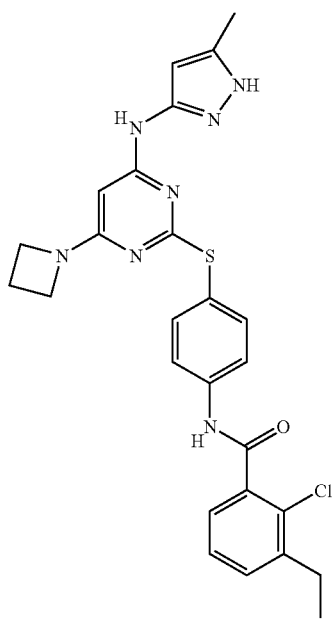
I-165
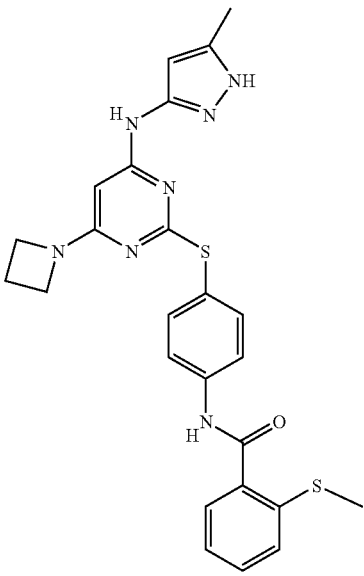
I-166
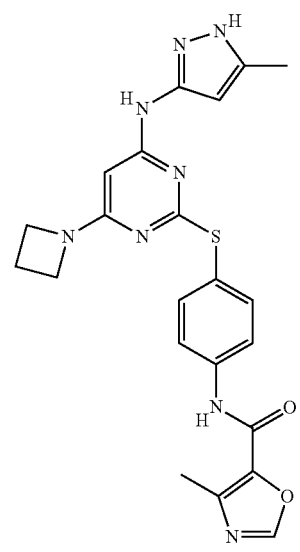
I-167

I-168
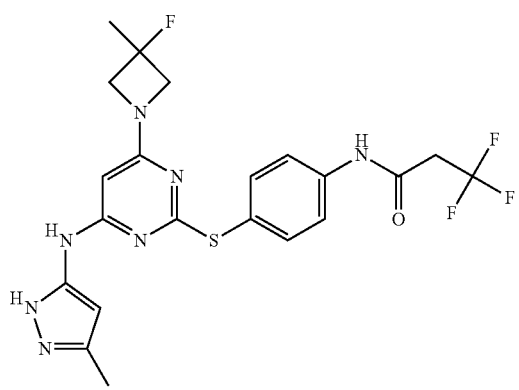
I-169
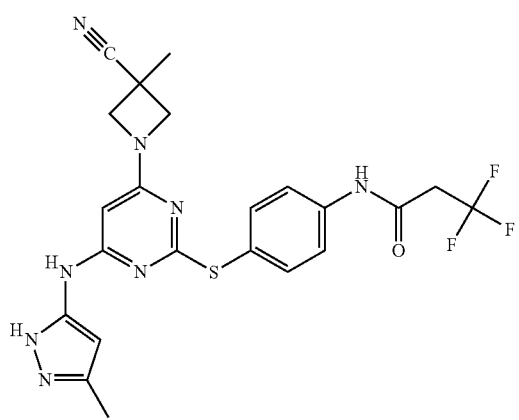
I-170
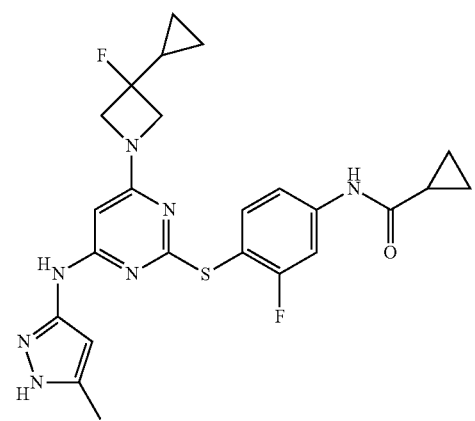
I-171
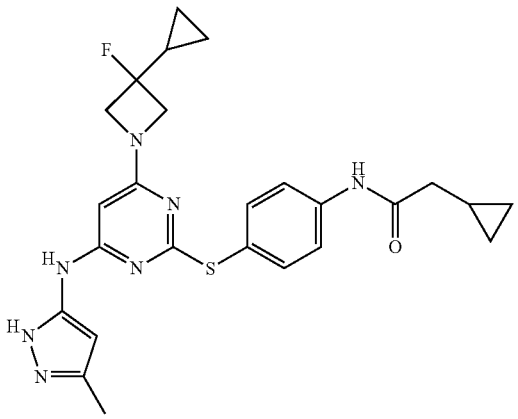
I-172
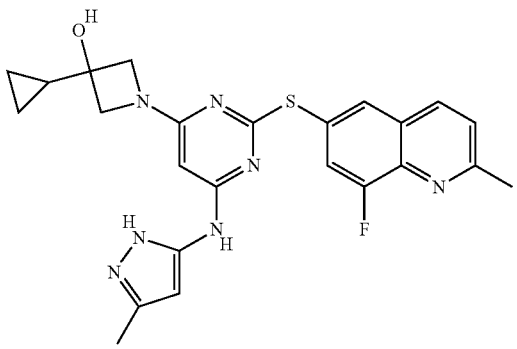
I-173
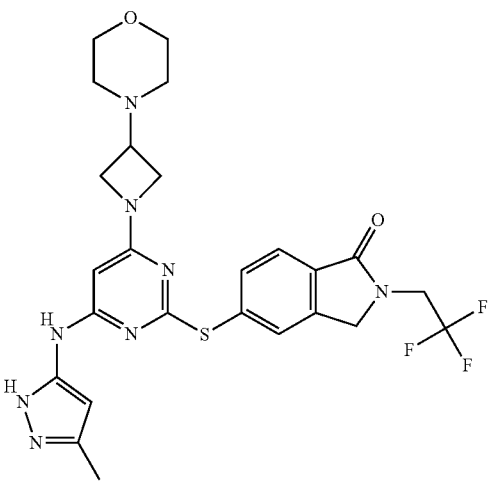

I-174
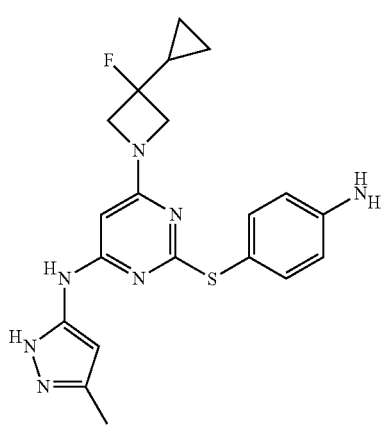
I-175
I-176
I-177
I-178
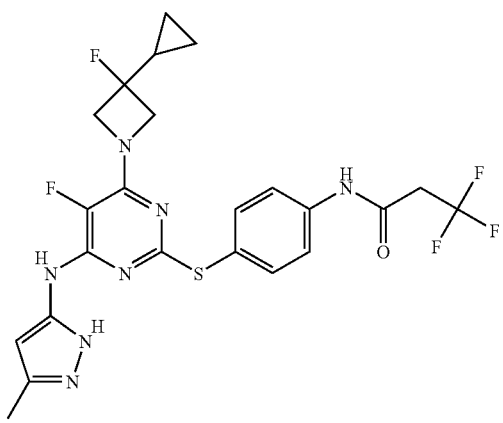
I-179
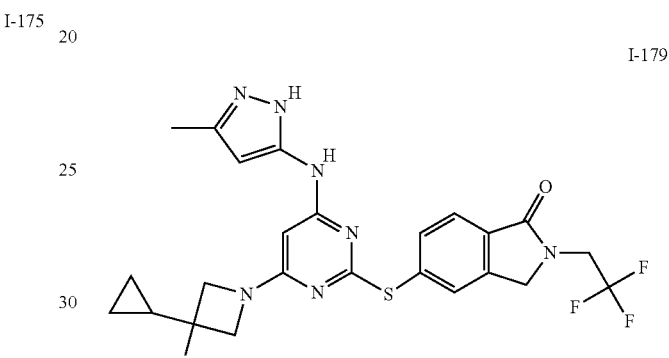
I-180
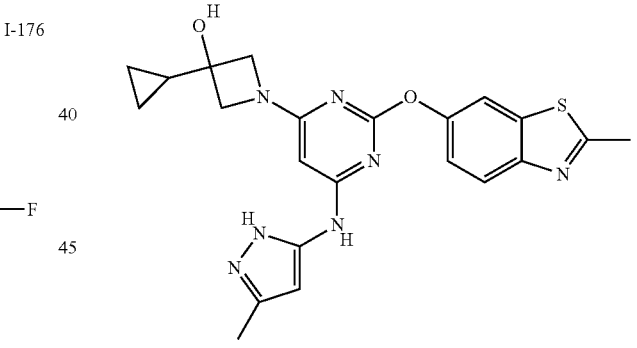
I-181
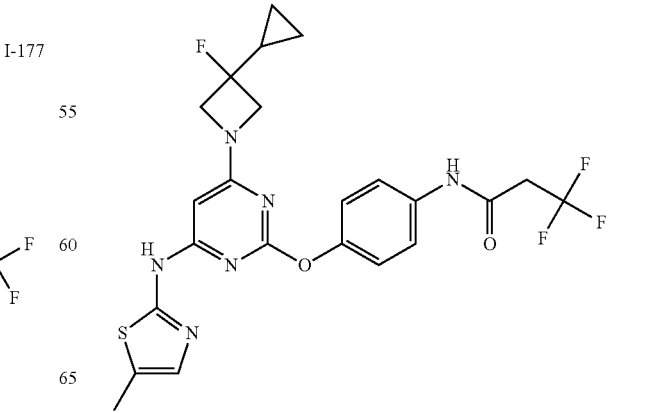

I-182
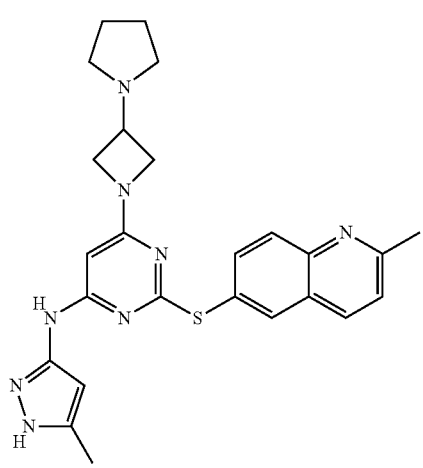
I-185
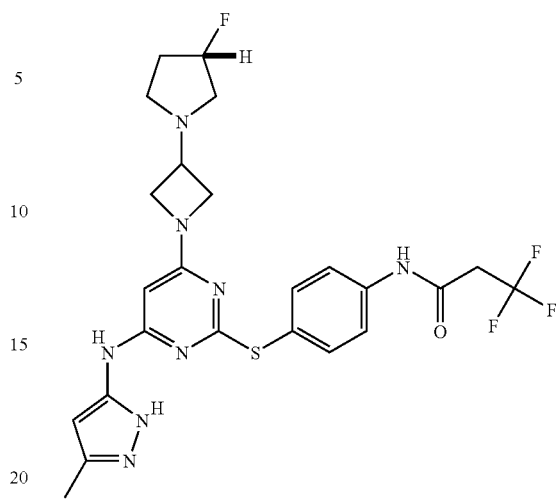
I-183
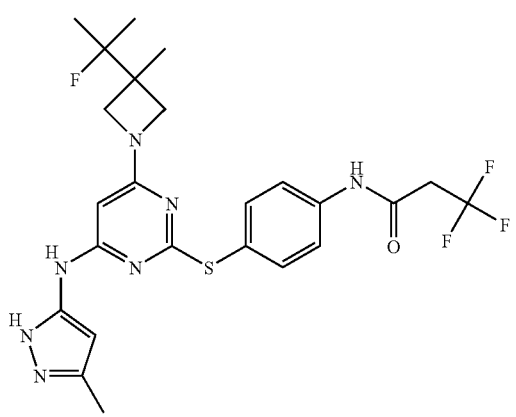
I-186
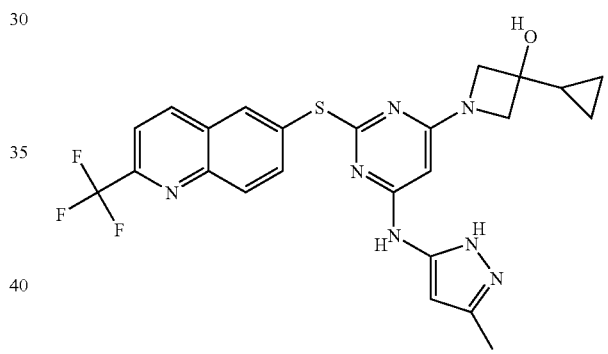
I-184
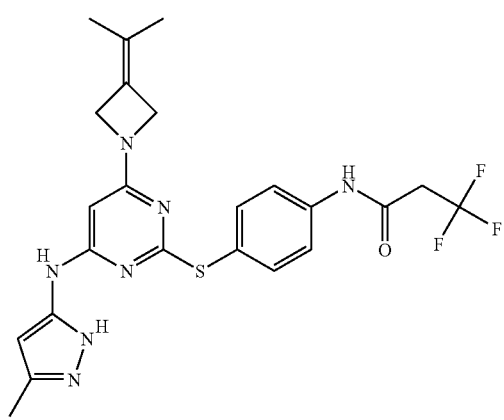
I-187
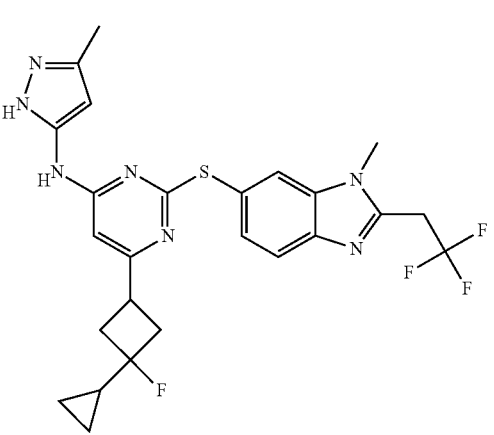

I-188
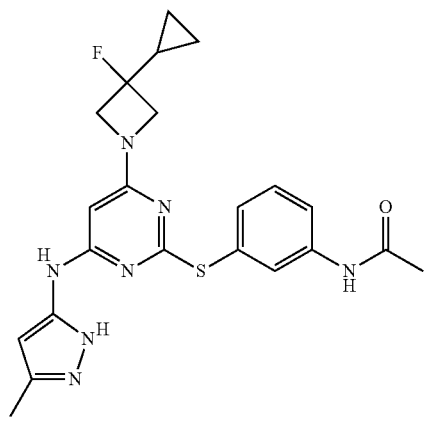
I-191
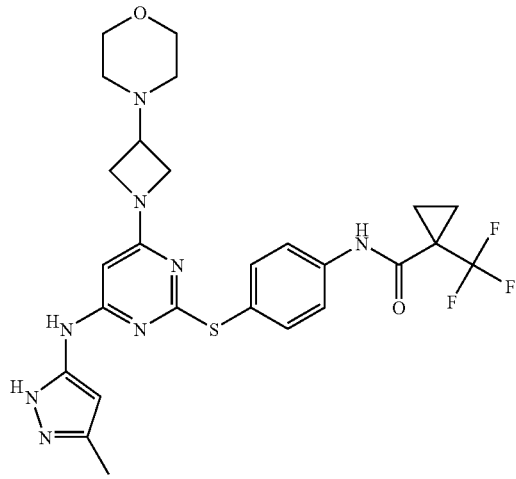
I-189
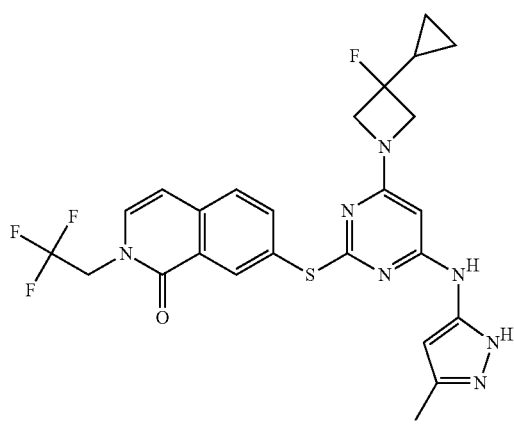
I-192
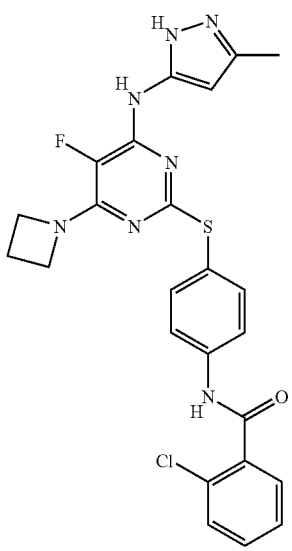
I-190
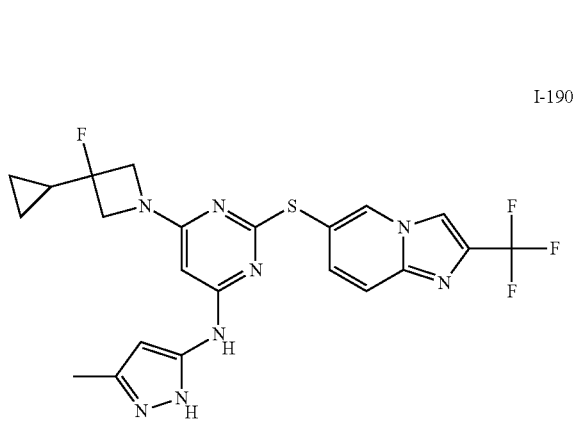
I-193
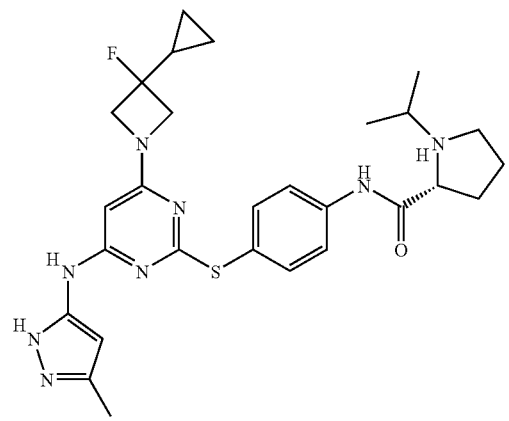

I-194
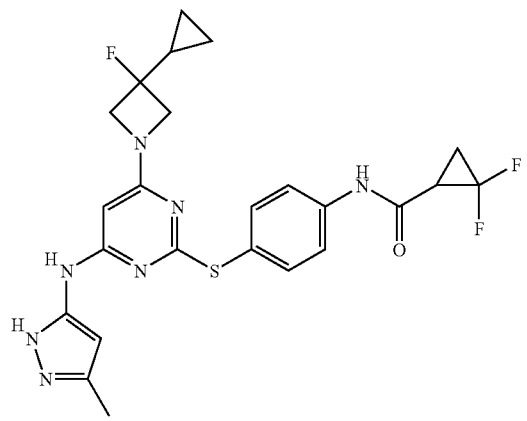
I-195
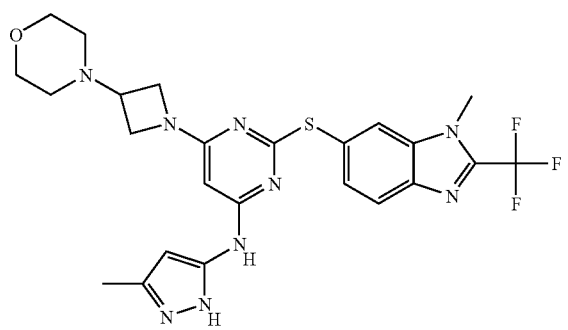
I-196
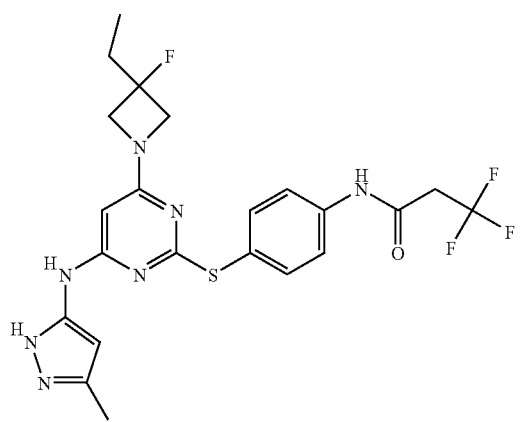
I-197
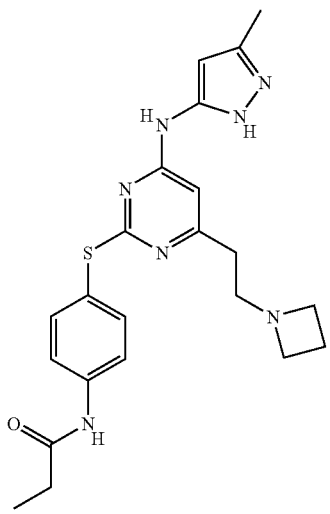
I-198
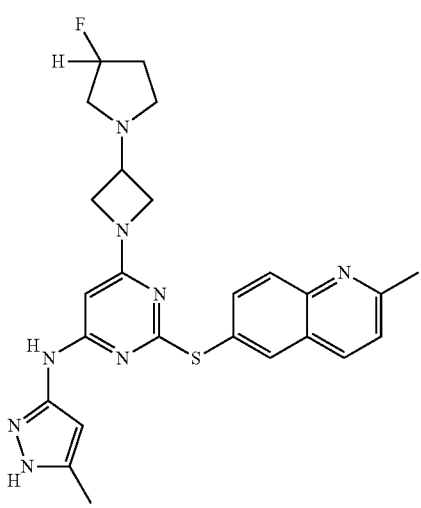
I-199
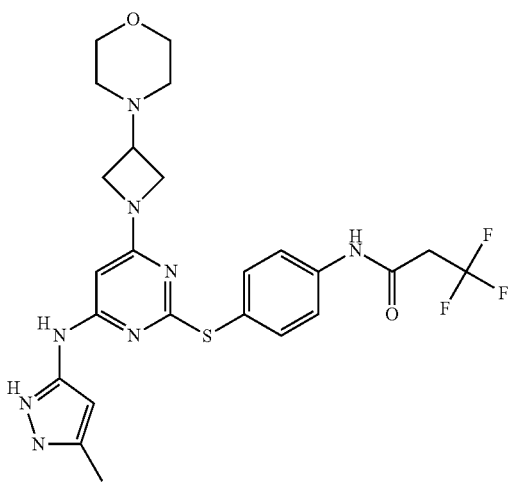

I-200
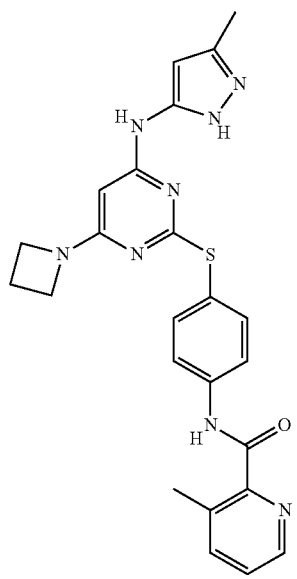
I-201
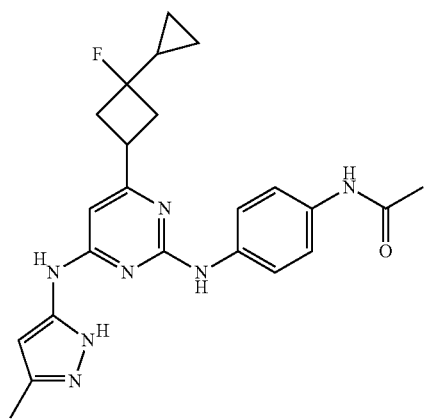
I-202
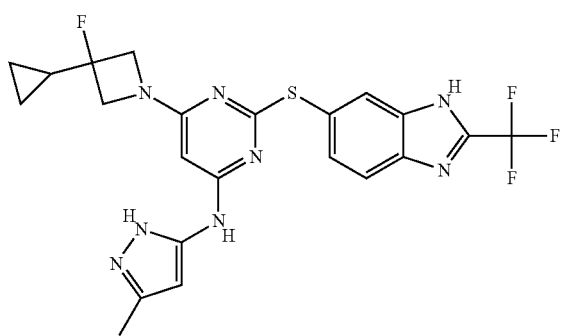
I-203
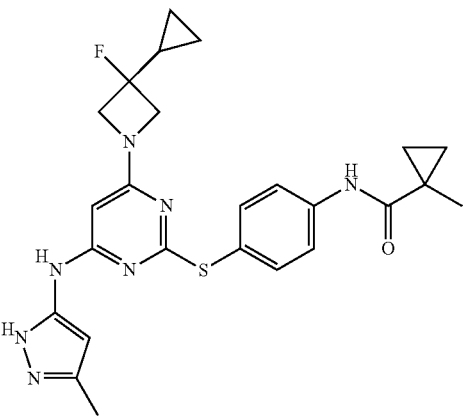
I-204
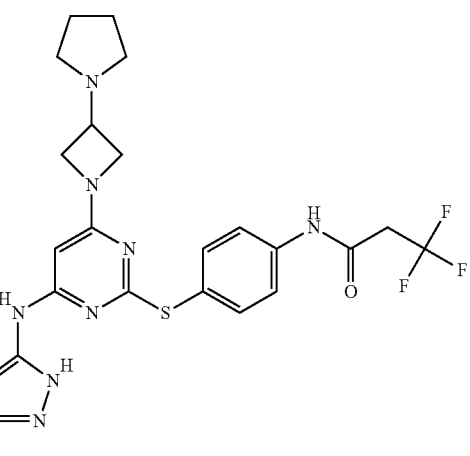
I-205
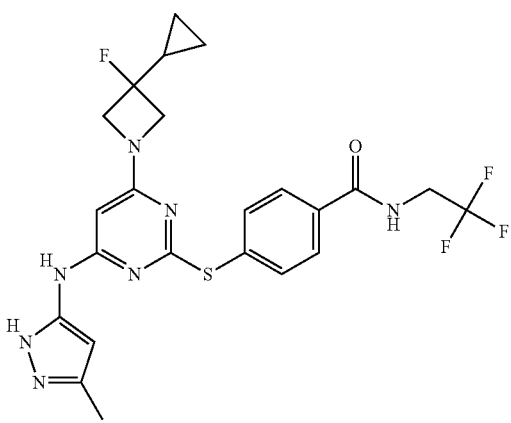

I-206
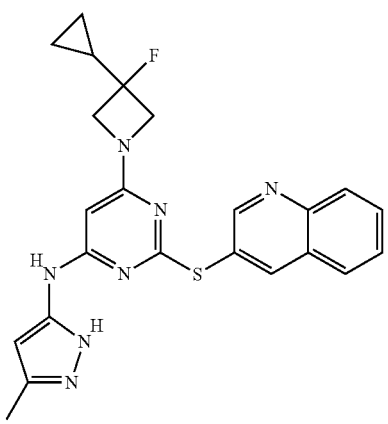
I-207
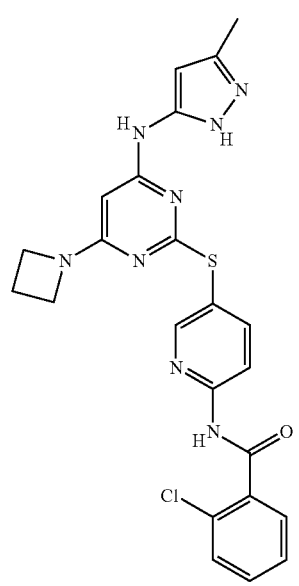
I-208
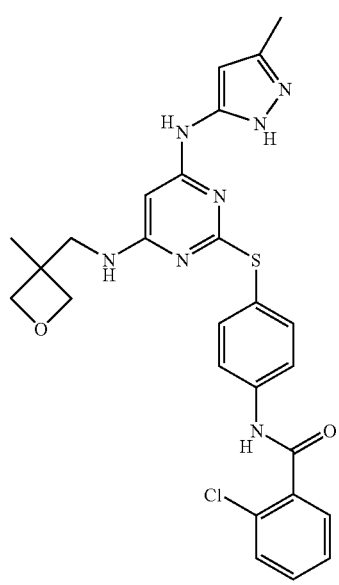
I-209
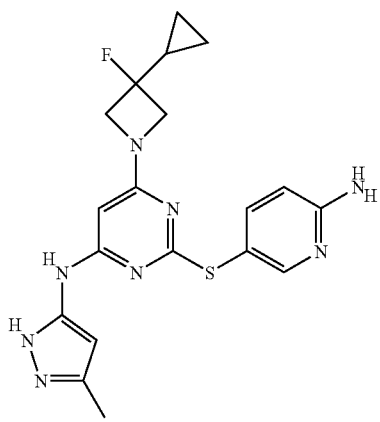
I-210
I-211
2. A method of inhibiting Aurora-A or Aurora-B protein kinase activity in an in vitro biological sample comprising contacting said biological sample with a compound of the following formula:

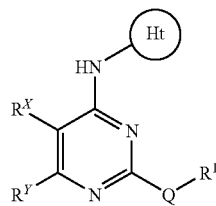

or a pharmaceutically acceptable salt thereof, wherein:

Ht is thiazolyl or pyrazolyl, wherein each ring is optionally and independently substituted with 0-1 occurrences of $R^2$ and 0-1 occurrences of $R^{2'}$;

Q is —O—, —NR'—, —S—, or —C(R')$_2$—;

$R^X$ is H, $C_{1-6}$aliphatic, $NO_2$, CN, halo, $NH_2$, $NH(C_{1-4}$aliphatic), $N(C_{1-4}$aliphatic)$_2$, $O(C_{1-4}$aliphatic), OH, or —N(C=O)($C_{1-4}$aliphatic); wherein said aliphatic is optionally substituted with 1-3 fluoro;

$R^Y$ is $T^2$-$R^{10}$ or L-Z—$R^{10}$;

$R^1$ is $T^3$-(Ring D);

Ring D is a 5-7 membered monocyclic aryl or heteroaryl ring, wherein said heteroaryl has 1-4 ring heteroatoms selected from O, N, and S; Ring D can optionally be fused with Ring D';

Ring D' is a 5-8 aromatic, or partially saturated ring containing 0-4 ring heteroatoms selected from nitrogen, oxygen or sulfur;

each substitutable ring carbon of Ring D and Ring D' is independently substituted by oxo, $T^4$-$R^5$, or V—Z—$R^5$;

each substitutable ring nitrogen of Ring D and Ring D' is independently substituted by —$R^4$;

each T, $T^3$, and $T^4$ is independently a $C_{1-4}$ alkylidene chain or is absent;

Z is a $C_{1-4}$ alkylidene chain or is absent;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON ($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N ($R^6$)C(O)—, —C($R^6$)$_2$N($R^6$)C(O)O—, —C($R^6$)=NN ($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON ($R^6$)—;

$T^2$ is independently absent or a $C_{1-10}$ alkylidene chain wherein up to six C units of the alkylidene chain are optionally replaced by —O—, —C(=O)—, —S(O)—, —S(O)$_2$—, —S—, or —N($R^4$)—; $T^2$ is optionally substituted with 0-6 $J^T$ groups;

$R^2$ and $R^{2'}$ are independently —R, -T-W—$R^6$, or $R^8$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^5$ is —R, -halo, —OR, —C(=O)R, —CO$_2$R, —COCOR, COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC (=O)R, —N($R^7$)COR, —N($R^7$)CO$_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$) SO$_2$R, or —OC(=O)N($R^7$)$_2$;

each R is hydrogen, a $C_{1-10}$ aliphatic, a $C_{6-10}$ aryl ring, a heteroaryl ring having 5-10 ring atoms, or a heterocyclyl ring having 4-10 ring atoms, the heteroaryl or heterocyclyl ring having 1-4 ring heteroatoms selected from nitrogen, oxygen, or sulfur, the aliphatic group and each R being optionally substituted by 0-6 $R^9$;

each $R^4$ is —$R^7$, —COR$^7$, —CO$_2$ (optionally substituted $C_{1-6}$ aliphatic), —CON($R^7$)$_2$, or —SO$_2$$R^7$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON ($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N ($R^6$)C(O)—, —C($R^6$)$_2$N($R^6$)C(O)O—, —C($R^6$)=NN ($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON ($R^6$)—;

W is —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N ($R^6$)—, —CO—, —CO$_2$—, —C($R^6$)$_2$OC(O)—, —C($R^6$)$_2$OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON ($R^6$)—, or —CON($R^6$)—;

each $R^6$ is independently hydrogen or $C_{1-6}$ aliphatic optionally substituted with 0-3 $J^6$; or two $R^6$ groups on the same nitrogen atom are taken together with the nitrogen atom to form a 4-8 membered heterocyclyl or heteroaryl ring; wherein said heterocyclyl or heteroaryl ring is optionally substituted with 0-4 $J^6$;

each $R^7$ is independently hydrogen; $C_{1-6}$ aliphatic; a 5-membered heteroaryl containing 0-4 heteroatoms selected from O, N, or S; or phenyl; each $R^7$ is optionally substituted with 0-3 $J^7$; or two $R^7$ on the same nitrogen are taken together with the nitrogen to form an optionally substituted 4-8 membered heterocyclyl or heteroaryl ring; wherein said heterocyclyl or heteroaryl ring is optionally substituted with 0-4 $J^7$;

each $R^8$ is halogen, —CN, or —NO$_2$;

each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$ N(R')$_2$, —OC(=O)R', —N(R')COR', —N(R')CO$_2$($C_{1-6}$ aliphatic), —N(R')N(R')$_2$, —N(R')CON(R')$_2$, —N(R') SO$_2$N(R')$_2$, —N(R')SO$_2$R', —OC(=O)N(R')$_2$, =NN (R')$_2$, =N—OR', =NR', or =O;

each $R^{10}$ is a 4-membered heterocyclic ring containing 1 heteroatom selected from O, NR$^{11}$, and S; each $R^{10}$ is optionally substituted with 0-6 occurrences of J;

each J and $J^T$ is independently R, -halo, —OR, —C(=O)R, —CO$_2$R, —COCOR, COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$) CO$_2$($C_{1-6}$ aliphatic), —N($R^4$)N($R^4$)$_2$, =NN($R^4$)$_2$, =N—OR, =NR, =O, —N($R^7$)CON($R^7$)$_2$, —N($R^7$) SO$_2$N($R^7$)$_2$, —N($R^4$)SO$_2$R, —OC(=O)N($R^7$)$_2$, or —OP(=O)(OR")$_2$; or each $J^6$ and $J^7$ is independently NH$_2$, NH($C_{1-4}$aliphatic), N($C_{1-4}$aliphatic)$_2$, halogen, $C_{1-4}$aliphatic, OH, O($C_{1-4}$ aliphatic), NO$_2$, CN, CO$_2$H, CO$_2$($C_{1-4}$aliphatic), O(halo$C_{1-4}$aliphatic), or halo$C_{1-4}$aliphatic;

2 J or $J^T$ groups, on the same atom or on different atoms, together with the atom(s) to which each set of J or $J^T$ atoms are bound, form a 3-8 membered saturated, partially saturated, or unsaturated ring having 0-2 heteroatoms selected from O, N, or S; wherein 1-4 hydrogen atoms on the ring formed by the 2 J or $J^T$ groups is optionally replaced with halo, $C_{1-3}$alkyl, or —O($C_{1-3}$alkyl); wherein said $C_{1-3}$alkyl is optionally substituted with 1-3 fluorine; or two hydrogen atoms on the same atom in the ring formed by the 2 J or $J^T$ groups are optionally replaced with oxo;

each $R^{11}$ is —$R^7$, —$COR^7$, —$CO_2$ (optionally substituted $C_{1-6}$ aliphatic), —$CON(R^7)_2$, or —$SO_2R^7$;

each R' is independently hydrogen or a $C_{1-6}$ aliphatic group optionally substituted with 0-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), $CONH_2$, CONH($C_{1-4}$aliphatic), CON($C_{1-4}$aliphatic)$_2$, O(halo$C_{1-4}$ aliphatic), or halo$C_{1-4}$aliphatic; or, two R', together with the atom(s) to which they are attached, form =O, an optionally substituted 3-6 membered carbocyclyl, or heterocyclyl;

each R" is independently H or $C_{1-2}$alkyl.

\* \* \* \* \*